(12) United States Patent
Malyshev et al.

(10) Patent No.: US 12,178,838 B2
(45) Date of Patent: Dec. 31, 2024

(54) SYNTHETIC NEUROMODULATORY PEPTIDES

(71) Applicant: Lactocore, Inc., Plymouth, MI (US)

(72) Inventors: Anton Malyshev, Plymouth, MI (US); Igor Doronin, Plymouth, MI (US); Gennady Babkin, Plymouth, MI (US); Askar Kuchumov, Plymouth, MI (US)

(73) Assignee: Lactocore, Inc., Plymouth, MI (US)

( * ) Notice: Subject to any disclaimer, the term of this patent is extended or adjusted under 35 U.S.C. 154(b) by 547 days.

(21) Appl. No.: 17/437,331

(22) PCT Filed: Mar. 13, 2020

(86) PCT No.: PCT/US2020/022623
§ 371 (c)(1),
(2) Date: Sep. 8, 2021

(87) PCT Pub. No.: WO2020/186155
PCT Pub. Date: Sep. 17, 2020

(65) Prior Publication Data
US 2022/0175873 A1    Jun. 9, 2022

Related U.S. Application Data

(60) Provisional application No. 62/818,458, filed on Mar. 14, 2019.

(51) Int. Cl.
| | |
|---|---|
| *A61K 38/07* | (2006.01) |
| *A61K 9/00* | (2006.01) |
| *A61K 45/06* | (2006.01) |
| *A61P 25/00* | (2006.01) |
| *A61P 25/22* | (2006.01) |
| *A61P 25/28* | (2006.01) |
| *C07K 5/10* | (2006.01) |

(52) U.S. Cl.
CPC .......... *A61K 38/07* (2013.01); *A61K 9/0043* (2013.01); *A61K 45/06* (2013.01); *A61P 25/22* (2018.01); *A61P 25/28* (2018.01)

(58) Field of Classification Search
CPC ...... A61K 38/07; A61K 45/06; A61K 9/0043; C07K 5/1008; C07K 5/101; C07K 5/1016; C07K 5/1019; C07K 5/1021; C07K 5/1024; A61P 25/00; A61P 25/22; A61P 25/28
See application file for complete search history.

(56) References Cited

FOREIGN PATENT DOCUMENTS

| EP | 2123666 B1 | 5/2013 |
|---|---|---|
| JP | H 05194254 A | 8/1993 |
| WO | WO 2008108285 A1 | 9/2008 |

OTHER PUBLICATIONS

WO 2008/108285 ESPACENET English translation of Description and Claims; Sep. 12, 2008. (Year: 2008).*
Campbell, et al., "Drug development of intranasally delivered peptides," Therapeutic Delivery, vol. 3, No. 4, pp. 557-568, 2012.
Cervato, et al., "Studies on the antioxidant activity of mil caseins," International Journal of Food Sciences and Nutrition, vol. 50, pp. 291-296, 1999.
Gebauer, et al., "Effects of anxiolytics in zebrafish: similarities and differences between benzodiazepines, buspirone and ethanol," Pharmacol. Biochem. Behav. vol. 99, pp. 480-486, 2011.
Grover, "Use of Allosteric Targets in the Discovery of Safer Drugs," Med Princ Pract, vol. 22, pp. 418-426, 2013.
Kahn, et al., "Zebrafish models in neuropsychopharmacology and CNS drug discovery," British Journal of Pharmacology, vol. 174, No. 13, pp. 1925-1944, 2017.
Kamiński S., et al., "Polymorphism of bovine beta-casein and its potential effect on human health," J. Appl. Genet. No. 48, pp. 189-198, 2007.
Lau, et al., "Therapeutic peptides: Historical perspectives, current development trends, and future directions," Bioorganic & Medicinal Chemistry, vol. 26, pp. 2700-2707, 2018.
Maximino, et al., "Fingerprinting of Psychoactive Drugs in Zebrafish Anxiety-Like Behaviors," PLoS ONE, vol. 9, No. 7, 8 pages, 2014.
Maximino, "Scototaxis as anxiety-like behavior in fish," Nature Protocols, vol. 5, No. 2, pp. 209-216, 2010.
Maximino, et al., "Role of serotonin in zebrafish (*Danio rerio*) anxiety: Relationship with serotonin levels and effect of buspirone, WAY 100635, SB 224289, fluoxetine and para-chlorophenylalanine (pCPA) in two behavioral models," Neuropharmacology, vol. 71, pp. 83-97, 2013.
Meredith, et al., "Intranasal Delivery of Proteins and Peptides in the Treatment of Neurodegenerative Diseases," The AAPS Journal, vol. 17, No. 4, pp. 780-787, Jul. 2015.
Miclo, "Characterization of alpha-casozepine, a tryptic peptide from bovine alpha(s1)-casein with benzodiazepine-like activity," FASEB J. No. 15, pp. 1780-1782, 2001.
Mizushige, et al., "Characterization of Tyr-Leu-Gly, a novel anxiolytic-like peptide released from bovine αS-casein," FASEB J., vol. 27, No. 7, pp. 2911-2917, 2013.
Morimoto, "Therapeutics peptides for CNS indications: Progress and challenges," Bioorganic & Medicinal Chemistry, vol. 26, pp. 2859-2862, 2018.
Parker, et al, "The utility of zebrafish to study the mechanisms by which ethanol affects social behavior and anxiety during early brain development," Prog. Neuro-Psychopharmacology Biol. Psychiatry, vol. 55, pp. 94-100, 2014.
Porto, et al., "In Silico optimatization of a guava antimicrobial peptide enables combinatorial exploration for peptide design," Nature Communications, vol. 9, No. 1490, 12 pages, 2018.

(Continued)

*Primary Examiner* — Julie Ha
(74) *Attorney, Agent, or Firm* — Morgan, Lewis & Bockius LLP

(57) ABSTRACT

A pharmaceutical composition comprising a synthetic neuromodulatory peptide is described. The invention discloses neuromodulatory peptides as defined in the claims and methods of using such molecules for therapeutic application. The neuromodulatory peptides included in the composition have been found to be effective in treatment of depression and other mood disorders, including anxiety.

20 Claims, 78 Drawing Sheets

Specification includes a Sequence Listing.

(56) References Cited

OTHER PUBLICATIONS

Ramerstorfer, et al., "The GABAA receptor α+ β-interface: a novel target for subtype selective drugs," J. Neurosci., vol. 31, No. 3, pp. 870-877, 2011.
Rival, et al., "Caseins and Casein Hydrolysates. 1. Lipoxygenase Inhibitory Properties," J. Agric. Food Chem., vol. 49, pp. 287-294, 2001.
Song, et al., "Single Binding Pockets Versus Allosteric Binding," J.B. Brown (ed.), Computational Chemogenomics, Methods in Molecular Biology, vol. 1825, pp. 295-326, 2018.
Walstra, et al., *Dairy science and technology*, 2nd ed. Taylor & Francis Group, Section A6: Amino Acid Sequences of Caseins, pp. 750-751, 2006.
Wilkinson, et al., "A new generation of antidepressants: an update on the pharmaceutical pipeline for novel and rapid-acting therapeutics in mood disorders based on glutamate/GABA neurotransmitter systems," Drug Discovery Today https://doi.org/10.1016/j.drudis.2018.11.007, 2018.
Wilson, et al., "Thromboxane A2-induced contraction of rat caudal arterial smooth muscle involves activation of $Ca^{2+}$ entry and $Ca^{2+}$ sensitization: Rho-associated kinase-mediated phosphorylation of MYPT1 at Thr-855, but not Thr-697," The Biochemical Journal, vol. 389 (Pt 3):763-74, 2005.
Yamakage, et al., "Calcium channels—basic aspects of their structure, function and gene encoding; anesthetic action on the channels—a review," Canadian Journal of Anaesthesia, vol. 49, No. 2, pp. 151-164, 2002.
Zolotarev, et al., "Anxiolytic activity of the neuroprotective peptide HLDF-6 and its effects on brain neurotransmitter systems in BALB/c and C57BL/6 mice," Journal of Psychopharmacology, vol. 30, No. 9, pp. 922-935, 2016.
International Search Report & Written Opinion, PCT Application No. PCT/US20/22623, dated Sep. 1, 2020, 12 pages.

\* cited by examiner

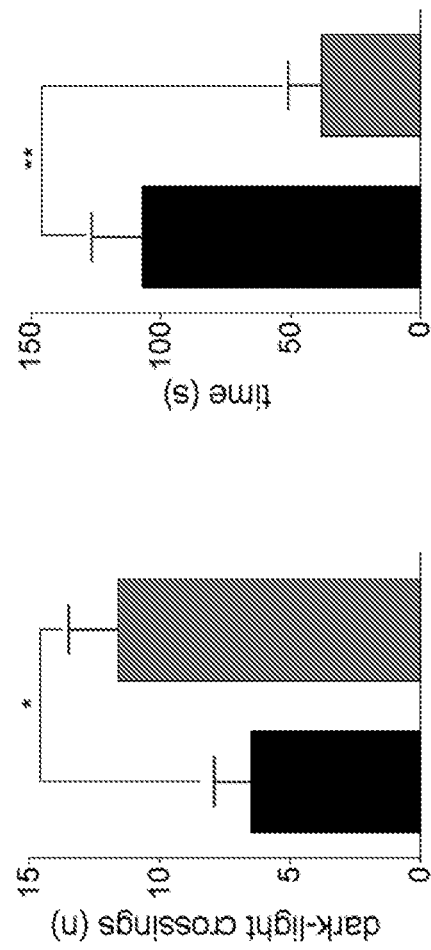
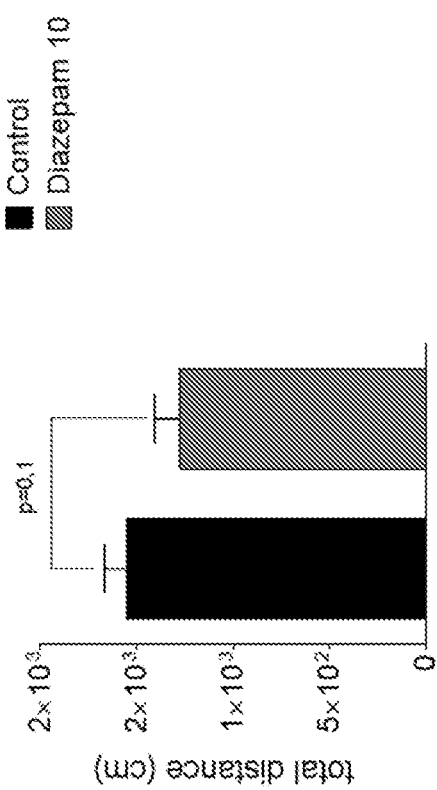
FIG. 5A  FIG. 5B  FIG. 5C

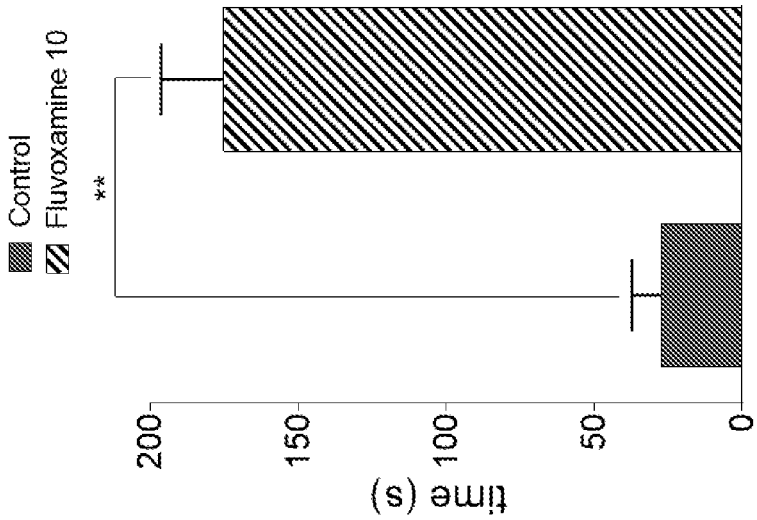
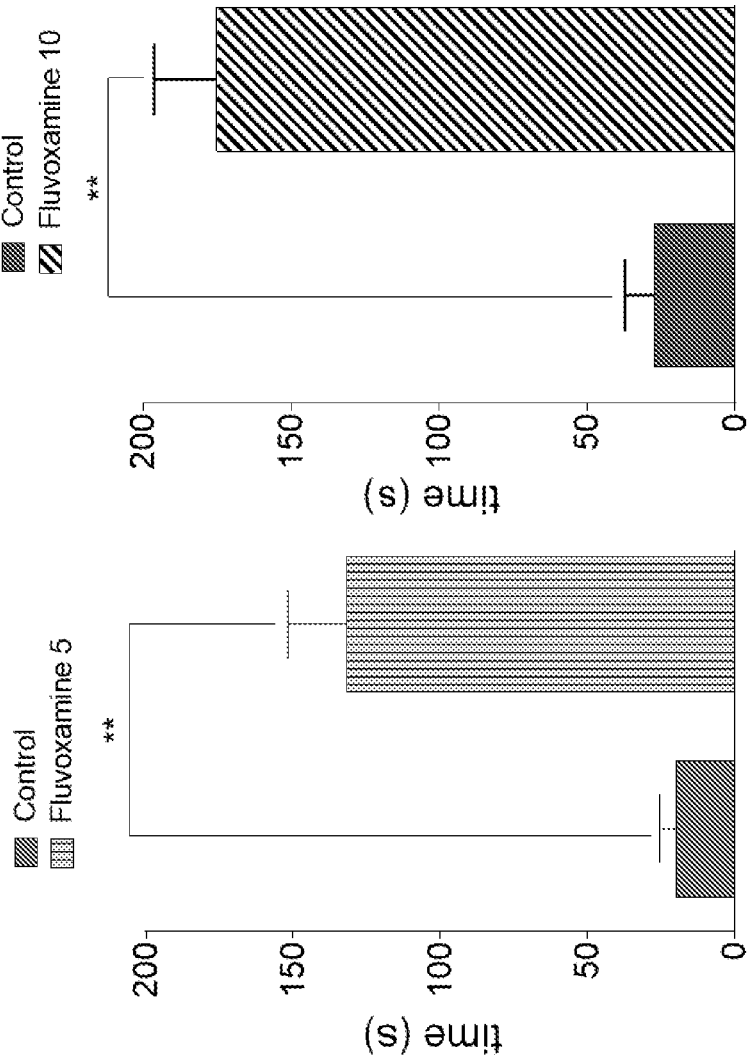

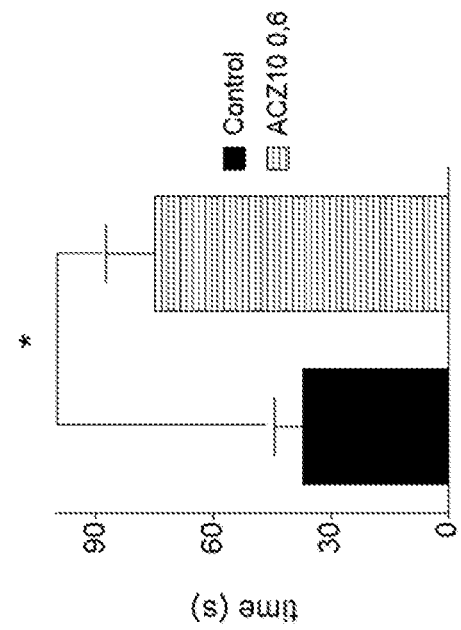
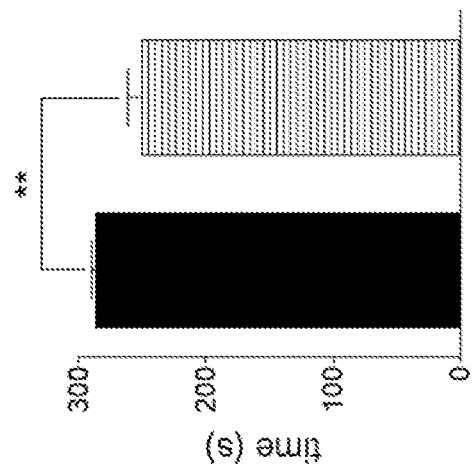
FIG. 7A
FIG. 7B

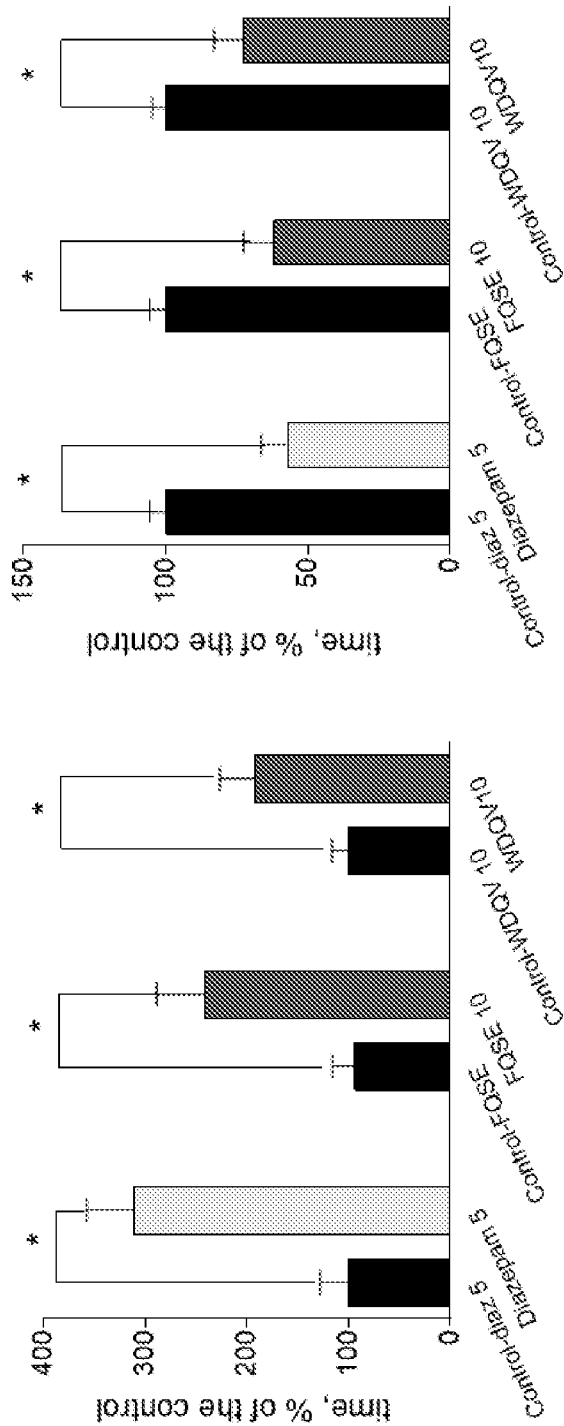

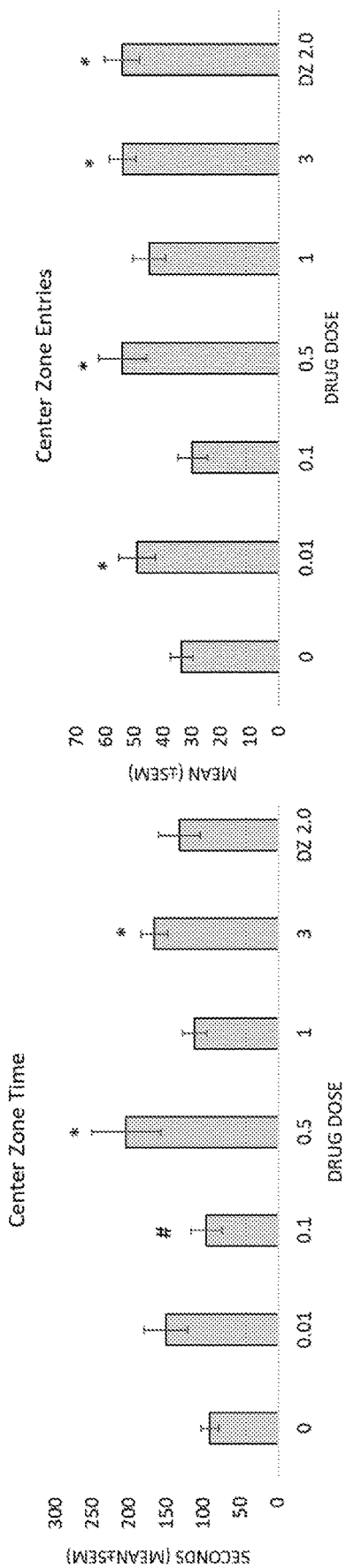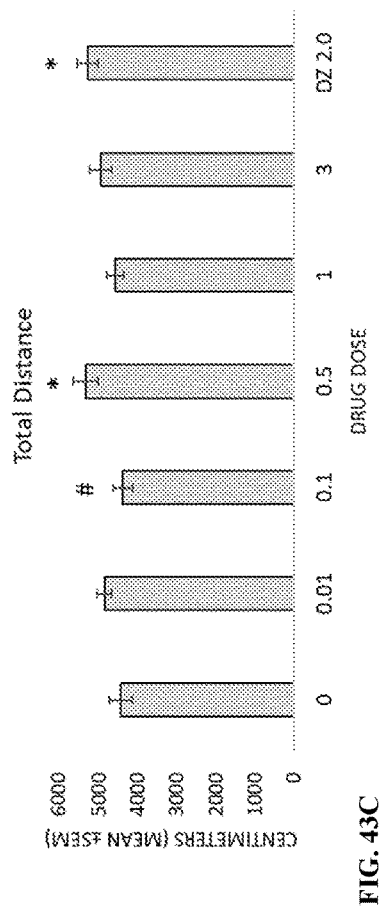
FIG. 43A
FIG. 43B
FIG. 43C

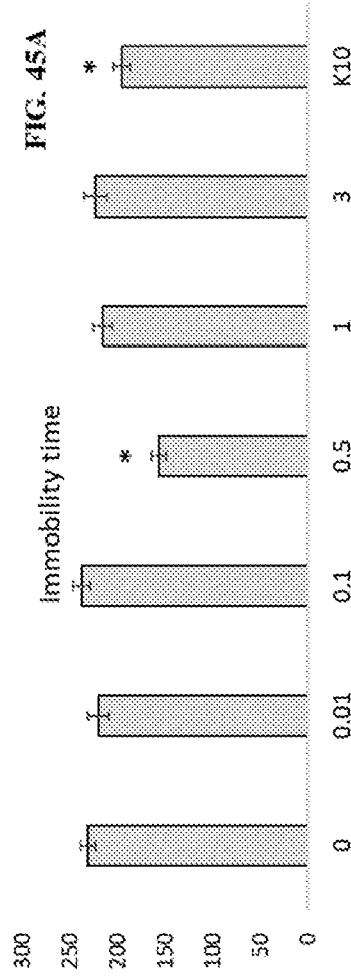
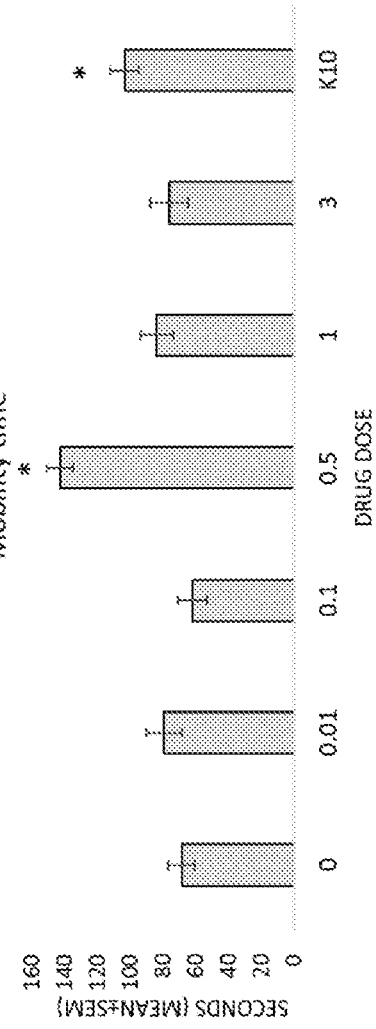

| day: | 1 | 14 | 22 | | 48 | 55 | 58 | 59 | 61 | 62 |
|---|---|---|---|---|---|---|---|---|---|---|
| | adaptation | SP1, selection | | CUMS | | SP2, selection | | EPM | | SI |

| | 65 | 66 | 67 | | 69 | | 72 | 75 | 76 | 79 | 80 |
|---|---|---|---|---|---|---|---|---|---|---|---|
| | | FUST | | NSFT | | | SP T | FST | | sacrifice | |

FIG. 46

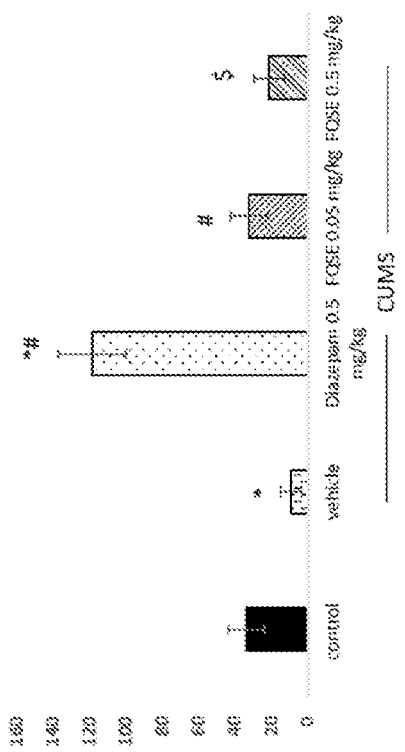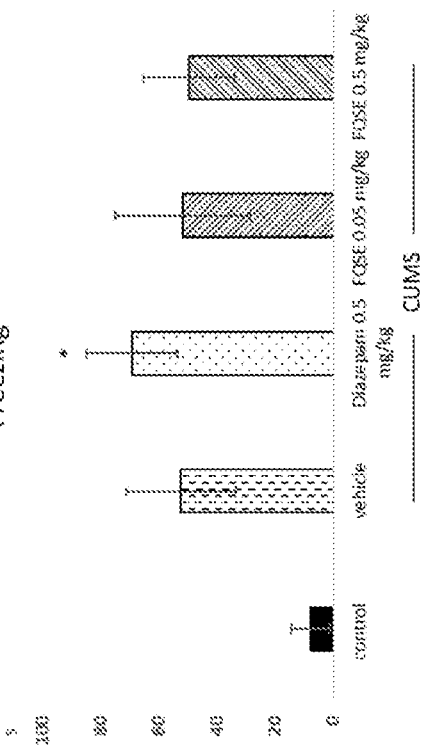
FIG. 47 A
FIG. 47 B

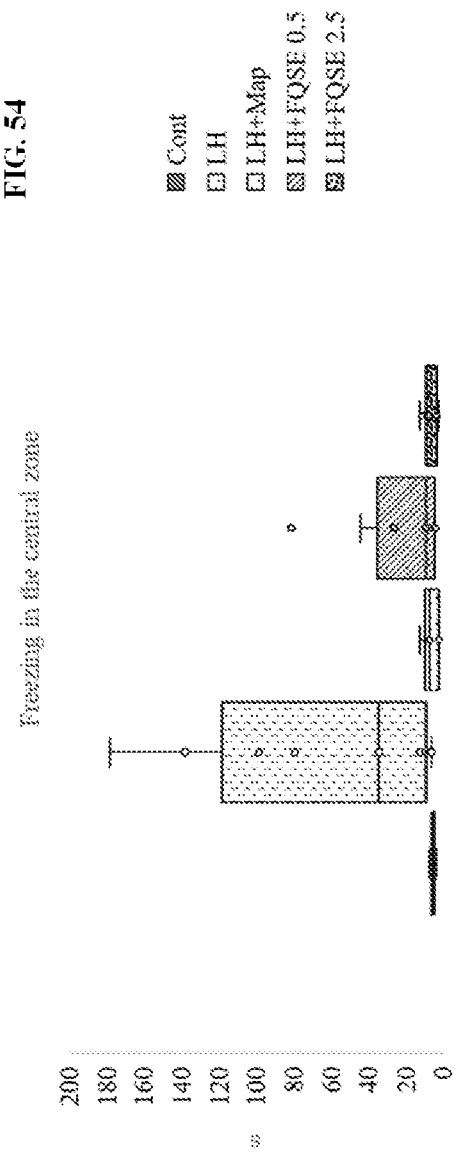

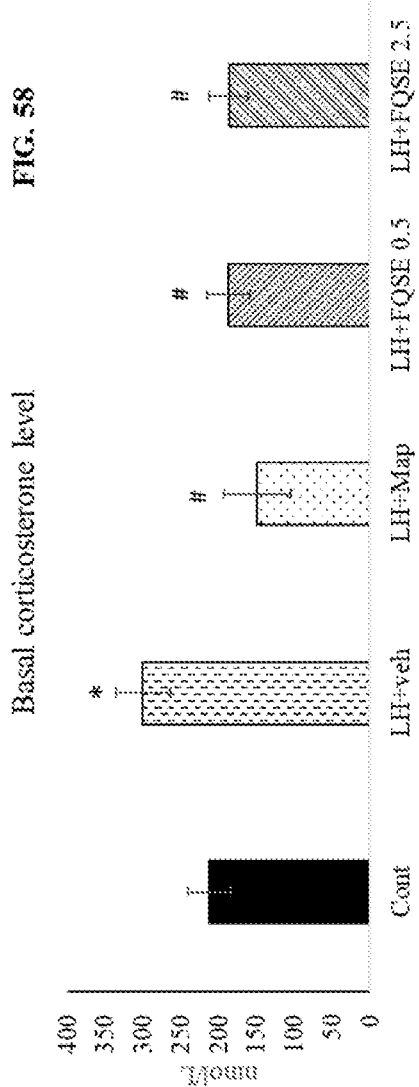

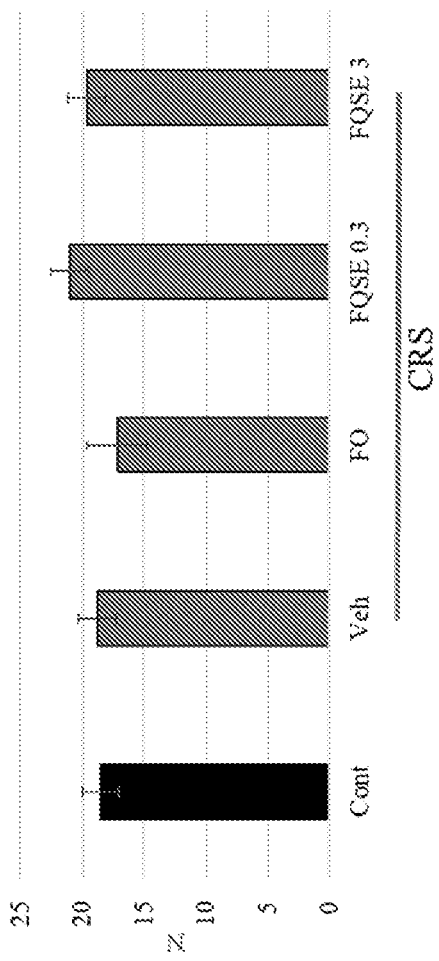

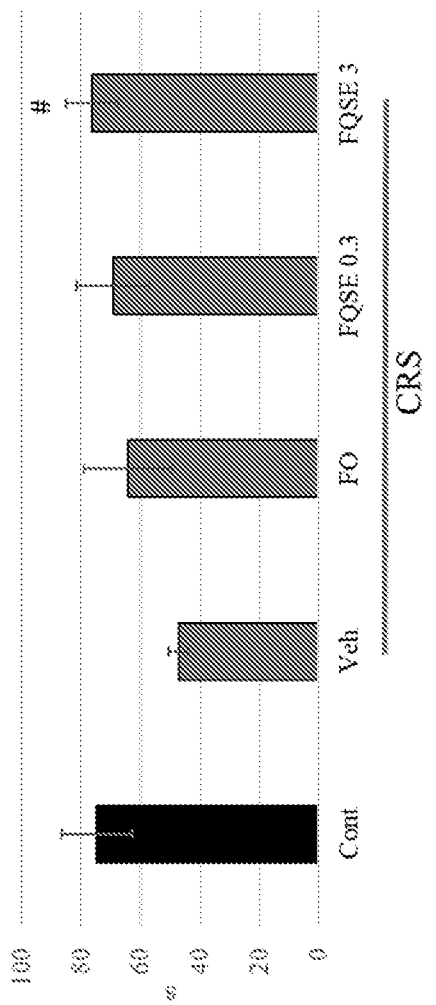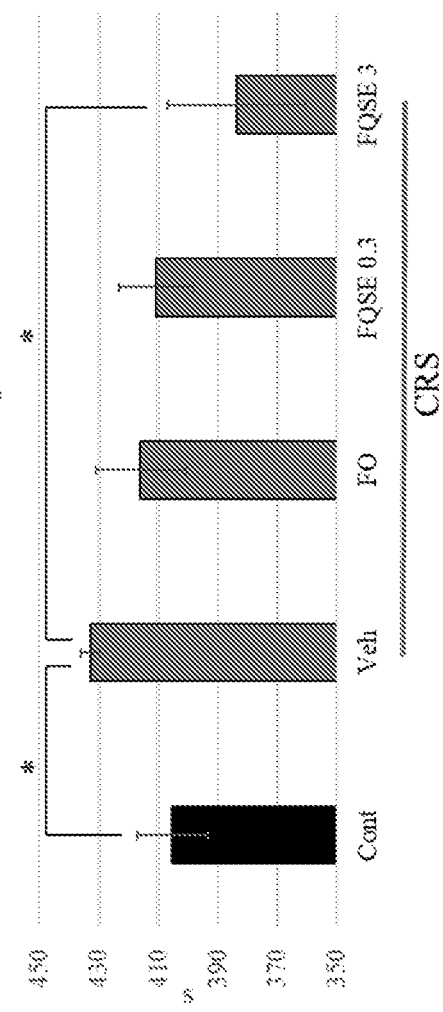

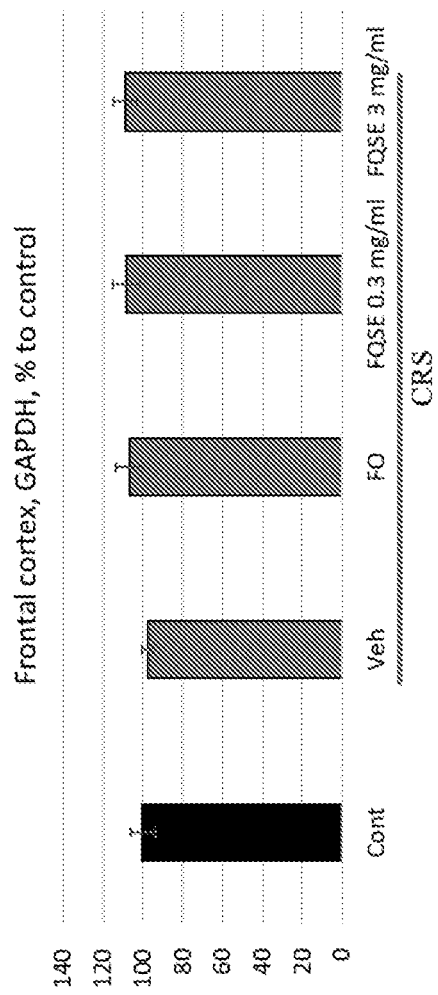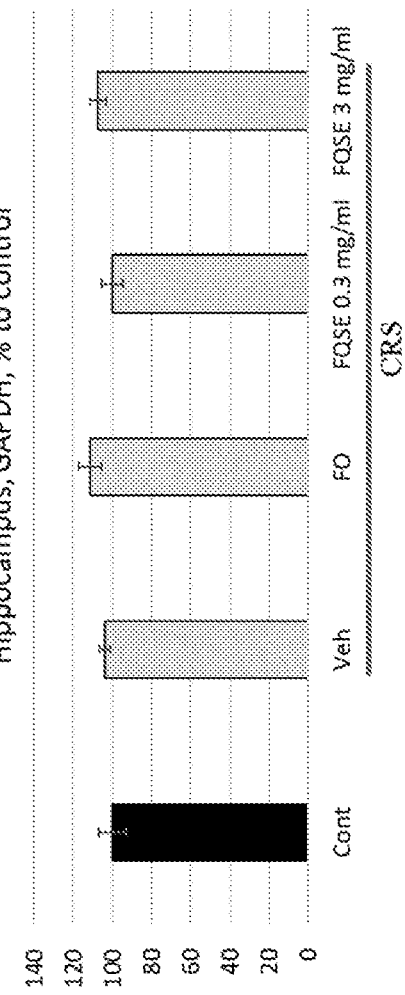

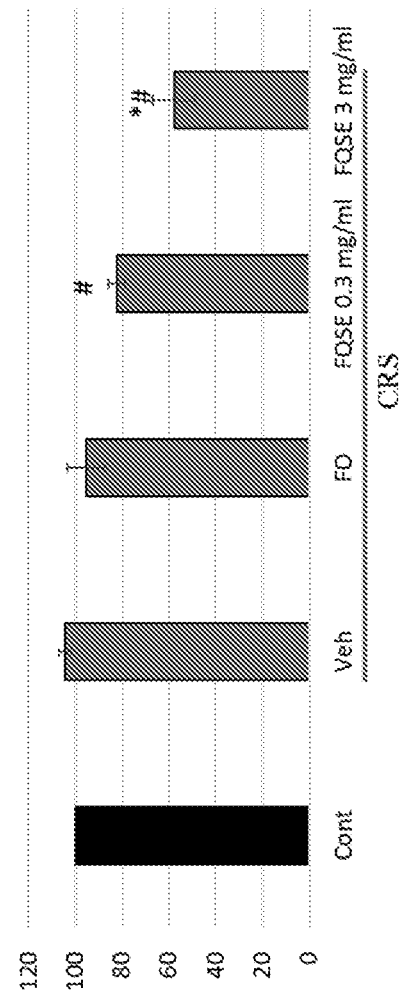
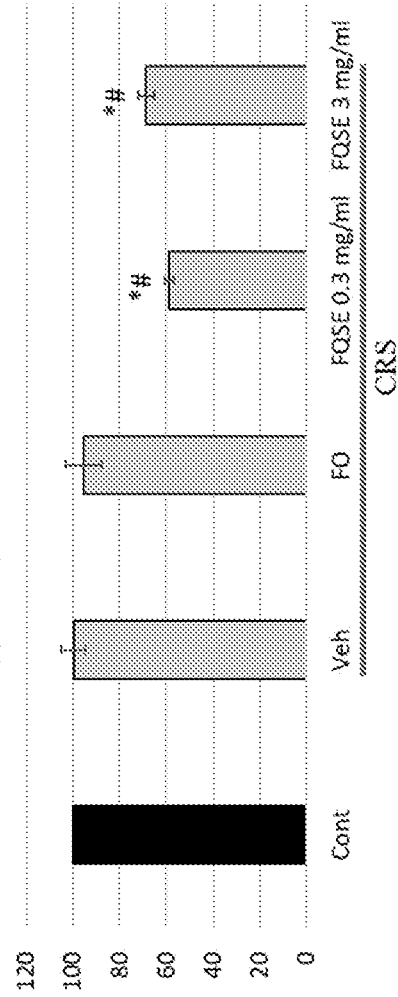
FIG. 64A
FIG. 64B

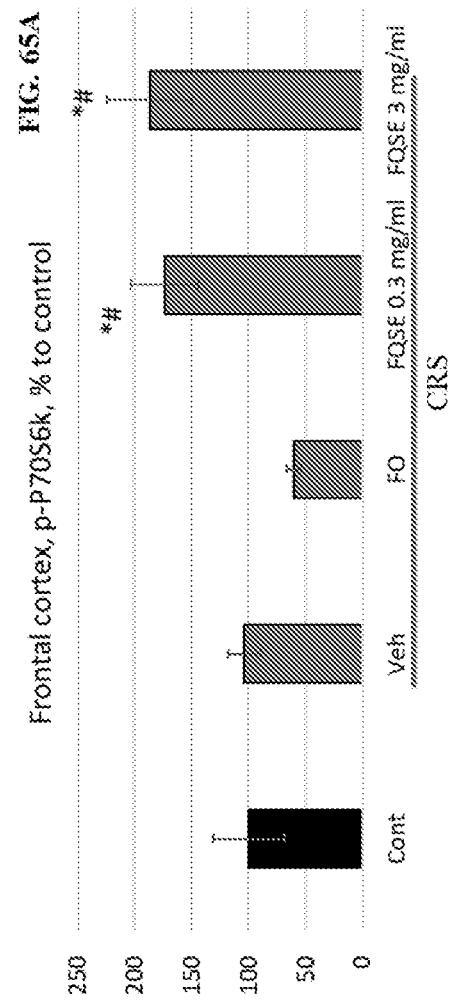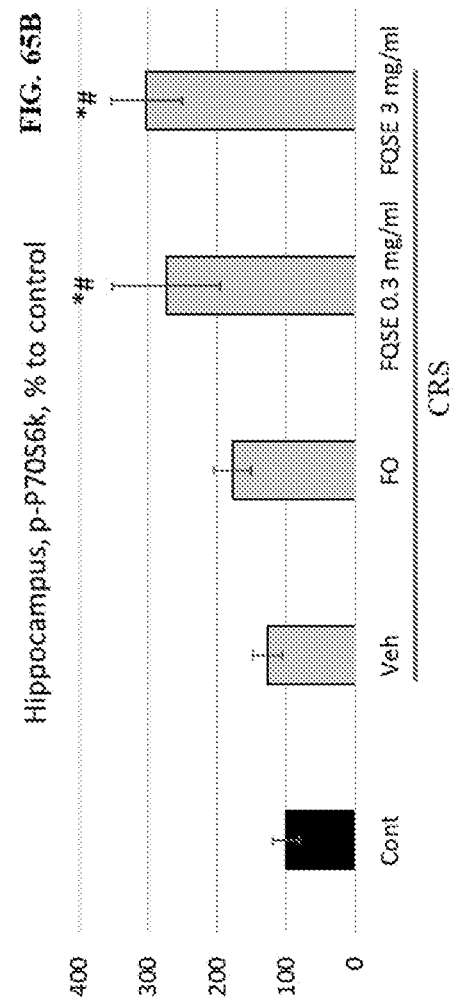

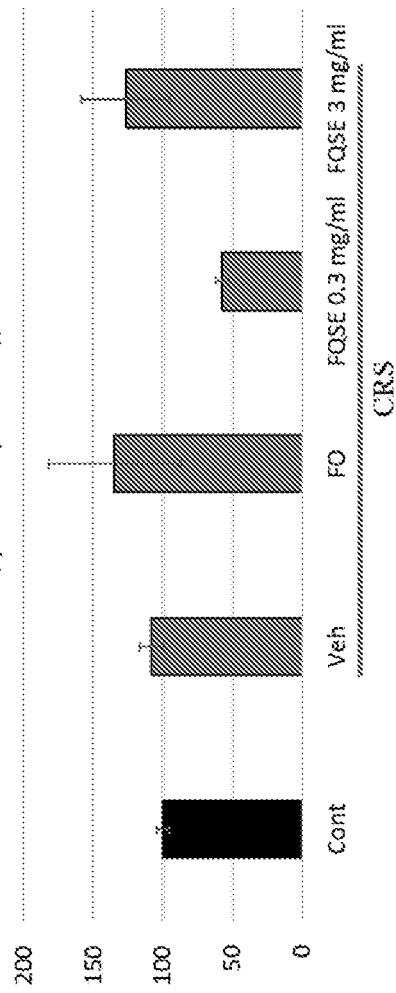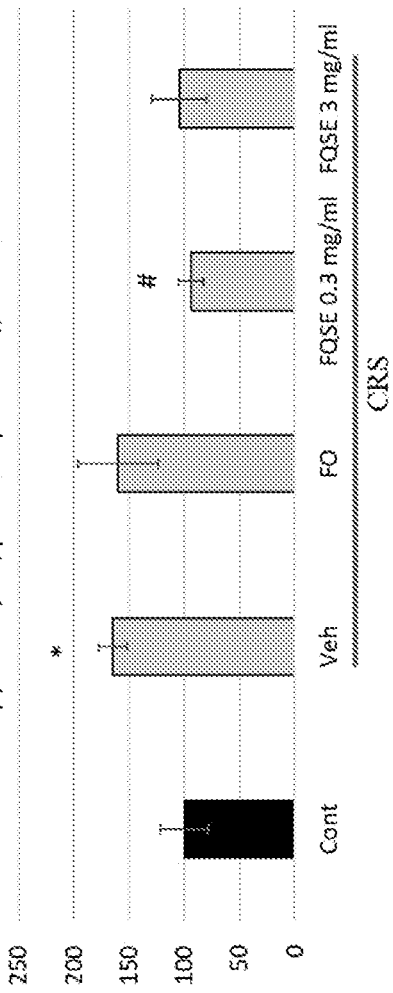

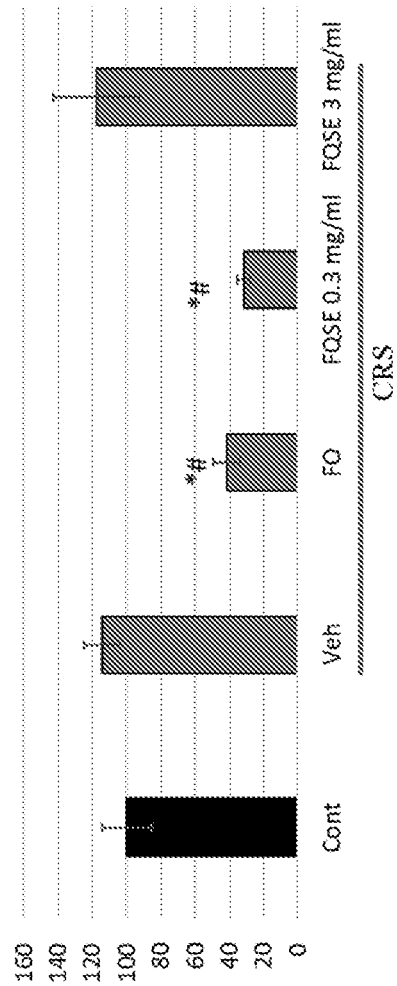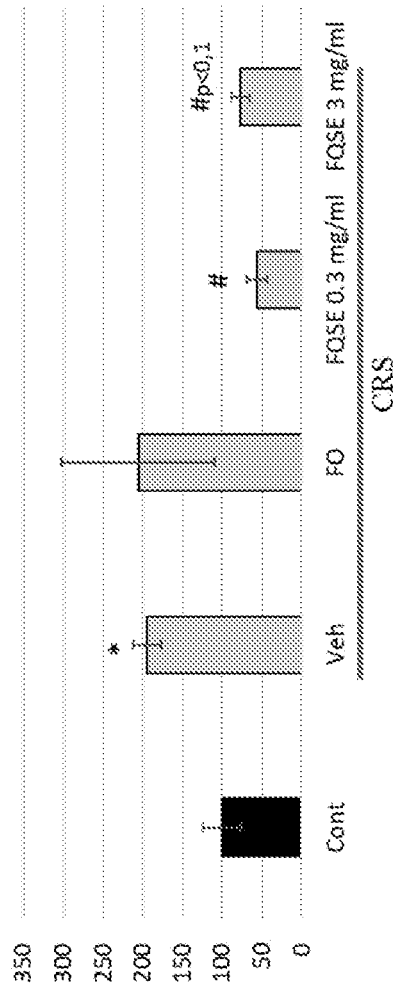

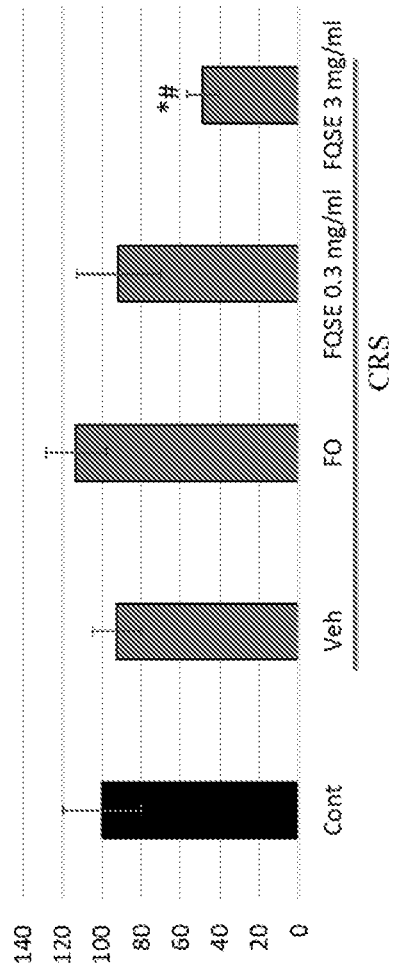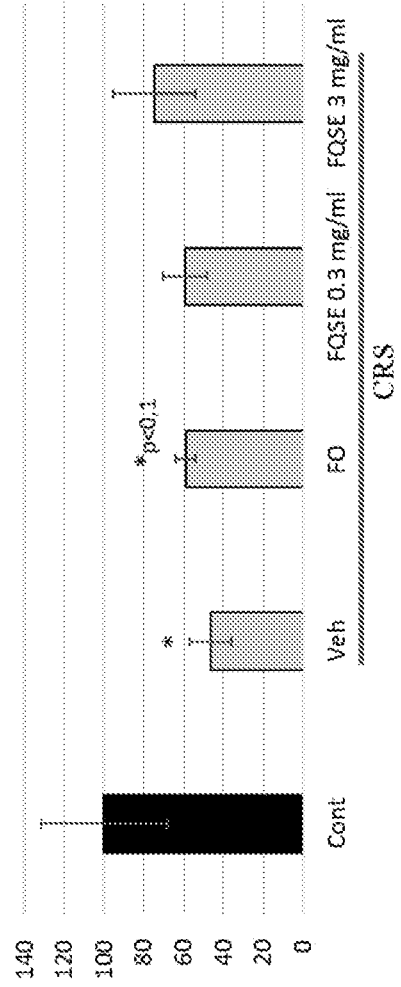

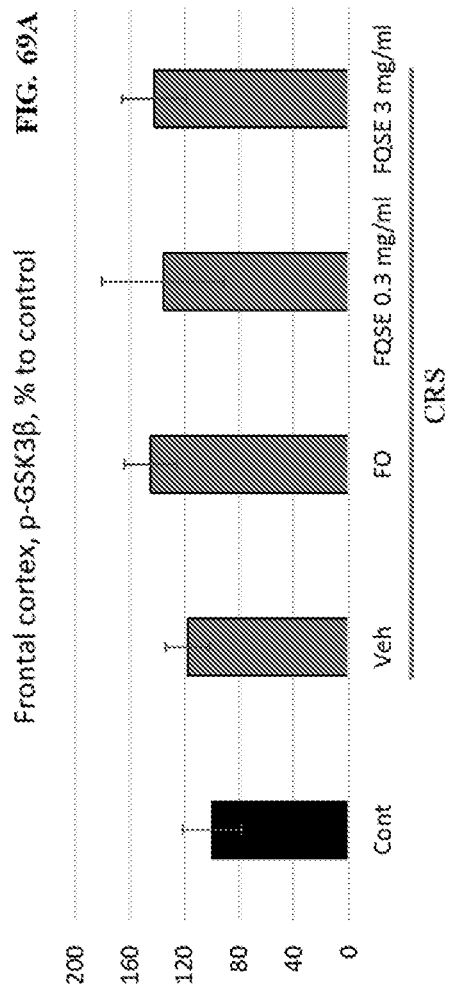
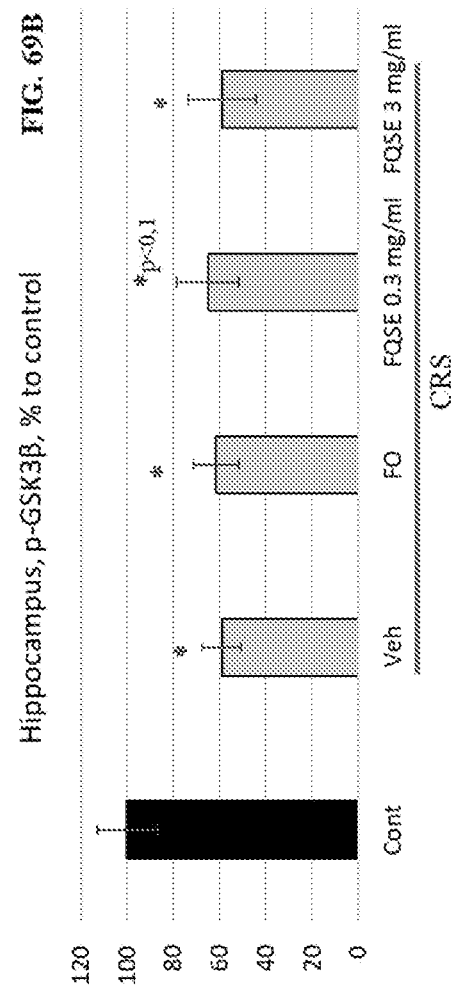

SEQUENCE LISTING

```
<160> NUMBER OF SEQ ID NOS: 36

<210> SEQ ID NO 1
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 1

Tyr Leu Gln Tyr
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 2

Tyr Gln Leu Tyr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 3

Tyr Leu Glu Gln
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 4

Gln Tyr Leu Tyr
1
```

```
<210> SEQ ID NO 5
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 5

Tyr Leu Lys Tyr
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 6

Tyr Leu Lys Thr
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 7

Phe Leu Leu Tyr
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 8

Tyr Gln Lys Phe
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 9

Leu Tyr Gln Glu
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 10

Phe Gln Ser Glu
1
```

```
<210> SEQ ID NO 11
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 11

Phe Tyr Gln Lys
1

<210> SEQ ID NO 12
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 12

Tyr Leu Gly Tyr
1

<210> SEQ ID NO 13
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 13

Pro Phe Thr Glu
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 14

Trp Asp Gln Val
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 15

Pro Glu Val Phe
1

<210> SEQ ID NO 16
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 16

Leu Ser Arg Tyr
1
```

```
<210> SEQ ID NO 17
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 17

Leu Leu Arg Phe
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 18

Met Pro Leu Trp
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 19

Lys Tyr Gln Phe
1

<210> SEQ ID NO 20
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 20

Tyr Gln Phe Leu
1

<210> SEQ ID NO 21
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 21

Phe Phe Val Ala
1

<210> SEQ ID NO 22
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 22

Lys Thr Val Tyr
1

<210> SEQ ID NO 23
```

```
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 23

Phe Ser Asp Ile
1

<210> SEQ ID NO 24
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 24

Ser Phe Ser Asp
1

<210> SEQ ID NO 25
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 25

Leu Leu Tyr Gln
1

<210> SEQ ID NO 26
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 26

Asp Lys Thr Glu
1

<210> SEQ ID NO 27
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 27

Tyr Tyr Val Pro
1

<210> SEQ ID NO 28
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 28

Phe Thr Glu Ser
1

<210> SEQ ID NO 29
<211> LENGTH: 4
```

```
<212> TYPE: PRT
<213> ORGANISM: Artificial Sequence
<220> FEATURE:
<223> OTHER INFORMATION: Synthetic Sequence

<400> SEQUENCE: 29

Gly Thr Gln Tyr
1

<210> SEQ ID NO 30
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 30

Phe Leu Gly Ala
1

<210> SEQ ID NO 31
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 31

Tyr Thr Asp Ala
1

<210> SEQ ID NO 32
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 32

Tyr Pro Ser Tyr
1

<210> SEQ ID NO 33
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 33

Phe Pro Lys Tyr
1

<210> SEQ ID NO 34
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 34

Tyr Pro Phe Pro Gly Pro Ile
1               5

<210> SEQ ID NO 35
<211> LENGTH: 10
<212> TYPE: PRT
```

```
<213> ORGANISM: Artificial Sequence
<220> FEATURE:
<223> OTHER INFORMATION: Synthetic Sequence

<400> SEQUENCE: 35

Tyr Leu Gly Tyr Leu Glu Gln Leu Leu Arg
1               5                   10

<210> SEQ ID NO 36
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 36

Phe Leu Pro Tyr
1
```

SYNTHETIC NEUROMODULATORY PEPTIDES

PRIORITY

The present application is a U.S. National Stage Application under 37 U.S.C. § 371 of International Application No. PCT/US2020/022623, filed Mar. 13, 2020, which claims priority to U.S. Provisional Patent Application No. 62/818,458, filed Mar. 14, 2019, the contents of which are hereby incorporated by reference herein in their entireties.

FIELD

The present disclosure relates to compositions that include proteins, such as peptide therapeutic agents, to treat depression and other psychiatric disorders.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: LACT-001 Sequence Listing ST25.txt; date recorded: Sep. 8, 2021; file size: 5,9475,862 bytes).

BACKGROUND

Depression, which manifests in many conditions affecting a subject's mood, affects millions of people worldwide and its treatment is still generally inadequate. Although various drugs for treatment of depression and associated conditions have been developed, the drugs are typically not specific enough and are ineffective for about 40 percent of patients. Also, it usually takes weeks before a patient can benefit from a therapeutic action of a drug. Moreover, many known drugs have various side effects. An anxiety disorder, although different from depression, often accompanies depression. Many anxiolytic drugs have issues similar to antidepressants. The challenge in discovering effective treatments for depression and anxiety includes identifying appropriate targets to upregulate or downregulate. Another challenge is to design safe, low cost therapeutics that are specific to those targets and that are able to alleviate depression and anxiety symptoms within a relatively short timeframe.

Accordingly, there remains a need to develop effective and safe therapeutics for treatment of depression and associated disorders.

SUMMARY

In various aspects, the present invention provides compositions and methods that are useful for treatment of various mental, behavioral, affective, neurotic, and emotional disorders, including depression, anxiety, and stress-related disorders. In some aspects, a synthetic neuromodulatory peptide, such as, for example, tetrapeptide, in the form of a pharmaceutical composition can be used for treatment of depression and other mood disorders. In some embodiments, a composition is provided that comprises a synthetic neuromodulatory peptide, that is defined by the general formula I: $R_1R_2R_3R_4(I)$, wherein $R_1$ is selected from the amino acids W, F, and D, $R_2$ is a hydrophilic amino acid, $R_3$ is a hydrophilic amino acid, and $R_4$ is selected from the amino acids V and E. In some embodiments, the synthetic neuromodulatory peptide consists of amino acids F, Q, S, and E. In some embodiments, the synthetic neuromodulatory peptide consists of amino acids D, K, T, and E. In some embodiments, the synthetic neuromodulatory peptide consists of amino acids W, D, Q, and V. The synthetic neuromodulatory peptide, or an analog thereof, in accordance with the described embodiments does not include proline. In some embodiments, $R_1$ is different from Y and $R_2$ is different from L.

The neuromodulatory peptides and their analogs described herein are developed to modulate GABA-A receptors. Furthermore, in some embodiments, neuromodulatory peptides and their analogs described herein can modulate voltage-gated calcium channels (VGCC). In view of the known link between GABA-A receptors and psychiatric disorders, including anxiety and depression, the neuromodulatory peptide of the present disclosure is effective at preventing or treating various depression-anxiety spectrum disorders as well as neurodegenerative disorders, including Alzheimer's disease and Parkinson's disease. Non-limiting examples of conditions that can be treated using the described neuromodulatory peptide include anxiety disorders such as, e.g., separation anxiety disorder, selective mutism, specific phobia (SP), social anxiety disorder (SAD), panic disorder, agoraphobia, substance/medication-induced anxiety disorder and anxiety disorder due to another medication condition, generalized anxiety disorder (GAD), post-traumatic stress disorder (PTSD), major depressive disorder (MDD), treatment-resistant depression (TRD), postpartum depression (PPD), bipolar disorder or bipolar depression, obsessive-compulsive disorder (OCD), and attention deficit hyperactivity disorder (ADHD), social phobia, agitation in Alzheimer's disease, aggression in Alzheimer's disease, and obsessive-compulsive disorder.

In some aspects, the tetrapeptides can be optionally chemically modified. The chemical modification can be selected from amidation, methylation, and acetylation of one or more of the amino acids. Additional chemical modifications can include addition of formyl, pyroglutamyl (pGlu), one or more fatty acids, urea, carbamate, sulfonamide, alkylamine, or any combination thereof. The composition can include a pharmaceutically acceptable carrier. In some embodiments, the composition can further include a delivery vehicle which can be, e.g., a liposome, a nanoparticle, or a polysaccharide. The composition can be administered to a subject determined to be in need of treatment via various routes, and in some aspects the composition is formulated for intranasal administration.

BRIEF DESCRIPTION OF THE FIGURES

FIG. 1A. Time spent in and out of the social, or "shoal," zone. FIG. 1B. Time spent in and out of the social, or "shoal" zone. FIG. 1C. Time spent in the light chamber. The ordinate represents time in seconds (FIGS. 1A and 1B) or percentage of the control group (FIG. 1C). The data are shown as the mean, error bars indicate the standard error of the mean, "*" indicates $p<0.05$, "" indicates $p<0.01$, and "**" indicates $p<0.0001$, according to Mann-Whitney U-test.

FIGS. 5A, 5B, and 5C illustrate effect of diazepam at a dose of 10 mg/kg on the behavioral parameters of *Danio rerio*. FIG. 5A. The number of transitions between the light and dark compartments of the experimental light/dark box. The ordinate represents the number of transitions. FIG. 5B. The latent period of the exit from the dark compartment to the light one. The ordinate represents the time in seconds. FIG. 5C. An average distance covered in the open field test. The ordinate represents the length in centimeters. The data are shown in the form of an average, error bars indicate the standard error of the mean, "*" indicates p<0.05, and "**" indicates p<0.01 according to Mann-Whitney U-test.

FIGS. 6A and 6B illustrate effect of fluvoxamine at doses of 5 mg/kg (FIG. 6A) and 10 mg/kg (FIG. 6B) on the time spent by the tested animals at the surface of the aquarium in the open field test. The ordinate represents the time in seconds. The data are shown as the mean, error bars indicate the standard error of the mean, and "**" indicates p<0.01 according to Mann-Whitney U-test.

FIGS. 7A and 7B illustrate effect of Alpha-Casozepine-10 (ACZ-10) at a dose of 0.6 mg/kg on the behavioral parameters of *Danio rerio*. FIG. 7A. Time spent near the social zone. FIG. 7B. Time spent at the surface in the open field test. The ordinate represents the time in seconds. The data are shown as the mean, error bars indicate the standard error of the mean, "*" indicates p<0.05, and "**" indicates p<0.01 according to Mann-Whitney U-test.

FIG. 8A. Time spent in the "social zone." The ordinate represents the time in seconds. FIG. 8B. An average length covered in the open field test. The ordinate represents the length in centimeters. The data are shown as the mean, error bars indicate the standard error of the mean; and indicates p<0.05 according to the Mann-Whitney U-test.

FIG. 10A. Time spent in the upper part of aquarium. FIG. 10B. Latent period of leaving the bottom. The ordinate represents time in seconds. The data are shown as the mean, error bars indicate the standard error of the mean, and "*" indicates p<0.05 according to the Mann-Whitney U-test.

FIG. 11A. Time spent in the upper part of the aquarium, in % relatively to the control group. FIG. 11B. Latent period of leaving the bottom, in % relatively to the control group. The ordinate shows values in % relatively to the control group. The data are shown as the mean, error bars indicate the standard error of the mean, and "*" indicates p<0.05 according to the Mann-Whitney U-test.

FIG. 12A. Time spent in the light compartment of the LDB. FIG. 12B. Time spent in the dark compartment of the LDB. The ordinate represents the time in seconds. The data are shown as the mean, error bars indicate the standard error of the mean, and "*" indicates p<0.05 according to the Mann-Whitney U-test.

FIG. 13A. Time spent in the light compartment of the LDB, in % relatively to the control group. FIG. 13B. Time spent in the dark compartment of the LDB, in % relatively to the control group. The ordinate represents the values in % relatively to the control group. The data are shown as the mean, error bars indicate the standard error of the mean, and "*" indicates p<0.05, and "**" indicates p<0.01 according to Mann-Whitney U-test.

FIG. 14A. Time spent outside the shoaling compartment. FIG. 14B. Latent period of leaving the shoaling compartment. The ordinate represents the time in seconds. The data are shown as the mean, error bars indicate the standard error of the mean, and "*" indicates p<0.05—according to the Mann-Whitney U-test.

FIG. 15A. Time spent outside the shoaling compartment, in % relatively to the control group.

FIG. 15B. Latent period of leaving the shoaling compartment, in % relatively to the control group. The ordinate represents the values in % relatively to the control group. The data are shown as the mean, error bars indicate the standard error of the mean, and "*" indicates p<0.05, and "**" indicates p<0.01 according to Mann-Whitney U-test.

FIG. 16A. Time spent close to the surface of water. FIG. 16B. Comparison of the effects of FQSE (SEQ ID NO:10) (1 mg/kg) and fluvoxamine (10 mg/kg), the time spent close to the surface of water, in % relatively to the control group. The ordinate represents the values in % relatively to the control group. The data are shown as the mean, error bars indicate the standard error of the mean, and "*" indicates p<0.05 according to the Mann-Whitney U-test.

FIG. 17A. Latent period of coming up to water surface. FIG. 17B. Comparison of FQSE (SEQ ID NO:10) (1 mg/kg) and fluvoxamine (10 mg/kg) effects, latent period of coming up to water surface, % relative to control group. The ordinate represents the values in % relatively to the control group. The data are shown as the mean, error bars indicate the standard error of the mean, and "*" indicates p<0.05, and "**" indicates p<0.01 according to Mann-Whitney U-test.

FIG. 19A. Time spent close to the surface (open field). FIG. 19B. Time spent in the light compartment of the LDB. FIG. 19C. Time spent outside the shoaling compartment. The ordinate represents the time in seconds. The data are shown as the mean, and error bars indicate the standard error of the mean.

FIG. 20A. Time spent close to the surface (open field). FIG. 20B. Time spent in the light compartment of the LDB. FIG. 20C. Time spent outside the shoaling compartment. The ordinate represents the time in seconds. The data are shown as the mean, and error bars indicate the standard error of the mean.

FIG. 21A. Time spent outside the shoaling compartment.

FIG. 21B. Latent period of visiting the shoaling compartment. FIG. 21C. Time spent near the shoaling compartment. The ordinate represents time in seconds. The data are shown as the mean, error bars indicate the standard error of the mean, "*" indicates $p<0.05$, and "**" indicates $p<0.01$ according to the Mann-Whitney test.

FIG. 24A. Length of the track, along the ordinate axis, in cm. FIG. 24B. Mean velocity, the ordinate axis shows velocity, in cm/sec. The data are shown as the mean, and error bars indicate the standard error of the mean.

FIG. 25A. Time spent close to the surface (open field). FIG. 25B. Time spent in the light compartment of the LDB. FIG. 25C. Time spent outside the shoaling compartment. The ordinate represents the time in seconds.

FIG. 26A. Time spent close to the surface (open field). FIG. 26B. Time spent in the light compartment of the LDB. FIG. 26C. Time spent outside the shoaling compartment. The ordinate axis shows time in seconds. The data are presented as the mean, and error bars indicate the standard error of the mean.

FIG. 27A. Time spent (in total) in the light compartment of the LDB, in seconds. FIG. 27B. Time spent (in dynamics within the minutes of the test) in the light compartment of the LDB, in seconds. FIG. 27C. Time spent (in total) in the dark compartment of the LDB, in seconds. FIG. 27D. Time spent (in dynamics within the minutes of the test) in the dark compartment of the LDB, in seconds. The ordinate axis shows time in seconds. The data are presented as the mean, the error bar define the standard error of the mean, and "*" indicates $p<0.05$ according to the Fisher criteria.

FIGS. 28A and 28B illustrate comparison of effects of WDQV (SEQ ID NO:14) at a dose of 10 mg/kg in the light/dark box test to effects of diazepam (5 mg/kg) and FQSE (SEQ ID NO:10) (10 mg/kg), and respective controls. FIG. 28A. Time spent in the light compartment of the LDB, in seconds. FIG. 28B. Time spent in the dark compartment of the LDB, in seconds. The data are presented as the mean, the error bar define the standard error of the mean, and "*" indicates $p<0.05$ according to the Mann-Whitney test.

FIGS. 43A, 43B and 43C illustrate the behavior of rats in the OF test. FIG. 43A. Effects of various doses of FQSE (SEQ ID NO:10) and diazepam (DZ) on center zone time (in seconds). FIG. 43B. Effects of various doses of FQSE (SEQ ID NO:10) and diazepam (DZ) on the number of center zone entries. FIG. 43C. Effects of various doses of FQSE (SEQ ID NO:10) and diazepam (DZ) on total distance traveled (centimeters, cm). Each bar represents mean±SEM. *–$p<0.05$ vs vehicle (0), #–$p<0.05$ vs diazepam (DZ). One-way ANOVA with Fisher's Least Significant Difference (LSD) post-hoc test.

FIGS. 45A and 45B illustrate the behavior of rats in the FST. FIG. 45A. Effects of various doses of FQSE (SEQ ID NO:10) and ketamine (10 mg/kg, K10) on immobility time (in seconds). 45B. Effects of various doses of FQSE (SEQ ID NO:10) and ketamine (10 mg/kg, K10) on mobility time (in seconds). Each bar represents mean±SEM. *–$p<0.05$ vs vehicle (0). One-way ANOVA with Fisher's Least Significant Difference (LSD) post-hoc test.

FIG. 46 illustrates the schedule of the experiments. SPT—Sucrose Preference Test (Sucrose Solution Preference Test), CUMS—Chronic Mild Stress test (Chronic Unpredictable Mild Stress), EPM—Elevated Plus Maze (Elevated Plus Maze test), SI—Social Interaction (Social Interaction test), FUST—Female Urine Sniffing Test (Sexual Motivation and Anhedonia Test), NSFT—Novelty Suppressed Feeding Test (Suppression of Food Consumption in a New Environment), FST—Forced Swim Test (Forced Swimming Test).

FIGS. 47A and 47B illustrate the behavior of rats in the EPM test after CUMS and one injection of drugs. FIG. 47A. The time spent on the open arms, in seconds. FIG. 47B. The time spent freezing, in seconds. Each bar represents mean±SEM. *–$p<0.05$ represents significant differences from the control group, and #–$p<0.05$—significant differences from the CUMS+veh group, $–$p<0.05$ vs. Diazepam group. Kruskal-Wallis with Dunn's multiple comparison test.

FIG. 53A. Shows conditioned place aversion following exposure to predator odor or no odor. Testing was conducted 24 h post-conditioning. FIG. 53B. Conditioned place aversion following exposure to no odor in groups pre-treated after no odor exposure and prior to testing conducted 24 h post-conditioning. FIG. 53C. Conditioned place aversion following exposure to predator odor in groups pre-treated after odor exposure and prior to testing conducted 24 h post-conditioning. Each bar represents mean±SEM. *–$p<0.05$ between groups. One-Way ANOVA with Student Newman-Keuls test.

FIG. 54 illustrates the duration of the latent period in the OF test in LH paradigm, in seconds. The results presented as box and whiskers plot with maximal and minimum values. *—significant difference from the control group, #—significant difference from the LH group, $p<0.05$. Kruskal-Wallis with Dunn's multiple comparison test.

FIG. 55A. Duration of vertical motor activity of animals (rears), in seconds. FIG. 55B Horizontal motor activity (mileage), number of sectors. The results presented as box and whiskers plot with maximal and minimum values. *—significant difference from the control group. One-way ANOVA with Tukey test.

FIG. 56A. Time spent in the open arms, in seconds. FIG. 56B. The number of stretch-attended postures from the closed arms of the maze, N. The results presented as box and whiskers plot with maximal and minimum values.

FIG. 57A. Duration of immobilization, in seconds. FIG. 57B. Duration of active swimming, in seconds. Each bar represents mean±SEM. *—significant difference from the control group; &—difference from the control group at the trend level ($p<0.1$); #—a significant difference from the LH group, $p<0.05$. One-way ANOVA with Fisher LSD post hoc test.

FIG. 58 illustrates basal corticosterone level in rat plasma, nmol/L. Each bar represents mean±SEM. *—$p<0.1$—a tendency to statistical significance in comparison with the Control group, #$p<0.05$—significant differences compared to the LH group. One-way ANOVA with Fisher LSD post hoc test.

FIG. 60 illustrates total distance traveled (number of squares) in OFT by animals after CRS and drug treatment. Each bar represents mean±SEM.

FIGS. 61A and 61B illustrate the performance of rats in the FST after CRS and drug treatment. FIG. 61A. The time spent active (active swimming+climbing), in seconds. FIG. 61B. Time spent inactive swimming (passive swimming+immobilization), in seconds. Each bar represents mean±SEM. *—statistically significant differences at $p≤0.05$; #–$p<0.05$ vs. "CRS+Veh" group. One-way ANOVA with Fisher LSD post hoc test.

FIGS. 63A and 63B illustrate the integral area of GAPDH obtained by Western Blotting (normalized to total protein) compared to the control group, %. FIG. 63A. GAPDH content in cerebral cortex. FIG. 63B. GAPDH content in hippocampus. Each bar represents mean±SEM.

FIGS. 64A and 64B illustrate the integral area of BDNF obtained by Western Blotting (normalized to total protein) compared to the control group, %. FIG. 64A. BDNF content in cerebral cortex. FIG. 64B. BDNF content in hippocampus. Each bar represents mean±SEM. *–$p<0.05$ in comparison with the control group, and #–$p<0.05$ in comparison with the "CRS+veh" group. One-way ANOVA with Fisher LSD post hoc test.

FIGS. 65A and 65B illustrate the integral area of p70s6k (Thr421/Ser424) obtained by Western Blotting (normalized to total protein) compared to the control group, %. FIG. 65A. p70s6k (Thr421/Ser424) content in cerebral cortex. FIG. 65B. p70s6k (Thr421/Ser424) content in hippocampus. Each bar represents mean±SEM. *–$p<0.05$ in comparison with the control group, and #–$p<0.05$ in comparison with the "CRS+veh" group. One-way ANOVA with Fisher LSD post hoc test.

FIGS. 66A and 66B illustrate the integral area of p-ERK1 (Thr202) obtained by Western Blotting (normalized to total protein) compared to the control group, %. FIG. 66A. p-ERK1 (Thr202) content in cerebral cortex. FIG. 66B. p-ERK1 (Thr202) content in hippocampus. Each bar represents mean±SEM. *–$p<0.05$ in comparison with the control group, and #–$p<0.05$ in comparison with the "CRS+veh" group. One-way ANOVA with Fisher LSD post hoc test.

FIGS. 67A and 67B illustrate the integral area of p-ERK 2 (Tyr204) obtained by Western Blotting (normalized to total protein) compared to the control group, %. FIG. 67A. p-ERK 2 (Tyr204) content in cerebral cortex. FIG. 67B. p-ERK 2 (Tyr204) content in hippocampus. Each bar represents mean±SEM. *–$p<0.05$ in comparison with the control group, and #–$p<0.05$ in comparison with the "CRS+veh" group. One-way ANOVA with Fisher LSD post hoc test.

FIGS. 68A and 68B illustrate the integral area of p-PKC (PKC gamma Thr514) obtained by Western Blotting (normalized to total protein) compared to the control group, %. FIG. 68A. p-PKC (PKC gamma Thr514) content in cerebral cortex. FIG. 68B. p-PKC (PKC gamma Thr514) content in hippocampus. Each bar represents mean±SEM. *–$p<0.05$ in comparison with the control group, and #–$p<0.05$ in comparison with the "CRS+veh" group. One-way ANOVA with Fisher LSD post hoc test.

FIGS. 69A and 69B illustrate the integral area of p-GSK3β (Ser9) obtained by Western Blotting (normalized to total protein) compared to the control group, %. FIG. 69A. p-GSK3β (Ser9) content in cerebral cortex. FIG. 69B. p-GSK3β (Ser9) content in hippocampus. Each bar represents mean±SEM. *–$p<0.05$ in comparison with the control group. One-way ANOVA with Fisher LSD post hoc test.

FIG. 75A. The time spent on open arms, s. FIG. 75B. The number of open arm entries. FIG. 75C. Anxiety index (AI), %. The results are expressed as the mean±SEM. * $p<0.05$ represents significant differences vs. control group, #$p<0.05$—vs. "bicuculline" group, $ $p<0.05$—vs. "bicuculline+FQSE (SEQ ID NO:10)" group. One-way ANOVA with Fisher's LSD post hoc test.

DETAILED DESCRIPTION

Figure 1C:
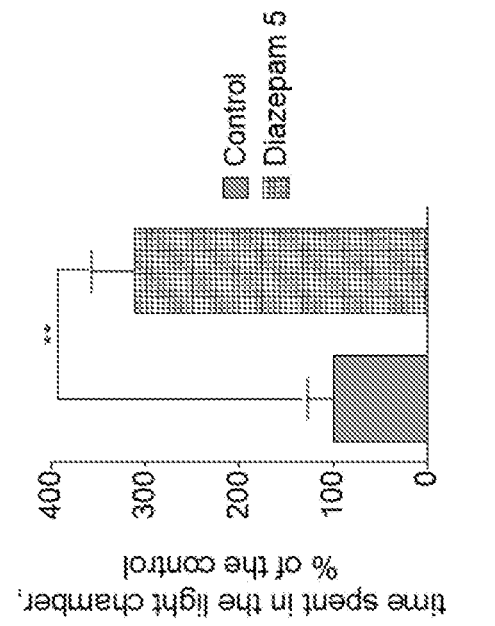
FIGS. 1A, 1B, and 1C illustrate effect of diazepam at a dose of 1.25 mg/kg (FIG. 1A) and 5 mg/kg (FIG. 1B and FIG. 1C) on the behavioral parameters of *Danio rerio*.

The peptide compositions are provided herein, which have use in, for instance, treatment of depression, anxiety, associated mood conditions, and stress-related disorders. In some aspects, peptide-based neuromodulatory therapeutical compositions for a range of psychiatric conditions within the spectrum of depressive and anxiety disorders were developed. Central nervous system (CNS) targets were selected to achieve high specificity and efficacy of neuromodulatory peptide compositions. In combination with anticipated safety profile of peptides, the compositions in accordance with the present disclosure provide safe and effective treatment.

In embodiments in accordance with the present disclosure, a GABA-A receptor, which is an ionotropic receptor, was selected as a target for the described group of neuromodulatory peptides. The endogenous ligand of GABA-A is gamma-aminobutyric acid (GABA) which is the major inhibitory neurotransmitter in the central nervous system. GABA-A receptors are the predominant type of GABA receptors in the brain. GABA-A receptors are composed of 5 subunits. There are at least 19 different isoforms of the subunits encoded by different genes and grouped into α, β, γ, δ, ε, and σ subunits, of which α, β, and γ are more fully studied. See Nutt (2006). GABA-A Receptors: Subtypes, Regional Distribution, and Function. Journal of clinical sleep medicine, 2: S7-11. The active site of the GABA-A receptor is the binding site for GABA and several drugs, and GABA binds at the junction between subunits α and β. The GABA-A-receptor can be modulated by a number of therapeutic agents, including benzodiazepines, barbiturates, anesthetics, ethanol, zinc, and neurosteroids. Benzodiazepines (BDZ) bind to a so-called benzodiazepine binding site situated at the interface between the α- and γ-subunits of α- and γ-subunit containing GABA-A receptors. Barnard (1998) Subtypes of gamma-aminobutyric acid A receptors: classification on the basis of subunit structure and receptor function. Pharmacol. Rev. 50 (2): 291-313. Thus, benzodiazepines bind to a receptor site on the GABA-A receptor protein complex that is distinct from the GABA binding site. Once a benzodiazepine binds to the site on the GABA-A receptor, the benzodiazepine allosterically changes the conformation of the GABA-A receptor, increasing the affinity of the GABA-A receptor to GABA. Neurosteroids, at the same time, bind to GABA-A-receptors at a site that is distinct from the recognition sites for GABA, benzodiazepines, and barbiturates. This results in allosteric modulation of GABA binding or channel gating. Neurosteroid modulation lacking subunit selectivity suggested that neurosteroids are binding to a site that is conserved throughout most members of the GABA-A-receptor family. The effect of neurosteroids on the GABA-A-receptor depends on the type of steroids (agonist or antagonist), the type of receptors (synaptic of extrasynaptic), the subunit compositions, and the intrinsic structure of the steroid. Wang, M. (2011). Neurosteroids and GABA-A receptor function. Front. Endocrinol. 2,44.

The inventors of the present disclosure discovered neuromodulatory peptides with novel structures and having binding capacity to the allosteric BDZ site between the α- and γ-subunits and/or another allosteric modulatory site of GABA-A receptor such as a binding site between the α- and β-subunits and/or binding to the neurosteroid site of GABA-AR. Anxiolytic and antidepressant activity of these peptides was discovered to be comparable to diazepam and fluvoxamine. This was confirmed by experiments on zebrafish (*Danio rerio*) and rodents, as discussed in more detail in Examples below.

In some embodiments, neuromodulatory peptides in accordance with various embodiments of the present disclosure may modulate voltage-gated calcium channels (VGCC), also referred to as voltage-dependent calcium channels (VDCCs), that are a group of voltage-gated ion channels found in the membrane of excitable cells (e.g., muscle, glial cells, neurons, etc.) with a permeability to the calcium ion $Ca^{2+}$. See Yamakage et al. Calcium channels—basic aspects of their structure, function and gene encoding; anesthetic action on the channels—a review. Canadian Journal of Anaesthesia. 2002. 49 (2):151-64. At physiologic or resting membrane potential, VGCCs are normally closed; and they are activated (i.e., opened) at depolarized membrane potentials. The concentration of $Ca^{2+}$ ions is normally several thousand times higher outside the cell than inside, and activation of VGCCs allows a $Ca^{2+}$ influx into the cell, which, depending on the cell type, results in activation of calcium-sensitive potassium channels, muscular contraction, excitation of neurons, up-regulation of gene expression, or release of hormones or neurotransmitters. Wilson et al. Thromboxane A2-induced contraction of rat caudal arterial smooth muscle involves activation of $Ca^{2+}$ entry and $Ca^{2+}$ sensitization: Rho-associated kinase-mediated phosphorylation of MYPT1 at Thr-855, but not Thr-697. The Biochemical Journal. 2005. 389 (Pt 3):763-74.

It was shown that THDOC (tetrahydrodeoxycorticosterone; 3α,21-dihydroxy-5α-pregnan-20-one), DHEA (dehydroepiandrosterone) and pregnenolone act as VGCC antagonist by reversibly blocking VGCC in adult mammalian hippocampal neurons. Reddy & Kulkarni, Development of neurosteroid-based novel psychotropic drugs. Prog Med Chem. 2000; 37:135-75. THDOC is a positive allosteric modulator of the GABAA receptor, and has sedative, anxiolytic and anticonvulsant effects. Reddy & Rogawski. Stress-induced deoxycorticosterone-derived neurosteroids modulate GABA(A) receptor function and seizure susceptibility. The Journal of Neuroscience. 200. 22 (9): 3795-805. Benzodiazepines such as, e.g., diazepam, flurazepam, and desalkylflurazepam, and other positive GABAAR modulators were shown to directly inhibit activity of L-type VGCCs (L-VGCCs). Earl & Tietz. Inhibition of recombinant L-type voltage-gated calcium channels by positive allosteric modulators of GABAA receptors. J Pharmacol Exp Ther. 2011 April; 337(1):301-311. Gabapentinoid drugs (e.g., gabapentin and pregabalin), which are analogs of GABA, may work through direct inhibition of VGCCs. Patel et al. Mechanisms of the gabapentinoids and α2 δ-1 calcium channel subunit in neuropathic pain. Pharmacol Res Perspect. 2016 Feb. 27; 4(2).

The inventors of the present disclosure have computationally created a set of peptides, wherein the peptides in the set were hypothesized to be GABA-A allosteric modulator peptides with the affinity to the BDZ and neurosteroid (NS) binding site of GABA-A. Another set of experiments evaluated another binding site between the α- and β-subunits (referred to as an alpha-beta or α-β binding site). A three-dimensional docking algorithm was used to select more relevant peptides from the peptide sets. As a result, a family of tetrapeptides having novel sequences was identified. In some aspects, a number of tetrapeptides were computationally generated as potential drugs, and a subset of the tetrapeptides was tested. In some aspects, in vivo behavioral testing has confirmed that three illustrative peptides, FQSE (SEQ ID NO:10), DKTE (SEQ ID NO:26), and WDQV (SEQ ID NO:14), have both anxiolytic and antidepressant activity comparable to diazepam and fluvoxamine, as discussed in more detail below.

The inventors of the present disclosure designed and evaluated neuromodulatory peptides that were estimated to have binding capacity to the BDZ (alpha-gamma) site and/or to the alpha-beta site and/or neurosteroid site of GABA-AR. In some aspects, the inventors of the present disclosure conducted the computational analysis and experiments in animal models as described herein, and, as a result, a group of tetrapeptides defined by a following general formula was identified: $R_1R_2R_3R_4(I)$.

In some aspects, the $R_1$ is an amino acid located in the BDZ site or in an α-β binding site or neurosteroid site of GABA-AR. The N-terminus of the peptide can be located in the BDZ site or in an α-β binding site or neurosteroid site of GABA-AR or in close proximity to the BDZ site or in an α-β binding site or neurosteroid site of GABA-AR. Alternatively, the C-terminus of the peptide can be located in the BDZ site or in an α-β binding site or neurosteroid site of GABA-AR. In the following description herein, the peptide is defined as a sequence extending from the N-terminus to the C-terminus. In some aspects, a tetrapeptide in accordance with the present disclosure does not include proline.

In some embodiments, the peptide is defined such that $R_1$ is an amino acid different from Y, and $R_2$ is an amino acid different from L, and the isoelectric point of the peptide is less than 6.

The inventors evaluated efficacy of the three illustrative peptides, FQSE (SEQ ID NO:10), DKTE (SEQ ID NO:26), and WDQV (SEQ ID NO:14), as well as tested other (known) test substances, using in vivo and in vitro models, as discussed in more details below in the Examples section.

It has previously been observed that an increased anxiety of zebrafish is associated with an enhanced time spent in a dark compartment of a light/dark box (an increase in scototaxis—the desire to be in a dark shelter), as well as with an intensification of the shoaling reflex expressed in the desire for close contact with other zebrafish. Increased time spent at the top (or decreased time spent in the bottom) in the novel tank test is also associated with anxiolysis in fish: such changes in Danio rerio behavior under the influence of antidepressant fluoxetine (SSRI) have been previously described. See Egan, R. J. (2009). Understanding behavioral and physiological phenotypes of stress and anxiety in zebrafish. Behav. Brain. Res., 205(1):38-44. An increase in scototaxis was shown to be caused by a shift in the exploratory-hiding motivation balance towards the hiding, and the shoaling reflex is the basic protective response of shoaling fish to a predator. Maximino (2011) Pharmacological analysis of zebrafish (Danio rerio) scototaxis. Prog Neuropsychopharmacol Biol Psychiatry 35: 624-631; Nguyen (2014) Aquatic blues: Modeling depression and antidepressant action in zebrafish. Prog. Neuro-Psychopharmacology Biol. Psychiatry 55:26-39. Thus, the Danio rerio is a suitable model for evaluating potential anxiolytic substances.

The findings by the inventors of the present disclosure are consistent with the published data on the subject, according to which Danio rerio behavior under the conditions of the open field, a light/dark box, and an apparatus assessing the shoaling reflex is an adequate model for assessing anxiety-like behavior, as well as evaluating the effects of antidepressant and anxiolytic drugs (Maximino (2014). Fingerprinting of Psychoactive Drugs in Zebrafish Anxiety-Like Behaviors. PLoS One. 9. P. e103943). The FQSE (SEQ ID NO:10) emerged in zebrafish testing as a leader peptide with robust anxiolytic-like activity and showed no sedative effects.

According to the results obtained in the Open Field test (OFT), the Elevated Plus Maze (EPM) test, and the Marble Burying (MB) test, administration of FQSE (SEQ ID NO:10) (via intraperitoneal injection) to mice resulted in a pronounced anxiolytic-like effect. In the Forced-Swim test (FST) the peptide administration resulted in antidepressant-like effect.

The inventors observed the effects of various doses of FQSE (SEQ ID NO:10) after intranasal administration on the behavior of Sprague-Dawley rats in the open field, elevated plus maze and forced swim test. The behavioral changes after FQSE (SEQ ID NO:10) administration partially recapitulate those observed in diazepam-treated rats in OF and EPM test and ketamine-treated in FST. The most prominent anxiolytic-like and antidepressant-like effects of the peptide were seen at a dose of 0.5 mg/kg and 0.01 mg/kg, depending of behavioral paradigm. The results propose dose-dependent activity of FQSE (SEQ ID NO:10), with maximal efficacy at an intranasal dose of 0.5 mg/kg.

FQSE (SEQ ID NO:10) at doses of 0.05 and 0.5 mg/kg showed an antidepressant-like effect in various behavioral tests in the model of Chronic Mild Unpredictable Stress (CUMS). At the same time, FQSE (SEQ ID NO:10) at a dose of 0.05 mg/kg showed an anxiolytic effect in Novelty-Suppressed Feeding Test (NSFT) and slight anxiolytic-like effect in EPM, without signs of sedation.

The findings by the inventors revealed that the dose of 0.5 mg/kg of FQSE (SEQ ID NO:10) significantly attenuated predator odor-induced place aversion to a greater degree than Doxazosin (DOX).

The study of the effects in the Learned-Helplessness (LH) paradigm showed that FQSE (SEQ ID NO:10) has dose-dependent, anxiolytic-like effects in OF and EPM tests, and antidepressant-like effects in the FST and the dexamethasone test (DXMT). FQSE (SEQ ID NO:10) administration prevented the hyperactivation of the hypothalamic-pituitary-adrenal (HPA) axis and its dysregulation, which was manifested in animals in response to stress.

It was found that FQSE (SEQ ID NO:10) administration has a positive neurotropic effect after chronic administration in the model of Chronic Restraint Stress (CRS). The inventors compare the obtained results of molecular mechanisms of action of the FQSE (SEQ ID NO:10) with the described activity of the GABAA modulators.

Unlabeled FQSE (SEQ ID NO:10) specifically replaces [$^3$H]-FQSE (SEQ ID NO:10) at low concentrations: sites of specific binding of the [$^3$H]-FQSE (SEQ ID NO:10) in rat cortex membranes were found with IC50=$2*10^6$ M. It was also found that diazepam and pregnenolone (both are ligands for GABAAR) have some degree of affinity (IC50~$10^{-4}$ M) for the [$^3$H]-FQSE (SEQ ID NO:10) binding sites in rat cortex membranes.

It was shown that FQSE (SEQ ID NO:10) suppresses LPS-induced expression of pro-inflammatory cytokines TNF-alpha, IL-1b and Il-6 in murine primary glial cells that could indicate its role in the regulation of neuroinflammation. The obtained data highly correlate with the previously shown Western blot results where it was revealed that FQSE (SEQ ID NO:10) was able to normalize stress induced ERK ½ (MAPK pathway participants) phosphorylation levels. Inhibited expression of proinflammatory cytokines observed in the present study could be also considered as a result of GABAA-triggered MAPK repression (Lee (2013). Neurotransmitters and microglial-mediated neuroinflammation. Curr. Prot. Pept. Sci., 14(1), 21-32).

The findings by the inventors revealed that FQSE (SEQ ID NO:10) can penetrate blood-brain barrier. The greatest affinity for peptide FQSE (SEQ ID NO:10) was found in olfactory bulbs where its contents were significantly higher than in other brain regions. It was also found that a higher level of peptide FQSE (SEQ ID NO:10) presented in the prefrontal cortex, hippocampus and hypothalamus compared to other brain regions.

In some aspects, a composition is provided that comprises a synthetic neuromodulatory peptide that is defined by the general formula I: $R_1R_2R_3R_4$(I), wherein $R_1$ is selected from the amino acids W, F, and D; $R_2$ is a hydrophilic amino acid; $R_3$ is a hydrophilic amino acid; and $R_4$ is selected from the amino acids V and E.

In some embodiments, $R_1$ is W. In other embodiments, $R_1$ is F. In yet further embodiments, $R_1$ is D.

In some embodiments, $R_2$ is a hydrophilic amino acid, the hydrophilic amino acid being selected from a polar and positively charged hydrophilic amino acid, a polar and neutral of charge hydrophilic amino acid, and a polar and negatively charged hydrophilic amino acid. In some embodiments, the polar and neutral of charge hydrophilic amino acid is an amino acid different from L, and positively charged hydrophilic amino acid is selected from R and K, H. In some embodiments, the polar and neutral of charge hydrophilic amino acid is selected from N, Q, S, T, and C. In some embodiments, the polar and negatively charged hydrophilic amino acid is selected from D and E, C, Y.

In some embodiments, $R_2$ can be selected from D, Q, and K, such that $R_2$ can be any one of D, Q, and K.

In some embodiments, $R_3$ is a hydrophilic amino acid, the hydrophilic amino acid being selected from a polar and positively charged hydrophilic amino acid, a polar and neutral of charge hydrophilic amino acid, and a polar and negatively charged hydrophilic amino acid. In some embodiments, the polar and positively charged hydrophilic amino acid is selected from R and K. In some embodiments, the polar and neutral of charge hydrophilic amino acid is selected from N, Q, S, T, and C. In some embodiments, the polar and negatively charged hydrophilic amino acid is selected from D and E. In some embodiments, $R_3$ is selected from Q, S, and T.

In some embodiments, $R_4$ is selected from V and E.

In some embodiments, $R_1$ is selected from W, F, and D, $R_2$ is selected from D, Q, and K, $R_3$ is selected from Q, S, and T, and $R_4$ is selected from V and E. In such embodiments, the synthetic neuromodulatory peptide can include any of the amino acids as indicated above. Thus, in some embodiments, $R_1$ is W, $R_2$ is D, $R_3$ is Q, and $R_4$ is V. In such embodiments, the composition can be capable of binding to a benzodiazepine and neurosteroid binding site of a GABA-A receptor. Also, the composition can be capable of binding to an α-β binding site of a GABA-A receptor.

In some embodiments, $R_1$ is F, $R_2$ is Q, $R_3$ is S, and $R_4$ is E. In such embodiments, the composition can be capable of binding to a benzodiazepine and neurosteroid binding sites of a GABA-A receptor. Also, in such embodiments, the composition can be capable of binding to an α-β binding site of a GABA-A receptor.

In some embodiments, $R_1$ is D, $R_2$ is K, $R_3$ is T, and $R_4$ is E. In such embodiments, the composition can be capable of binding to a benzodiazepine and neurosteroid binding site of a GABA-A receptor. Also, in such embodiments, the composition can be capable of binding to an α-β binding site of a GABA-A receptor.

An isoelectric point (pI) value of the neuromodulatory peptide in accordance with any of the embodiments described herein is less than about 6. In some embodiments, the isoelectric point (pI) value of the neuromodulatory peptide is between about 3.5 and about 4.5. In further embodiments, the isoelectric point (pI) value of the neuromodulatory peptide is between about 3.3 and about 4.2.

In some aspects, a composition is provided that comprises a synthetic neuromodulatory peptide that is defined by the general formula Ia:

$$R_1R_2R_3R_4 \tag{Ia}$$

wherein $R_1$ is selected from the amino acids W, F, and D, $R_2$ is selected from the amino acids D, Q, and K, $R_3$ is a polar and neutral of charge hydrophilic amino acid, and $R_4$ is selected from the amino acids V and E. In some embodiments, $R_3$ is a polar and neutral of charge hydrophilic amino acid that is selected from N, Q, S, T, P, and C.

In at least some embodiments, $R_1$ is F, $R_2$ is Q, $R_3$ is S and $R_4$ is E. In at least some embodiments, $R_1$ is D, $R_2$ is K, $R_3$ is T, and $R_4$ is E. In at least some embodiments, $R_1$ is W, $R_2$ is D, $R_3$ is Q, and $R_4$ is V.

The neuromodulatory peptide in accordance with the present disclosure can be in the form of a pharmaceutical composition. The composition can be administered to a subject in need of a treatment, e.g., a subject diagnosed with a disorder manifesting in depression and/or anxiety.

In some embodiments, the peptide, or more than one peptide, in accordance with the present disclosure can be included as an active ingredient in a foodstuff. In these embodiments, the peptide can be included in a composition that is a food preparation. The food composition can include any non-active ingredients. Furthermore, the food composition can include, in addition to the peptide(s) in accordance with the present disclosure, other active ingredients that do not affect the effectiveness of the peptide.

In some embodiments, a peptide in accordance with the present disclosure is an active ingredient of the composition. In other embodiments, the active ingredient of the composition is an analog of the peptide, which can be an N-terminal modified analog or a C-terminal modified analog. The peptide in accordance with the present disclosure is optionally chemically modified. In some embodiments, the chemical modification is selected from amidation, methylation, and acetylation of one or more of $R_1$, $R_2$, $R_3$, and $R_4$, as described herein for either Formula I or Ia. In other embodiments, other various types of peptide backbone and/or side chain modifications can be performed. In some embodiments, chemical modifications can include addition of formyl, pyroglutamyl (pGlu), one or more fatty acids, urea, carbamate, sulfonamide, alkylamine, or any combination thereof.

For example, in some embodiments, the peptide can be a "pseudo-peptide" where the regular peptide bond (CO—NH) is replaced with one of an isosteric or isoelectronic analog. For example, the reduced amide (CH2-NH) can be isosterically introduced into the peptide. In some embodiments, the peptide can be made in the form of azapeptide, where α-Carbon of the peptide backbone is replaced with nitrogen (without changing the amino acids residues). As a further example of a chemical modification, the synthetic neuromodulatory peptide in accordance with the present disclosure can be a retro-inverso peptide where a D-amino acid is used in a reversed sequence. As yet another example, in some embodiments, the synthetic neuromodulatory peptide in accordance with the present disclosure can be peptidomimetic having its side chains appended to the nitrogen atom of the peptide backbone, rather than to the α-carbons. In this way, the synthetic neuromodulatory peptide can be, in some embodiments, a peptoid, or poly-N-substituted glycine.

In some embodiments, the synthetic neuromodulatory peptide can be optionally modified by incorporating non-natural amino acids into certain positions in the peptide. Non-limiting examples of the non-natural amino acids include D-amino acids, N-methylated (or N-alkylated) amino acids, alpha-substituted alpha-amino acids, beta-substituted alpha-amino acids, beta-amino acids, and gamma-amino acids.

In some embodiments, the synthetic neuromodulatory peptide can be modified by cyclization of the peptide. In some embodiments, the synthetic neuromodulatory peptide can be modified such that the peptide is a beta-turn mimetics peptide. In some embodiments, phenylalanine (F) in the peptide, if present, can be replaced with nitro-, amino-, fluoro-phenylalanine, or other inhibitors of proteases.

In some embodiments, the composition in accordance with the present disclosure comprises a pharmaceutically acceptable carrier.

In some embodiments, the composition in accordance with the present disclosure comprises a delivery vehicle. The delivery vehicle can be selected from a liposome, a nanoparticle, and a polysaccharide. In some embodiments, the polysaccharide can be selected from cyclodextrin, chitosan, cellulose, and alginate.

The composition in accordance with the present disclosure can be formulated for various routes of administration. Non-limiting examples of routes of administration include inhalation, intranasal, oral, intravenous, intramuscular, and subcutaneous.

In some embodiments, the composition is formulated for intranasal administration. The composition formulated for intranasal administration can include at least one inhibitor of nasal mucosa proteases. Non-limiting examples of the inhibitors include one or more compounds selected from bestatine, comostate amylase, leupeptin, aprotinin, bacitracin, amastatine, boroleucine, puromycin, a bile salt, and a fusidic acid (e.g., disodium ethylene-diaminetetraacetate). The intranasal delivery is a noninvasive route of administration for the therapeutic peptides and provides an alternative to intravenous or subcutaneous injections.

In some embodiments, the composition is formulated for administration by inhalation. In some embodiments, the composition formulated for administration by inhalation can be administered using a dry powder intranasal device.

In some embodiments, the composition is formulated for intravenous administration.

In some embodiments, the composition modulates gamma-aminobutyric acid A (GABA-A) receptor.

In some embodiments, a pharmaceutical composition is provided in accordance with any of the embodiments or any combination of the embodiments described herein, the pharmaceutical composition comprising a therapeutically effective amount of the composition and at least one pharmaceutically acceptable carrier, diluent, or excipient. Physiological saline, carbonate or bicarbonate buffers, among other possible diluents, may be used to dissolve the composition.

In some embodiments, a method for modulating gamma-aminobutyric acid A (GABA-A) receptor in a cell is provided. The method comprises contacting the cell with the composition in accordance with any of the embodiments or any combination of the embodiments described herein.

In some embodiments, a method for treating a mood disorder in a patient in need thereof is provided. The method comprises administering a therapeutically effective amount of the composition in accordance with any of the embodiments or any combination of the embodiments described herein to a patient in need thereof. The mood disorder can be depression. In some embodiments, the depression can be pediatric depression or youth depression. In some embodiments, the depression is selected from major depressive disorder, dysthymia, breakthrough depression, treatment-refractory depression, and depression associated with Parkinson's disease, depression associated with post-traumatic stress disorder, post-partum depression, bipolar depression. In some embodiments, the mood disorder can be a stress-related disorder.

In some embodiments, the mood disorder is an anxiety disorder. In some embodiments, the anxiety disorder is pediatric anxiety or youth anxiety. The anxiety disorder can be selected from separation anxiety disorder, selective mutism, specific phobia (SP), social anxiety disorder (SAD), panic disorder, agoraphobia, substance/medication-induced anxiety disorder and anxiety disorder due to another medication condition, generalized anxiety disorder (GAD), post-traumatic stress disorder (PTSD), major depressive disorder (MDD), treatment-resistant depression (TRD), postpartum depression (PPD), bipolar disorder or bipolar depression, obsessive-compulsive disorder (OCD), attention deficit hyperactivity disorder (ADHD), major depressive disorder (MDD), treatment-resistant depression (TRD), postpartum depression (PPD), bipolar disorder or bipolar depression, obsessive-compulsive disorder (OCD), and attention deficit hyperactivity disorder (ADHD), social phobia, agitation in Alzheimer's disease, aggression in Alzheimer's disease, and obsessive-compulsive disorder. In some embodiments, the mood disorder is schizophrenia. In some embodiments, the mood disorder is a post-traumatic stress disorder.

In some embodiments, a method for treating a mood disorder in accordance with any of the embodiments or any combination of the embodiments described herein is provided, the method further comprising administering an antidepressant. The antidepressant is optionally selected from the group consisting of serotonin reuptake inhibitors, selective norepinephrine reuptake inhibitors, combined action SSRI/SNRI, serotonin-2 antagonist/reuptake inhibitors, an antidepressant with alpha-2 antagonism plus serotonin-2 and serotonin-3 antagonism, an antidepressant with serotonin/norepinephrine/dopamine reuptake inhibition, an antidepressant with norepinephrine and dopamine reuptake inhibition, 5-HT-1alpha antagonist, 5-HT-1beta antagonist, 5-HT1A receptor agonists, 5-HT1A receptor agonists and antagonists, 5-HT2 receptor antagonists, viloxazine hydrochloride, dehydroepiandosterone, NMDA receptor antagonists, AMPA receptor potentiators, substance P antagonists/neurokinin-1 receptor antagonists, nonpeptide Substance P antagonist, neurokinin 2 antagonists, neurokinin 3 antagonists, corticotropin-releasing factor receptor antagonists, antiglucocorticoid medications, glucocorticoid receptor antagonists, cortisol blocking agents, nitric oxide synthesize inhibitors, inhibitors of phosphodiesterase, enkephalinase inhibitors, GABA-A receptor agonists, free radical trapping agents, atypical MAOI's, selective MAOI inhibitors, hormones, folinic acid, leucovorin, tramadol, and tryptophan in combination with an antipsychotic drug, wherein said antipsychotic drug is selected from the group consisting of an atypical antipsychotic drug, and a dopamine system stabilizer.

In some embodiments, a method for treating a mood disorder in accordance with any of the embodiments or any combination of the embodiments described herein is provided, the method further comprises administering an additional depression treatment optionally selected from agent one or more additional agents.

In some embodiments, the invention provides for the present compositions and methods that further comprise an additional agent and methods of administering the additional agent to a subject. In some embodiments, the invention pertains to co-administration and/or co-formulation. Any of the compositions described herein may be co-formulated and/or co-administered.

In embodiments, the additional agent is one or more of duloxetine (CYMBALTA oral), escitalopram oxalate (LEXAPRO oral), venlafaxine (EFFEXOR oral, EFFEXOR XR oral), sertraline (ZOLOFT oral), citalopram (CELEXA oral), trazodone oral (OLEPTRO ER oral), fluoxetine (PROZAC oral, PROZAC WEEKLY oral SARAFEM oral), bupropion (WELLBUTRIN oral, WELLBUTRIN SR oral, WELLBUTRIN XL oral, ZYBAN oral, APLENZIN oral, BUPROBAN oral, FORFIVO XL oral), desvenlafaxine (PRISTIQ oral), amitriptyline oral, milnacipran (SAVELLA oral), vilazodone (VIIBRYD oral), paroxetine (PAXIL oral, PAXIL CR oral, PEXEVA oral, BRISDELLE oral), mirtazapine (REMERON oral, REMERON SOLTAB oral), nortriptyline (AVENTYL or PAMELOR), methylphenidate (RITALIN oral, METHYLIN oral, QUILLIVANT XR oral), doxepin (SINEQUAN or ADAPIN oral), olanzapine/fluoxetine (SYMBYAX oral), imipramine (TOFRANIL oral, TOFRANIL-PM oral), vortioxetine (BRINTELLIX oral, phenelzine (NARDIL oral), levomilnacipran (FETZIMA oral), selegiline (EMSAM TRANSDERMAL), tranylcypromine (PARNATE oral), clomipramine (ANAFRANIL oral) fluvoxamine (LUVOX oral), desipramine (NORPRAMIN, PERTOFRANE), nefazodone, desvenlafaxine succinate oral, imipramine pamoate, paroxetine mesylate oral, trimipramine (SURMONTIL oral), maprotiline oral, protriptyline oral, phenelzine oral, tranylcypromine oral, amoxapine oral, isocarboxazid (MARPLAN oral), desvenlafaxine (KHEDEZLA oral), and desvenlafaxine fumarate oral.

In some embodiments, a method for treating a mood disorder in accordance with any of the embodiments or any combination of the embodiments described herein is provided, the method further comprises administering an additional anxiety treatment optionally selected from agent one or more of benzodiazepines selected from alprazolam (XANAX), clonazepam (KLONOPIN), diazepam (VALIUM), lorazepam (ATIVAN), oxazepam (SERAX), and chlordiazepoxide (LIBRIUM); beta blockers selected from propranolol (INDERAL) and atenolol (TENORMIN); tricyclic antidepressants selected from imipramine (TOFRANIL), desipramine (NORPRAMIN, PERTOFRANE), nortriptyline (AVENTYL or PAMELOR), amitriptyline (ELAVIL), doxepin (SINEQUAN or ADAPIN), clomipramine (ANAFRANIL); monoamine oxidase inhibitors (MAOIs) selected from phenelzine (NARDIL), tranylcypromine (PARNATE); selective serotonin reuptake inhibitors (SSRIs) selected from fluoxetine (PROZAC), fluvoxamine (LUVOX), sertraline (ZOLOFT), paroxetine (PAXIL), escitalopram oxalate (LEXAPRO), citalopram (CELEXA); serotonin-norepinephrine reuptake inhibitors (SNRIs) selected from venlafaxine (EFFEXOR), venlafaxine extended release (EFFEXOR XR) and duloxetine (CYMBALTA); mild tranquilizers such as buspirone (BUSPAR); and anticonvulsants selected from valproate (DEPAKOTE), pregabalin (LYRICA), and gabapentin (NEURONTIN).

In embodiments, the additional agent may be conjugated to the peptides in accordance with the present disclosure.

In embodiments, the present compositions may be fused to other moieties, e.g., an additional agent or a moiety to extend half-life in vivo. Apart from increasing stability, such moieties may also increase solubility of the molecule they are fused to. A moiety that increases solubility (e.g., prevents aggregation) may provide easier handling of the compositions, and particularly improve stability and shelf-life. A well-known example of such moiety is PEG (polyethylene glycol). This moiety is particularly envisaged, as it can be used as linker as well as solubilizing moiety. Other examples include peptides and proteins or protein domains, or even whole proteins (e.g., GFP). In this regard, it should be noted that, like PEG, one moiety can have different functions or effects. For instance, a flag tag (DYKDDDDK) is a peptide moiety that can be used as a label, but due to its charge density, it will also enhance solubilization. PEGylation has already often been demonstrated to increase solubility of biopharmaceuticals (e.g., Veronese and Mero (2008) The impact of PEGylation on biological therapies, BioDrugs; 22(5)315-29). Adding a peptide, polypeptide, protein or protein domain tag to a molecule of interest has been extensively described in the art. Examples include, but are not limited to, peptides derived from synuclein (e.g., Park et al., Protein Eng. Des. Sel. 2004; 17:251-260), SET (solubility enhancing tag, Zhang et al., Protein Expr Purif 2004; 36:207-216), thioredoxin (TRX), Glutathione-S-transferase (GST), Maltose-binding protein (MBP), N-Utilization substance (NusA), small ubiquitin-like modifier (SUMO), ubiquitin (Ub), disulfide bond C (DsbC), Seventeen kilodalton protein (Skp), Phage T7 protein kinase fragment (T7PK), Protein G BI domain, Protein A IgG ZZ repeat domain, and bacterial immunoglobulin binding domains (Hutt et al., J Biol Chem; 287(7):4462-9, 2012). The nature of the tag will depend on the application, as can be determined by the skilled person. For instance, for transgenic expression of the molecules described herein, it might be envisaged to fuse the molecules to a larger domain to prevent premature degradation by the cellular machinery. Other applications may envisage fusion to a smaller solubilization tag (e.g., less than 30 amino acids, or less than 20 amino acids, or even less than 10 amino acids) in order not to alter the properties of the molecules too much. Additional chemical modifications can include addition of formyl, pyroglutamyl (pGlu), one or more fatty acids, urea, carbamate, sulfonamide, alkylamine, or any combination thereof.

Apart from extending half-life, the present compositions may be fused to moieties that alter other or additional pharmacokinetic and pharmacodynamic properties. For instance, it is known that fusion with albumin (e.g., human serum albumin), albumin-binding domain or a synthetic albumin-binding peptide improves pharmacokinetics and pharmacodynamics of different therapeutic proteins (Langenheim & Chen (2009). Improving the pharmacokinetics/pharmacodynamics of prolactin, GH, and their antagonists by fusion to a synthetic albumin-binding peptide. J. Endocrinol., 203(3): 375). Another moiety that is often used is a fragment crystallizable region (Fc) of an antibody. The nature of these moieties can be determined by the person skilled in the art depending on the application.

In some embodiments, the peptides of the present disclosure can be administered as the sole pharmaceutical agent or in combination with one or more other pharmaceutical agents where the combination causes no unacceptable adverse effects.

The amount of the active ingredient to be administered in the treatment of one or more conditions can vary according to such considerations as the particular peptide and dosage unit employed, the mode of administration, the period of treatment, the age, weight, and sex of the patient treated, and the nature and extent of the condition treated. The composition in accordance with the present disclosure can be administered to a subject at the appropriate dose via a certain route.

In some embodiments, a dose of the peptide to be administered will generally range from about 0.001 mg/kg to about 200 mg/kg body weight, from about 0.01 mg/kg to about 100 mg/kg body weight, from about 0.01 mg/kg to about 50 mg/kg body weight, from about 0.01 mg/kg to about 40 mg/kg body weight, from about 0.01 mg/kg to about 30 mg/kg body weight, from about 0.01 mg/kg to about 5 mg/kg body weight, from about 0.01 mg/kg to about 10 mg/kg body weight, from about 0.1 mg/kg to about 10 mg/kg body weight, from about 0.1 mg/kg to about 20 mg/kg body weight, from about 0.1 mg/kg to about 30 mg/kg body weight, from about 0.1 mg/kg to about 40 mg/kg body weight, from about 0.1 mg/kg to about 50 mg/kg body weight. Clinically useful dosing schedules will range from one to three times a day dosing. A pharmaceutical composition with the neuromodulatory peptides described herein can also be administered as a single dose. Because of the safety and effectiveness of the composition, the single dose of the composition can be effective in alleviating depression- or anxiety-related symptoms. Treatment schedules can also be developed for a more prolonged treatment course. For example, in some embodiments, a pharmaceutical composition in accordance with embodiments of the present disclosure can be administered during more than one day, for instance, from 2 days to 60 days, or from 2 days to 50 days, or from 2 days to 40 days, or from 2 days for 30 days, and the daily dose can be within any of the above ranges. The administration for more than one day can be used for treatment of chronic symptoms or disorders, which can be any of various mental, behavioral, affective, neurotic, and emotional disorders, including depression, anxiety, and stress-related disorders.

A "subject" is a mammal, e.g., a human (e.g., a female or a male human), mouse, rat, guinea pig, dog, cat, horse, cow, pig, or non-human primate, such as a monkey, chimpanzee, baboon or rhesus, and the terms "subject" and "patient" are used interchangeably herein.

The peptides described herein can be administered in the form of sprays, for example, intranasal sprays.

The invention further provides kits that can simplify the administration of any agent described herein. An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agents described herein. In one embodiment, the kit comprises a container containing an effective amount of a composition of the invention and an effective amount of another composition, such those described herein.

The present disclosure is further illustrated by the following non-limiting examples.

EXAMPLES

Example 1: Computational Design of Peptides

A set of peptides from bovine milk hydrolysate was divided into 5 categories and was computationally converted into a set of all possible tetrapeptides by a sliding window with a step size of 1 amino acid. In total, 341 unique tetrapeptides were generated. For each peptide, a 3D docking algorithm was applied to fit a peptide to the BDZ site of a GABA-A receptor and to an interface between alpha and beta subunits of a GABA-A receptor, which resulted in up to 20 possible conformations per peptide. A total of 5650 unique peptide positions were generated. All positions were combined and the frequency with which an atom of a specific type (aromatic carbon, hydrogen bond donor/acceptor, etc.) is positioned in the given area, was calculated. Each conformation was weighed according to the spatial density map and normalized to the number of atoms and residues. The docking site was chosen to be bigger than the BDZ site, and thus to facilitate the evaluation of the results, peptides bigger than the BDZ site were assigned a score of 0.0. All the usual interactions (such as electrostatics, hydrogen bonds, etc) were accounted for at the stage of docking/fitting. Further, 100 tetrapeptides were preselected based on their scores.

Example 2: Selection of Four Peptides for Testing 2.1 Aim of the Study

To identify tetrapeptides which will have the maximum affinity to the benzodiazepine site of a GABA-A receptor among the given peptides, using computational methods.

2.2 Results

The given set of peptides from bovine milk hydrolysate divided into 5 categories was converted into a set of tetrapeptides. All possible tetrapeptides were generated from each peptide by a sliding window with a step size of 1 amino acid. In total, 341 unique tetrapeptides were generated.

Each peptide was modified in the following way: an acetyl "plug" was added to the N-terminus, while a methyl one—to the C-terminus.

For each peptide, docking to the BZD site of the GABA-A receptor was performed generating up to 20 conformations. A total of 5650 unique peptide positions were obtained. Later on, all the results were combined and the frequency with which an atom of this type (aromatic carbon, hydrogen bond donor/acceptor, etc.) gets into the given area was analyzed. Each conformation was weighed according to this spatial density map and normalized to the number of atoms and residues. Thus, a type of statistical analysis was performed. As the docking cell was admittedly bigger than the BZD site, to facilitate the assessment of the result, peptides which got outside the BZD site are assigned using the assessment mark of 0.0. The account of the usual interactions (such as electrostatics, hydrogen bonds, etc.) in the explicit form takes place at the stage of docking.

In this way, about 100 findings, with the value of the evaluation function 0.7:

| Short name | Pose name | Energy | Sequence ID |
|---|---|---|---|
| YLQY | YLQY_out_model16.pdb | 1.00 | SEQ ID NO: 1 |
| YQLY | YQLY_out_model9.pdb | 0.99 | SEQ ID NO: 2 |
| YQLY | YQLY_out_model11.pdb | 0.94 | SEQ ID NO: 2 |
| YLQY | YLQY_out_model5.pdb | 0.93 | SEQ ID NO: 1 |
| YLEQ | YLEQ_out_model10.pdb | 0.92 | SEQ ID NO: 3 |
| QYLY | QYLY_out_model10.pdb | 0.92 | SEQ ID NO: 4 |
| YLKY | YLKY_out_model9.pdb | 0.90 | SEQ ID NO: 5 |
| YLKY | YLKY_out_model19.pdb | 0.89 | SEQ ID NO: 5 |
| YLKT | YLKT_out_model4.pdb | 0.89 | SEQ ID NO: 6 |
| YQLY | YQLY_out_model3.pdb | 0.86 | SEQ ID NO: 2 |
| FLLY | FLLY_out_model10.pdb | 0.86 | SEQ ID NO: 7 |
| YQLY | YQLY_out_model20.pdb | 0.86 | SEQ ID NO: 2 |
| YQKF | YQKF_out_model2.pdb | 0.86 | SEQ ID NO: 8 |
| YLQY | YLQY_out_model14.pdb | 0.85 | SEQ ID NO: 1 |
| YLKY | YLKY_out_model6.pdb | 0.84 | SEQ ID NO: 5 |
| LYQE | LYQE_out_model8.pdb | 0.84 | SEQ ID NO: 9 |
| FQSE | FQSE_out_model5.pdb | 0.84 | SEQ ID NO: 10 |
| FLLY | FLLY_out_model7.pdb | 0.83 | SEQ ID NO: 7 |
| QYLY | QYLY_out_model11.pdb | 0.82 | SEQ ID NO: 4 |
| FYQK | FYQK_out_model5.pdb | 0.82 | SEQ ID NO: 11 |
| LYQE | LYQE_out_model2.pdb | 0.82 | SEQ ID NO: 9 |
| FLLY | FLLY_out_model11.pdb | 0.81 | SEQ ID NO: 7 |
| YLGY | YLGY_out_model15.pdb | 0.81 | SEQ ID NO: 12 |
| YLQY | YLQY_out_model12.pdb | 0.80 | SEQ ID NO: 1 |
| PFTE | PFTE_out_model11.pdb | 0.80 | SEQ ID NO: 13 |
| WDQV | WDQV_out_model11.pdb | 0.80 | SEQ ID NO: 14 |
| PEVF | PEVF_out_model16.pdb | 0.80 | SEQ ID NO: 15 |
| FLLY | FLLY_out_model13.pdb | 0.80 | SEQ ID NO: 7 |
| YLQY | YLQY_out_model13.pdb | 0.79 | SEQ ID NO: 1 |
| LSRY | LSRY_out_model12.pdb | 0.79 | SEQ ID NO: 16 |
| LLRF | LLRF_out_model2.pdb | 0.79 | SEQ ID NO: 17 |
| WDQV | WDQV_out_model15.pdb | 0.79 | SEQ ID NO: 14 |
| MPLW | MPLW_out_model17.pdb | 0.79 | SEQ ID NO: 18 |
| KYQF | KYQF_out_model10.pdb | 0.79 | SEQ ID NO: 19 |
| YLKY | YLKY_out_model7.pdb | 0.78 | SEQ ID NO: 5 |
| YLKT | YLKT_out_model5.pdb | 0.78 | SEQ ID NO: 6 |
| FYQK | FYQK_out_model13.pdb | 0.78 | SEQ ID NO: 11 |
| YQLY | YQLY_out_model7.pdb | 0.78 | SEQ ID NO: 2 |
| YQKF | YQKF_out_model14.pdb | 0.78 | SEQ ID NO: 8 |
| LLRF | LLRF_out_model5.pdb | 0.78 | SEQ ID NO: 17 |
| KYQF | KYQF_out_model16.pdb | 0.78 | SEQ ID NO: 19 |
| YQKF | YQKF_out_model3.pdb | 0.77 | SEQ ID NO: 8 |
| YLQY | YLQY_out_model18.pdb | 0.77 | SEQ ID NO: 1 |
| QYLY | QYLY_out_model17.pdb | 0.77 | SEQ ID NO: 4 |
| YQLY | YQLY_out_model8.pdb | 0.77 | SEQ ID NO: 2 |
| YQFL | YQFL_out_model8.pdb | 0.77 | SEQ ID NO: 20 |
| FFVA | FFVA_out_model6.pdb | 0.77 | SEQ ID NO: 21 |
| KTVY | KTVY_out_model8.pdb | 0.77 | SEQ ID NO: 22 |
| YQLY | YQLY_out_model13.pdb | 0.76 | SEQ ID NO: 2 |
| KYQF | KYQF_out_model11.pdb | 0.76 | SEQ ID NO: 19 |
| FSDI | FSDI_out_model14.pdb | 0.76 | SEQ ID NO: 23 |
| FFVA | FFVA_out_model5.pdb | 0.76 | SEQ ID NO: 21 |

-continued

| Short name | Pose name | Energy | Sequence ID |
|---|---|---|---|
| YLKY | YLKY_out_model13.pdb | 0.75 | SEQ ID NO: 5 |
| FFVA | FFVA_out_model7.pdb | 0.75 | SEQ ID NO: 21 |
| SFSD | SFSD_out_model14.pdb | 0.75 | SEQ ID NO: 24 |
| FLLY | FLLY_out_model8.pdb | 0.75 | SEQ ID NO: 7 |
| FFVA | FFVA_out_model12.pdb | 0.75 | SEQ ID NO: 21 |
| LLYQ | LLYQ_out_model5.pdb | 0.75 | SEQ ID NO: 25 |
| DKTE | DKTE_out_modeI20.pdb | 0.74 | SEQ ID NO: 26 |
| LLYQ | LLYQ_out_model6.pdb | 0.74 | SEQ ID NO: 25 |
| QYLY | QYLY_out_model8.pdb | 0.74 | SEQ ID NO: 4 |
| YYVP | YYVP_out_model13.pdb | 0.73 | SEQ ID NO: 27 |
| YQKF | YQKF_out_model13.pdb | 0.73 | SEQ ID NO: 8 |
| LSRY | LSRY_out_model9.pdb | 0.73 | SEQ ID NO: 16 |
| YQLY | YQLY_out_model19.pdb | 0.73 | SEQ ID NO: 2 |
| YLKT | YLKT_out_model14.pdb | 0.73 | SEQ ID NO: 6 |
| FTES | FTES_out_model15.pdb | 0.73 | SEQ ID NO: 28 |
| LSRY | LSRY_out_model4.pdb | 0.73 | SEQ ID NO: 16 |
| GTQY | GTQY_out_model13.pdb | 0.73 | SEQ ID NO: 29 |
| PEVF | PEVF_out_model7.pdb | 0.72 | SEQ ID NO: 15 |
| FLGA | FLGA_out_model7.pdb | 0.71 | SEQ ID NO: 30 |
| YTDA | YTDA_out_model10.pdb | 0.71 | SEQ ID NO: 31 |
| YPSY | YPSY_out_model18.pdb | 0.71 | SEQ ID NO: 32 |
| KTVY | KTVY_out_model2.pdb | 0.71 | SEQ ID NO: 22 |
| YPSY | YPSY_out_model19.pdb | 0.71 | SEQ ID NO: 32 |
| FTES | FTES_out_model12.pdb | 0.71 | SEQ ID NO: 28 |
| FPKY | FPKY_out_model9.pdb | 0.71 | SEQ ID NO: 33 |
| QYLY | QYLY_out_model18.pdb | 0.70 | SEQ ID NO: 4 |

It is possible to estimate the occurrence of separate tetrapeptides in the list of the best outcomes. As most peptides are situated linearly on the surface of proteins, the direction in relation to the BZD site can be determined. Below, F stands for Forward—N-terminus of a peptide is situated in the BZD site or in close proximity to it. R stands for Reverse—C-terminus of a peptide is situated in the BZD site—in these cases the peptide sequence should be regarded from C-terminus to N-terminus. Peptides that have only conformer R are not the peptides from the provided list:

YQLY 8 F/R (SEQ ID NO: 2)

YLQY 6 F/R (SEQ ID NO: 1)

YLKY 5 F/R (SEQ ID NO: 5)

QYLY 5 F/R (SEQ ID NO: 4)

FLLY 5 F/R (SEQ ID NO: 7)

YQKF 4 F (SEQ ID NO: 8)

FFVA 4 F (SEQ ID NO: 21)

YLKT 3 F (SEQ ID NO: 6)

KYQF 3 R (SEQ ID NO: 19)

LSRY 3 R (SEQ ID NO: 16)

FTES 2 F (SEQ ID NO: 28)

PEVF 2 R (SEQ ID NO: 15)

YPSY 2 F/R (SEQ ID NO: 32)

LYQE 2 F (SEQ ID NO: 9)

LLRF 2 R (SEQ ID NO: 17)

KTVY 2 R (SEQ ID NO: 22)

FYQK 2 F (SEQ ID NO: 11)

WDQV 2 F (SEQ ID NO: 14)

LLYQ 2 F (SEQ ID NO: 25)

DKTE 1 F (SEQ ID NO: 26)

YTDA 1 F (SEQ ID NO: 31)

FQSE 1 F (SEQ ID NO: 10)

FSDI 1 F (SEQ ID NO: 23)

PFTE 1 F (SEQ ID NO: 13)

MPLW 1 R (SEQ ID NO: 18)

GTQY 1 R (SEQ ID NO: 29)

SFSD 1 F (SEQ ID NO: 24)

YQFL 1 F (SEQ ID NO: 20)

FLGA 1 F (SEQ ID NO: 30)

YLEQ 1 F (SEQ ID NO: 3)

```
YLGY 1 R                        (SEQ ID NO: 12)

YYVP 1 F                        (SEQ ID NO: 27)

FPKY 1 R                        (SEQ ID NO: 33)
```

The best findings are quite uniformly situated in the BZD site.

2.3 Conclusion

By looking at the most suitable options, tetrapeptides of a known peptide YLGYLEQLLR were discovered. However, the other peptides were also discovered that significantly differ from those in the sequence, yet that differ insignificantly in the value of the evaluation function. For the further experimental validation, the following original peptides were chosen: FQSE (SEQ ID NO:10), WDQV (SEQ ID NO:14), DKTE (SEQ ID NO:26), and for negative control—FLPY (SEQ ID NO:36).

Moreover, computational methods were used to check whether the FQSE (SEQ ID NO:10) peptide may have an affinity to neurosteroid site of a GABA-A.

FQSE (SEQ ID NO:10) tetrapeptide was initially identified via the high-throughput combinatorial docking of all possible tetrapeptides into the extracellular domain of the GABA-A receptor. The preferential binding pocket for this peptide was found to be the BZD site. Then binding modes of FQSE (SEQ ID NO:10) were independently checked during the control docking run into the full GABA-A receptor model with the inclusion of its membrane-buried alpha-helical domains. This run demonstrated high preference of FQSE (SEQ ID NO:10) to the neurosteroid-binding site of GABA-A with all the best hits from 20 independent replicas positioned in it.

These experiments demonstrate that FQSE (SEQ ID NO:10) peptide binds the GABA-A receptor in two regions: the major binding mode corresponds to the neurosteroid site and the minor to the BZD site.

Example 3: Evaluation of Effects of Selected Peptides and Other Test Substances on Behavior of Zebrafish (*Danio rerio*)

The objective was to develop a standard protocol for evaluating the neurotropic activity of novel neuromodulatory peptides by analyzing the effect of psychoactive agents on behavior of zebrafish (*Danio rerio*). In particular, the effects of single injection of such antidepressant and anxiolytic agents as fluvoxamine and diazepam on scototaxis, locomotor activity, exploratory reactions, and social behavior of *Danio rerio* were evaluated.

3.1. Materials and Methods 3.1.1. Animal Maintenance

The zebrafish were kept in a flow-through ZebTEC Zebrafish housing system (manufactured by Tecniplast) at a temperature of 28° C., a pH of 6.8-7.5, an osmolality of 550-700 osmol/liter, with a light regimen of 12/12, and constant aeration. The zebrafish were fed a special diet twice a day. During the experiment the fish were fed in the evening on the day prior to the experiment and in the evening on the day of the experiment after its completion. All procedures involving animals were conducted in accordance with the European (Directive 2010/63/EU of the European Parliament and of the Council of 22 Sep. 2010 on the protection of animals used for scientific purposes) and the Russian ("GOST 33216-2014 Guidelines for the maintenance and care of laboratory animals. Rules for the maintenance and care of laboratory rodents and rabbits") bioethical guidelines.

3.1.2. Substances, Doses and Administration

Diazepam

Diazepam is a benzodiazepine anxiolytic that acts by binding to the benzodiazepine sites of GABA-A receptors (Cl-channels), prolonging their open state. Thus, in low, diazepam has been shown to produce an anxiolytic effect, while the high doses it can cause a strong sedative effect. In the described experiments, diazepam was administered at doses of 1.25 mg/kg, 5 mg/kg, and 10 mg/kg.

Fluvoxamine

Fluvoxamine, a known antidepressant representing a group of selective serotonin reuptake inhibitors (SSRIs), was administered to zebrafish at doses of 5 mg/kg and 10 mg/kg.

Beta-Casomorphin-7 (BCM-7)

BCM-7 is a fragment of the bovine's milk beta-casein (H-YPFPGPI-OH (SEQ ID NO:34); IUPAC: L-tyrosyl-L-prolyl-L-phenylalanyl-L-prolyl-glycyl-L-prolyl-L-isoleucine). BCM-7 is known for its opioid activity (e.g., analgesic and anxiolytic activity), mainly acting through mu-opioid receptors (Kaminski S., et al. (2007) Polymorphism of bovine beta-casein and its potential effect on human health. J. Appl. Genet. 48:189-198). BCM-7 was administered at a dose of 5 mg/kg in this study.

Alpha-Casozepine-10 (ACZ-10)

ACZ-10 is a fragment of the bovine's milk alpha-casein (H-YLGYLEQLLR-OH (SEQ ID NO:35); IUPAC: L-tyrosyl-L-leucyl-glycyl-L-tyrosyl-L-leucyl-L-alpha-glutamyl-L-glutaminyl-L-leucyl-L-leucyl-L-arginine). According to Miclo et al., 2001 (Miclo (2001) Characterization of alpha-casozepine, a tryptic peptide from bovine alpha(s1)-casein with benzodiazepine-like activity. FASEB J. 15:1780-2), ACZ-10 displays benzodiazepine-like activity due to its three-dimensional structure that allows it to bind to the benzodiazepine site of GABA-A receptors. A dose of 0.6 mg/kg of ACZ-10 was administered in this study.

Inventive Tetrapeptides

Four selected tetrapeptide ligands of GABA-A benzodiazepine site were tested, at two dose levels—1 mg/kg and 10 mg/kg. The peptides had the following primary structure: FQSE (SEQ ID NO:10), DKTE (SEQ ID NO:26), WDQV (SEQ ID NO:14), and FLPY (SEQ ID NO:36). Among these substances, FQSE (SEQ ID NO:10), DKTE (SEQ ID NO:26), and WDQV (SEQ ID NO:14) were the illustrative tetrapeptides, whereas FLPY (SEQ ID NO:36) was a negative control.

Administration

The tested substances were injected into the zebrafish intraperitoneally (ip) using an insulin syringe (0.5 ml, 30 g) 10 minutes before the test. The saline solution (0.9% NaCl) was used as a solvent. Anesthesia and immobilization of the animals were achieved by placing them in water at a temperature of 10° C. Control group fish received intraperitoneal injections of an equivalent volume of solvent, also after going through a pre-cooling procedure.

3.1.3. Equipment Setup

Figure 2:
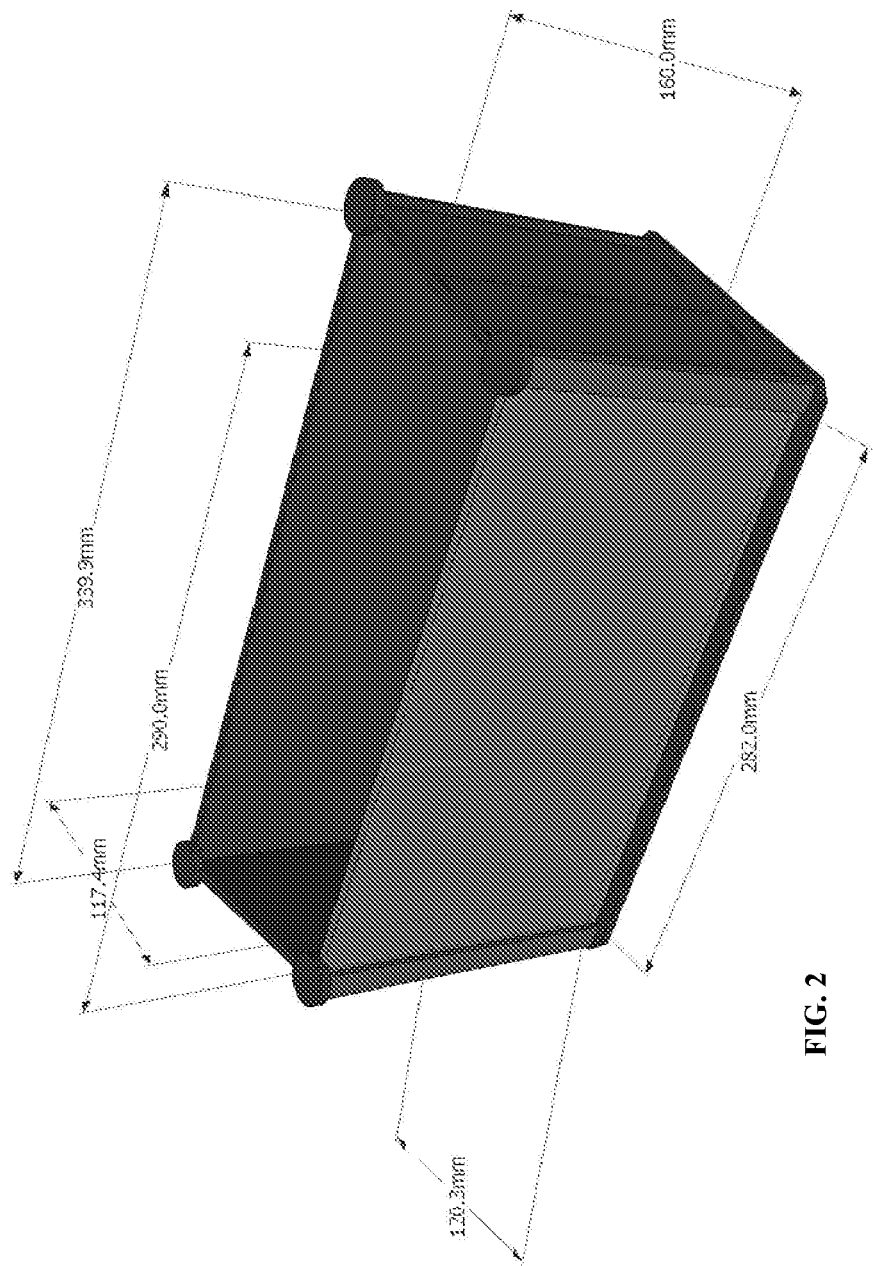
FIG. 2 is a perspective view of a system for fish behavioral testing employed in the Open Field Test.
Figure 3:
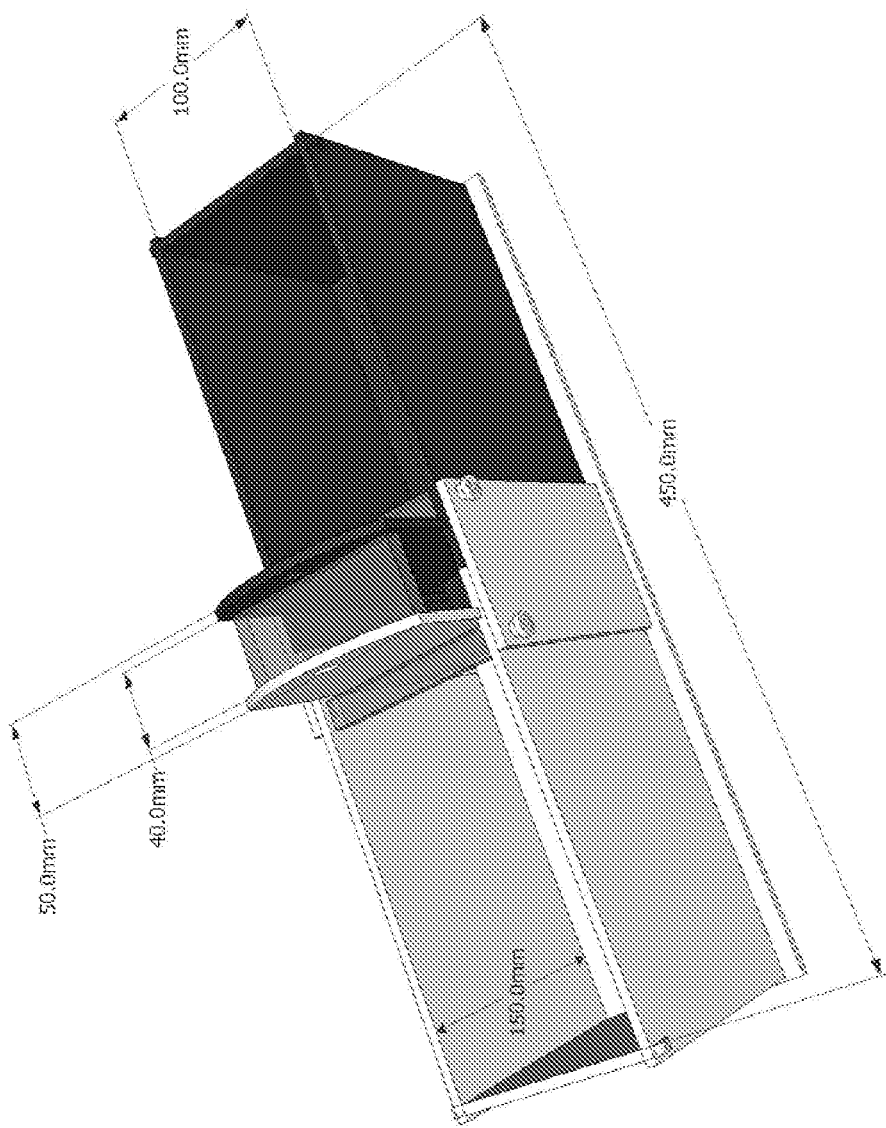
FIG. 3 is a perspective view of a system for fish behavioral testing employed in the Light/Dark preference test.

The Open Field test was conducted in a 4-liter trapezoid aquarium, the parameters of which are shown in FIG. 2. A base, back, and side walls of the aquarium were made of matte black plastic; the front panel (shorter wall) was made of transparent Plexiglas. The setup for the Light/Dark preference test consisted of three main parts: a launch compartment, a light compartment made of white plastic, and a dark compartment made of black plastic. Installation parameters are shown in FIG. 3. The bright lighting in these tests was provided by a lamp on a stand (LED lamp PL, 11 W, light flux≈600 Lm, about 500 Lx directly above the water surface), which was attached to the upper part of the aquarium.

Figure 4:
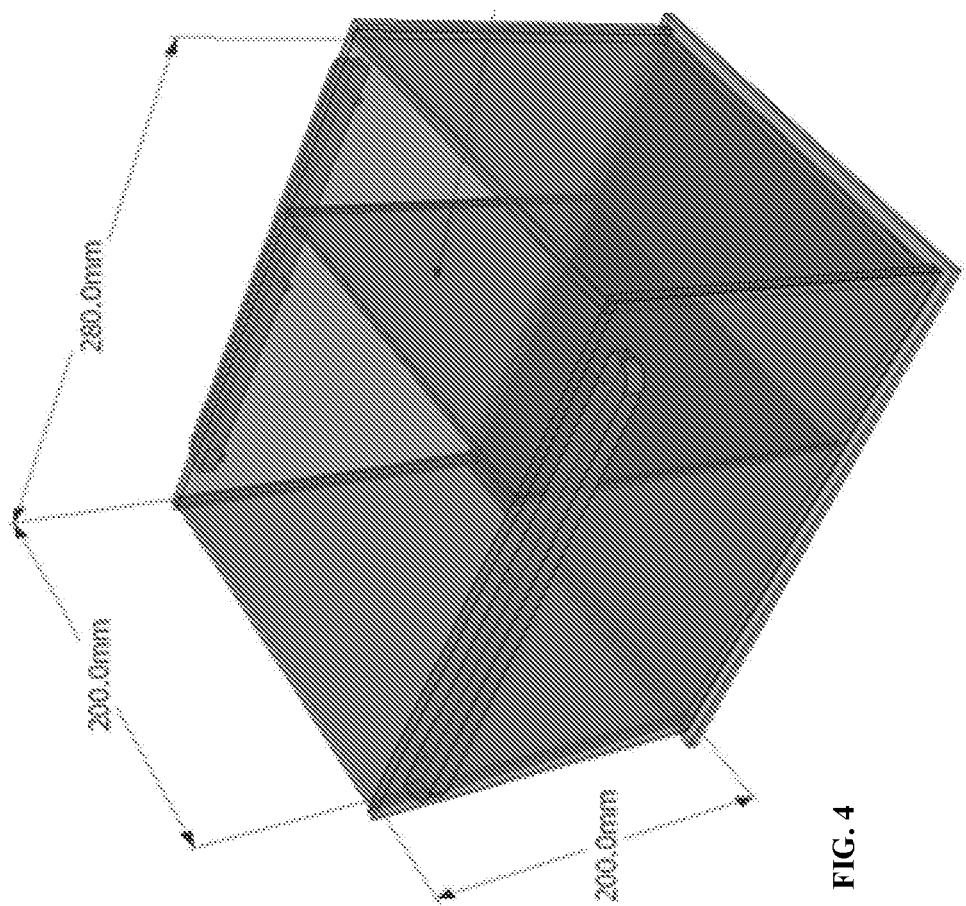
FIG. 4 is a perspective view of a system for fish behavioral testing employed in the shoaling behavior test.

A Plexiglas container with a removable partition (shown in FIG. 4) was used as a setup for investigating the shoaling behavior of zebrafish. A shoal of 5 adult *Danio rerio* specimens was placed into in the small compartment; and the test fish was placed in a large compartment. Diffused lighting in this installation was provided by the usual lighting of the room (about 200 Lx).

3.1.4. Behavioral Tests 3.1.4.1. The Open Field Test

The open field test was performed as described in Maximino et al., 2013. A video recording (background shooting) was started 20-30 seconds before the zebrafish were placed in the test aquarium. The experimental zebrafish was placed in an open field ("OF") aquarium using a net. The recording was being conducted for five minutes. The test was carried out using EthoVision XT software package (Noldus). The software registered the distance covered by the animal, its speed, the number of visits to the three conventional zones of the aquarium: "bottom," "center," and "middle" (lower, middle, and upper thirds of the aquarium, respectively), the time spent in these zones, and the latency of a visit to the middle and to the surface of the aquarium.

3.1.4.2. The Shoaling Behavior Test

The shoaling behavior test was performed as described in Parker et al., 2014. (Parker et al. (2014) The utility of zebrafish to study the mechanisms by which ethanol affects social behavior and anxiety during early brain development. Prog. Neuro-Psychopharmacology Biol. Psychiatry. 94-100). The video recording began simultaneously with placing the zebrafish in the set-up and recorded for 5 minutes. The videos were processed using RealTimer (OpenScience Ltd., Moskow, Russia). During the processing of the records, the residence time and the number of visits to the three conventional zones of the aquarium wall (near the "shoal" in the middle of the aquarium, and near the opposite side; all three were equal in size) were recorded.

3.1.4.3. The Light/Dark Box Test

The light/dark box (LDB) test was performed as described in Maximino et al., 2011. The zebrafish was placed in a light compartment of an LDB using a net, the camera was switched on simultaneously, and the behavior of the zebrafish was recorded for 5 minutes. The video was processed using RealTimer (OpenScience). During the processing of records, the residence time and the number of visits to the light and dark compartments of the test setup were recorded, as well as the latent period of visiting both compartments.

3.1.5. Data Analysis

The data obtained during the behavioral tests were evaluated using the STATISTICA platform. Both statistical processing of the data and constructing of visual representation of results (including graphs) were carried out in Graph Pad Prism 6.

The normality of the obtained data distribution was estimated with Kolmogorov-Smirnov normality test. The non-parametric test (the Mann-Whitney test) was applied to compare the parameters whose distribution did not correspond to the normal one. The use of a paired test was valid since paired control was recorded for each substance. The non-parametric Kruskal-Wallis test was used for multiple comparisons, while the latter were carried out according to Dunn's multiple comparison test. Results are presented on the graphs in the form of an average (mean), and the spread is shown as the standard error of the mean.

3.2. Evaluation of Effects of Test Substances on Behavior of *Danio rerio*

3.2.1. Diazepam

Figure 1A:
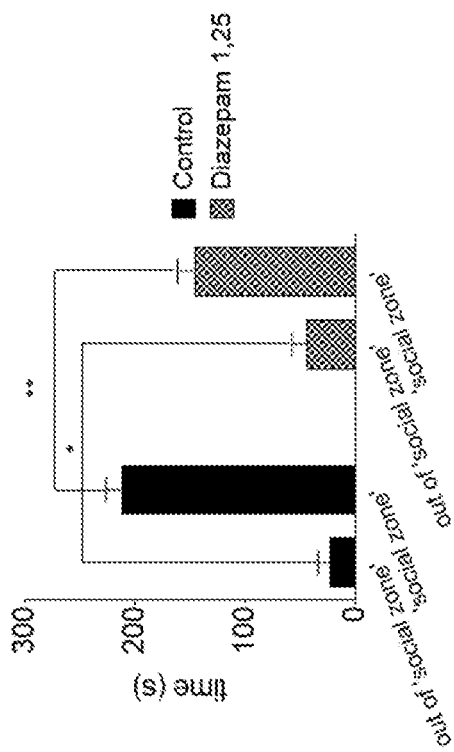
Figure 1B:
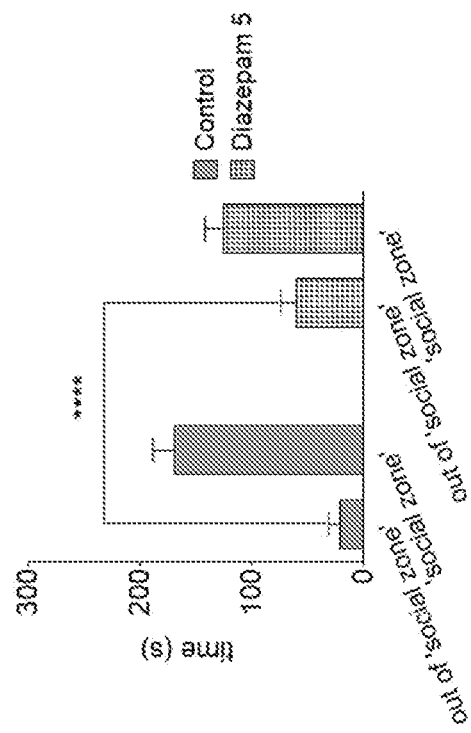

During an experimental session aimed at evaluating effects of diazepam on *Danio rerio* behavior, it was found that diazepam at doses of 1.25 mg/kg, 5 mg/kg, and 10 mg/kg (ip) changes the behavior of treated zebrafish as compared to the control animals. At a dose of 1.25 mg/kg, a statistically significant decrease in the time spent in the compartment near the "shoal" was detected (FIG. 1A), whereas other behavioral parameters did not change. An injection of diazepam at a dose of 5 mg/kg induced much more pronounced behavioral effects: the experimental zebrafish exhibited an increase in the time spent in the compartment near the wall opposite to the "shoal" (FIG. 1B). The time spent in the light chamber also increased dramatically (FIG. 1C). No effects of diazepam on *Danio rerio* behavior in the open field test were revealed.

Diazepam at a dose of 10 mg/kg caused an increase in the number of transitions between the light and dark compartments in the light/dark box (FIG. 5A) and a decrease in the time of the first exit (latent period) to the light chamber of the light/dark box (FIG. 5B). Under the influence of a high dose of diazepam, the zebrafish tended to cover a smaller distance during the open field test (FIG. 5C).

3.2.2. Fluvoxamine

Both dose levels of 5 mg/kg and 10 mg/kg of fluvoxamine produced a change in the behavior of treated zebrafish in the OFT, but not in the "shoal" and light/dark box tests. Fluvoxamine caused a statistically significant increase in the time spent at the surface of the aquarium of the open field (FIGS. 6A and 6B) at both doses. The time spent under light increased at about 6.8 times at a dose of 5 mg/kg and at about 7.2 times at a dose of 10 mg/kg.

3.2.3. Alpha-Casozepine-10 (ACZ-10)

Zebrafish receiving intraperitoneal injection of ACZ-10 demonstrated a statistically significant decrease in the time spent inside the shoaling compartment (FIG. 7A), as well as an approximately twofold increase in the residence time at the water surface in the open field test, as compared to the control group (FIG. 7B).

3.2.4. Beta-Casomorphin-7 (BCM-7)

Figures 8A, 8B:
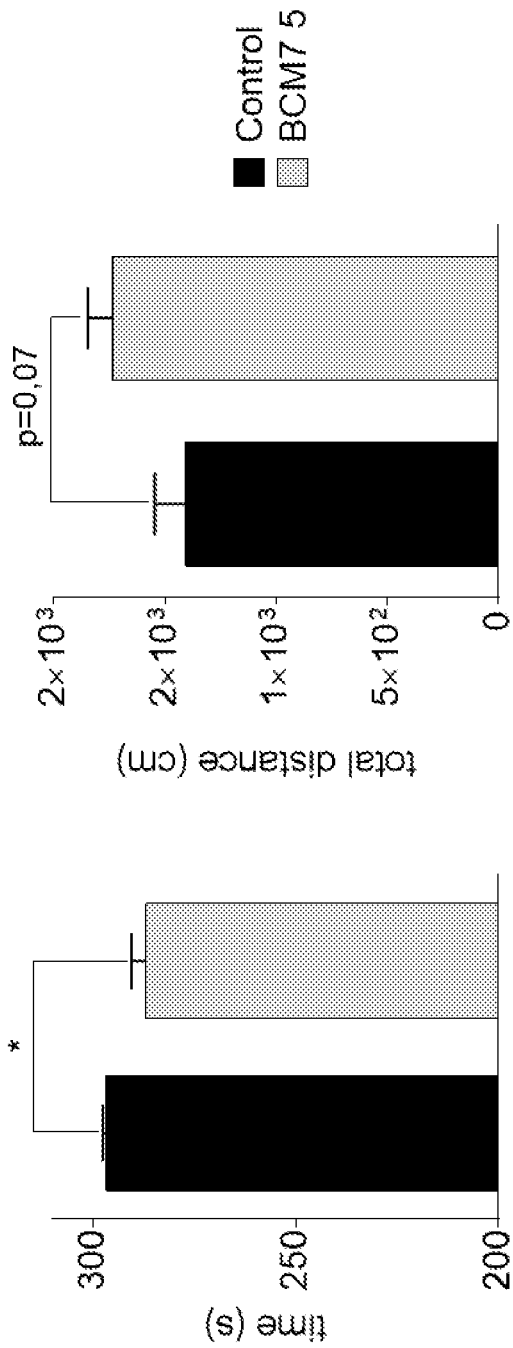
FIGS. 8A and 8B illustrate effect of Beta-Casomorphin-7 (BCM-7) at a dose of 5 mg/kg on the behavioral parameters of *Danio rerio*.

As shown in FIGS. 8A and 8B, zebrafish receiving intraperitoneal injections of beta-casomorphin (BCM-7) at a dose of 5 mg/kg showed a decrease in the time spent next to their specimens in the "shoal" test and a slight increase in run length (the trend to a significant difference in Mann-Whitney U-test p≈0.07) as compared to the control group.

3.2.5. Comparison of the Effects of Test Substances on Behavior of *Danio rerio*

Figure 9:
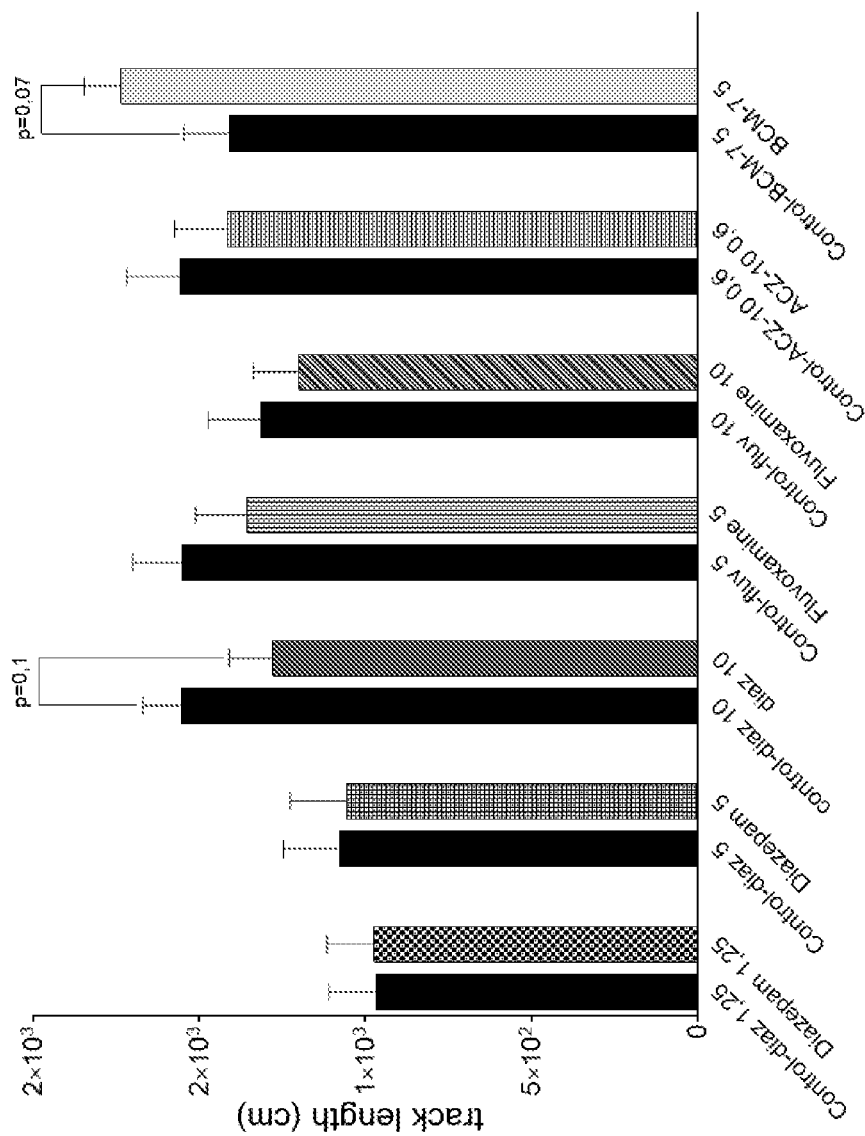
FIG. 9 illustrates an average length covered in the open field test by groups of fish exposed to diazepam at doses of 1.25 mg/kg ("Diaz 1.25"), 5 mg/kg ("Diaz 5"), and 10 mg/kg ("Diaz 10") and in the corresponding control groups ("Control-diaz 1.25," "Control-diaz 5," and "Control-diaz 10"), and by groups of fish exposed to fluvoxamine at doses of 5 mg/kg ("Fluv 5") and 10 mg/kg ("Fluv 10"), and the corresponding control groups ("Control-fluv 5") and ("Control-fluv 10"). In fish administered ACZ-10 (0.6 mg/kg) and BCM-7 (5 mg/kg), the corresponding controls are Control-ACZ10 and Control-BCM-7, respectively. The ordinate represents the length, in centimeters. The data are shown as the mean, and error bars indicate the standard error of the mean. p=0.1 and p=0.07—trends to statistical significance according to the Mann-Whitney U-test.

In the conducted experiments, only BCM-7 was shown to affect the average distance covered by the experimental zebrafish. The average distance covered parameter reflects the overall locomotor activity and, to some extent, the physical well-being of the tested zebrafish. But diazepam, fluvoxamine, and ACZ-10 did not demonstrate any significant effects on the average distance covered by the experimental zebrafish. No changes were observed in comparison with the corresponding control group, or between the successive control groups, as shown in FIG. 9.

The experiments described herein illustrate that diazepam, which is a typical representative of the benzodiazepine anxiolytic drugs, at a dose of 1.25 mg/kg reduces the shoaling reflex, and at a dose of 5 mg/kg reduces both the shoaling reflex and the severity of scototaxis in the light/ dark box. This indicates the reduction in the level of anxiety of the fish treated with diazepam in the described experimental settings. Diazepam at a dose of 10 mg/kg, in addition to anxiolytic effect in the light/dark box, caused a slight sedative effect, which was expressed in a tendency to decline in motor activity in the open field test. These results are consistent with results obtained at other studies which described similar effects of benzodiazepine anxiolytics (Gebauer et al. (2011) Effects of anxiolytics in zebrafish: similarities and differences between benzodiazepines, buspirone and ethanol. Pharmacol. Biochem. Behav. 99:480-486; Bencan (2009). Buspirone, chlordiazepoxide and diazepam effects in a zebrafish model of anxiety. Pharmacol. Biochem. Behav., 94(1): 75-80; Giacomini et al., (2016) Fluoxetine and diazepam acutely modulate stress induced behavior. Behav. Brain Res. 296).

Furthermore, in the described experiments, anxiolytic and positive neurotropic effects of the ACZ-10 and BCM-7 peptides on zebrafish behavior were observed after a single intraperitoneal injection. The inventors have discovered changes in zebrafish behavior, which indicate that neuropeptides are capable of producing a neurotropic effect in the spectrum of anxiety-depressive disorders. Notably, the efficacy profile of ACZ-10, which is more known as an anxiolytic, matched more closely the profile of fluvoxamine rather than diazepam. At the same time, BCM-7 showed only moderate anxiolytic efficacy. These results indicate that Danio rerio is a suitable model for screening of neurotropic effects of new drugs within the spectrum of anxiety-depressive disorders, where the new drugs are not limited to small molecules, but can also include peptides (e.g., oligopeptides).

3.2.6. The FQSE (SEQ ID NO:10) Tetrapeptide

Figure 10A:
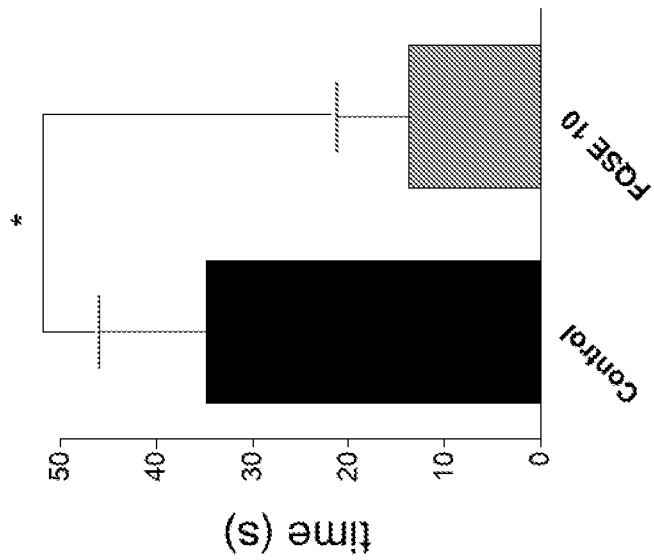
FIGS. 10A and 10B illustrate influence of neuromodulatory peptide FQSE (SEQ ID NO:10) on *Danio rerio* behavior in the open field test.
Figure 10B:
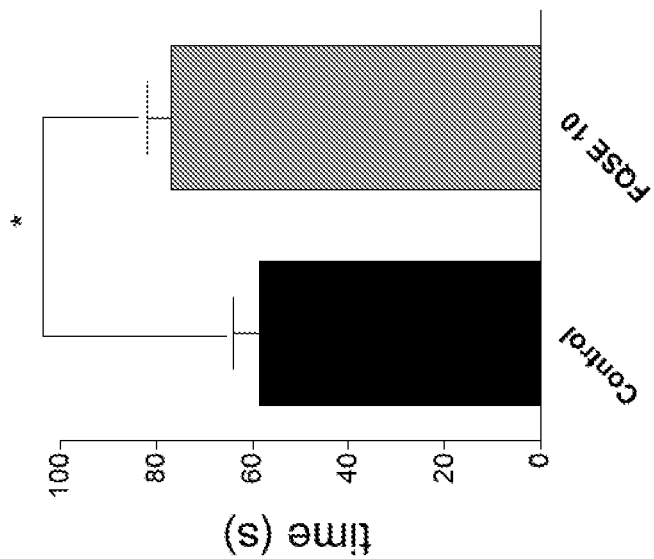

The FQSE (SEQ ID NO:10) peptide was studied at doses of 1 mg/kg and 10 mg/kg. In the described experiments, the most prominent changes in zebrafish behavior were observed at a dose of 10 mg/kg. Thus, as shown in FIG. 10A, in the open field test, zebrafish demonstrated a statistically significant increase in the time spent in the upper part of the aquarium (iE. near the surface and in the central part, as opposed to being at the bottom). The same test has shown a noticeable decrease in the latent period of leaving the bottom part in the test group of zebrafish, as shown in FIG. 10B. This result shows a decrease in the anxiety of the zebrafish exposed to the influence of FQSE (SEQ ID NO:10) peptide at a dose of 10 mg/kg. As was observed in the experiments with fluvoxamine described herein, results of administering the open field test to zebrafish are a good indicator of fluvoxamine activity. Thus, the effects of FQSE (SEQ ID NO:10) observed in the open field test can be interpreted as indicative of an antidepressant effect of FQSE (SEQ ID NO:10).

Figure 11A:
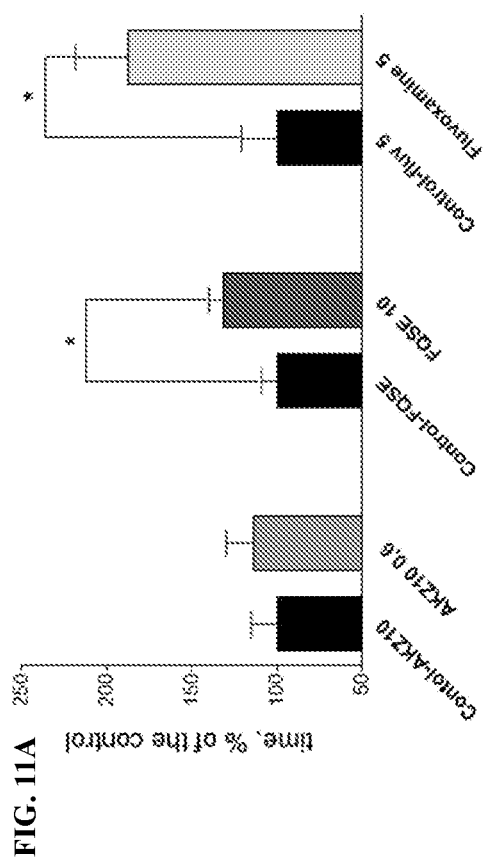
FIGS. 11A and 11B illustrate comparison of the effects of ACZ10, FQSE (SEQ ID NO:10) and fluvoxamine on *Danio rerio* behavior in the open field test.
Figure 11B:
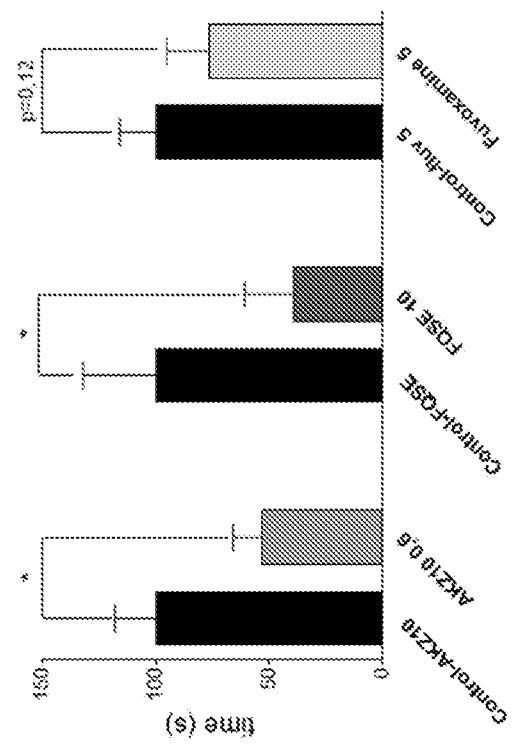

As shown in FIGS. 11A and 11B, when compared with other tested substances (ACZ-10 and fluvoxamine), FQSE (SEQ ID NO:10) at a dose of 10 mg/kg was shown to be more efficient as compared to ACZ-10 (0.6 mg/kg), which did not affect the time spent in the upper water column, although it decreased significantly the amount of LP while leaving the bottom of the test aquarium. The efficiency of FQSE (SEQ ID NO:10) as compared with fluvoxamine (5 mg/kg) is slightly lower: along with the same decrease in the LP of leaving the bottom (FIG. 11 B), FQSE (SEQ ID NO:10) increases the time spent in the upper part by 35%, while fluvoxamine increases it by more than 80%. Nevertheless, marked behavioral changes were observed under the influence of FQSE (SEQ ID NO:10), similar to those caused by the injection of fluvoxamine.

Figure 12B:
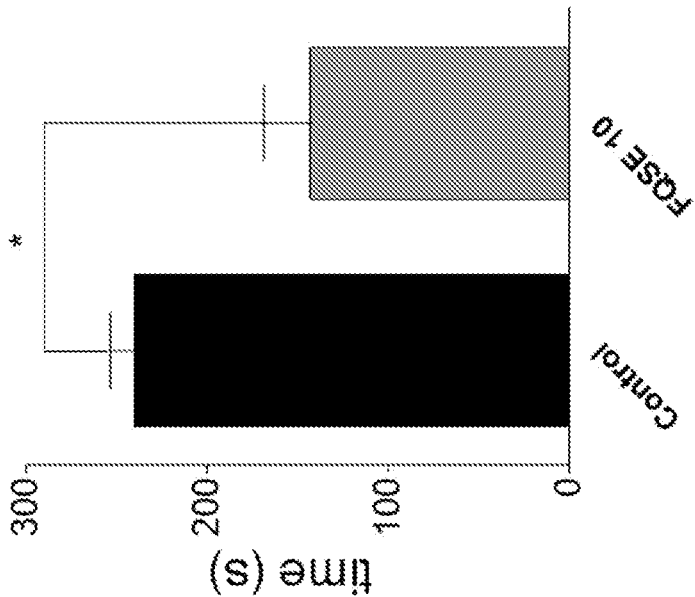
FIGS. 12A and 12B illustrate influence of FQSE (SEQ ID NO:10) on *Danio rerio* behavior in the light/dark box (LDB) test.
Figure 12A:
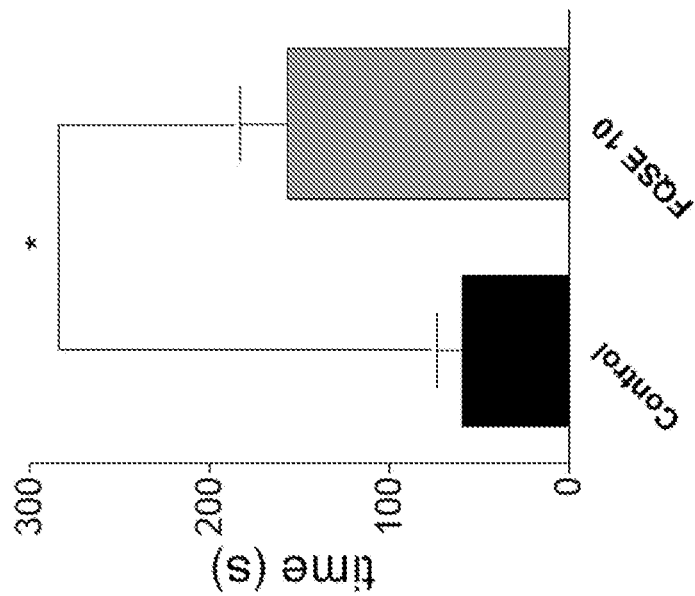
Figure 13B:
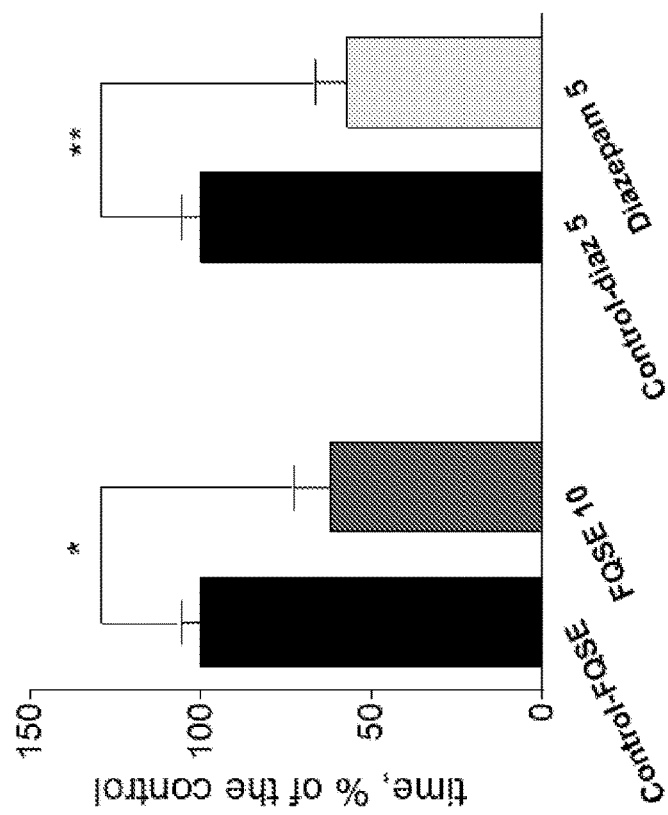
FIGS. 13A and 13B illustrate comparison of the effects of the test substances on *Danio rerio* behavior in the dark-light box test.
Figure 13A:
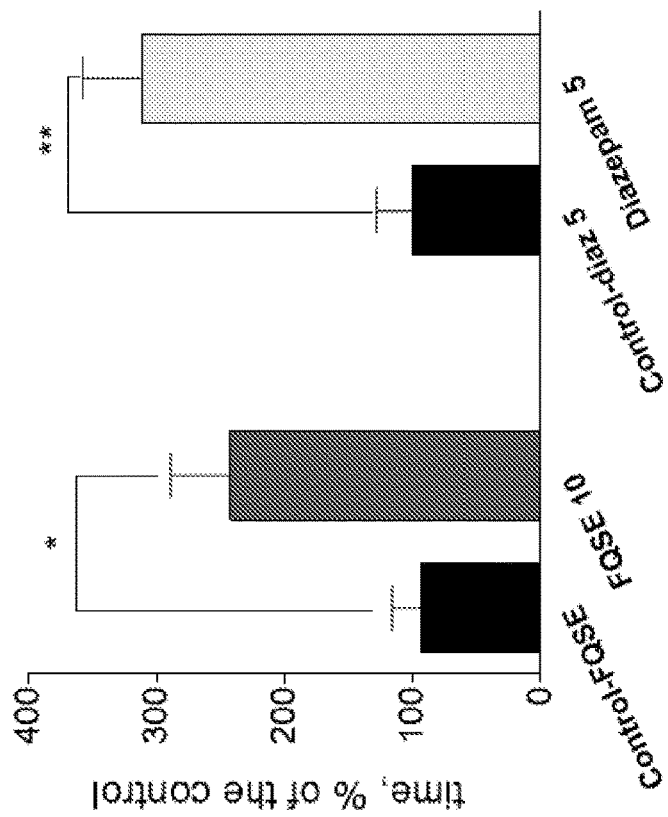

In the course of the light/dark box (LDB) test, the fish injected with a high dose of FQSE (SEQ ID NO:10) peptide demonstrated a statistically significant increase in time spent in the light compartment and a decrease in time spent in the dark one (FIGS. 12A and 12B). A similar effect was observed in benzodiazepine anxiolytic diazepam at a dose of 5 mg/kg (FIGS. 13A and 13B). A relative increase in the time spent in the light compartment after injecting FQSE (SEQ ID NO:10) amounted to approximately 140% compared with the control group, while injecting diazepam (5 mg/kg) led to approximately 210% increase. The decrease in the time spent in the dark compartment in both groups amounted to approximately 40% relatively to the control group.

A decrease in scototaxis (a pursuit of darkened spaces) was interpreted as a decrease in anxiety, as this parameter was significantly influenced by a typical anxiolytic drug diazepam and was not affected at all by fluvoxamine. Thus, it appears that FQSE (SEQ ID NO:10) at a dose of 10 mg/kg has a visible anxiolytic effect.

Figure 14B:
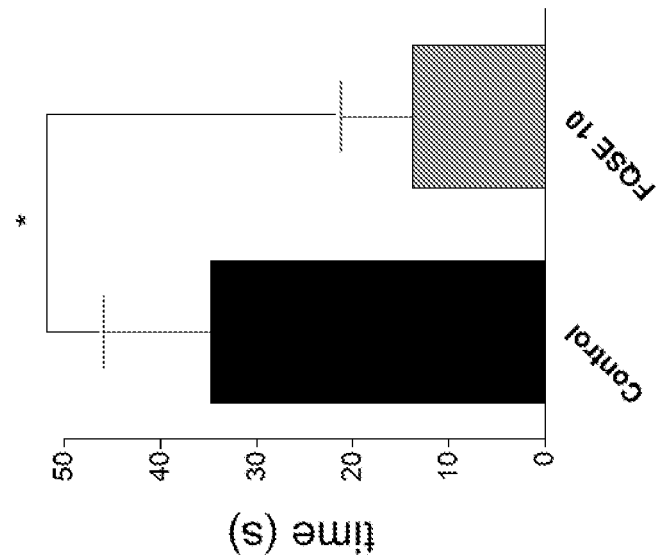
FIGS. 14A and 14B illustrate influence of FQSE (SEQ ID NO:10) on *Danio rerio* behavior in the shoaling test.
Figure 14A:
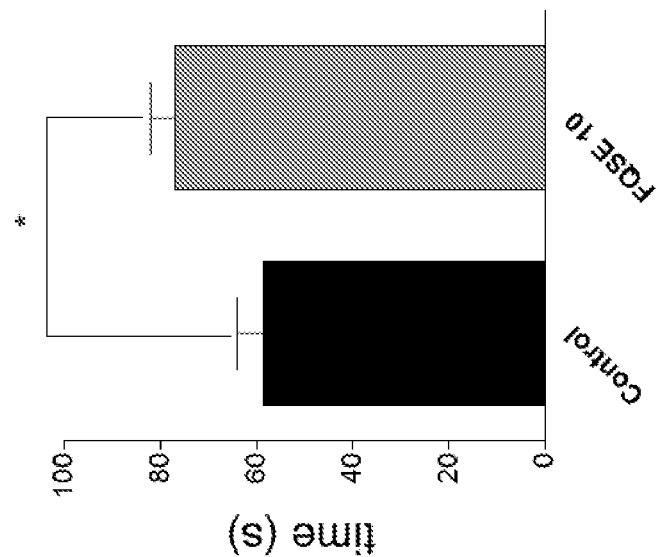

FIGS. 14A and 14B illustrate the influence of FQSE (SEQ ID NO:10) on Danio rerio behavior in the shoaling test. The shoaling behavioral test has demonstrated that under the influence of FQSE (SEQ ID NO:10) (10 mg/kg) the latent period of leaving the sector with the "shoal" (FIG. 14B) decreases, which is accompanied by a visible tendency to prolong the time spent outside the shoaling compartment (p=0.054 according to the Mann-Whitney U-test, FIG. 14A).

Figure 15A:
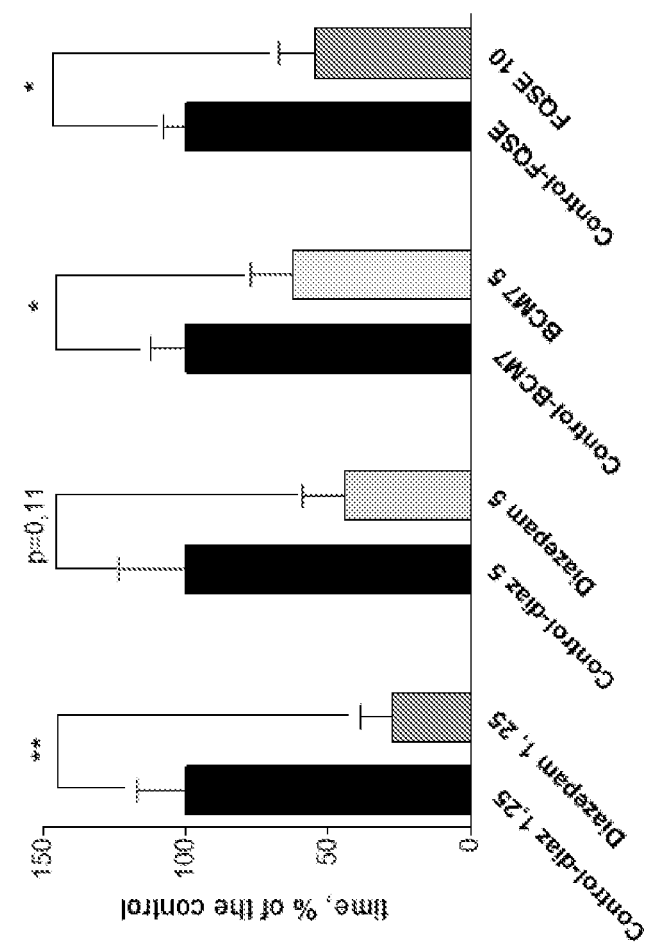
FIGS. 15A and 15B illustrate comparison of the effects of the test substances on *Danio rerio* behavior in the shoaling test.
Figure 15B:
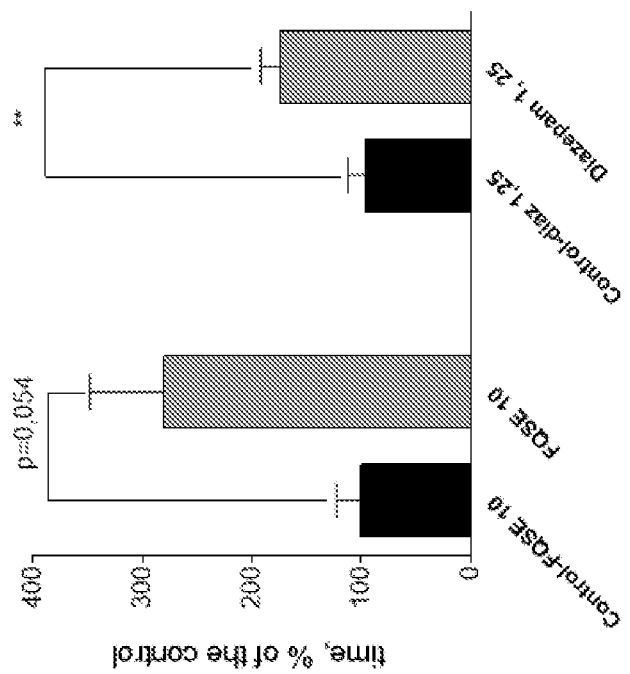
Figure 16B:
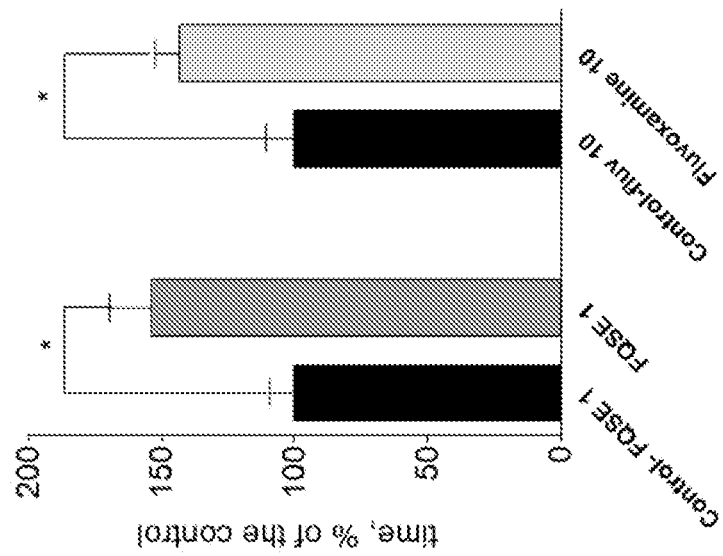
FIGS. 16A and 16B illustrate comparison of the effects of the test substances on *Danio rerio* behavior in the open field test.
Figure 16A:
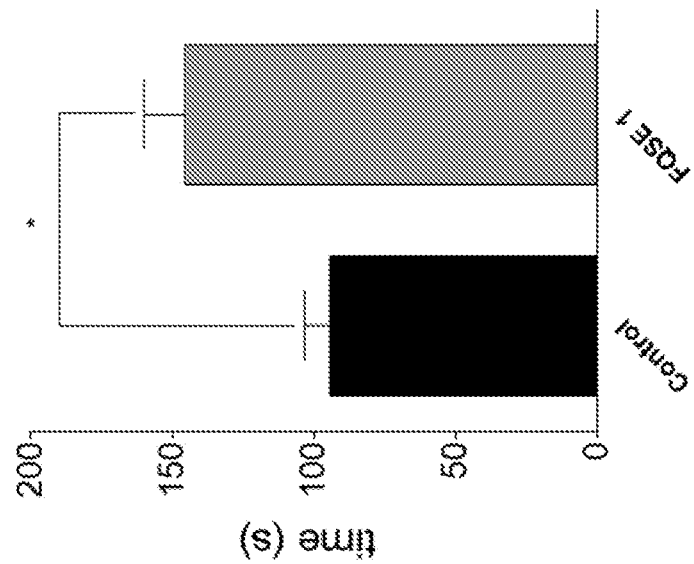

FIGS. 15A and 15B illustrate comparison of the effects of diazepam, BCM-7, and the FQSE (SEQ ID NO:10) peptide on Danio rerio behavior in the shoaling test. A decrease in the latent period of leaving the "shoal" caused by FQSE (SEQ ID NO:10) at a dose of 10 mg/kg is weaker than that caused by diazepam at doses of 1.25 mg/kg and 5 mg/kg and is approximately on the same level as in BCM-7, which also did not demonstrate a statistically significant effect on the time outside the shoaling compartment (FIG. 15B). As it was noted before, increase in the time spent outside the "shoal" caused by the FQSE (SEQ ID NO:10) peptide can only be recognized as a tendency to increase, whereas diazepam (1.25 mg/kg) causes a statistically significant change (FIG. 15A). Shoaling reflex is usually interpreted as protective mechanism, which indicates an increased anxiety in the presence of natural predators, exposure to anxiogenic compounds or a new environment. Diazepam has a steady anxiolytic effect in this test, as it decreases the latent period of leaving the "shoal" (a fish quickly adapts and easily swims far away from its conspecifics) and increases the time spent outside the shoaling compartment.

Figure 17B:
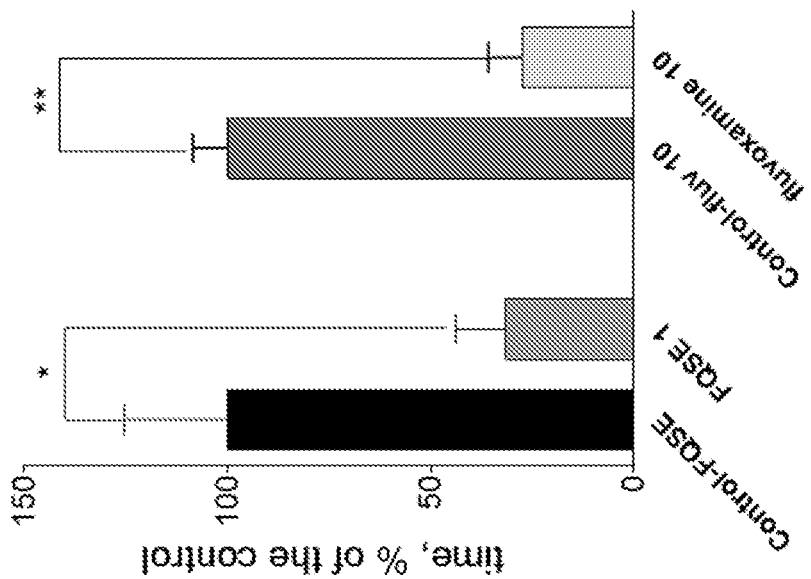
FIGS. 17A and 17B illustrate comparison of the effects of the test substances on *Danio rerio* behavior in the open field test.
Figure 17A:
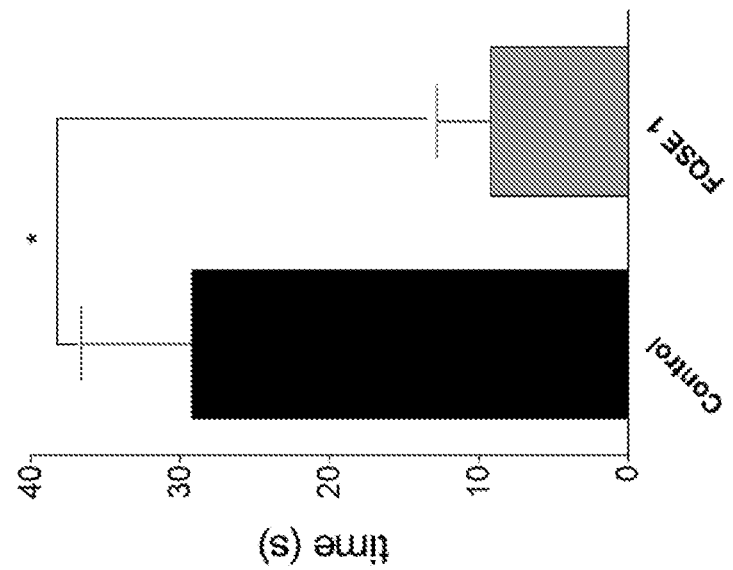

FIGS. 16A, 16B, 17A, and 17B illustrate the comparison of the effects of the FQSE (SEQ ID NO:10) peptide and fluvoxamine on Danio rerio behavior in the open field test. It is observed that, at a dose of 1 mg/kg, the FQSE (SEQ ID NO:10) peptide was effective in the open field test, statistically increasing both the time spent close to the surface of water (FIG. 16A) and the latent period of coming up to the surface (FIG. 17A). Moreover, the effects of FQSE (SEQ ID NO:10) at a low dose can be compared to those of fluvoxamine at a dose of 10 mg/kg (FIGS. 16B and 17B), iE. at a dose of 1 mg/kg FQSE (SEQ ID NO:10) demonstrates a steady antidepressant effect.

Figure 18:
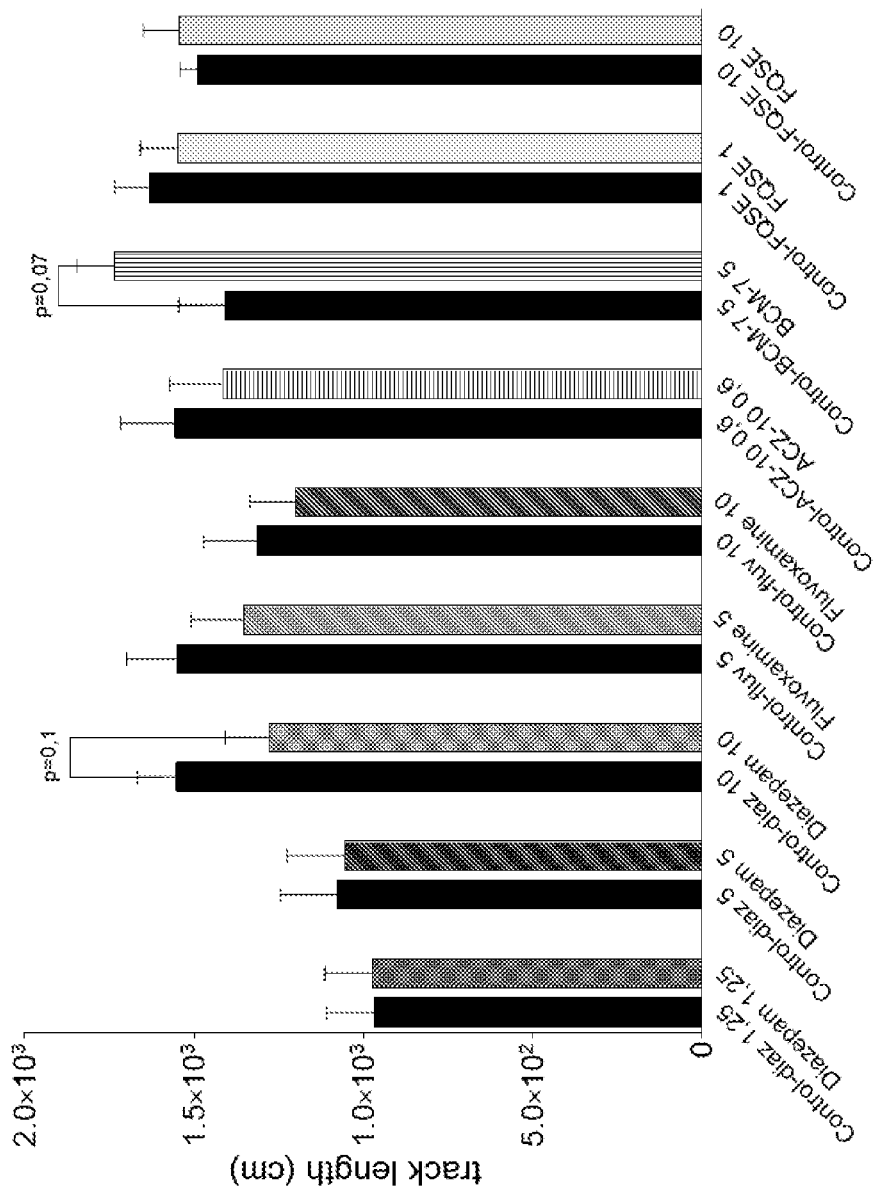
FIG. 18 illustrates an average track length in the open field test in the groups of fish administered diazepam at doses of 1.25 mg/kg ("Diazepam 1,25"), 5 mg/kg ("Diazepam 5") and 10 mg/kg ("Diazepam 10") and in the corresponding control groups ("Contr-diaz 1,25", "Contr-diaz 5," and "Contr-diaz 10"), as well as in the groups of fish treated with fluvoxamine at a dose of 5 mg/kg ("Fluvoxamine 5") and 10 mg/kg ("Fluvoxamine 10") and in corresponding control groups ("Control-fluv 5" and "Control-fluv 10"). For the groups of fish administered 0.6 mg/kg of ACZ-10 ("ACZ-10 0.6"), the control groups are named correspondingly "Control-ACZ, −10 0.6"; BCM-7 5 mg/kg—correspondingly "BCM-7 5" and "Control-BCM-7 5"; tetrapeptide FQSE (SEQ ID NO:10) at doses of 1 mg/kg and 10 mg/kg ("FQSE 1" and "FQSE 10")—"Control-FQSE 1" and "Control-FQSE 10." The ordinate represents the length in centimeters. The data are shown as the mean, and error bars indicate the standard error of the mean.
Figure 19B:
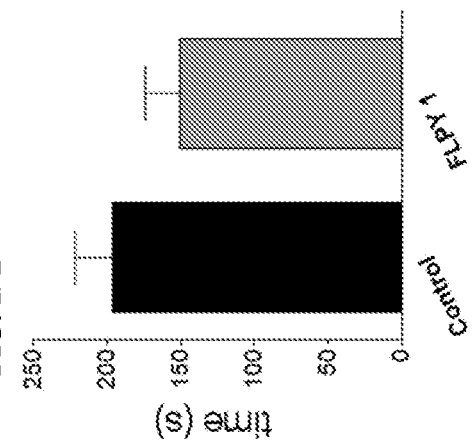
FIGS. 19A, 19B, and 19C illustrate behavioral parameters of *Danio rerio* after injecting FLPY (SEQ ID NO:36) at a dose of 1 mg/kg.
Figure 19A:
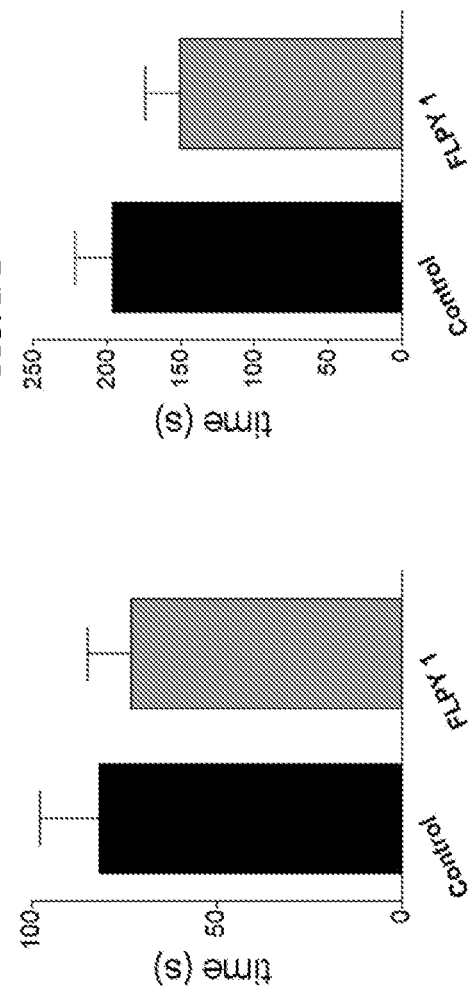
Figure 19C:
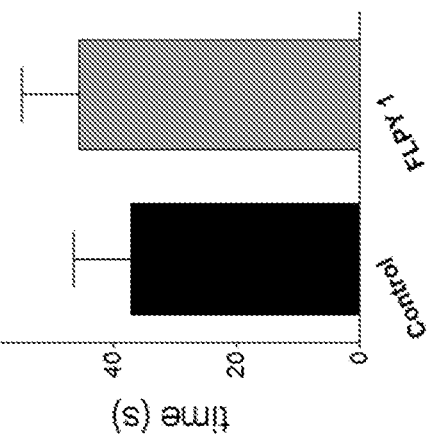
Figure 20B:
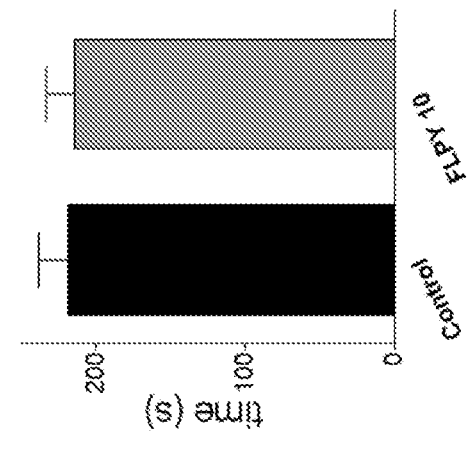
FIGS. 20A, 20B, and 20C illustrate behavioral parameters of *Danio rerio* after injecting FLPY (SEQ ID NO:36) at a dose of 10 mg/kg.
Figure 20A:
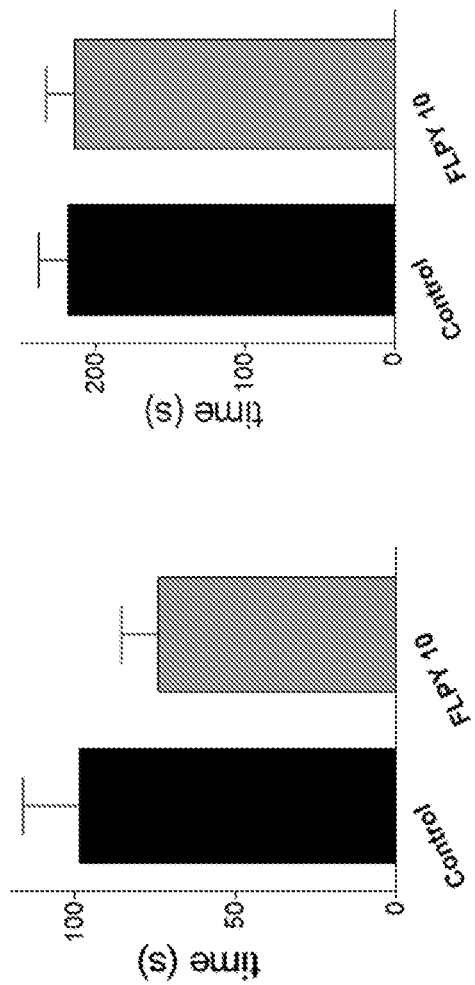
Figure 20C:
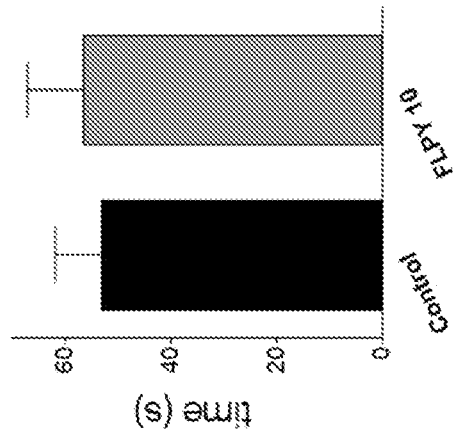

FIG. 18 illustrates an average track length in the open field test in the groups of zebrafish administered the test substances as follows: diazepam at doses of 1.25 mg/kg ("Diaz 1.25"), 5 mg/kg ("Diazepam 5") and 10 mg/kg ("Diazepam 10") and corresponding control groups ("Control-diaz 1.25," "Control-diaz 5," "Control-diaz 10");

fluvoxamine at doses of 5 mg/kg ("Fluvoxamine 5") and 10 mg/kg ("Fluvoxamine 10") and corresponding control groups ("Control-fluv 5" and "Control-fluv 10"); ACZ-10 at a dose of 0.6 mg/kg ("ACZ-10 0.6") and a corresponding control group ("Control-ACZ-10 0.6"); 5 mg/kg of BCM-7 ("BCM-7 5") and a corresponding control group ("Control-BCM-7 5"); tetrapeptide FQSE (SEQ ID NO:10) at doses of 1 mg/kg and 10 mg/kg ("FQSE 1" and "FQSE 10," respectively) and corresponding control groups ("Control-FQSE 1" and "Control-FQSE 10"). FIG. 18 illustrates that, at a dose 1 mg/kg, as well as at a dose of 10 mg/kg, FQSE (SEQ ID NO:10) had no significant influence on the locomotor activity of Danio rerio, which manifests itself in the absence of changes in the length of the track covered in the open field test.

These experiments illustrate that the FQSE (SEQ ID NO:10) peptide has a complex anxiolytic and antidepressant effect on the behavior of Danio rerio. The anxiolytic effect of FQSE (SEQ ID NO:10) was demonstrated in the light/dark box test. The increase in the time spent in the light compartment of the light/dark box is a result of the decrease in anxiety, which is further confirmed by the decrease in the shoaling reflex. The antidepressant effect of FQSE (SEQ ID NO:10) in the open field test was also observed. FQSE (SEQ ID NO:10) at a dose of 1 mg/kg demonstrates a steady antidepressant effect in the open field test, without changing the zebrafish behavior in the other tests.

3.2.7. The FLPY (SEQ ID NO:36) Tetrapeptide

In the described experiments, the FLPY (SEQ ID NO:36) tetrapeptide was used as a negative control. The effects of the FLPY (SEQ ID NO:36) peptide on behavior of Danio rerio were studied at two doses of FLPY (SEQ ID NO:36)—1 mg/kg and 10 mg/kg. As shown in FIGS. 19A, 19B, 19C, 20A, 20B, and 20C, neither of the doses of FLPY (SEQ ID NO:36), induced statistically significant changes of the basic behavioral parameters of the test zebrafish. This demonstrated a lack of an antidepressant or anxiolytic effect for the FLPY (SEQ ID NO:36) peptide.

3.2.8. The DKTE (SEQ ID NO:26) Tetrapeptide

Figure 21B:
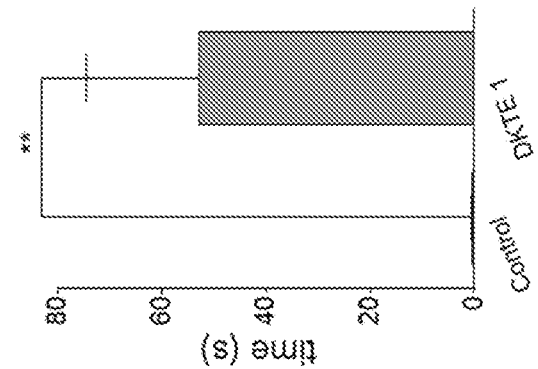
FIGS. 21A, 21B, and 21C illustrate behavioral parameters of *Danio rerio* in the shoaling test after injecting DKTE (SEQ ID NO:26) at a dose of 1 mg/kg.
Figure 21A:
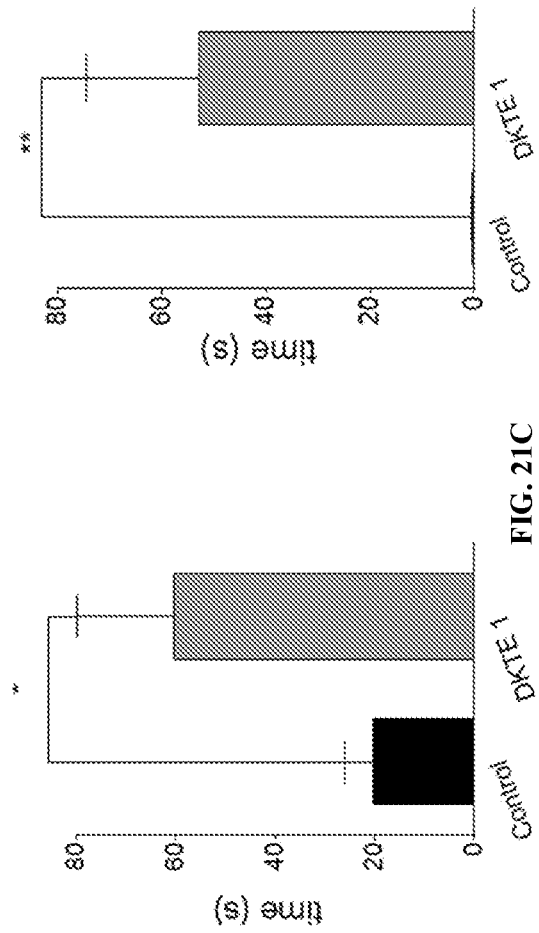
Figure 21C:
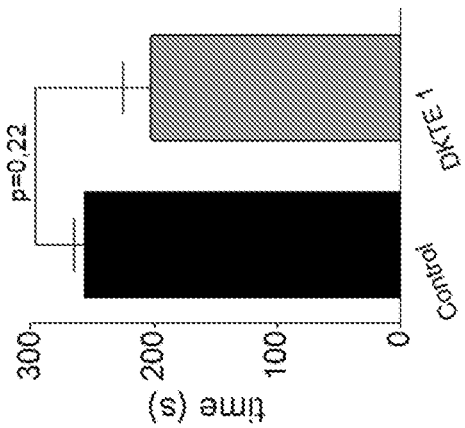

The effects of the DKTE (SEQ ID NO:26) peptide on behavior of Danio rerio were studied at two doses of DKTE (SEQ ID NO:26)—1 mg/kg and 10 mg/kg. FIGS. 21A, 21B, and 21C illustrate parameters of behavioral of Danio rerio in the shoaling test. Abdominal injection of DKTE (SEQ ID NO:26) to zebrafish at a dose of 1 mg/kg caused a decrease in the shoaling reflex, which was expressed in the statistically significant increase in the time spent by the zebrafish of the test group close to the wall opposite the shoaling compartment (FIG. 21A), as well as in the latent period of visiting the "shoal" (FIG. 21B). A decrease in the time spent in the shoaling compartment in this group is at the level of tendency (FIG. 21C).

Figure 22:
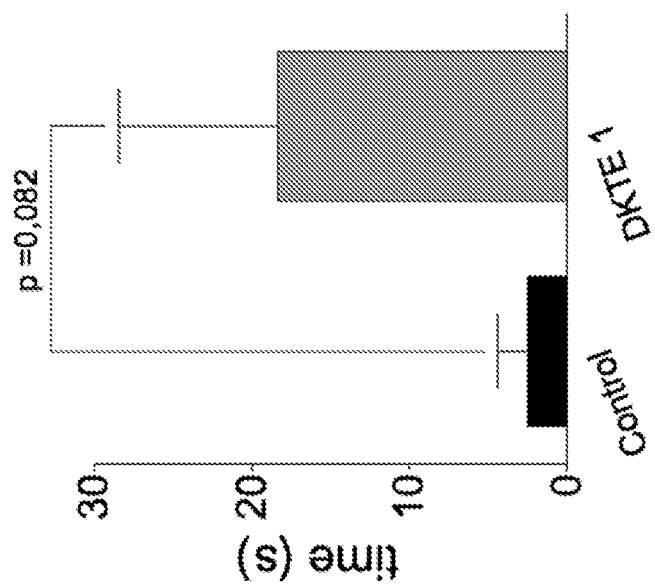
FIG. 22 illustrates measurements of a latent period of visiting the bottom in the open field test, for a control group ("Control") and a group administered 1 mg/kg of DKTE (SEQ ID NO:26) ("DKTE 1"). The ordinate shows time in seconds.

FIG. 22 illustrates a latent period of visiting the bottom of the aquarium in the open field test. As shown in FIG. 22, the open field test has shown that the DKTE (SEQ ID NO:26) peptide at a dose of 1 mg/kg causes an increase in the latent period of visiting the bottom of the aquarium for the test zebrafish.

Figure 23:
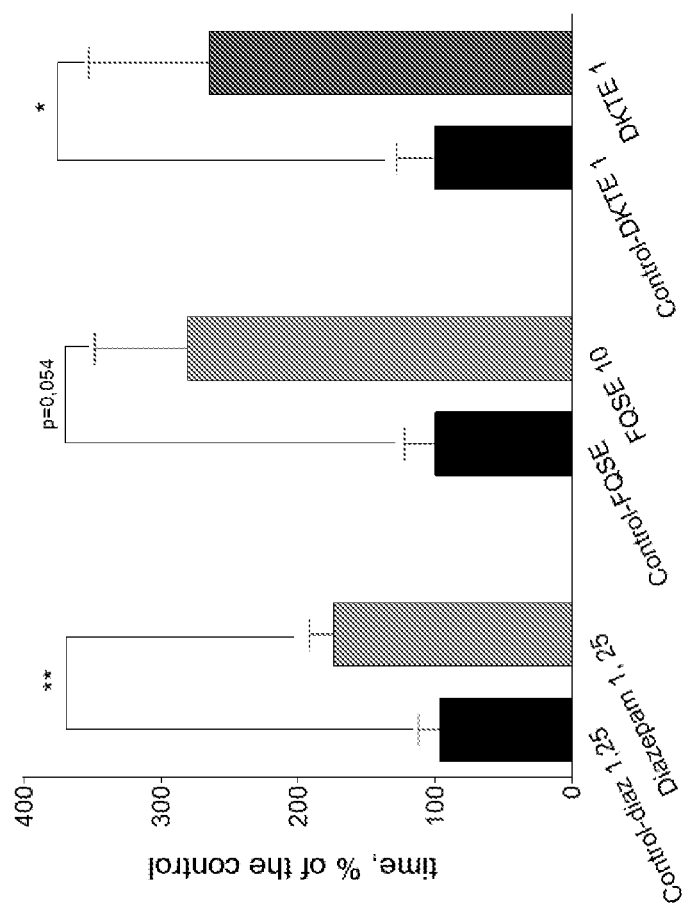
FIG. 23 illustrates comparison of the effects of the test substances on the behavior of *Danio rerio* in the shoaling test. Time spent outside the shoaling department is shown in % relatively to the control group. The following groups are illustrated: 1.25 mg/kg Diazepam ("Diazepam 1,25"), 1.25 mg/kg control diazepam ("Control-diaz 1,25"), 10 mg/kg FQSE (SEQ ID NO:10) ("FQSE 10"), 10 mg/kg control FQSE (SEQ ID NO:10) ("Control-FQSE"), 1 mg/kg DKTE (SEQ ID NO:26) ("DKTE 1"), and 1 mg/kg control DKTE (SEQ ID NO:26) ("Control-DKTE 1"). The ordinate shows time change, in % relatively to the control group. The data are shown as the mean, error bars indicate the standard error of the mean, and "*" indicates $p<0.05$, "**" indicates $p<0.01$ according to the Mann-Whitney test.

FIG. 23 illustrates comparison of effects of diazepam, the FQSE (SEQ ID NO:10) peptide and the DKTE (SEQ ID NO:26) peptide on behavior of Danio rerio in the shoaling test. When comparing the effects of the DKTE (SEQ ID NO:26) peptide at a dose of 1 mg/kg on the shoaling behavior with the effects of diazepam and the FQSE (SEQ ID NO:10) peptide, it was observed that the effects of DKTE (SEQ ID NO:26) at this dose were comparable to those the effects of diazepam (1.25 mg/kg), as shown in FIG. 23. At the same time, as also shown in FIG. 23, the influence of DKTE (SEQ ID NO:26) at 1 mg/kg on the shoaling activity was higher than that of FQSE (SEQ ID NO:10) at a dose of 10 mg/kg, which statistically only showed a tendency to increase the activity. Furthermore, in view of no observed efficacy of the DKTE (SEQ ID NO:26) peptide in the light/dark box test and the weak effect of DKTE (SEQ ID NO:26) peptide in the open field test, it can be concluded that DKTE (SEQ ID NO:26) at a dose of 1 mg/kg overall has a weaker anxiolytic effect, when compared to FQSE (SEQ ID NO:10).

Figure 24A:
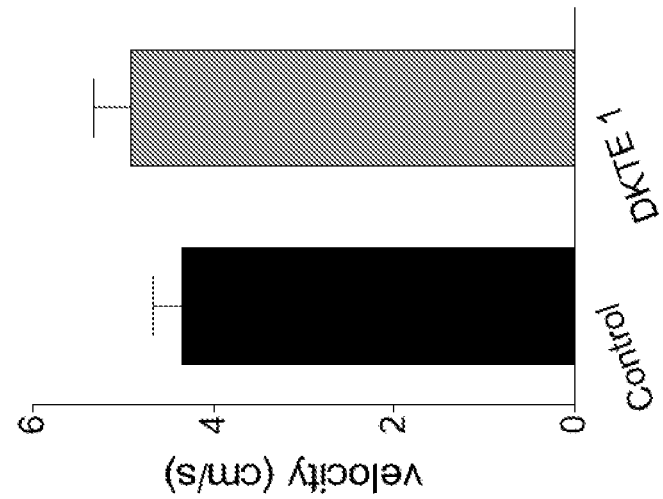
FIGS. 24A and 24B illustrate parameters of locomotor activity of DKTE (SEQ ID NO:26) at a dose of 1 mg/kg in the open field test.
Figure 24B:
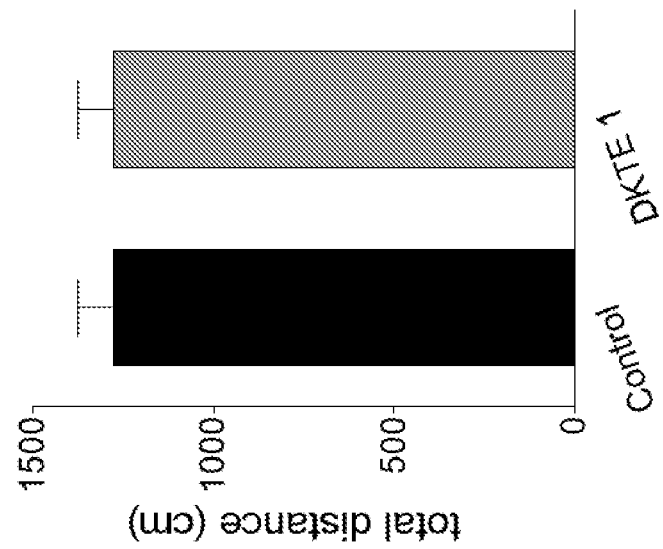

FIGS. 24A and 24B illustrate parameters of locomotor activity (a length of the track and a mean velocity) of DKTE (SEQ ID NO:26) at a dose of 1 mg/kg in the open field test. It is shown that DKTE (SEQ ID NO:26) at a dose of 1 mg/kg did not affect these parameters of motor activity.

Figure 25B:
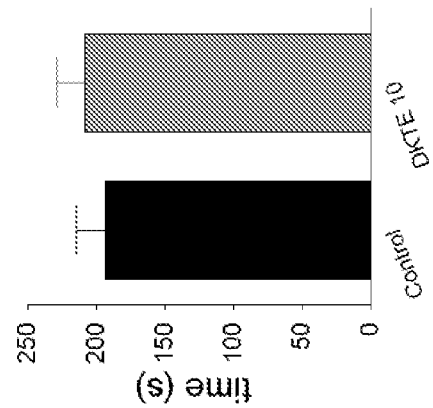
FIGS. 25A, 25B, and 25C illustrate behavioral parameters of *Danio rerio* after injecting DKTE (SEQ ID NO:26) at a dose of 10 mg/kg.
Figure 25C:
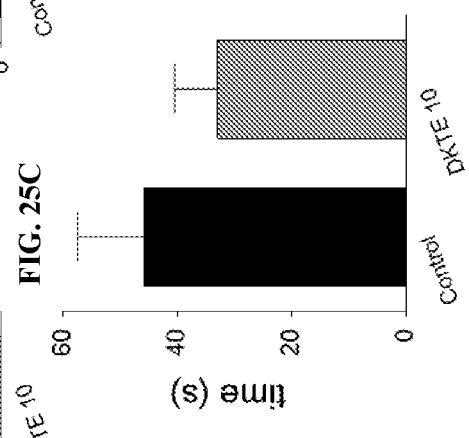
Figure 25A:
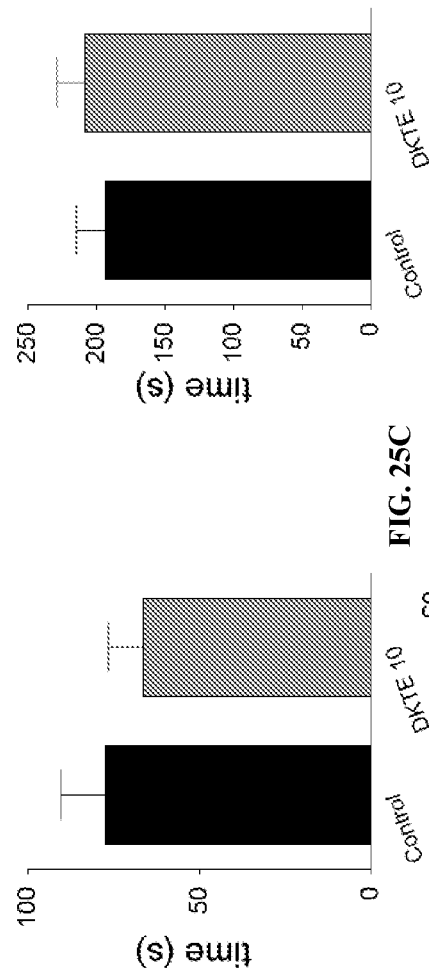

FIGS. 25A, 25B, and 25C illustrate parameters of Danio rerio behavior after injecting Danio rerio with DKTE (SEQ ID NO:26) at a dose of 10 mg/kg. In particular, FIG. 25A shows a time spent close to the surface (in the open field), FIG. 25B shows a time spent in the light compartment of the light/dark box, and FIG. 25C shows a time spent outside the shoaling compartment as measured in the shoaling test. As shown, the intraperitoneal injection of DKTE (SEQ ID NO:26) at a dose of 10 mg/kg did not cause any statistically significant changes in the behavioral parameters of Danio rerio in the open field, light/dark box and shoaling tests. This may by an indication that the dosage of 10 mg/kg is beyond an effective concentration range for the DKTE (SEQ ID NO:26) peptide.

As shown in these experiments, the DKTE (SEQ ID NO:26) peptide at a dose of 1 mg/kg demonstrates anxiolytic activity in the shoaling test. A decrease in the time spent outside the shoaling compartment under the influence of DKTE (SEQ ID NO:26) in this dosage can be compared to the decrease in the same parameter caused by diazepam at a dose 1.25 mg/kg. In the open field test DKTE (SEQ ID NO:26) (1 mg/kg) has caused a slight antidepressant effect which manifests itself in an increasing latent period of visiting the bottom. At a dose of 10 mg/kg. DKTE (SEQ ID NO:26) has not shown any behavioral effects in any of the tests.

3.2.9. The WDQV (SEQ ID NO:14) Tetrapeptide

Figure 26B:
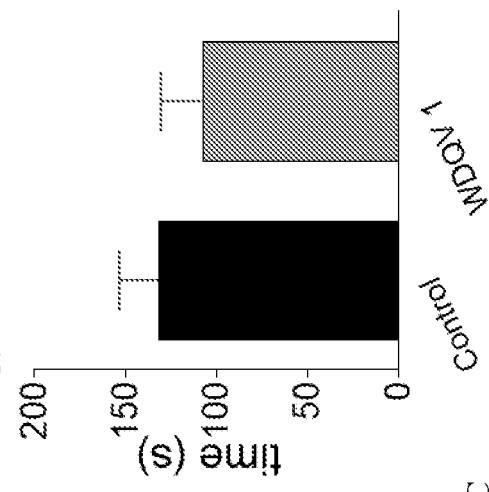
FIGS. 26A, 26B, and 26C illustrate behavioral parameters of *Danio rerio* after injecting WDQV (SEQ ID NO:14) at a dose of 1 mg/kg.
Figure 26A:
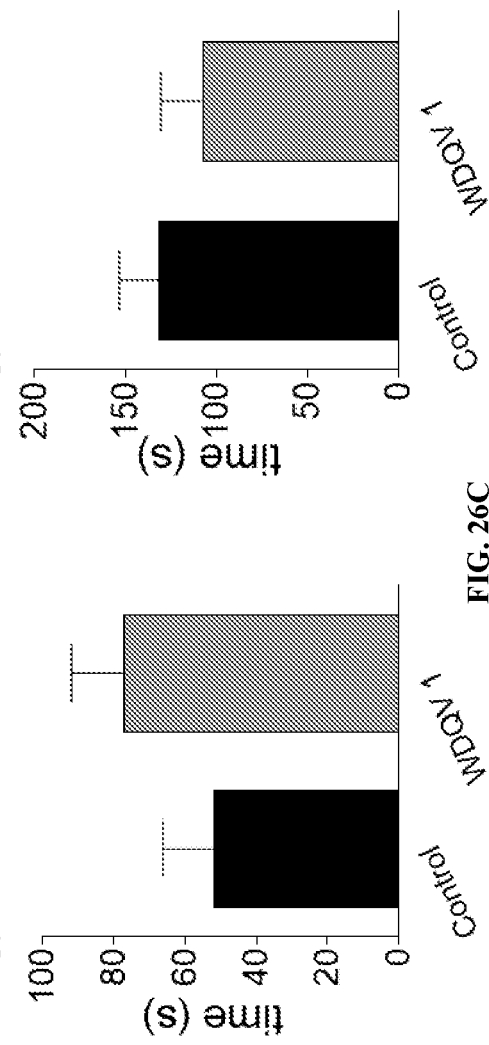
Figure 26C:
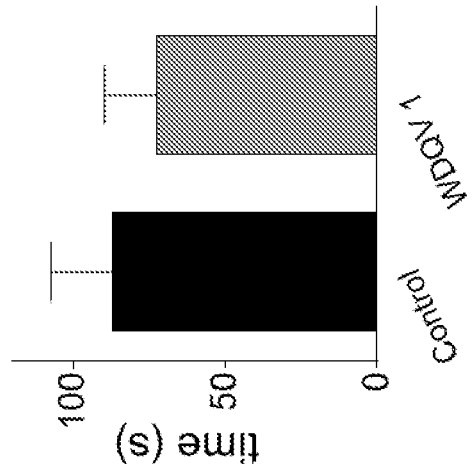

The effects of the WDQV (SEQ ID NO:14) peptide on behavior of Danio rerio were studied at two doses of WDQV—1 mg/kg and 10 mg/kg. FIGS. 26A, 26B, and 26C illustrate parameters of behavior of Danio rerio after injecting WDQV (SEQ ID NO:14) at a dose of 1 mg/kg. As shown in these figures, at the dose of 1 mg/kg, no significant effects of the WDQV (SEQ ID NO:14) peptide on the fish behavior were observed in all three behavioral tests—the open field, light/dark box, and shoaling tests.

Figure 27B:
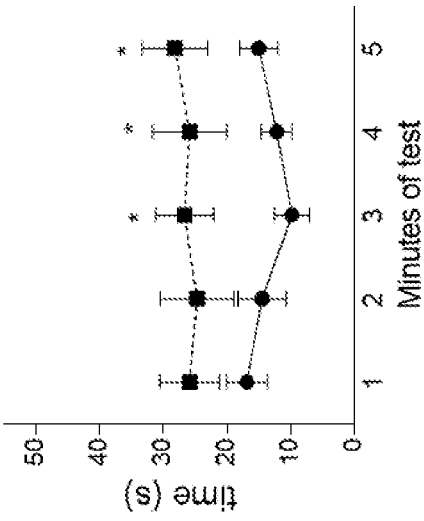
FIGS. 27A, 27B, 27C, and 27D illustrate behavioral parameters of *Danio rerio* after injecting WDQV (SEQ ID NO:14) at a dose of 10 mg/kg in the light/dark box test.
Figure 27D:
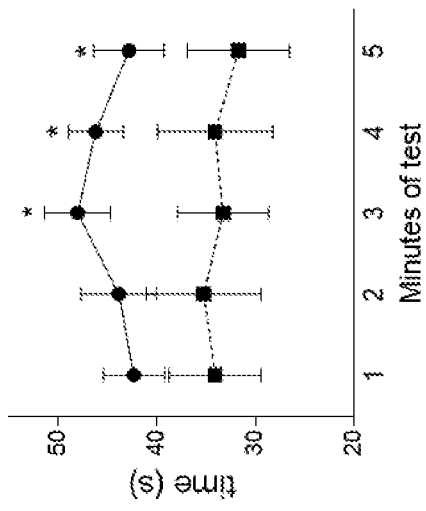
Figure 27A:
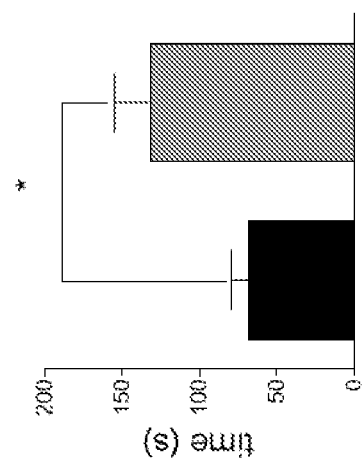
Figure 27C:
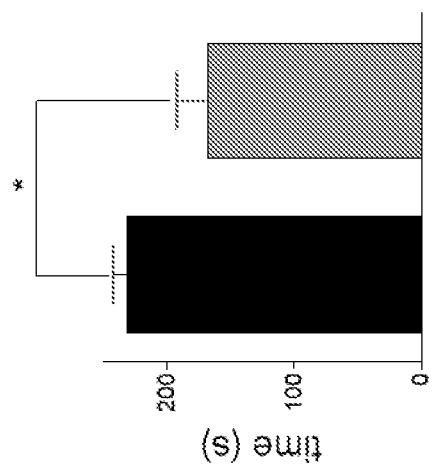

FIGS. 27A, 27B, 27C, and 27D illustrate behavioral parameters of Danio rerio after injecting WDQV (SEQ ID NO:14) at a dose of 10 mg/kg in the light/dark box test. As shown in FIGS. 27A and 27C, at the dose of 10 mg/kg, the peptide WDQV (SEQ ID NO:14) only affected fish behavior in the light/dark box test. The fish from the test group demonstrated an increase in time spent in the light compartment of the light/dark box, both in total during all 5 minutes of the test, and from third till fifth minute of the test. Accordingly, at 10 mg/kg of WDQV (SEQ ID NO:14), a reduction in the time spent in the dark compartment of the LDB was observed, both in total time, as well as in dynamics, as shown in FIGS. 27B and 27D.

FIGS. 28A and 28B illustrate comparison of the effects of WDQV (SEQ ID NO:14) (10 mg/kg) in the light/dark box test with diazepam (5 mg/kg) and FQSE (SEQ ID NO:10) (10 mg/kg). It was observed that the WDQV (SEQ ID NO:14) peptide has an anxiolytic efficacy profile similar to that of diazepam and FQSE (SEQ ID NO:10).

Figure 29:
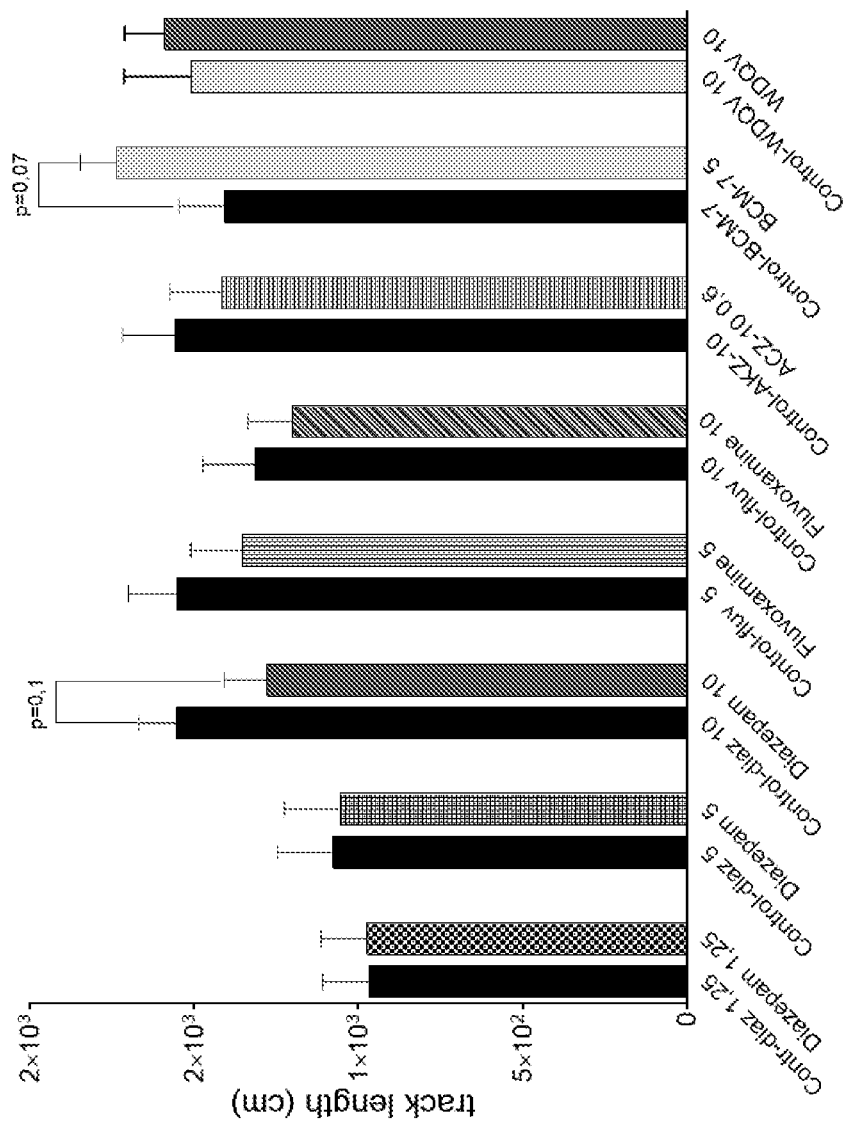
FIG. 29 illustrates an average track length in the open field test in the groups of fish administered diazepam at doses of 1.25 mg/kg ("Diazepam 1,25"), 5 mg/kg ("Diazepam 5") and 10 mg/kg ("Diazepam 10") and in the corresponding control groups ("Contr-diaz 1,25," "Control-diaz 5," and "Control-diaz 10"), as well as in the groups of fish administered fluvoxamine at doses of 5 mg/kg ("Fluvoxamine 5") and 10 mg/kg ("Fluvoxamine 10") and in corresponding control groups ("Control-fluv 5" and "Control-fluv 10"). For the group of fish administered 0.6 mg/kg of ACZ-10 ("ACZ-10 0.6"), a corresponding control group is "Control-ACZ-10"; for the group of fish administered 5 mg/kg of BCM-7 ("BCM-7 5") a corresponding control group is "Control-BCM-7"; and for the group of fish administered tetrapeptide WDQV (SEQ ID NO:14) at a dose of 10 mg/kg ("WDQV 10") a corresponding control group is "Control-WDQV 10".

FIG. 29 illustrates an average track length in the open field test in the groups of zebrafish administered the test substances as follows: diazepam at doses of 1.25 mg/kg ("Diazepam 1,25"), 5 mg/kg ("Diazepam 5") and 10 mg/kg ("Diazepam 10") and corresponding control groups ("Contr-diaz 1.25," "Control-diaz 5," "Control-diaz 10"); fluvoxamine at doses of 5 mg/kg ("Fluvoxamine 5") and 10 mg/kg ("Fluvoxamine 10") and corresponding control groups ("Control-fluv 5" and "Control-fluv 10"); ACZ-10 at a dose of 0.6 mg/kg ("ACZ-10 0.6") and a corresponding control group ("Control-ACZ-10"); BCM-7 "BCM-7 5" and a corresponding control group ("Control-BCM-7"); tetrapeptide WDQV (SEQ ID NO:14) at a dose of 10 mg/kg ("WDQV 10") and a corresponding control group ("Control-WDQV 10"). FIG. 29 illustrates that, at a dose 10 mg/kg, the WDQV (SEQ ID NO:14) peptide did not demonstrate any behavioral effects, particularly, there was no influence of the tetrapeptide on the motor activity in the open field test.

These experiments demonstrate that WDQV (SEQ ID NO:14) tetrapeptide at a dose of 10 mg/kg demonstrated an anxiolytic effect in the light/dark box test similar to the one observed after injection of diazepam (5 mg/kg) and FQSE (SEQ ID NO:10) (10 mg/kg). However, other tests did not reveal any effect of the WDQV (SEQ ID NO:14) peptide (10 mg/kg) on the behavior of *Danio rerio*. At a dose of 1 mg/kg, WDQV (SEQ ID NO:14) also did not have any marked effects on the zebrafish behavior. In sum, it can be concluded that WDQV (SEQ ID NO:14) has a positive neurotropic effect, although a somewhat less distinctive than that of diazepam and the FQSE (SEQ ID NO:10) tetrapeptide, which both showed a wider spectrum of behavioral effects.

Example 4: Determination of Neurotropic Activity of FQSE (SEQ ID NO:10) Peptide in Mice The objective of this experiment was to identify the potential neurotropic effect of different doses of FQSE (SEQ ID NO:10) peptide on the behavior of BALB/C mice after acute intraperitoneal injections. The effects of administering of FQSE (SEQ ID NO:10) peptide on behavior of BALB/C mice was compared to the effects of administering diazepam to BALB/C mice. The effects of both FQSE (SEQ ID NO:10) peptide and diazepam on behavior of the mice were assessed using the Marble Burying test, the Elevated Plus Maze test, the Porsolt swim test (two-day modification) and the Open Field test. These tests are techniques for measuring stress- and anxiety-related behavior in animal models to evaluate effectiveness of potential anti-depressant and anxiolytic agents.

In the experiments conducted in this study, BALB/C mice were subjected to the Open Field, Elevated Plus Maze, and Marble Burying tests to determine anxiolytic effects of diazepam and FQSE (SEQ ID NO:10) peptide on the mice. According to the results obtained in the Open Field test, the Elevated Plus Maze test, and the Marble Burying test, administration of diazepam (via intraperitoneal injection) to mice resulted in a pronounced anxiolytic effect. These findings confirm that the mice model is a valid model for testing effects of drugs, including peptides, that bind to the GABA-A receptor. Furthermore, in this study, BALB/C mice subjected to the Porsolt swim test (two-day modification) to determine antidepressant effects of diazepam and FQSE (SEQ ID NO:10) peptide on the mice. The FQSE (SEQ ID NO:10) peptide at doses ranging from 1 mg/kg to 20 mg/kg showed an antidepressant effect.

4.1. Materials and Methods 4.1.1. Animal Models

Seventy-nine male BALB/C mice were used as subjects in this example. Body weight of each specimen at the beginning of the experiment was between about 18 grams and about 20 grams. All animals were free from species-specific pathogens (SPF status according to the FELASA list, 2014). The animals were kept in conditions of free access to water and food. The room was air-conditioned (exchange rate not less than 15 r/h) with a 12 h:12 h light-dark cycle (lights on at 09:00 am), air temperature 20-24°±2° C. (possible fluctuations of the limits no more than 2° C. per day), 30-70% humidity. For the study, the mice were separated into six different groups and the tested substances were administered to the groups as shown in Table 1. Taking into account the division into the groups, an interval between the tests was one day. All procedures involving animals were conducted in accordance with the European (Directive 2010/63/EU of the European Parliament and of the Council of 22 Sep. 2010 on the protection of animals used for scientific purposes) and the Russian ("GOST 33216-2014 Guidelines for the maintenance and care of laboratory animals. Rules for the maintenance and care of laboratory rodents and rabbits") bioethical guidelines.

TABLE 1

Experimental groups

| Group name | Group size | Testing substance | Test |
| --- | --- | --- | --- |
| 1. Intact control | 13 | Intraperitoneal injections of solvent according to the experimental group study design | Marble burying test Elevated plus maze test, Porsolt swim test (two-day modification), Open field test. |
| 2. Peptide FQSE (SEQ ID NO: 10), 1 mg/kg | 13 | Intraperitoneal injections of FQSE (SEQ ID NO: 10) at a dose of 1 mg/kg | |
| 3. Peptide FQSE (SEQ ID NO: 10), 5 mg/kg | 13 | Intraperitoneal injections of FQSE (SEQ ID NO: 10) at a dose of 5 mg/kg | |
| 4. Peptide FQSE (SEQ ID NO: 10), 10 mg/kg | 13 | Intraperitoneal injections of FQSE (SEQ ID NO: 10) at a dose of 10 mg/kg | |
| 5. Peptide FQSE (SEQ ID NO: 10), 20 mg/kg | 14 | Intraperitoneal injections of FQSE (SEQ ID NO: 10) at a dose of 20 mg/kg | |

TABLE 1-continued

| | | Experimental groups | |
|---|---|---|---|
| Group name | Group size | Testing substance | Test |
| 6. Comparison drug Diazepam | 13 | Intraperitoneal injections of the comparison drug Diazepam at a dose of 0.75 mg/kg | |

After an adaptation period, the test substance was intraperitoneally injected into mice. Behavioral parameters were measured in 30 minutes after injection. The tests were administered as follows: day 1—the Open field test, day 3—the Elevated plus maze test, day 5—the Marble burying test, days 12-13—the Porsolt swim (two-day modification) test.

4.1.2. Statistical Analysis

Statistical data analysis was performed using nonparametric criteria (Manna-Whitney) for not normally distributed samples or using one-way analysis of variance (ANOVA) followed by Fisher's LSD test for normally distributed samples.

4.1.3. The Open Field Test

In the Open field test, the installation is an arena with a diameter of 63 cm, illuminated by bright light (500 lux) (OpenScience, Russia). The following parameters were measured during 5-minute experiment: a total distance (cm), a time of motion (if the speed is more than 5 cm/s), an immobility (if the speed is less than 0.2 cm/sec), a mean and maximum velocity, and a number of episodes of motor activity and "freezing". The same set of parameters, as well as latent period and time duration of stay, were recorded for the central sector of the arena. Defecations and rearing (animal raise upright on hind limbs) were assessed visually (File and Wardill (1975) Validity of head-dipping as a measure of exploration in a modified hole-board. Psychopharmacol., 44, 53-59). The test is designed to measure the level of motor and exploratory activity.

4.1.4. The Elevated Plus Maze Test

In the elevated plus maze test, a test arena includes two open and two closed arms crossed in the middle. The arm length is 30 cm, the height of the closed arms side walls is 15 cm. The entire installation is raised 70 cm above the floor. The open arms have bright uniform illumination of about 400 lux, and the closed arms have illumination of about 30-40 lux. Mice were placed at the junction of the four arms of the maze (center), facing an open arm. The following behavioral parameters were automatically registered by the EthoVision, Noldus program within 5 minutes of the experiment: a total distance (cm), a time of motion (if the speed is more than 5 cm/s), an immobility (if the speed is less than 0.2 cm/sec), a mean and maximum velocity, and the number of episodes of motor activity and "freezing". The same set of parameters, as well as a latent period and the duration of stay, were measured for the central sector, open and closed arms separately. (Manufactured by OpenScience, Russia).

4.1.5. The Marble Burying Test

In the marble burying test, the installation is a standard T3 cage (19 cm×29 cm×13 cm) filled with bedding material. The standard glass marbles (15 mm in diameter, weight 5.2 g, arbitrary color) were used for the test. Twenty marbles were evenly spaced on the surface in 4 rows, 5 pieces each. The animal was placed in the testing cage for 30 minutes. At the end of the period, after the animal was carefully removed, the number of marbles that were more than two-thirds covered with bedding material was counted.

4.1.6. The Porsolt Swim Test (Two-Day Modification)

In the Porsolt Swim test, two tests were conducted in two days. The installation is a transparent cylinder, 30 cm in height, 10 cm in diameter, filled with water (temperature about 21-23° C.) to the mark of 25 cm height. On the first day each animal was placed into the cylinder for 10 minutes. Behavioral parameters were not registered. On the second day, the animals were placed into the cylinder for 5 minutes. The following parameters were measured: duration of active (vigorous movements of all limbs) and passive (weak movements of hind limbs) swimming, as well as immobility (immobilization) (Porsolt et al. (1977) Behavioral despair in mice: a primary screening test for antidepressants. Arch Int Pharmacodyn Ther. 229(2):327-36). After each test, the mice were placed into a heated cell to dry.

4.2. Evaluation of Anxiolytic Effects of Test Substances

The following tests were used for the evaluation of the anxiolytic effects of the peptide at different doses (1 mg/kg, 5 mg/kg, 10 mg/kg, 20 mg/kg): day 1—the Open Field test, day 3—the Elevated Plus Maze Test, day 5—the Marble Burying test. Diazepam (0.75 mg/kg) was used as a drug of comparison. All substances were injected intraperitoneally in a volume of 10 µl of solution per 1 gram of animal weight 30 minutes prior to behavioral testing.

In animal models, the state of anxiety can be defined as a conflict of defensive and exploratory motivations. Accordingly, if the defensive motivation prevails, then the emotional state of heightened anxiety is formed, and, conversely, if the exploratory motivation prevails, then a conclusion can be made about a calm emotional state of animals. Thus, the anxiolytic effect of the drug can manifest itself both in the attenuation of the defensive motivation or in the strengthening of the exploratory component, and in the combined multidirectional influence on these two components. Often the effect of anxiolytics is defined as a shift of the conflict between the defensive and exploratory motivations towards the latter.

Figure 30:
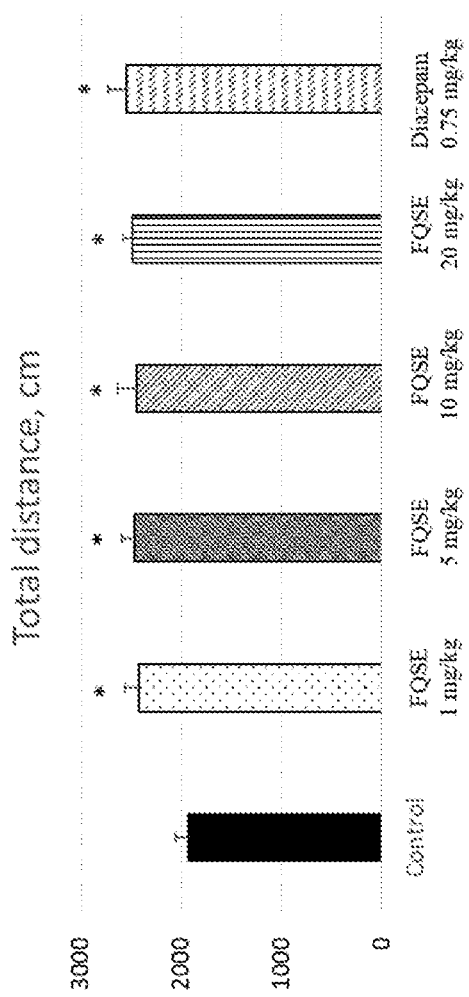
FIG. 30 illustrates a total distance in the Open Field test performed in mice, in cm, for the FQSE (SEQ ID NO:10) peptide at concentrations 1 mg/kg, 5 mg/kg, 10 mg/kg, 20 mg/kg. Each bar represents an average total distance±SEM. Significant difference is denoted by the "*" symbol (one-way ANOVA followed by Fisher's LSD test; $p<0.05$).

4.2.1. Evaluation of Effects of Test Substances on Mice Behavior Using the Open Field Test The open field test was used for the evaluation of initial effects of drugs on motor (total distance), and exploratory (rears, time in center, center entries) activities. As shown in FIG. 30, the total distance in the group "Diazepam" (2542.2±179.77) was significantly higher in comparison with the control group (1925.6±129.31). The similar tendencies were revealed for all four groups with the FQSE (SEQ ID NO:10) peptide administration: FQSE 1 mg/kg (2423±133.81), FQSE 5 mg/kg (2464±124.67 cm), FQSE 10 mg/kg (2441±185.97), FQSE 20 mg/kg (2478±100.41).

Figure 31:
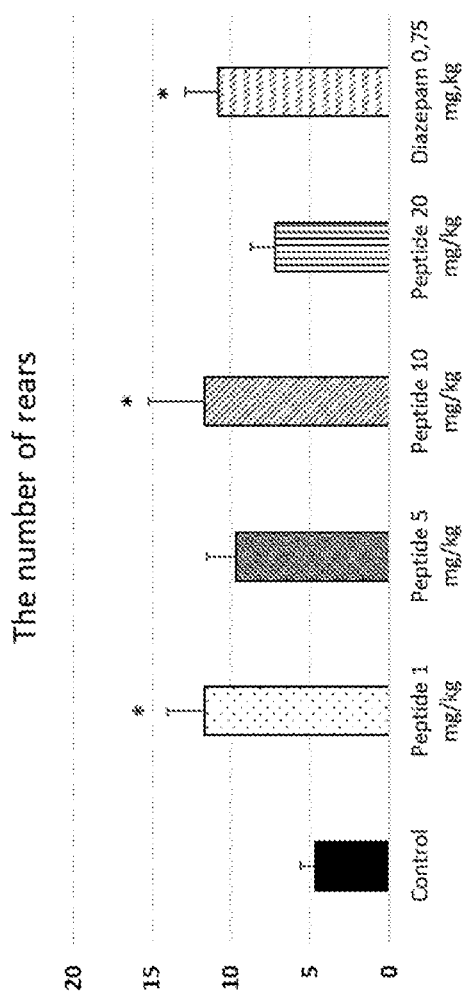
FIG. 31 illustrates a number of rearings in the Open Field test performed in mice, for the FQSE (SEQ ID NO:10) peptide at concentrations 1 mg/kg, 5 mg/kg, 10 mg/kg, and 20 mg/kg. Each bar represents an average number of rearings per group±SEM. Significant difference is denoted by the "*" symbol (one-way ANOVA followed by Fisher's LSD test; $p<0.05$).
Figure 32:
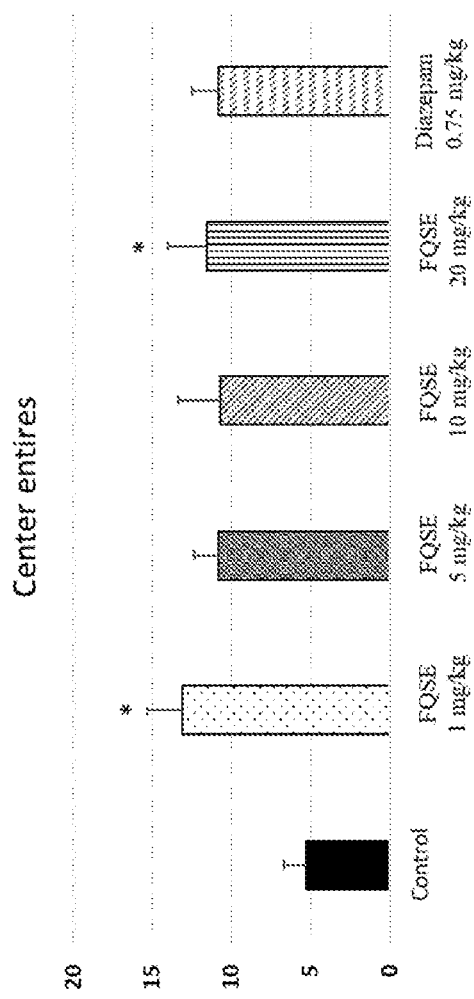
FIG. 32 illustrates a number of center entries in the Open Field test performed in mice, for the FQSE (SEQ ID NO:10) peptide at concentrations 1 mg/kg, 5 mg/kg, 10 mg/kg, and 20 mg/kg. Each bar represents an average number of center entries per group±SEM. Significant difference is denoted by the "*" symbol (one-way ANOVA followed by Fisher's LSD test; $p<0.05$).

FIGS. 31 and 32 show the parameters that reflect exploratory activity of the animals ("Number of rearings" and "Number of center entries," respectively). In the Diazepam group, the number of rearings was significantly higher (10.8±2.1) in comparison with the control group (4.7±0.94), while the number of center entries and the time the animals spent in the center were not significantly different between Diazepam and control groups. For the groups FQSE 1 mg/kg and FQSE 10 mg/kg, the number of rearings was significantly higher (11.7±2.3 and 11.7±3.6, respectively) in comparison with the control group. For animals that received the peptide at a dose of 1 mg/kg and 20 mg/kg, number of center entries (13.1±2.26 and 11.6±2.5, respectively) were significantly higher in comparison with the control group (5.3±1.44).

Figure 33:
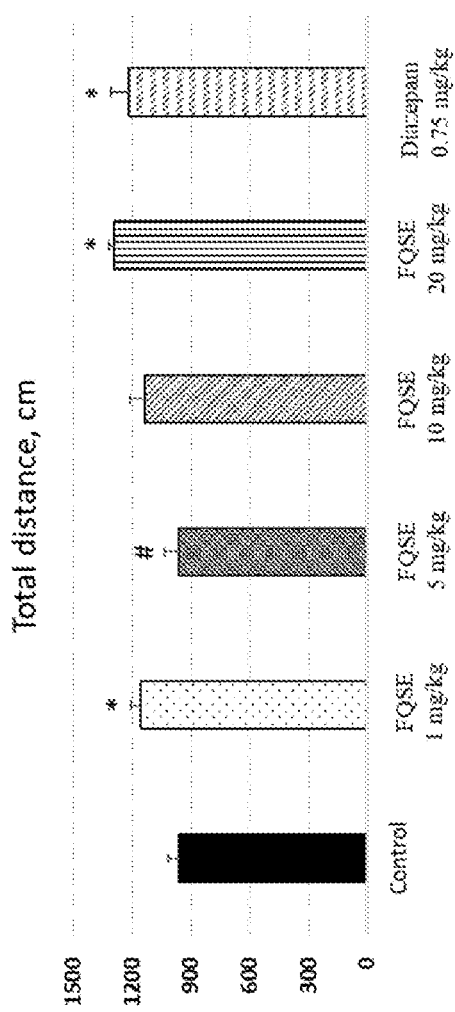
FIG. 33 illustrates a total distance in Elevated Plus Maze test, cm, performed in mice, for the FQSE (SEQ ID NO:10) peptide at concentrations 1 mg/kg, 5 mg/kg, 10 mg/kg, and 20 mg/kg. Each bar represents an average total distance±SEM. Significant difference from the control group is denoted by the "*" symbol, significant difference from the Diazepam group is denoted by the "#" symbol (one-way ANOVA followed by Fisher's LSD test; p<0.05).
Figure 34:
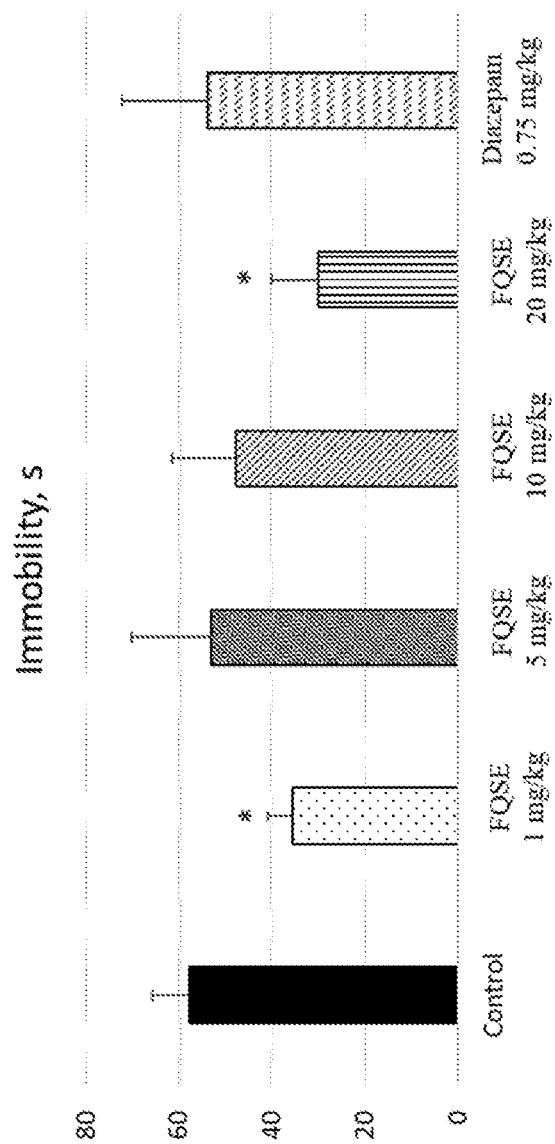
FIG. 34 illustrates immobility, s, for the Elevated Plus Maze test, performed in mice, for the FQSE (SEQ ID NO:10) peptide at concentrations 1 mg/kg, 5 mg/kg, 10 mg/kg, and 20 mg/kg. Each bar represents an average immobility time per group±SEM. Significant difference from the control group is denoted by the "*" symbol (one-way ANOVA followed by Fisher's LSD test; p<0.05).

4.2.2. Evaluation of Effects of Test Substances on Mice Behavior Using the Elevated Plus Maze Test Two groups of behavioral parameters that characterize the anxiolytic effect of drug administration were identified in the elevated plus maze test. The first group of parameters is associated with the motor activity of animals. This group includes such parameters as immobility, measured time (in seconds) without movements, and a total distance, measured in cm. An overall increase of motor activity may indicate a decrease of the passive-defensive motivational component (iE. on the anxiolytic drug effect). FIG. 33 demonstrates the total distance parameter. It was revealed that this parameter in the Diazepam group (1219±91.4) was significantly higher in comparison with the control group (960±56). The FQSE (SEQ ID NO:10) peptide injection at doses of 1 mg/kg and 20 mg/kg also led to an increase of the total distance (1156±48.2 and 1290±30.5, respectively), while the immobility time decreased (FIG. 34) (36.6±3.97 and 30.1±3.07, respectively) in comparison with the control values (57.7±7.05).

Figure 35:
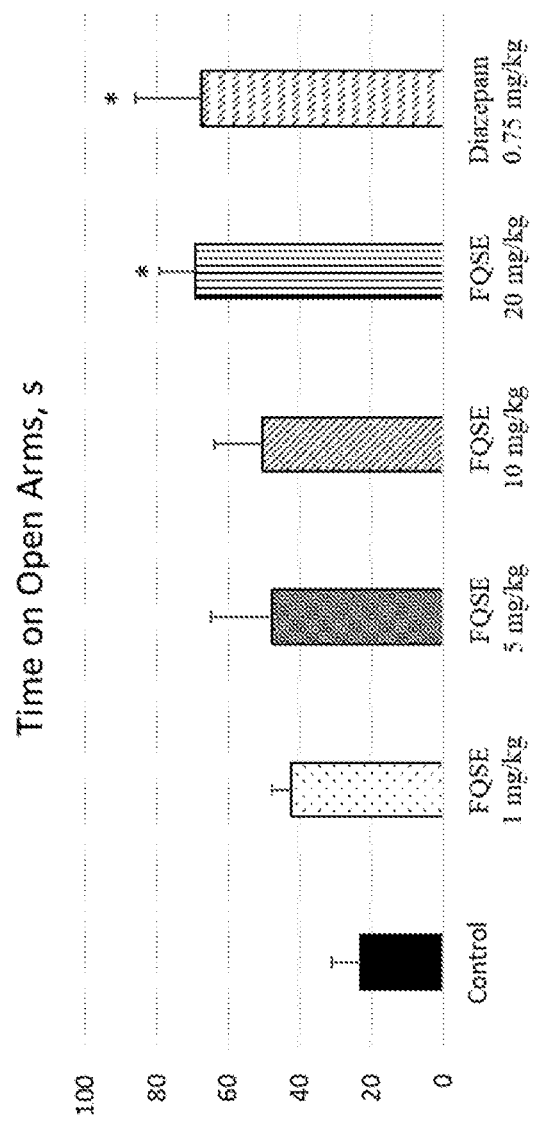
FIG. 35 illustrates a time on open arms in the Elevated Plus Maze test, s, for the FQSE (SEQ ID NO:10) peptide at concentrations 1 mg/kg, 5 mg/kg, 10 mg/kg, and 20 mg/kg. Each bar represents an average time on open arms per group±SEM. Significant difference from the control group is denoted the "*" symbol (one-way ANOVA followed by Fisher's LSD test; p<0.05).
Figure 36:
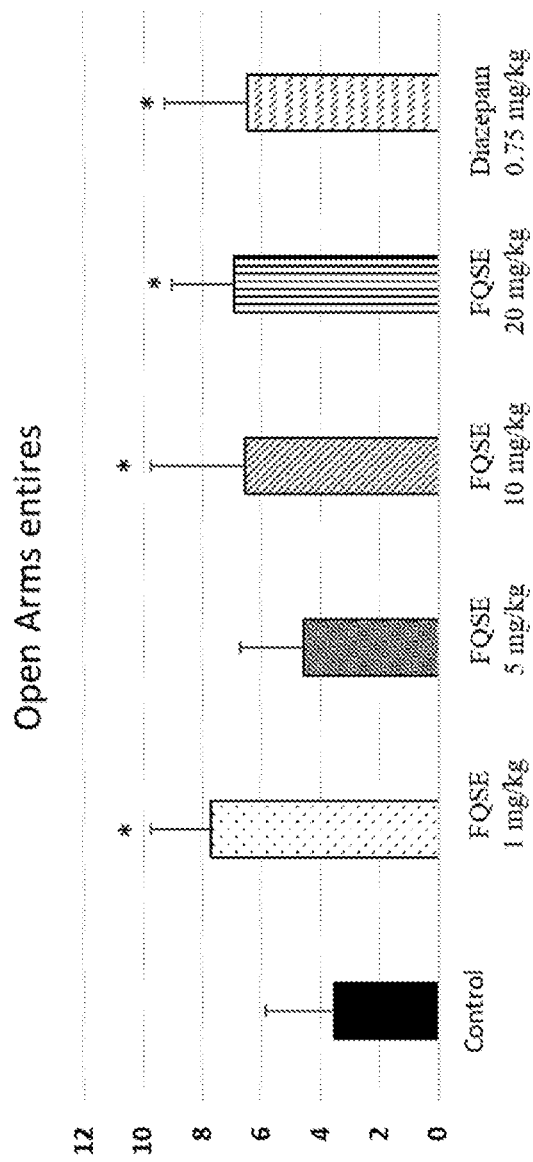
FIG. 36 illustrates open arms entries in the Elevated Plus Maze test for the FQSE (SEQ ID NO:10) peptide at concentrations 1 mg/kg, 5 mg/kg, 10 mg/kg, and 20 mg/kg. Each bar represents an average number of open arms entries per group±SEM. Significant difference from the control group is denoted by the "*" symbol (one-way ANOVA followed by Fisher's LSD test; p<0.05).
Figure 37:
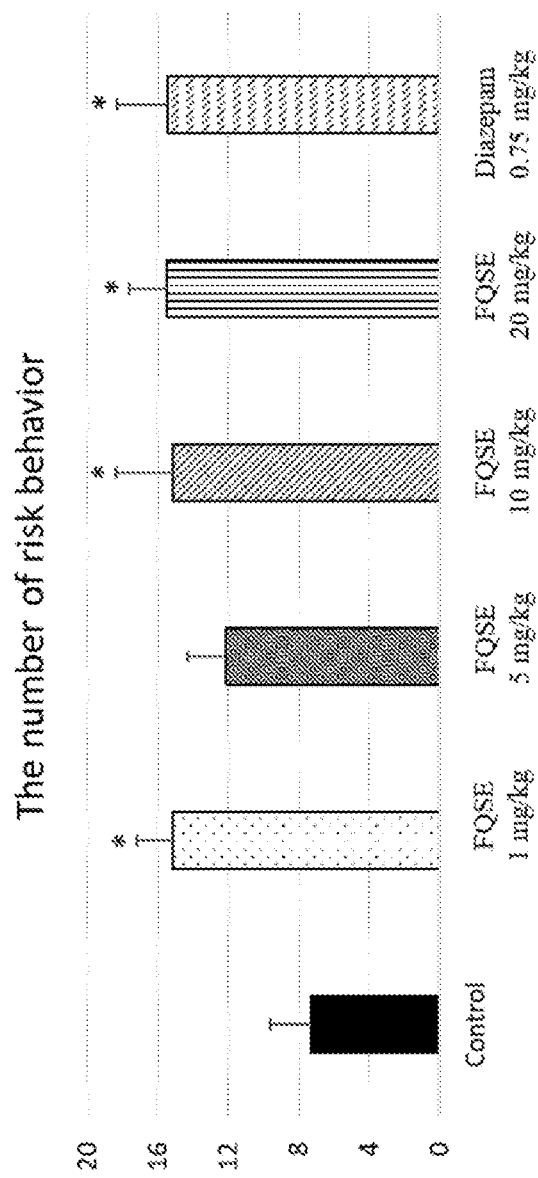
FIG. 37 illustrates a number of occurrences of risk behavior in the Elevated Plus Maze test for the FQSE (SEQ ID NO:10) peptide at concentrations 1 mg/kg, 5 mg/kg, 10 mg/kg, and 20 mg/kg. Each bar represents an average number of risk behavior per group±SEM. Significant difference from the control group is denoted by the "*" symbol (one-way ANOVA followed by Fisher's LSD test; p<0.05).
Figure 38:
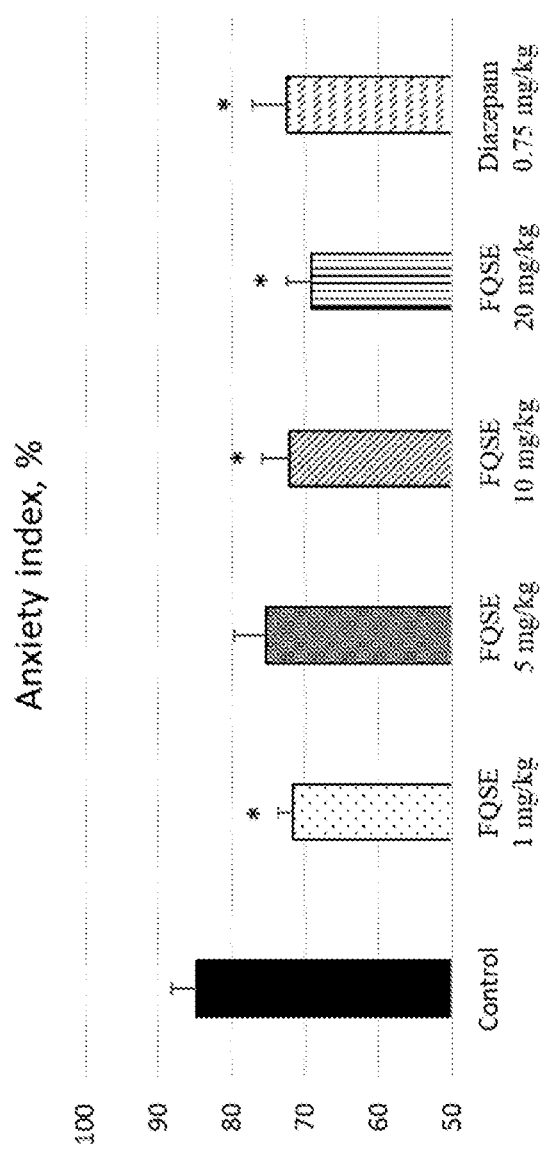
FIG. 38 illustrates anxiety index in the Elevated Plus Maze test for the FQSE (SEQ ID NO:10) peptide at concentrations 1 mg/kg, 5 mg/kg, 10 mg/kg, and 20 mg/kg. Each bar represents an average anxiety index per group±SEM. Significant difference from the control group is denoted by the "*" symbol (one-way ANOVA followed by Fisher's LSD test; p<0.05).

The second group of parameters includes a time on open arms (in seconds) (FIG. 35), a number of open arms entries (FIG. 36), a number of risk behavior (number of rearings and dangle events, as shown in FIG. 37]), and an anxiety index (FIG. 38). The anxiety index (AI) was calculated using the following formula:

AI=100*(1-(time on open arms/total test time+open arms entries/total number of entries)/2)

An increase in the time spent on the open arms, and an associated decrease of anxiety index, are the standard metrics of exploratory motivation increase and anxiety reduction. These observations indicate the anxiolytic action of the substance.

According to the experimental results of the tests described herein, intraperitoneal injections of Diazepam resulted in a pronounced anxiolytic effect: during the analysis of the behavioral parameters in response to Diazepam administration, it was revealed that "Time on open arms" (67.4±18.43), "Open arms entries" (6.5±0.99), "The number of risk behavior" (15±2.8) in the Diazepam group were significantly higher in comparison with the control group (23±8.12; 3.5 0.81; 7±2.3, respectively), which resulted in a statistically significant decrease in the "Anxiety index" in the Diazepam group (73±4.7%) in comparison with the Control group (85±3.4%).

The similar results were observed for the peptide administration groups. "Time on open arms" was significantly increased in the FQSE 20 mg/kg group (69.1±9.98) in comparison with the Control group (23±8.12). "Open arms entries" and "The number of risk behavior" were significantly higher in the FQSE 1 mg/kg (7.7 S0.79; 15±2.1), FQSE 10 mg/kg (6.5±1.07; 15±3.2), and FQSE 20 mg/kg (6.9±0.79; 16±2.1) groups than in the Control group (3.5±0.81; 7±2.3). Thus, "Anxiety index" for animals from these groups was also below the control values and was 72±2% in the FQSE 1 mg/kg group; 72±3.8% in the FQSE 10 mg/kg group, and 69±3.3% in the Peptide 20 mg/kg group.

Figure 39:
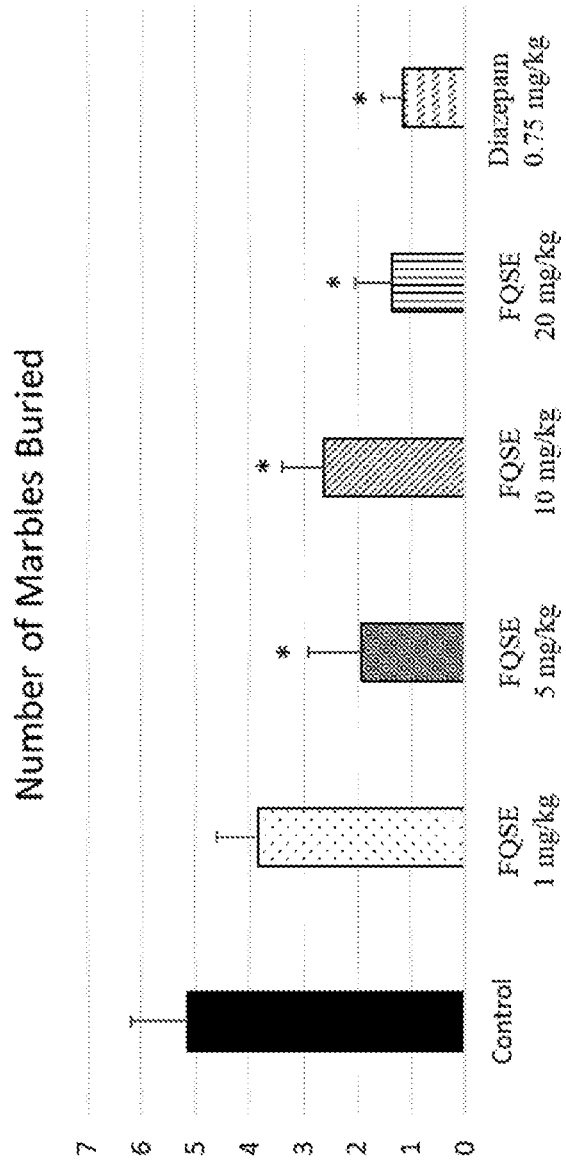
FIG. 39 illustrates the results of the Marble Burying test (number of marbles buried) for the FQSE (SEQ ID NO:10) peptide at concentrations 1 mg/kg, 5 mg/kg, 10 mg/kg, and 20 mg/kg. Each bar represents an average number of buried marbles per group±SEM. Significant difference from the control group is denoted by the symbol (one-way ANOVA followed by Fisher's LSD test; p<0.05).

4.2.3. Evaluation of Effects of Test Substances on Mice Behavior Using the Marble Burying Test Animals perceive shiny marbles located in an experimental area as a stress factor, a negative stimulus that has to be buried in bedding material, so mice do not have to have visual and tactile contacts with it. A reduction in the number of buried marbles (FIG. 39) under the influence of the drug administration in 30 minutes experiment indicates a decrease in anxiety level of animals. According to the acquired data, an average number of marbles buried by animals in the control group was 5.2±1.04, while animals of the Diazepam group buried significantly a smaller number of marbles—1.2±0.39. A decrease in the number of buried marbles was also observed in the following groups: FQSE 5 mg/kg (1.9±0.99), FQSE 10 mg/kg (2.6±0.877) and FQSE 20 mg/kg (1.4±0.68).

4.3. Evaluation of Antidepressant Effects of Test Substances

For the evaluation of antidepressant effects of drugs, the Porsolt swim test (two-day modification) was used. These behavioral tests are the main methods for evaluation of the depression component of animal behavior and the influence of test drugs on it.

4.3.1. The Porsolt Swim Test (Two-Day Modification)

A two-day modification lets the animal to adapt to test conditions on the first day of experiment, and this allowed for a more informed evaluation of behavioral responses on the second day. According to the literature, the longer the duration of immobilization time (the time the animal spends in a "freezed" state), the more depressed the animal is. A significant reduction in immobilization time under the drug influence characterizes its ability to demonstrate an antidepressant effect and regulate a depression-like behavior.

Figure 40:
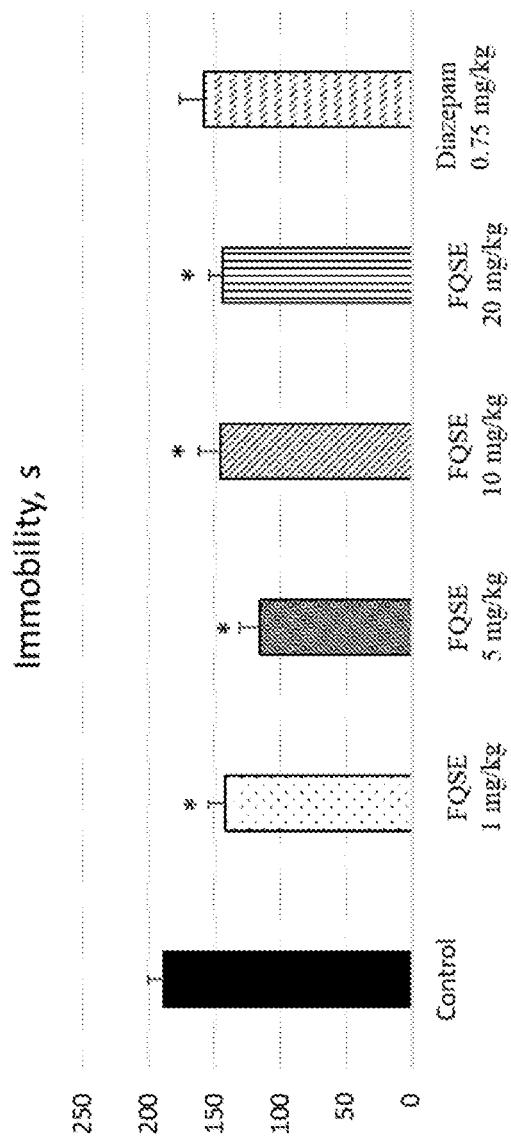
FIG. 40 illustrates immobility in the Porsolt swim test (two-day modification), s, for the FQSE (SEQ ID NO:10) peptide at concentrations 1 mg/kg, 5 mg/kg, 10 mg/kg, and 20 mg/kg. Each bar represents an average duration of immobility total time per group±SEM. Significant difference from the control group is denoted by the "*" symbol (one-way ANOVA followed by Fisher's LSD test; p<0.05).
Figure 41:
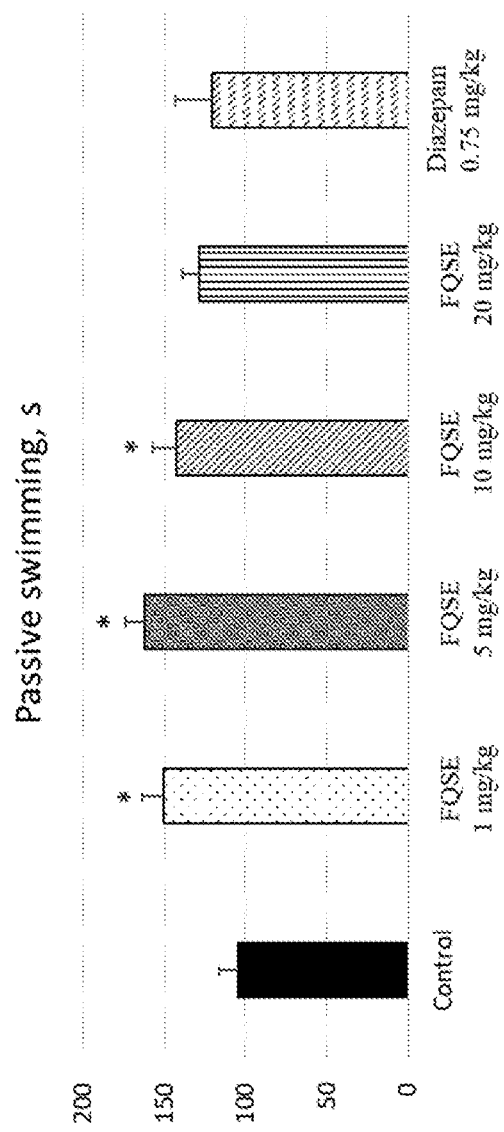
FIG. 41 illustrates a passive swimming time duration in the Porsolt swim test (two-day modification), s, for the FQSE (SEQ ID NO:10) peptide at concentrations 1 mg/kg, 5 mg/kg, 10 mg/kg, and 20 mg/kg. Each bar represents an average duration of passive swimming per group±SEM. Significant difference from the control group is denoted by the "*" symbol (one-way ANOVA followed by Fisher's LSD test; p<0.05).
Figure 42:
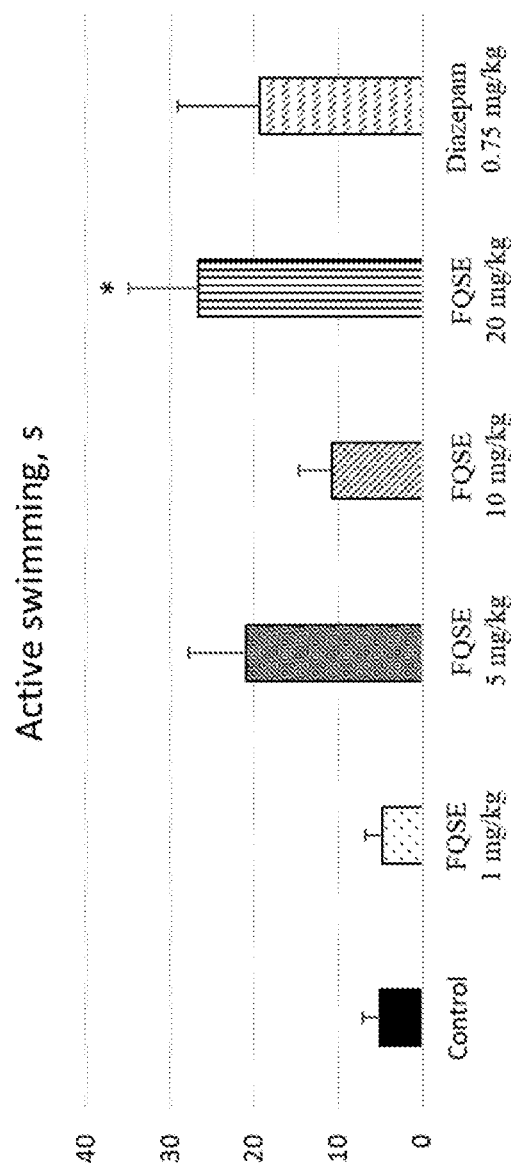
FIG. 42 illustrates an active swimming time duration in the Porsolt swim test (two-day modification), s, for the FQSE (SEQ ID NO:10) peptide at concentrations 1 mg/kg, 5 mg/kg, 10 mg/kg, and 20 mg/kg. Each bar represents an average duration of passive swimming per group±SEM. Significant difference from the control group is denoted by the "*" symbol (one-way ANOVA followed by Fisher's LSD test; p<0.05).

According to results of the experiments described herein, intraperitoneal injections of Diazepam at a dose of 0.75 mg/kg did not lead to the changes in any tested parameter (duration of active and passive swimming, immobility time) (FIGS. 40, 41, 42). On the contrary, injections of the study peptide FQSE (SEQ ID NO:10) (FIG. 40) resulted in a decrease of the total time of immobility in all experimental groups: FQSE 1 mg/kg (142±12.7), FQSE 5 mg/kg (115±15.4), FQSE 10 mg/kg (145±16.5) and FQSE 20 mg/kg (144±10.2), and these results are significantly different from the control group (189±11.1). In addition, for the groups FQSE 5 mg/kg, FQSE 10 mg/kg, and FQSE 20 mg/kg, an increase in the duration of passive swimming was observed (151±12.5, 162±12.1, and 143±14.6, respectively), in comparison with the control values (105±11.1). It should be mentioned that the administration of the peptide at a dose of 20 mg/kg significantly increased the time of active swimming (when the animal moves four limbs simultaneously) to 27±8.3 sec, while an average value in the control group was 5±2 sec.

4.4. Comparison of Anxiolytic-Like and Antidepressant-Like Effects of Test Substances The inventors of the present disclosure have discovered, based on the results obtained in three different behavioral tests (the Open Field test, the Elevated Plus Maze test, and the Marble Burying test), that the intraperitoneal administration (a single injection) of the FQSE (SEQ ID NO:10) peptide at doses ranging from 1 mg/kg to 20 mg/kg, 30 minutes prior the experiments resulted in a pronounced anxiolytic-like effect. Similarly, a single intraperitoneal injection of diazepam at a dose of 0.75 mg/kg into BALB/C mice 30 minutes before the behavioral tests resulted in a pronounced anxiolytic-like effect of diazepam.

According to the results obtained in the Open Field test, the Elevated Plus Maze test, and the Marble Burying test, administration of diazepam (via intraperitoneal injection) to mice resulted in a pronounced anxiolytic-like effect. These findings are consistent with the information from the scientific literature, which confirms that the mice model is a valid model for testing effects of drugs, including peptides that bind to the GABA-A receptor. The conclusion about the anxiolytic effect of the drug was based on the following data: an increase in motor and exploratory activities in the Open Field test; an increase of such parameters as "Time on open arms", the number of "Open arms entries" and "Risk behavior", and a decrease of the "Anxiety index" parameter in the Elevated Plus Maze test; a decrease in the number of buried marbles in the Marble Burying test. All of the peptide doses used in this study led to an increase of animal motor activity in the Open Field test. An increase of exploratory activity (based on the "Open arms entries" parameter) was observed for the FQSE 1 mg/kg and FQSE 20 mg/kg test groups. The Elevated Plus Maze test revealed a decrease of the "Anxiety index" parameter in the FQSE 1 mg/kg, FQSE 10 mg/kg and FQSE 20 mg/kg groups. Thus, based on the results obtained in three different behavioral tests, it can be concluded that the intraperitoneal administration of the peptide at doses from 1 mg/kg to 20 mg/kg 30, minutes prior the experiments results in a pronounced anxiolytic-like effect.

In the experiments conducted by the inventors of the present disclosure, BALB/C mice were subjected to the Porsolt swim test (two-day modification) test to determine antidepressant effects of diazepam and FQSE (SEQ ID NO:10) peptide on the mice. A single Intraperitoneal injection of Diazepam at a dose of 0.75 mg/kg to BALB/C mice did not induce an antidepressant effect. However, according to results of the Porsolt swim test, a single intraperitoneal injection of FQSE (SEQ ID NO:10) peptide at doses ranging from 1 mg/kg to 20 mg/kg showed an antidepressant effect. In addition, the diazepam injection led to a sedative side effect, while intraperitoneal injections of FQSE (SEQ ID NO:10) peptide at all dose levels ranging from 1 mg/kg to 20 mg/kg did not cause negative, suppressive effects on CNS.

Example 5: The Effects of Intranasal Administration of Peptide FQSE (SEQ ID NO:10) in Behavioral Tests for Anxiety and Depression in Male Sprague Dawley Rats The aim of the study was to evaluate the effective intranasal (i.n.) dose of peptide in behavioral tests for anxiety and depression in rats.

5.1. Materials and Methods.
5.1.1. Animals

A total of 110 male Sprague Dawley rats (Charles River, Wilmington, MA) were used for the studies. Rats were initially housed 3-5 to a cage in polypropylene cages housed in circular towers (Animal Care Systems, Inc, Centennial, CO) located within a temperature- and humidity-controlled vivarium that was maintained on a 12:12 light/dark cycle (lights on at 6 AM). Rats weighed about 250-350 gm at the start of the experiment and were at least 100 days old. Food and water were available ad libitum throughout the study. All procedures were approved by the University of Houston Institutional Animal Care and Use Committee in accordance with the National Institutes of Health Guidelines.

5.1.2. Drugs and Test Articles

Diazepam (DZ 2.0, Sigma-Aldrich, St. Louis, MO, USA, 2 mg/kg, IP) and Ketamine (Miller Veterinary Supply, Fort Worth, TX, 10 mg/kg, IP) were made up in sterile saline. The five doses of FQSE (SEQ ID NO:10) (0.01, 0.1, 0.5, 1 and 3 mg/kg, CS, Menlo Park, CA) were prepared fresh for each test day in sterile saline and administered intranasally (i.n.) 30 minutes prior to testing. Fifteen rats per group per peptide dose were tested with the exception that there were twenty rats in the vehicle (0) group. Each dose was administered in a randomized order across rats. Prior to dosing, the rats were lightly anesthetized (till loss of righting reflex) with isoflurane (2.5%, 0.5 L/min oxygen), placed in the recumbent position, then a thin plastic pipette (Fischer Scientific) inserted into the nares and peptide administered at a volume of 15-20 uL per nares. Individuals performing the behavioral tests were blind to drug treatment.

5.1.3. Behavioral Apparatus and Testing Procedures.
Open Field (OF)

Open field tests occurred in open field apparatus constructed of gray Plexiglas (17"L×17" W×12" H (43.2 cm×43.2 cm×30.5 cm; Noldus, Leesburg, VA) with digital cameras positioned above the arenas to detect different measures of activity using specialized software (Ethovision, XT12). Rats were first allowed to acclimate to the testing room for 30 minutes while in their home cage. The test was initiated by placing the animal in the center of the open field chamber and behavior recorded for 30 minutes. The observer was not in the room during testing. Testing was conducted under red-light. Arenas were cleaned thoroughly between subjects with LpH disinfectant.

Elevated Plus Maze (EPM)

Rats were first allowed to acclimate to the testing room for 30 minutes while in their home cage. During testing, a rat was placed on the maze which consists of two open arms (45-cm long×10-cm wide), two closed arms (45-cm long× 10-cm wide×30-cm high), and a middle compartment (4-cm long×4-cm wide) forming the shape of a plus located 50-cm above the floor, for 5-min. The test session was digitally recorded for later analyses (Ethovision, XT12). All testing was conducted under red lighting. An experimenter observed the rat during testing through a specialized observation window built into the door of the behavioral testing room. The apparatus was cleaned with LpH disinfectant after each animal's run.

Forced Swim Tests (FST)

Rats were first allowed to acclimate to the testing room for 30 minutes while in their home cage. The forced swim tests were conducted using Plexiglas cylinders (10 in width, 18 in height) filled with water maintained at approximately 25° C. On day 1, rats were first habituated (15 minutes) to the forced swim apparatus by being placed into the water facing the cylinder wall. Forced swim tests (5 minutes) occurred the following day. Activity was recorded by digital cameras and analyzed with specialized software (Ethovision XT12).

5.1.4. Statistical Analysis

Center zone time, center zone entries for the open field tests, % time on the open arm in the EPM tests and immobility and mobility times in the FST were analyzed with a 1×7 One-Way ANOVA with drug dose (0, 0.01, 0.1, 0.5, 1.0, 3.0, diazepam 2.0 or ketamine 10 mg/kg) as the primary factor. Pairwise multiple comparisons procedures were conducted using the Student-Newman-Keuls Method or Fisher's Least Significant Difference (LSD) post-hoc test. Statistical significance was set at $P<0.05$.

5.2. Results
OFT

Center zone time following administration of various drug doses is presented in FIG. 43A. Analysis revealed a significant main effect ($P<0.05$) for drug dose. Post-hoc multiple comparisons of center zone time across drug doses indicated a significant difference between control (90.9±11.6 s) and two doses of FQSE (SEQ ID NO:10): 0.5 mg/kg (204.1±46.6 s; P=0.0017) and 3 mg/kg (166.2±18.4 s; P=0.038) of the peptide. Center zone entries following administration of various drug doses are presented in FIG. 43B. Analysis revealed a significant main effect (P<0.05) for drug dose. Post-hoc multiple comparisons of center zone entries across drug doses indicated significant differences between vehicle (33.6±3.9) and four test groups: 0.01 mg/kg (49.1±6.5; P=0.048), 0.5 mg/kg (54.2±8.3; P=0.009), 3 mg/kg (54.1±4.6; P=0.011), diazepam (54.3±6.2; P=0.0089). Total distance (cm) following administration of various drug doses are presented in FIG. 43C. Analysis revealed a significant main effect (P<0.05) for drug dose. Fisher's LSD post-hoc test yielded significant differences between vehicle (4441±292 cm) and two test groups: 0.5 mg/kg (5338±316.2 cm; P=0.014) and diazepam (5289±263 cm; P=0.02).

EPM

Figure 44:
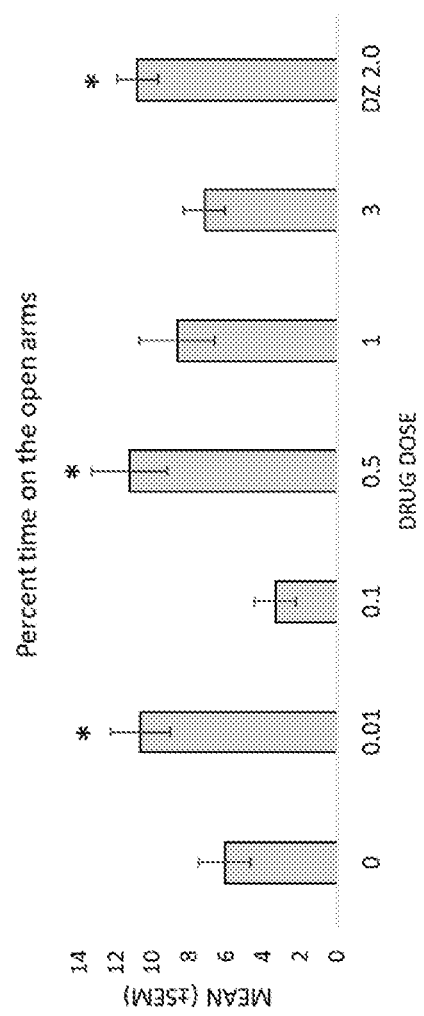
FIG. 44 illustrates the effects of various doses of FQSE (SEQ ID NO:10) and diazepam (DZ) on percent time spent on the open arms (%) in the EPM. *–$p<0.05$ vs vehicle (0). One-way ANOVA with Fisher's Least Significant Difference (LSD) post-hoc test.

Percent time on the open arm following EPM tests is presented in FIG. 44. Analysis revealed a significant main effect (P<0.05) for drug dose. Fisher's LSD post-hoc test revealed significant differences between vehicle (6.1±1.4%), two test groups: 0.01 mg/kg (10.6±1.6%; P=0.032), 0.5 mg/kg (11.3±2.05%; P=0.015) and diazepam (10.8±1.11%; P=0.028).

FST

Results from the forced swim tests for immobility are presented in FIG. 45A. Analysis of immobility measures revealed a significant main effect for drug dose (P<0.001). Fisher's LSD post-hoc test indicated significant differences between vehicle (231.1±7.99 s) and two drug doses: 0.5 mg/kg (157.1±7.98 s; P<0.0001) and ketamine 10 mg/kg (196.4±8.9 s; P<0.008). Ketamine was also associated with a significant decrease in immobility compared to 0.1 mg/kg peptide (238.1±9.19 s; P=0.003). No significant differences were noted between any of the other test doses. Mobility measures are presented in FIG. 46B. Analysis of mobility measures revealed a significant main effect for drug dose (P<0.001). Fisher's LSD post-hoc test indicated significant differences between 0.5 mg/kg (142.9±7.98 s; P<0.0001) and vehicle (68.6±7.99 s). Mobility following ketamine administration (103.6±8.9 s) was also greater compared to the vehicle (P=0.008) and 0.1 mg/kg peptide dose (P=0.0032). No significant differences were noted between any of the other test doses.

5.3. Discussion

This study addresses the behavioral effects of various doses of FQSE (SEQ ID NO:10) tetrapeptide in comparison with diazepam or ketamine administration.

In the OF, it was uncovered that the FQSE (SEQ ID NO:10) treatment resulted in the increment of distance travelled (at a dose of 0.5 mg/kg) as well as the increment in time spent in the center (at a dose of 0.5 and 3 mg/kg) and the number of center entries (at a dose of 0.01, 0.5, 3 mg/kg). The behavior of animals in OF test reflects the balance between the exploratory motivation and fear in novel environment. The decline in thigmotaxis together with increased locomotion suggests the reduction of anxiety in rats which received FQSE (SEQ ID NO:10). The most prominent effect of the peptide was observed at a dose of 0.5 mg/kg and it was comparable to those of diazepam. The peptide at all doses didn't cause sedation.

In the EPM, it was observed the reduction of time spent on the open arms after FQSE (SEQ ID NO:10) treatment at a dose of 0.01 and 0.5 mg/kg. The EPM test has a strong predictive validity for screening anxiolytic drugs. The behavioral outcomes of FQSE (SEQ ID NO:10) treatment in this test suggest anxiolytic-like activity of the peptide at a dose of 0.01 and 0.5 mg/kg.

The FS test is a valid tool for evaluating drugs with potential antidepressant-like activity. In the current study, a significant reduction of time spent immobile and increased—spend actively swimming after FQSE (SEQ ID NO:10) administration at a dose of 0.5 mg/kg were observed. These changes are similar to those observed after ketamine treatment and suggest antidepressant-like effect of the peptide. Rats treated with other doses of peptide did not differ from animals, which received saline.

5.4. Conclusion

In the current study, the effects of various doses of FQSE (SEQ ID NO:10) on the behavior of Sprague-Dawley rats in the open field were assessed using the elevated plus maze and forced swim test. The behavioral changes after FQSE (SEQ ID NO:10) administration partially recapitulate those, observed in diazepam-treated rats in OF and EPM test and ketamine-treated in FST. The most prominent anxiolytic-like and antidepressant-like effects of the peptide were seen at a dose of 0.5 mg/kg and 0.01 mg/kg, depending of behavioral paradigm. The results propose dose-dependent activity of FQSE (SEQ ID NO:10), with maximal efficacy at an intranasal dose of 0.5 mg/kg.

Example 6: The Study on the Anxiolytic and Antidepressant Effects of FQSE (SEQ ID NO:10) Peptide in the Model of Chronic Unpredictable Mild Stress (CUMS)

The aim of this study was to investigate the anxiolytic and antidepressant potential of different doses of FQSE (SEQ ID NO:10) peptide after chronic intranasal administrations in CUMS model.

6.1. Materials and Methods.

6.1.1. Animals 110 male rats of the Wistar line from the Stolbovaya laboratory animal nursery were used in the experiment. The animals were kept in standard as required for biological laboratories (Laboratory Animal Regulations and Guidelines, Moscow, 2003). Environmentally friendly hardwood shavings were used as bedding (TU 5313-001-1897639-92). The rats had free access to food and water. Daylight simulation lasted from 7:00 to 19:00 and illumination during the light time was 70-90 lux. The temperature in the permanent holding room was 24° C. All procedures involving animals were conducted in accordance with the European (Directive 2010/63/EU of the European Parliament and of the Council of 22 Sep. 2010 on the protection of animals used for scientific purposes) and the Russian ("GOST 33216-2014 Guidelines for the maintenance and care of laboratory animals. Rules for the maintenance and care of laboratory rodents and rabbits") bioethical guidelines.

All experiments with animals were performed according to the rules of humane treatment of laboratory animals. For this experiment, the requirements of the following orders were undertaken: Order MZ RF 267 from 19 Jun. 2003 "Rules of Laboratory Practice of the Russian Federation", "Manual on Experimental (Preclinical) Study of New Pharmacological Substances", 2005 (Second Edition) and the "Guidelines for Maintenance and Breeding of Laboratory Animals in Nurseries and Experimental Biological Laboratories (Vivariums A) and Their Use in Scientific, Educational and Industrial Purposes", M., 2003.

After delivery to the vivarium, the animals were kept in quarantine for 2 weeks (adaptation period) before the start of the experiment.

6.1.2. Experimental Protocol

The experimental protocol is shown in FIG. 46. At the onset of the experiment, the animals were placed in individual cells to conduct a sucrose preference test and determine the level of anhedonia for the elimination of the animals with a sucrose preference index lower than 65% (SP1).

Animals that met the selected criteria were divided into a group of native controls (n=10) and a group subjected to chronic unpredictable mild stress (CUMS) (n=52).

6.1.3. Stress Protocol

During stress, the animals were placed in individual cells and exposed to stressful conditions each day for 26 days. Two stressors were used daily, applied in the following order:

Day 1. 10 am-6 pm, rats were placed in a cold room for an hour. From 6 PM to 10 am the lights were turned on and off every 2 hours.

Day 2. 10 am-6 pm, cage tilted to 45°. From 6 PM to 10 am water deprivation.

Day 3. 10 am-6 pm, stroboscopic light. From 6 PM to 10 am the light was left on overnight.

Day 4. 10 am-6 pm, wet bedding. From 6 PM to 10 am the animals were put in a small mouse cage.

Day 5. 10 am-6 pm, no bedding. From 6 PM to 10 am the lights were turned on and off every 2 hours.

Day 6. 10 am-6 pm, a new rat was placed in the cage (6-month-old). From 6 PM to 10 am the light was left on overnight.

Day 7. 10 am-6 pm, white noise. From 6 PM to 10 am a stroboscopic light was turned on at night.

Day 8-26. Repetition of previously used stressors in the specified sequence.

After the stress procedure, the animals were retested for sucrose preference (SP2) to assess the effectiveness of the stress and identify rats showing signs of anhedonia. As a result of the evaluation 1 rat was excluded from the native control group due to low sucrose preference values (<65%). 40 animals were selected for the experimental groups.

6.1.4. Experimental Groups

All selected animals were divided into the following groups: 1) "CUMS+vehicle" in which 10 males received saline i.n. 2) "CUMS+0.05" in which 10 males were administered 0.05 mg/kg i.n. of the experimental drug dissolved in saline, 3) "CUMS+0.5" in which 10 males were administered 0.5 mg/kg/i.n. of the experimental drug dissolved in saline, 4) "CUMS+Diaz" in which 10 males were administered 0.5 mg/kg/i.p. of Diazepam, and 5) "Control" in which 9 males were administered saline intraperitoneally and intranasally. Experimental substances were administered daily starting from the 58-59 day of the experiment. The administration took place 30 minutes before the start of behavioral testing. On days when there were no tests, the substances were administered in the morning.

TABLE 2

The number of injections of the studied substances to the beginning of behavioral testing

| Test | Number of Peptide Injections |
|---|---|
| Elevated Plus Maze (Days 58-59) | 1 |
| Social Interaction (Days 61-62) | 4 |
| Female Urine Sniffing test (Days 65-66) | 8 |
| Novelty Suppressed Feeding (Days 68-69) | 11 |
| Sucrose Preference (Days 73-75) | 16 |
| Porsolt Forced Swimming Test (Days 75-76) | 18 |
| Collecting Brain Samples (End of Experiment, Days 79-80) | 22 |

6.1.5. Behavioral Tests

Sucrose Preference Test (SPT)

A test was used to determine the preference for a sucrose solution to assess the state of anhedonia (rejection of pleasure), a key symptom of depression. Animals were subjected to 2 drinkers for 24 hours with free access to them. One contained only water, the other—1% sucrose solution. The day before the test, the rats were presented with a 2% sucrose solution for 2 hours in the evening. During testing, the drinkers were swapped in order to avoid developing a place preference. The drinkers were pre-weighed, and the volume of liquid consumed was calculated based on the mass difference. The measured parameters included the volume of regular water, sweet water, and the total volume of liquid consumed. The preference index was calculated using the formula:

The volume of sweet water consumed*100%/Total volume of liquid consumed.

Elevated Plus Maze Test (EPM)

The Elevated Plus Maze test was used to assess the level of anxiety, motor, and exploratory activity of laboratory animals. The apparatus consisted of two closed and two open arms opposite to each other (arm's length 45 cm) with the height of the sides of the closed arm −10 cm. The entire installation was raised on a stand 70 cm above the base. Rats were placed in the center of the maze with their heads facing the open arm. Within 5 minutes the number of exits to open arms and time spent in them, the number of transitions between arms, the time of rest, the duration and number of grooming acts, the number of stretch-attend postures into the open arms of the maze, and the number of rears were recorded. Normally, rodents tend to stay in the dark arms. An important indicator of the anxiolytic effect of the drug is increased number and duration of exits to the open arms of the maze.

Social Interaction Test (SI)

To assess the social activity and depressive state of the animals, a test that evaluates a social interaction of rodents was used. In the test, a juvenile male aged 1 month was placed in the home cage. Within 10 minutes the duration and number of social contacts with the juvenile male and number of threatening and aggressive contacts were recorded. Social contacts were considered to be the reaction of following and sniffing the juvenile male, etc. (Vishnivetskaya et al. (2007). Effect of MAO A deficiency on different kinds of aggression and social investigation in mice. Aggress. Behav. 33(1), 1-6). Normally, a juvenile male does not pose any danger to an adult rat, so rats in calm states demonstrate fairly high social interaction indicators and low aggressiveness. Signs of aggression are the result of deviations in behavior and decreased social contact may indicate the presence of depressive behavior.

Novelty Suppressed Feeding Test (NSFT)

To assess anxiety and food motivation, a test for eating behavior in a new environment was used. In this test, a laboratory animal that had previously been subjected to food deprivation for 24 hours was placed in a square arena (50×50×40 cm) for 5 minutes (Jiao et al. (2019). Influence of Xiaoyaosan on depressive-like behaviors in chronic stress-depressed rats through regulating tryptophan metabolism in hippocampus. Neuropsych. Dis. Treat. 15, 21). A treat (a food pellet) was placed in the brightly lit center of the arena. The time to start eating and the duration of consumption were recorded. Due to fear of open lit spaces by rodents, this test is used to assess the level of anxiety. Animals that show high levels of anxiety do not normally approach the treat. Anxiolytic drugs significantly reduce the time to start eating. Chronic administration of antidepressants also leads to a decrease in the latency to start eating in this test.

Female Urine Sniffing Test (FUST)

The FUST test was used to evaluate anhedonia, sexual motivation, and exploratory behavior associated with a depressive condition in rodents (Gould et al. (2009). Mood and anxiety related phenotypes in mice. Humana Press). The test was performed under dim light (3 Lux) in a cage with bedding. In the first stage of the experiment, the animal was presented for 3 minutes with a cotton swab moistened with distilled water. The latency of the approach to the swab, the time, and the number of sniffs were recorded. After a 45-minute break, the rat was presented with a cotton swab moistened with the urine of a female of the same line in estrus. The latency of the approach to the swab, the time and the number of sniffs were also recorded. To determine the preference, an index was calculated using the formula: time spent sniffing urine*100%/total sniffing time. Mature males show a high level of interest towards the swab with female urine, showing a high sexual motivation. It is expressed as a decreased latency of approach to the moistened swab and a longer duration of the interaction. At the same time, low rates of interaction with the swab may indicate a disturbance of exploratory behavior and development of anhedonia—the main symptom of clinical depression.

Porsolt Swimming Test

The forced swim test is a rodent behavioral test used for the evaluation of antidepressant drugs, antidepressant efficacy of new compounds, and experimental manipulations that are aimed at rendering or preventing depressive-like states. During the test, each animal was placed in a cylinder filled with water (temperature 24° C.) to 30 cm for 8 minutes. The vessel diameter was 31 cm and height 40 cm. In the last 6 minutes, the duration of active (vigorous movement of all limbs) and passive (weak strokes of the hind limbs) swimming and immobility duration were recorded. The immobility parameter reflects the animal's state of desperation and refusal to attempt to escape from the experimental setup. This may reflect the state of apathy and motor retardation that occurs in clinical depression.

6.1.6. Statistical Analysis

The Shapiro-Wilk criterion was used to check the distribution of data and based on this, parametric or non-parametric statistical comparison criteria were selected.

Parametric analysis in the case of normal distribution within the number of stands, time of social interaction, index of female urine preference and sucrose preference was performed using ANOVA variance analysis and Tukey multiple comparison criterion for post hoc analysis. Nonparametric analysis (in the case of an abnormal distribution) was performed using the Kruskal-Wallis test with the Dunn multiple comparison test for post hoc analysis. Differences were considered significant at $p<0.05$.

6.2. Results.

6.2.1. EPM

The test was performed to determine the level of anxiety in rats, which may be increased in animals with a depressive-like phenotype.

Testing for normality using the Shapiro-Wilk test did not confirm the normal distribution of data in groups, so the results will be evaluated using non-parametric criteria. The results of applying the Kruskal-Wallis criterion revealed a significant effect of the Treatment factor (H (4, N=49)=21.5; p=0.0002) on time spent on the open arms. A significant decrease of this parameter in animals from the "CUMS+ veh" group (p=0.04) in comparison with the control group was revealed, which suggests the development of anxious phenotype (FIG. 47A). There was no difference between control and peptide-treated animals, which suggests normalization of the stress level. FQSE (SEQ ID NO:10) at a dose of 0.05 mg/kg also showed a trend towards increment of this parameter in comparison with vehicle treatment (p=0.07), which may suggest a mild anxiolytic effect of the peptide. An increase in the time spent on the open arms were revealed for animals treated with diazepam after chronic stress compared to stressed animals treated with a solvent (p=0.0001) and both doses of the peptide (p=0.05 vs. FQSE (SEQ ID NO:10) 0.05 and p=0.009 vs. FQSE (SEQ ID NO:10) 0.5) (FIG. 47A), which reflects its strong anxiolytic effect.

Moreover, there was a significant main effect for Treatment (H (4, N=49)=12.6; p=0.013) on the freezing time in the EPM test. An increase of freezing was observed only in animals treated with diazepam (p=0.006 vs. control group) (FIG. 47B), which may be a result of a strong sedative effect of the drug.

6.2.2. SI

The social interaction test indicates interest in social contacts in rats, which may be reduced in a depressive-like state.

Figure 48:
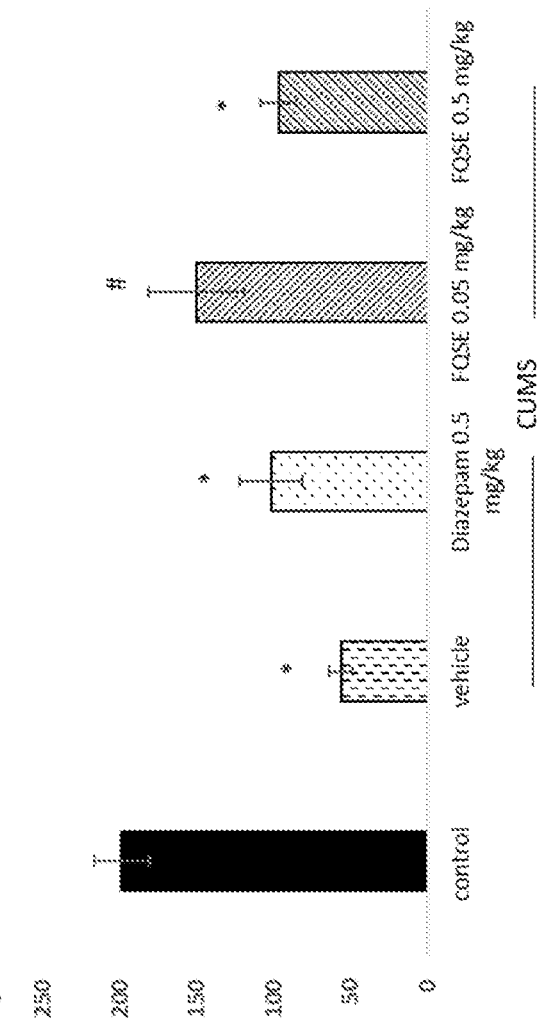
FIG. 48 illustrates the duration of social interactions (in seconds) in SI test after CUMS and four injections of drugs. Each bar represents mean±SEM. *–$p<0.05$ represents significant differences from the control group, and #–$p<0.05$—significant differences from the CUMS+veh group. One-way ANOVA with Fisher's LSD test.

Testing for normality using the Shapiro-Wilk test confirmed normal distribution and so the results will be evaluated using parametric criteria. One-way ANOVA revealed a significant effect of Treatment (F (4, 44)=7.5; p=0.0001) on the time of social contacts. Through multiple pairwise comparisons of groups using Tukey test, a significant decrease was observed in the duration of social contacts in groups of stressed animals which received solvent (p=0.0002), diazepam (p=0.01) and FQSE (SEQ ID NO:10) at a dose of 0.5 mg/kg (p=0.007) compared to control non-stressed rats. While the animals receiving the peptide at a dose of 0.05 mg/kg did not differ in this parameter from the control ones the duration of social contacts in comparison with the CUMS+veh group was significantly higher (p=0.01) (FIG. 48).

6.2.3. FUST

Figure 49:
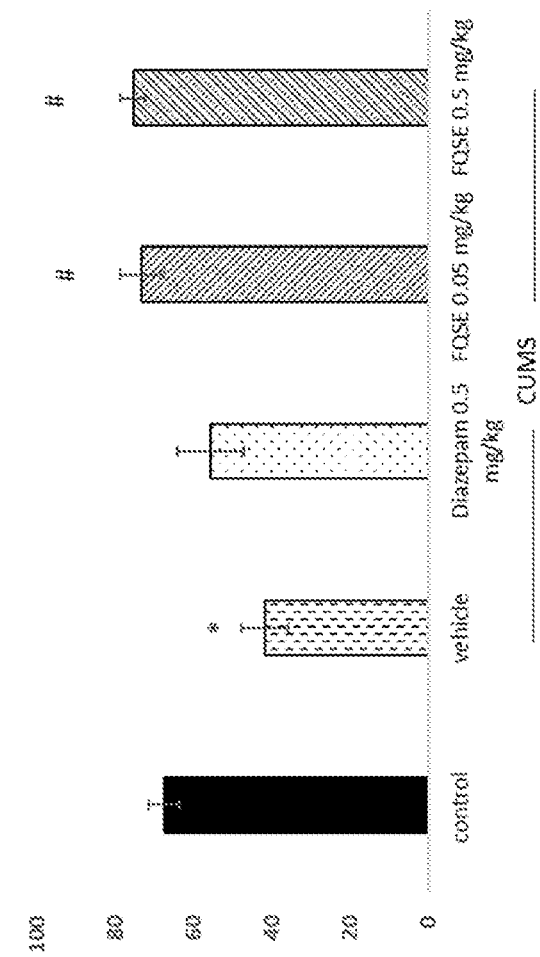
FIG. 49 illustrates the female urine preference index (in %) in the FUST after CUMS and eight injections of the drugs. Each bar represents mean±SEM. *–$p<0.05$ represents significant differences from the control group, and #–$p<0.05$—significant differences from the CUMS+veh group. One-way ANOVA with Fisher's LSD test.

Testing for normality confirmed normal distribution so the results will be evaluated using parametric criteria. One-way ANOVA showed a significant effect for Treatment (F (4, 44)=5,8073; p=0.0007) on the female urine preference index. Post hoc analysis revealed a decrease in the group of stressed animals receiving solvent compared to the control group (p=0.03). Administration of the peptide at doses of 0.05 and 0.5 mg/kg led to increased preference for female urine in rats in comparison with animals that had undergone stress and received vehicle (p=0.003 and p=0.001) (FIG. 49). Diazepam had no effect on animal behavior in this test.

6.2.4. NSFT

The NSFT test was performed to determine the level of anxiety in rats.

Figure 50:
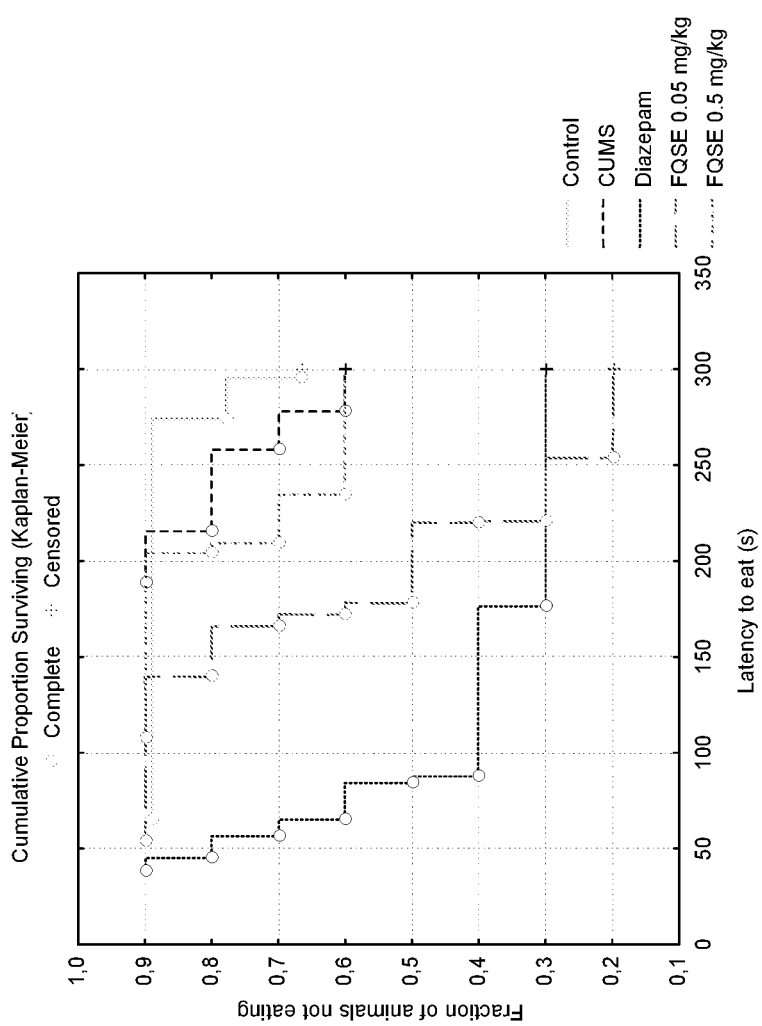
FIG. 50 illustrates Kaplan-Mayer Survival Curves. On the x axis—Latency (in seconds) to start eating, Y—the proportion of animals that did not start eating. Introduction of substances has been carried out for eleven days. *–$p<0.05$ represents significant differences from the control group, and #–$p<0.05$—significant differences from the CUMS+veh group. Chi-square criterion with Cox-Mantel test.

The latency to start eating was assessed using Kaplan-Meyer multiplier estimates, which take into account the censored variables. The resulting curves are shown in FIG. 50.

The use of the Chi-square criterion revealed significant differences between the groups (Chi sq=12.1; df=4; p=0.01). The groups were compared using the Cox-Mantel test. It was shown that chronic stress did not lead to an increase in the latency to approach food (F (6, 8)=1.3 p=0.35 vs. control group). It should be noted that in the control group more than 60% of animals did not approach food, which is due to the high level of stress in this test. The introduction of diazepam led to a significant decrease in latency compared to the control and CUMS+veh. groups (F (6, 14)=3.5; p=0.02 and F (8, 14)=3.2; p=0.02, respectively). A similar effect was observed in the group of rats receiving the peptide at a dose of 0.05 mg/kg; a significant increase in time was observed compared to the control and CUMS+veh. groups (F (6, 16)=4.2; p=0.009 and F (8, 16)=3.71 p=0.01). Animals receiving FQSE (SEQ ID NO:10) at a dose of 0.5 mg/mg did not differ from the control group and stressed animals receiving saline.

6.2.5. SPT

This test characterizes the degree of anhedonia in animals that have undergone chronic stress.

Figure 51:
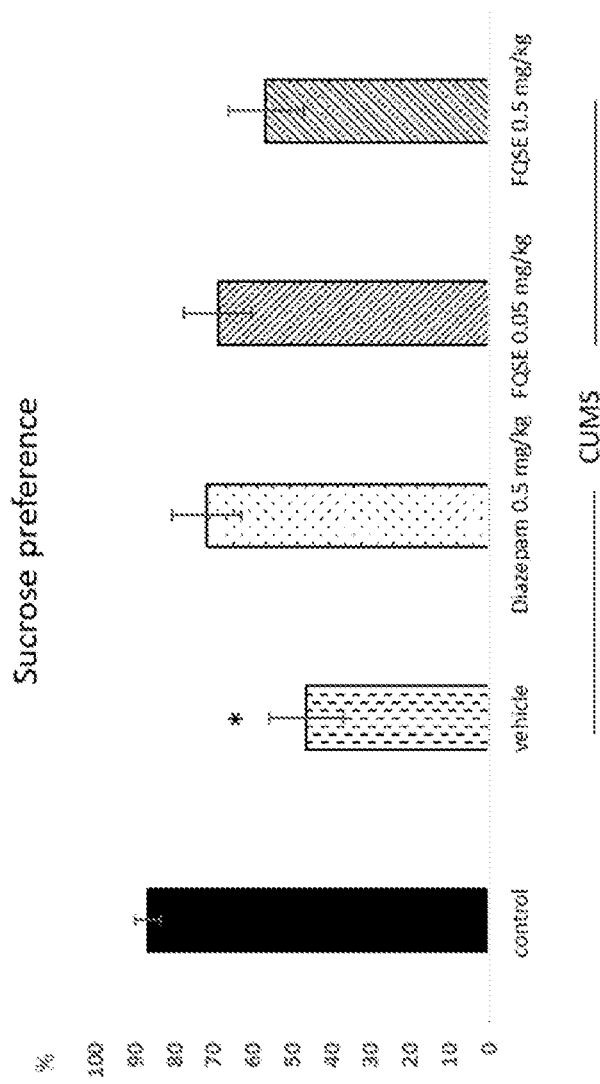
FIG. 51 illustrates the sucrose preference index (in %) after CUMS and sixteen injections of the studied substances. Each bar represents mean±SEM. *–$p<0.05$—significant differences from the control group. Kruskal-Wallis with Dunn's multiple comparison test.

Testing for normality using the Shapiro-Wilk test did not confirm normal distribution so the results will be evaluated using non-parametric criteria. The results of Kruskal-Wallis showed a significant effect of the Treatment factor on the sucrose preference index (H (4, N=49)=11.8; p=0.018). Animals that underwent stress and received a solvent had a significantly lower index than control animals (p=0.017). Stressed animals receiving diazepam and peptide showed no significant changes in comparison with the control or CUMS+veh groups (FIG. 51).

6.2.6. FST

A widely used test for evaluating the potent antidepressant activity of substances.

Figure 52:
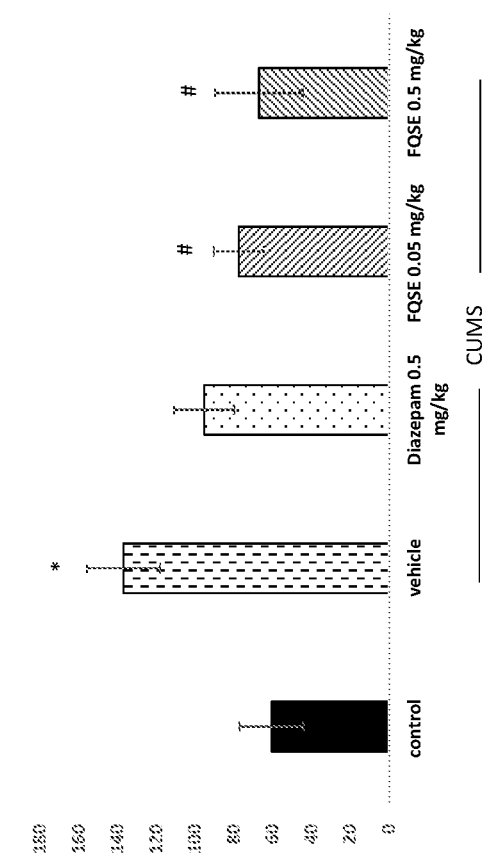
FIG. 52 illustrates time spent immobile (in seconds) in the FST after CUMS and eighteen injections of the studied substances. Each bar represents mean±SEM. *–$p<0.05$ represents significant differences from the control group, and #–$p<0.05$—significant differences from the CUMS+veh group. Kruskal-Wallis with Dunn's multiple comparison test.

Testing for normality using the Shapiro-Wilk test did not confirm the normal distribution so the results will be evaluated using non-parametric criteria. The results of the Kruskal-Wallis test revealed a significant effect of the Treatment on the immobilization time (H (4, N=49)=12.2; p=0.01). A significant increase in immobilization in the CUMS+veh group was observed in comparison with the control group (p=0.04). FQSE (SEQ ID NO:10) at a dose of 0.5 mg/kg significantly reduced the immobilization time in this test compared to the CUMS+veh. group (p=0.03) (FIG. 52). Diazepam and peptide at a dose of 0.05 mg/kg did not differ from either control or stressed group receiving saline.

6.3. Discussion

The model of chronic stress led to the development of a persistent depressive-like condition observed in all the behavioral tests used. Diazepam administration at a dose of 0.5 mg/kg produced only an anxiolytic effect in EPM and NSFT tests and had no effect on animals' behavior in tests for a depressive-like condition (Table 3).

The experimental drug studied had an antidepressant-like effect in the Porsolt test, the social interaction test, and affected the anhedonia level in the female urine preference test. The peptide at both doses had an antidepressant-like effect as well, but not in all behavioral tests. The most pronounced effect of the peptide in both doses was observed in the FUST test. The antidepressant effect of FQSE (SEQ ID NO:10) was observed after the 4th injection.

At a dose of 0.05 mg/kg, FQSE (SEQ ID NO:10) had an anxiolytic-like effect in NSFT. It should be noted that in this test, an anti-anxiety effect was observed after the chronic administration of clinically used antidepressants; selective serotonin reuptake inhibitors (SSRIs).

6.4. Conclusions

This model of unpredictable chronic stress leads to the development of a persistent depressive state in rats.

Administration of diazepam has a prominent anxiolytic and sedative effects.

FQSE (SEQ ID NO:10) at doses of 0.05 and 0.5 mg/kg has an antidepressant-like effect in various behavioral tests.

FQSE (SEQ ID NO:10) at a dose of 0.05 mg/kg showed an anxiolytic effect in NSFT and slight anxiolytic-like effect in EPM, without signs of sedation.

TABLE 3

The results obtained in the model of chronic stress after the introduction of the studied substances.

| | CUMS | | | |
|---|---|---|---|---|
| Test | Vehicle | Diazepam | FQSE (SEQ ID NO: 10) 0.05 mg/kg | FQSE (SEQ ID NO: 10) 0.5 mg/kg |
| EPM (1 administration) | — | anxiolytic and sedative effects | slight anxiolytic-like effect | — |
| SI (4 administrations) | depressive-like behavior | — | antidepressant-like effect | — |
| FUST (8 administrations) | anhedonia, depressive-like behavior | — | antidepressant-like effect | antidepressant-like effect |
| NSFT (11 administrations) | — | anxiolytic effect | anxiolytic effect | — |
| SP (16 administrations) | anhedonia, depressive-like behavior | — | — | — |
| FST (18 administrations) | depressive-like behavior | — | — | antidepressant-like effect |

Example 7: Effects of FQSE (SEQ ID NO:10) in an Animal Model of Post-Traumatic Stress Disorder (PTSD)

To date, there is no effective treatment for PTSD now: the first line treatment of PTSD includes SSRIs, though a report from the Institute of Medicine concluded that the available evidence was inadequate to support the efficacy of SSRIs or other pharmacotherapy in PTSD (Treatment of posttraumatic stress disorder: An assessment of the evidence. Washington, DC: National Academies Press. Institute of Medicine; 2008). Clearly, the discovery of novel pharmacotherapeutic treatments for anxiety represents a large unmet medical need.

The aim of the study was to evaluate the effects of FQSE (SEQ ID NO:10) peptide in the model of PTSD.

7.1. Materials and Methods.
7.1.1. Animals and Housing

A total of 120 male Sprague Dawley rats (Charles River, Wilmington, MA) were used for the studies. Rats were initially housed 3-5 to a cage in polypropylene cages in circular towers (Animal Care Systems, Inc, Centennial, CO) located within a temperature- and humidity-controlled vivarium that was maintained on a 12:12 light/dark cycle (lights on at 6 AM). Rats weighed about 250-350 gm at the start of the experiment and were at least 100 days old. Food and water were available ad libitum throughout the study. All procedures were approved by the University of Houston Institutional Animal Care and Use Committee in accordance with the National Institutes of Health Guidelines.

7.1.2. Animals and Housing

Doxazosin (DOX, Sigma-Aldrich, St. Louis, MO, USA, 1 mg/kg, IP) was prepared in sterile saline. Previously it has been shown that DOX is effective in the treatment of some PTSD symptoms in veterans (Rodgman et al. (2016). Doxazosin XL reduces symptoms of posttraumatic stress disorder in veterans with PTSD: a pilot clinical trial. J. Clin. Psychiat., 77(5), e561-565).

The two doses of FQSE (SEQ ID NO:10) (0.05 and 0.5 mg/kg, CS, Menlo Park, CA) were prepared fresh for each test day in sterile saline and administered intra-nasally 30 minutes prior to testing. Each dose was administered in a randomized order across groups. Prior to dosing, the rats were lightly anesthetized (till loss of righting reflex) with isoflurane (2.5%, 0.5 L/min oxygen), placed in the recumbent position, then a thin plastic pipette (Fischer Scientific) inserted into the nares and peptide administered at a volume of 15-20 uL per nares. The same procedure with isoflurane was used to administer doxazosin however the drug was administered IP. Individuals performing behavioral tests were blind to drug treatment.

7.1.3. Behavioral Apparatus and Testing Procedures

Predator odor stress exposure and conditioned place aversion protocols were based on previously published studies (Edwards et al. (2013). Traumatic stress reactivity promotes excessive alcohol drinking and alters the balance of prefrontal cortex-amygdala activity. Transl. Psychiatry, 3(8), e296; Roltsch et al. (2014). Predator odor stress alters corticotropin-releasing factor-1 receptor (CRF1R)-dependent behaviors in rats. Neuropharmacology, 79, 83-89; Whitaker et al. (2015). Blunted hypothalamo-pituitary adrenal axis response to predator odor predicts high stress reactivity. Physiol. Behav., 147, 16-22). Rats were exposed to no odor (sterile saline) or predator odor (bobcat urine, PMart, Sandy Point, ME) using a place conditioning apparatus (MED Associates, Fairfax, VT) consisting of two compartments (8×8×11 in) that differed in both visual (wall color) and tactile (floor texture) cues connected by a smaller middle compartment (5×8×11 in). Compartments were divided by automated guillotine doors. A non-biased conditioning method was used so that rats did not prefer one chamber over another. Between 8-10 am (AM), rats were placed in the middle compartment and guillotine doors raised and allowed to explore the conditioning apparatus for 15 minutes (habituation). Time in each compartment and activity were recorded via infra-red sensors and tabulated with commercially available software (MED Test, ver 4.2.0.0, MED Associates, Fairfax, VT). Between 2-4 pm (PM), rats were again allowed to explore the conditioning apparatus and time and activity recorded (pre-conditioning baseline). Twenty-four hours later rats were randomly assigned to a chamber and exposed to saline (AM) while confined to the conditioning compartment for 15 minutes. In the evening (PM) on the same day, rats were confined in the opposite compartment and exposed to predator odor (or no odor) for 15 minutes. During the pairings a 2×2 inch square piece of filter paper placed in a weigh boat was infused with 5 mLs of saline or bobcat urine and put under the grid floor of the chamber. The day after predator-odor stress, rats were placed in the center compartment and allowed to explore the entire apparatus for 15 minutes. Rats did not have direct access to the bobcat urine. The entire apparatus was cleaned with disinfectant after each conditioning session.

7.1.4. Statistical Analysis

The statistical analysis was conducted using time in the odor-paired compartment subtracted from baseline measures for 117 rats. Analysis of time in designated chambers between no odor and odor exposed groups administered vehicle was conducted using an independent t-test. Potential differences between groups that were not odor exposed and odor exposed groups were analyzed using One-Way ANOVA with drug dose as the primary factor. Significant main effects were followed by pairwise multiple comparison procedures (Student Newman-Keuls Method). Significance was set at $P<0.05$.

7.2. Results

Figure 53B:
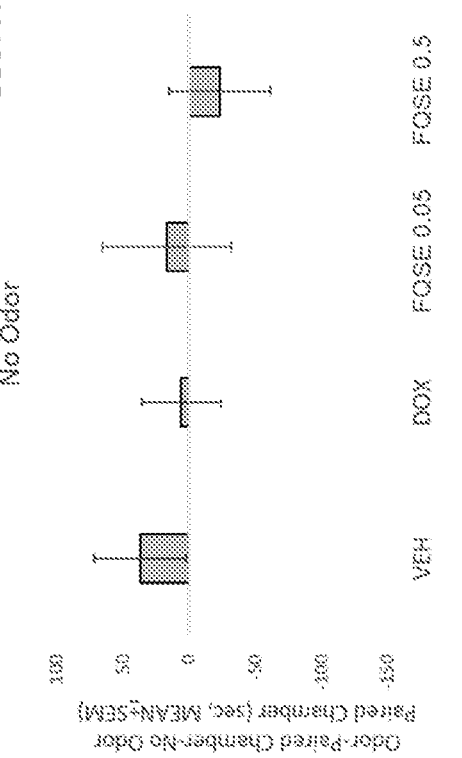
FIGS. 53A, 53B and 53C illustrate the behavior of rats in the predator odor stress exposure and conditioned place aversion paradigms.
Figure 53C:
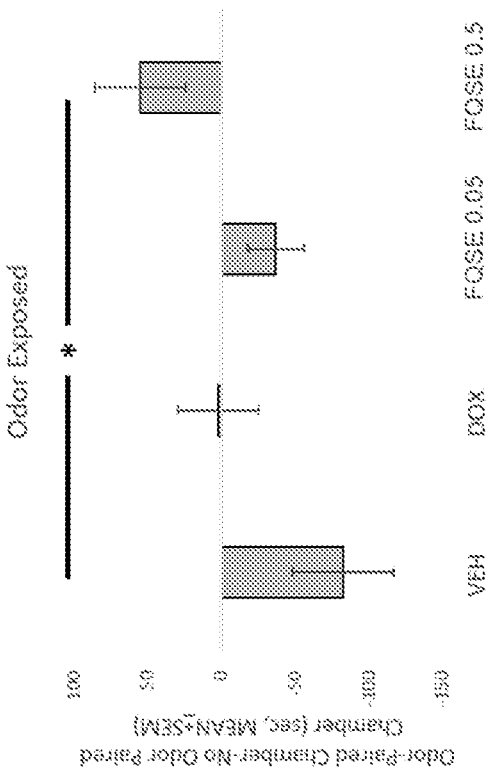
Figure 53A:
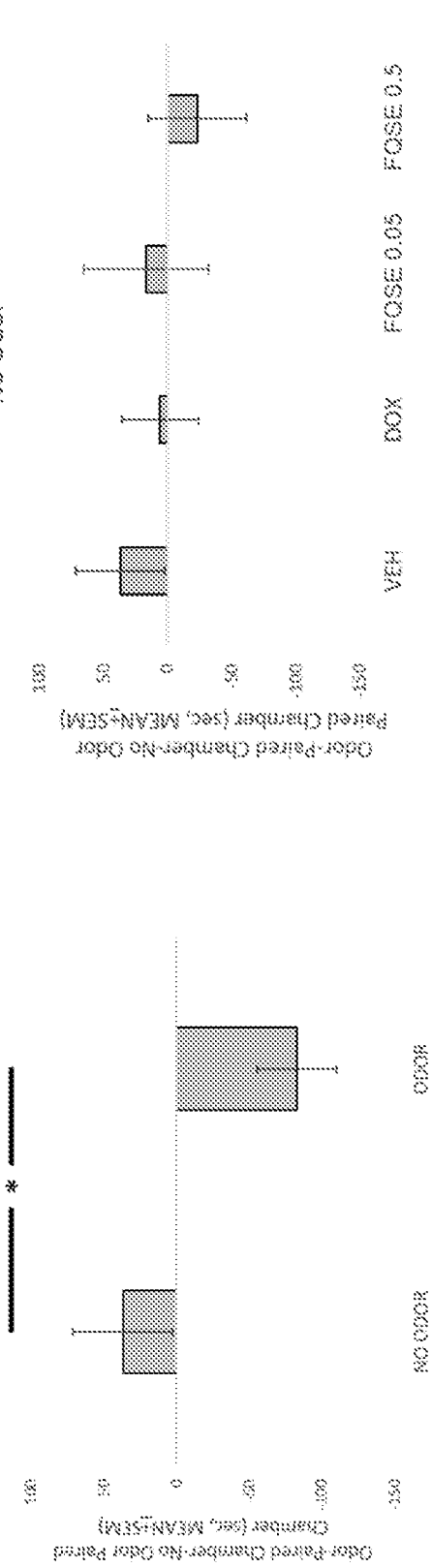

FIG. 53A shows no odor and odor exposed groups treated with VEH. Analysis confirms predator-odor exposure produced a significant (t (27)=2.690, P=0.012) conditioned place aversion at 24 hours post-exposure. As presented in FIG. 53B, ANOVA revealed no significant differences in treatment groups following no exposure to predator odor (P=0.746). Analysis of times from groups exposed to predator odor revealed a significant main effect for drug dose (F (3,57)=2.780, P=0.050). Post-hoc multiple comparisons yielded a significant difference between the highest peptide dose (FQSE (SEQ ID NO:10) 0.5) and VEH (P=0.036) (FIG. 53C) and a trend toward a significant difference between low peptide dose (FQSE (SEQ ID NO:10) 0.05) and the high peptide dose (P=0.159).

7.3. Conclusions

This report describes the effects of a peptide test article administered intra-nasally on tests in an animal model of PTSD. Primary findings include:1) confirmation of predator-odor induced conditioned place aversion as demonstrated previously, 2) no apparent adverse effects of drug or peptide and 3) significant attenuation of predator odor-induced place aversion in rats administered the highest dose of the peptide.

Predator odor-induced place aversion, an animal model of PTSD, was robust and replicates previous studies (Edwards et al. (2013). Traumatic stress reactivity promotes excessive alcohol drinking and alters the balance of prefrontal cortex-amygdala activity. Transl. psychiatry, 3(8), e296). Analysis of groups that received DOX and peptide and were not exposed to predator odor demonstrated normal behavior as no significant effects were found for the time in randomly paired chambers. Total activity (not shown) also did not differ between groups. As shown in FIG. 53C, the highest dose of the peptide (FQSE (SEQ ID NO:10)0.5) completely attenuated predator-odor induced place aversion. DOX, a medication that has shown efficacy in humans with PTSD (Rodgman et al. (2016). Doxazosin XL reduces symptoms of posttraumatic stress disorder in veterans with PTSD: a pilot clinical trial. J. Clin. Psychiat., 77(5), e561-565), also attenuated predator odor-induced place aversion however there was not a significant difference from VEH using the statistical model employed. Taken together, the data support further development of the peptide test article as a potential treatment for PTSD.

Example 8: The Study of the Effects of Intranasal Administration of FQSE (SEQ ID NO:10) on the Behavioral and Endocrine Parameters of Rats in "Learned Helplessness" Model of Depression The aim of the study is to investigate the potential antidepressant and anxiolytic effect of intranasal administration of the peptide GABA-AR modulator FQSE (SEQ ID NO:10) on the behavioral and endocrine parameters of rats in the "learned helplessness" (LH) depression model.

8.1. Materials and Methods.
8.1.1. Animals

The study was performed on 45 adult male Wistar rats 220-250 g, (average weight 230 g) from the "Collection of laboratory mammals of different taxonomic affiliations" of the IPh RAS, supported by the program of bioresource collections of the FANO of Russia, kept in standard conditions. All procedures involving animals were conducted in accordance with the European (Directive 2010/63/EU of the European Parliament and of the Council of 22 Sep. 2010 on the protection of animals used for scientific purposes) and the Russian ("GOST 33216-2014 Guidelines for the maintenance and care of laboratory animals. Rules for the maintenance and care of laboratory rodents and rabbits") bioethical guidelines.

8.1.2. Test Substance

Peptide GABA-A modulator FQSE (SEQ ID NO:10) (LC) was administered intranasally (i.n) daily for 10 days at a dose of 0.5 mg/kg or 2.5 mg/kg. To prepare solutions of the FQSE (SEQ ID NO:10) peptide, 0.3% bicarbonate buffer was prepared (3 g of sodium bicarbonate $NaHCO_3$ per 1 liter of $ddH_2O$, pH 8; to prepare the solution, the buffer was collected through a filter nozzle with a 0.45 μm Millex syringe (Millipore)). A solution for i.n. administration of 2.5 mg/kg in a volume of 20 μl (single administration) contained 0.575 mg FQSE (SEQ ID NO:10), and a solution for intranasal administration of 0.5 mg/kg in a volume of 10 μl (single administration) contained 0.115 mg of FQSE (SEQ ID NO:10). Weigh was measured on an analytical balance, with an accuracy of 0.0001 g, the solution was prepared with a margin of 0.5 ml. For the experiment, a freshly prepared FQSE (SEQ ID NO:10) solution was used; for the second day, this solution was stored in a refrigerator at +4° C.

8.1.3. Drug of Comparison

The tetracyclic antidepressant Maprotiline (Lyudiomil), a monoamine reuptake inhibitor, was used as a positive control. Animals received a daily intraperitoneal injection (i.p) of Maprotiline for ten days (M9651, Merck, 4.5 mg/kg, dissolved in saline: 200 μl per administration).

8.1.4. Learned Helplessness (LH) Model

The classical paradigm of "learned helplessness" (LH) was used as an experimental model of depression (Seligman et al. (1975). Learned helplessness in the rat. J. Comp. Physiol. Psychol., 88(2):534-541). The state of "learned helplessness" according to modern concepts adequately reflects anxiety-depressive syndrome, reproducing the main signs of a person's endogenous depression, including the severity of effects of helplessness, hopelessness, and characteristic endocrine disorders. To develop LH, rats were subjected to uncontrolled unavoidable aversive stress (electro cutaneous irritation). The animals were stimulated with electric current (1 mA, 1 Hz, 15 sec) in a closed space of a 13×16×26 cm-sized cage with a conductive floor using an interval of different durations between applying current to the chamber floor so that each rat received 60 stimulations within an hour, which resulted in the development of a persistent depressive-like state. Stimulation was performed automatically using a software randomizer.

8.1.5. «Open Field» Test (OF)

The Open Field test is a classic method for assessing the level of motor activity and exploratory behavior of rodents in new stressogenic conditions. The test was performed in a cage of 90×90×45 cm without a roof, the floor of which was laid out on squares 15×15 cm and lit from above by a 60 W lamp. On the 5th day after stressing in the LH model, the rat was placed in the center of the OF. The following parameters were measured for 5 minutes: latency to start of moving, the number of crossed squares (outside, intermediate and central), the duration of the rears and immobilization time.

8.1.6. «Elevated Plus-Maze» Test (EPM)

EPM testing allows characterizing the behavior of rodents under the variable stress conditions, which makes it possible to assess the level of animal anxiety and anxiolytic effects of drugs. On the 6th day after the experimental exposure, the rats were tested one at a time for 5 min in the EPM installation, located at a height of 75 cm above the floor, and consisting of 2 open illuminated and 2 closed arms with exits. The time spent by the animal inside and outside the closed arms (in the open arms and in the center), the number of transitions between the arms, the number of stretch-attended postures were evaluated. Usually, animals tend to stay in the closed arms, anxiolytic treatment results in an increment of the time spent on the open arms of the maze (Pellow et al. (1985). Validation of open: closed arm entries in an elevated plus-maze as a measure of anxiety in the rat. J. Neurosci. Methods, 14(3), 149-167; Walf et al. (2007). The use of the elevated plus maze as an assay of anxiety-related behavior in rodents. Nat. Protoc., 2(2), 322-328).

8.1.7. «Porsolt Forced Swimming Test», One-Day Modification (FS)

Porsolt's swimming tests (FS) are standard tests for detecting the potent antidepressant-like properties of substances by evaluating the motor activity of rats placed in a glass cylinder. Cylinders have a diameter of 30 cm and a height of 90 cm, ⅔ filled with water with a temperature of 26±1° C. In a one-day modification of the Porsolt test (Porsolt et al. (1977). Behavioral despair in mice: a primary screening test for antidepressants. Arch. Int. Pharmacodyn. Ther., 229(2), 327-336; Slattery et al. (2012). Using the rat forced swim test to assess antidepressant-like activity in rodents. Nat. Protoc., 7(6):1009-14) animals were placed in a cylinder and the following parameters were measured for 5 minutes: the time of active and passive swimming, time spent immobile.

8.1.8. Dexamethasone Test (DXMT)

Evaluation of the stress-evoked release of glucocorticoid hormones (corticosterone, an analog of cortisol in humans)

and its suppression by the introduction of synthetic glucocorticosteroid was performed on the 9-10th day after the development of LH in a two-day dexamethasone test according to the scheme, taking into account the specificity of the circadian rhythm of HPA axis function in rats (Zhukov (1993) The dexamethasone suppression test in genetically different rats exposed to inescapable and escapable electric shocks. Psychoneuroendocrinology, 18(7): 467-474).

On the first day of the test (DXMT1) at 10:00 AM, animals were injected intraperitoneally with saline, then at 04:00 PM on the same day peripheral blood samples were taken to determine the basal level of the hormone, which caused stress, and 30 minutes after taking the rat from the cage and receiving initial sample, re-taken blood to measure hormone stress level.

To study the sensitivity of the HPA system to feedback signals, rats were injected with dexamethasone (10 μg/kg, intraperitoneally) the next day (DXMT2) at 10 am. The procedure for taking blood from the tail vein was repeated after 6 and 6.5 hours. The corticosterone content was determined by enzyme-linked immunosorbent assay with reagent kits "Corticosterone-ELISA" ("Hema", RF) in two parallel samples.

The experimental data were processed by calculating the mean and standard error of the mean in the studied subgroups of animals, n=9 for each point.

8.1.9. Experimental Design

Laboratory rats were divided into 5 experimental groups of 9 animals each:

"Control"—the injection control group had a 10-day daily intranasal administration of the solvent (0.3% bicarbonate buffer). "LH"—a group of animals subjected to stress, in which a depressive state of "learned helplessness" was developed. Pharmacotherapy was not performed in the LH group; the development of experimental depression was studied. "LH+FQSE (SEQ ID NO:10)0.5"—a LH group with pharmacological correction, receiving 10-day daily intranasal administration of FQSE (SEQ ID NO:10) at a dosage of 0.5 mg/kg. "LH+FQSE (SEQ ID NO:10) 2.5"—a pharmacologically corrected LH group that received 10-day daily intranasal administration of FQSE (SEQ ID NO:10) at a dosage of 2.5 mg/kg. "LH+Map."—the comparison drug group. Maprotiline was injected intraperitoneally at a dosage of 4.5 mg/kg ten days daily to develop experimental depression.

8.1.10. Statistical Analysis

For a normally distributed data, a one-way analysis of variance (ANOVA) using the post-hoc Tukey test was used. For abnormally distributed data, the Kruskal-Wallis test was used, followed by multiple comparisons using Dunn's test. The significance threshold was 0.05. Data are presented as mean±standard error of the mean, or as a median and interquartile range with minimum and maximum values.

8.2. Results 8.2.1. OF

The LH group was characterized by significantly increased freezing (which corresponds to motor inhibition in patients suffering depression) in comparison with the control group. It was especially vivid in the initial period in the center of the maze (p=0.01, FIG. 54). In addition, there was significantly reduced the time of vertical exploratory activity (p=0.03, FIG. 55A), which indicates the anxiety of animals and a decrease in their exploratory activity. Chronic administration of FQSE (SEQ ID NO:10) 2.5 mg/kg (i/n) and Maprotiline 4.5 mg/kg (i/p) led to a significant decrease in freezing time when animals were placed in the center of the OF, in comparison with LH group (p=0.04 and p=0.044, respectively, FIG. 54). Daily administration of Maprotiline resulted in a 2.3-fold decrease in the number of animals showing immobilization after LH; in the FQSE (SEQ ID NO:10)-treated groups, this indicator also decreased: 1.75-fold in the 2.5 mg/kg group, and 1.4-fold in the 0.5 mg/kg group, however, the average time of immobilization in all animals of these groups was not significantly different from the LH group.

Figure 55A:
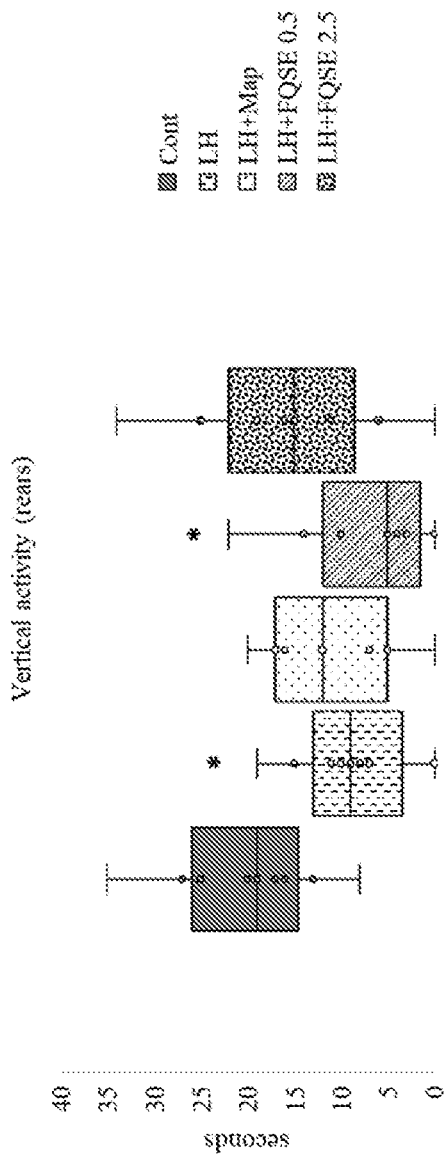
FIGS. 55A and 55B illustrate the behavior of rats in the OF test in LH paradigm.
Figure 55B:
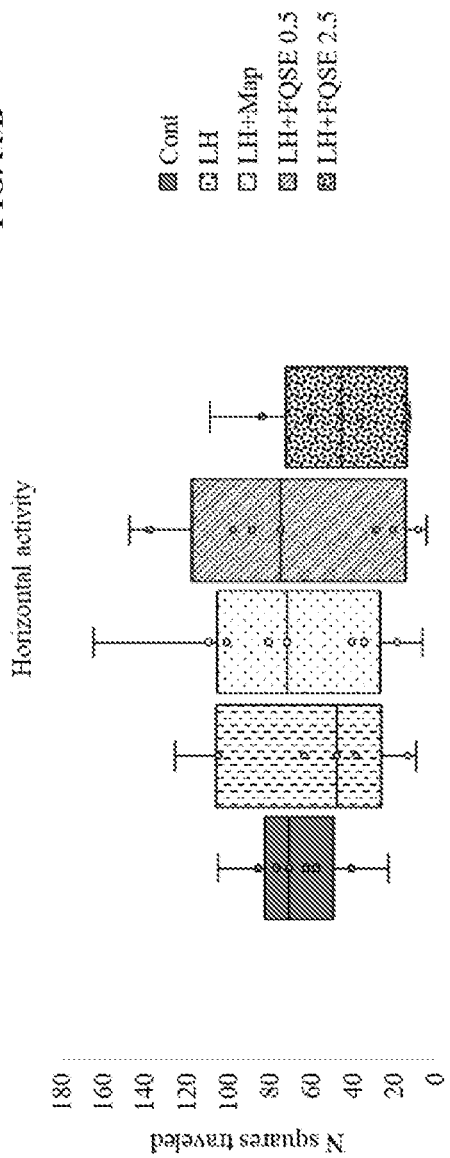

A significant decrease in vertical activity was also noted in the group of animals that underwent LH and received the peptide at a dose of 0.5 mg/kg (p=0.01, FIG. 55A). The "LH+Map" and "LH+FQSE (SEQ ID NO:10) 0.5" groups did not differ either from the control group nor from the LH group, which may indicate a partial correction of the negative effect of unavoidable stress by these substances. The motor activity of animals did not change in all experimental groups (FIG. 55B).

8.2.2. EPM

In the EPM test, there was an almost complete absence of entries to open arms in the control and LH groups. This result may indicate a high degree of novelty and stress in this test. At the same time, animals treated with Map or FQSE (SEQ ID NO:10) appeared on the arms more often, but these

TABLE 4

The general plan of the experiment, drug administration and testing (explanation in the text).

Figure 56A:
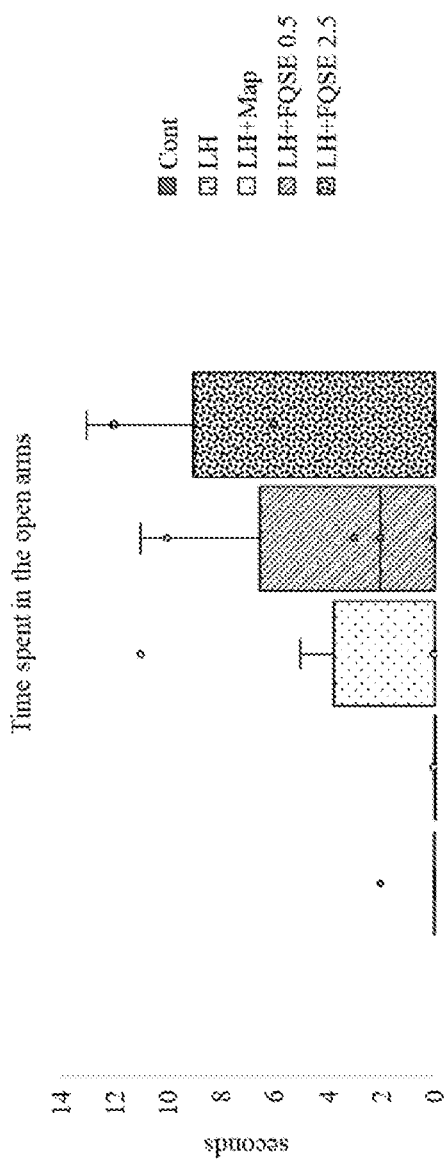
FIGS. 56A and 56B illustrate the behavior of rats in the EPM test in LH paradigm.
Figure 56B:
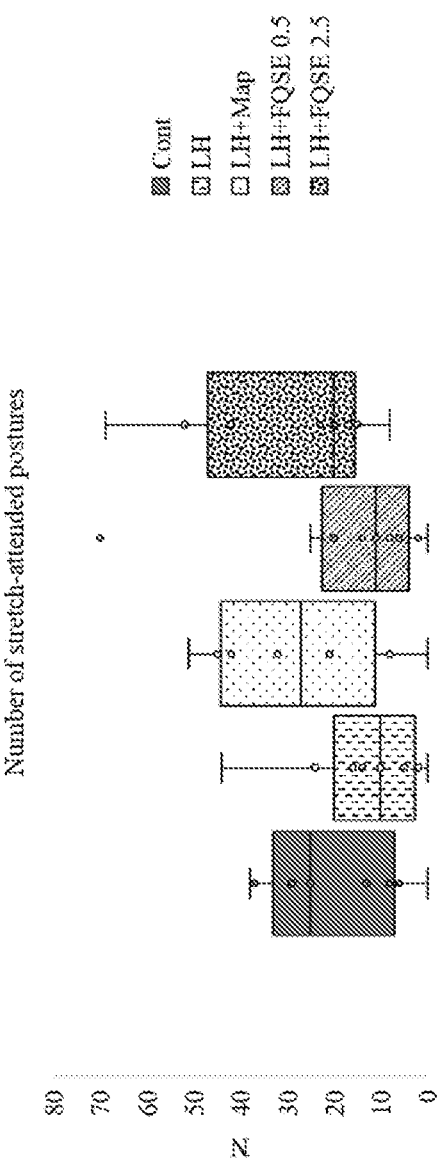

| Day | | 1 | 2 | 3 | 4 | 5 | 6 | 7 | 8 | 9 | 10 |
|---|---|---|---|---|---|---|---|---|---|---|---|
| Control i/n i/p | stress | saline i/n | saline i/n | saline i/n | saline i/n | OF + saline OF | EPM + saline EPM | Saline i/n | FS + saline FS | DXMT1 + saline DXMT1 | DXMT2 + saline DXMT2 |
| i/p + FQSE (SEQ ID NO: 10) 0.5 mg | stress | FQSE (SEQ ID NO: 10) i/n | FQSE (SEQ ID NO: 10) i/n | FQSE (SEQ ID NO: 10) i/n | FQSE (SEQ ID NO: 10) i/n | OF + FQSE (SEQ ID NO: 10) | EPM + FQSE (SEQ ID NO: 10) | FQSE (SEQ ID NO: 10) i/n | FS + FQSE (SEQ ID NO: 10) | DXMT1 + FQSE (SEQ ID NO: 10) | DXMT2 + FQSE (SEQ ID NO: 10) |
| i/p + FQSE (SEQ ID NO: 10) 2.5 mg | stress | FQSE (SEQ ID NO: 10) i/n | FQSE (SEQ ID NO: 10) i/n | FQSE (SEQ ID NO: 10) i/n | FQSE (SEQ ID NO: 10) i/n | OF + FQSE (SEQ ID NO: 10) | EPM + FQSE (SEQ ID NO: 10) | FQSE (SEQ ID NO: 10) i/n | FS + FQSE (SEQ ID NO: 10) | DXMT1 + FQSE (SEQ ID NO: 10) | DXMT2 + FQSE (SEQ ID NO: 10) |
| i/p + MAP | stress | Map i/p | Map i/p | Map i/p | Map i/p | OF + Map | EPM + Map | Map i/p | FS + Map | DXMT1 + Map | DXMT2 + Map | differences did not reach statistical significance (FIG. 56A). The number of stretch-attended postures from closed sleeves also did not differ between groups (FIG. 56B).

8.2.3. FS

Figure 57A:
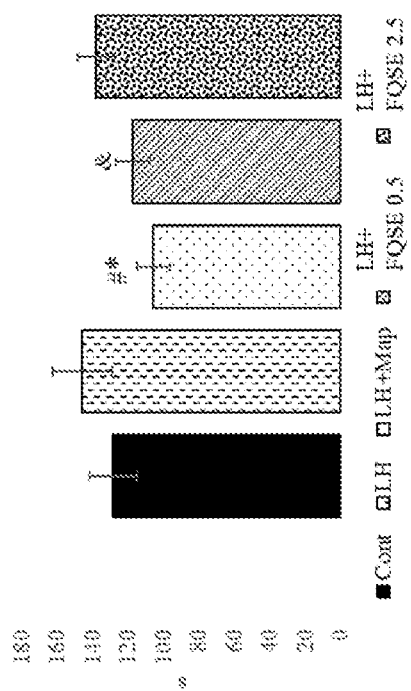
FIGS. 57A and 57B illustrate the behavior of rats in the FST in LH paradigm.
Figure 57B:
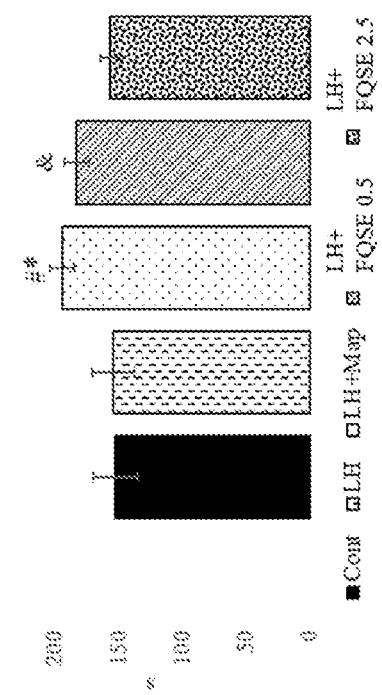

The administration of the antidepressant Maprotiline after stress conditions led to a significant reduction of the time spent immobile in the forced swimming test in comparison with the control and LH groups (p=0.02 and p=0.03, respectively, FIG. 57A), and an increase in active swimming time (p=0.01 and p=0.02, respectively, FIG. 57B). The introduction of FQSE (SEQ ID NO:10) at a dose of 0.5 mg/kg, but not 2.5 mg/kg, led to a decrease of immobilization and, accordingly, an increase in active swimming at the level of the trend in comparison with a control group (p=0.09 and p=0.08, respectively).

8.2.4. DXMT

A study of basal levels of corticosterone (CS) in rat plasma showed a trend to increase the hormone content in animals that underwent stress and received saline injections compared with animals in the control group (p=0.07). This result indicates the hyperactivation of the HPA axis. At the same time, rats treated with Map and FQSE (SEQ ID NO:10) in both doses did not differ from the unstressed animals and had a significantly lower level of CS compared to the LH group (p<0.02), which indicates a decrease in animals' stress reactivity (FIG. 58). It is interesting to note that in a previous study on the prevention of experimental depression in this model with the high-dose antidepressant lyudiomil (Maprotiline) (Rybnikova et al. (2008). The possible use of hypoxic preconditioning for the prophylaxis of post-stress depressive episodes. Neurosci. Behav. Physiol., 38(7), 721-726) resulted in a decrease in blood corticosterone levels below the control levels.

The dexamethasone test is a marker of primary depression. According to clinical data, in healthy subjects, in the case of dexamethasone introduction, the cortisol level decreases due to inhibition of the secretion of corticoliberin and ACTH by the negative feedback loop. In patients with endogenous depression, such a decrease in the cortisol level is less pronounced, since the negative feedback mechanism is violated in this disease. The weak effect of dexamethasone on the level of cortisol in the blood (a positive test result), indicates the presence of endogenous depression.

Figure 59:
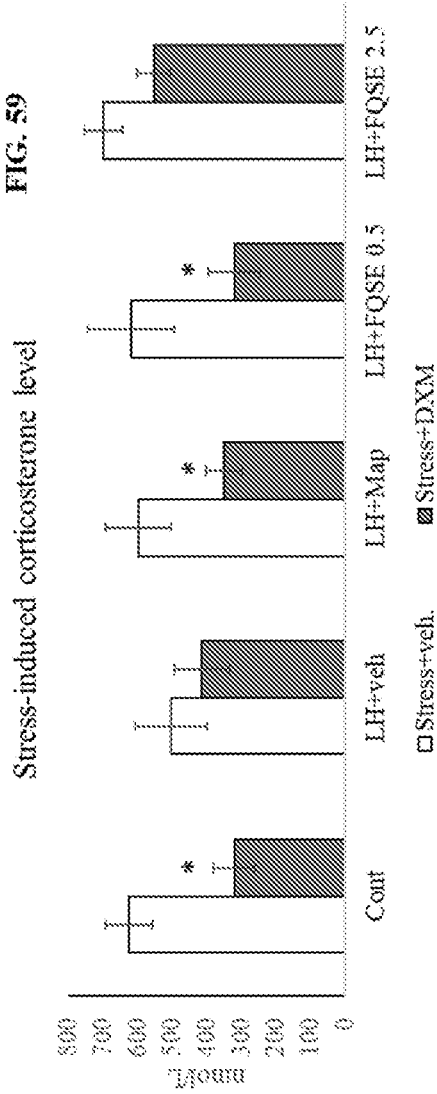
FIG. 59 illustrates stress-induced changes in the rat plasma corticosterone after acute stress and saline/dexamethasone (DXM) administration, nmol/L. Each bar represents mean±SEM. *–$p<0.05$—significant differences from the corresponding "stress+veh" group. One-way ANOVA with a Fisher LSD post-hoc test.

The DXM test revealed impaired regulation of the pituitary-adrenal system in glucocorticoid negative feedback in rats of the LH group. Injection of dexamethasone to these animals practically did not reduce either basal or stress levels of CS compared to more than 50% inhibition in control rats (FIG. 59, Table 2). It was found that the introduction of Map and FQSE (SEQ ID NO:10) at a dose of 0.5 mg/kg, but not 2.5 mg/kg, led to a significant suppression of the stress-induced increase in CS in blood after administration of DXM (FIG. 59, Table 5), which may indicate normalization of inhibition of HPA system in rats of these groups.

Administration of FQSE (SEQ ID NO:10) at a dose of 2.5 mg/kg had a less pronounced effect on the suppression of the stress hormone level by an exogenous glucocorticoid: A in the LH+FQSE (SEQ ID NO:10) 2.5 group was twice lower than the control, but at the same time it exceeded this value in the LH group (table 2, A (FR-DXM)).

TABLE 5

The magnitude of suppression of the corticosterone stress release by the introduction of an exogenous steroid.

| Control | LH | LH + FQSE (SEQ ID NO: 10) 0.5 | LH + FQSE (SEQ ID NO: 10) 2.5 | LH + Map. |
|---|---|---|---|---|
| 303.6 | 88.9 | 298.8 | 146.2 | 248.5 |

The magnitude of suppression—Δ between the Saline and DXM in the stress level of corticosterone, nmol/l 8.3. Conclusions The results of the study indicate that a ten-day intranasal administration of the peptide GABA-A modulator FQSE (SEQ ID NO:10) has a dose-dependent, anxiolytic-like (effect on time spent in open arms in EPM, immobilization time in OF), and antidepressant-like (DXMT, decrease in immobilization time in FS test) effects. And apparently, it prevents the hyperactivation of the hypothalamic-pituitary-adrenocortical hormonal system and the disturbance of its regulation by the feedback mechanism, which was manifested in animals in response to stress.

Thus, the peptide GABA-A modulator FQSE (SEQ ID NO:10) exhibits stress-protective properties and demonstrates effectiveness in the correction of post-stress anxiety. These data, combined with the absence of visible behavioral side effects for the studied dosages of the drug, suggest the prospect of further study of FQSE (SEQ ID NO:10) and the possibility of its application in anxiety-depressive disorders.

Example 9: The Study of the Neurotropic Effects of Intranasal Administration of FQSE (SEQ ID NO:10) in the Model of Chronic Restraint Stress The aim of the study was to evaluate the behavioral effects of FQSE (SEQ ID NO:10) administration as well as to analyze the relative levels of BDNF, p-p70S6k, p-ERK (1 and 2), p-GSK3β and p-PKC proteins in the brain structures of rats treated with FQSE (SEQ ID NO:10) after chronic restraint stress (CRS).

9.1. Materials and Methods.

9.1.1. Animals

The experiment was performed on male Sprague-Dawley rats aging from three to four months (n=50). The animals were kept in the vivarium of the Institute with free access to food and water and natural alternation of daily illumination. All procedures involving animals were conducted in accordance with the European (Directive 2010/63/EU of the European Parliament and of the Council of 22 Sep. 2010 on the protection of animals used for scientific purposes) and the Russian ("GOST 33216-2014 Guidelines for the maintenance and care of laboratory animals. Rules for the maintenance and care of laboratory rodents and rabbits") bioethical guidelines.

9.1.2. Chronic Restraint Stress Model

To simulate a depressive state, experimental animals were placed in the individual restrainers ("Open Science", Russia) for six hours daily for 14 days (hereinafter "chronic restraint stress=CRS"). In order to study the neurotrophic effect of FQSE (SEQ ID NO:10), the animals were divided into 5 groups, 10 individuals each. The groups are as follows: Group 1, control unstressed animals, receiving 10 μl (a pair of 5 μl doses) of saline intranasally; Group 2, stressed animals, receiving 10 pI of saline intranasal (CRS+Veh); Group 3, stressed animals, receiving fluoxetine (FO) at a dose of 5 mg/kg intraperitoneal (CRS+FO, positive control); Group 4, stressed animals, receiving a peptide drug at a dose of 0.3 mg/kg in 10 pl of saline intranasal (CRS+FQSE (SEQ ID NO:10) 0.3); Group 5, stressed animals, receiving a peptide drug at a dose of 3 mg/kg in 10 ml of saline intranasal (CRS+FQSE (SEQ ID NO:10) 3). The administration of drugs was carried out daily, 30 minutes before placing rats in the restrainers. Doses of FQSE (SEQ ID NO:10) were selected based on the results of preliminary studies.

9.1.3. Behavioral Testing

The changes in motor activity and emotional state of animals were evaluated in the Open Field (OFT) and Porsolt Forced Swimming tests (FST) fourteen days after the start of the experiment. In all cases, the animals were injected with drugs 30 minutes before testing. The OF test was designed as a square box, with sides of 90 cm and a height of 35 cm. The floor of the installation was divided into 25 squares. For three minutes the horizontal and vertical motor activity was measured. The total number of crossed squares, as well as the length of the distance, traveled, and the number of rears was counted. The FST was carried out in a glass cylinder, 40 cm high and 19 cm in diameter with water temperature 24° C. During the 8-minute experiment, the time spent active (active swimming+climbing) and inactive swimming (immobility+passive swimming) were calculated. Recording and analysis of behavioral experiments were carried out using the video surveillance system for animal behavior "Any Maze".

9.1.4. Brain Samples Preparation

At the end of the behavioral examination, the rats were decapitated, and their brains extracted for subsequent western blot analysis. A total of 51 samples of homogenized brain tissue from Sprague-Dawley rats (3-4 months old) were received from the Customer. 25 samples were homogenates of the cerebral cortex, 26 samples were homogenates of the hippocampus isolated from rat brain. The amount of homogenized tissue in each sample was less than 50 mg. Homogenization was performed in buffer (50 mM Tris-HCl, pH 7.5, 0.15 M NaCl, 1% NP-40, 0.1% SDS) in the ratio of 1 ml of buffer per 100 mg of sample. They were Incubated in ice for 30 minutes. Then the samples were centrifuged at 12000 g, 15 minutes, +4° C.

9.1.5. Experimental Design

The analysis of total protein levels in the studied samples was provided using trichloroethane according to the standard method (Ness et al. (2015). Western blot optimized exercise: an efficient and more environmentally friendly approach in the lab classroom. Biochem. Mol. Biol. Educ., 43 (5), 358-365).

All the steps necessary for the analysis of protein levels of BDNF, p-p70S6k (Thr421/Ser424), p-ERK (one and two), (Thr202/Tyr204), p-GSK3β (Ser9), p-PKC (PKCG gamma Thr514) and the GAPDH reference protein were provided in the studied samples using Western blotting.

The following procedures were performed:

Electrophoretic separation of proteins was carried out according to Laemmli in a 12% denaturing polyacrylamide gel (PAGE: 0.375 M Tris-HCl, pH 8.8, 0.1% SDS, 12% acrylamide) at 10 V/cm. Thermo Scientific high-quality protein kit was used as markers.

Transfer of proteins from the gel to the nitrocellulose membrane (PVDF 0.45 um) was provided in transfer buffer (25 mM Tris, 190 mM glycine, 10% EtOH, pH 8.3) overnight at room temperature. Transfer quality (if necessary) was evaluated by staining all bands on the membrane with non-specific AmidoBlack dye.

The membrane was washed with PBS-T solution (8 mM $Na_2HPO_4$, 150 mM NaCl, 2 mM $KH_2PO_4$, 3 mM KCl, 0.05% Tween® 20, pH 7.4) and blocked (with skimmed milk powder or BSA, depending on the antibodies) for 60 minutes at room temperature.

The membrane was washed and incubated overnight at +4° C. with primary antibodies to the target protein in a dilution recommended by the manufacturer. After that, the membrane was washed again and incubated with secondary antibodies conjugated to horseradish peroxidase for 1 hour. The membrane was stained with a Thermo Scientific SuperSignal™ West Dura Extended Duration Substrate chemiluminescent substrate. Analysis of stained membranes was performed on a ChemiDoc detection and imaging system (Bio-Rad, USA).

The integral areas of the spots obtained were calculated as a quantitative assessment and then normalized to the amount of protein in the sample.

9.1.6. Statistical Analysis

The data were processed in Statistica 10 using one-way ANOVA with a posteriori Fisher's criterion for comparison between groups. In the case of deviation from the normal distribution, the Kruskal-Wallis ANOVA test was used with post hoc Dunn's multiple comparison test. Statistically significant differences were considered at $p \leq 0.05$ and the data are presented as mean±SE.M.

9.2. Results 9.2.1. Behavioral Effects of FQSE (SEQ ID NO:10) in the CRS Model 9.2.1.1. OF The total distance traveled changed neither after stress exposure nor after drug treatment: there were no significant differences in horizontal activity observed between groups (FIG. 60).

9.2.1.2. FST

There was no effect of stress or FO treatment on the duration of active swimming in animals. However, rats that experienced stress and received FQSE (SEQ ID NO:10) at a dose of 3 mg/kg, has spent more time active swimming than animals from "CRS+Veh" group (FIG. 61A).

The duration of low activity behavior was higher in the subgroup of animals which experienced stress and received vehicle injections. Administration of the peptide at a dose of 3 mg/kg significantly reduced time spent passive swimming in the FST compared with the "CRS+Veh" (FIG. 61B). The introduction of FO had no effect on the behavior of rats in this test.

9.2.2. Discussion of the Behavioral Effects of FQSE (SEQ ID NO:10) in the CRS Model Chronic predictable stress (CPS) is one of the main tools for modeling the anxiety-depressive phenotype in rodents. However, it is often noted that chronic immobilization stress is a weak stressful effect. The degree of reproducibility of this model varies from laboratory to laboratory. In this study, it was planned to evaluate the behavior of rats after chronic administration of the peptide FQSE (SEQ ID NO:10) against immobilization stress.

In the Open Field test, no change in horizontal motor activity (MA) in stressed animals was detected. The peptide had no effect on motor activity.

In the Porsolt Swimming Test, the stress did not lead to a change in time spent in active swimming. However, there was a significant impact on the duration of low active behavior (the total time of passive swimming and immobilization). This effect was eliminated with the administration of 3 mg/kg of the peptide. There was a shift in the ratio of active and passive swimming towards a decrease in inactive swimming.

9.2.3. Conclusion

According to the literature, CPS leads to decreased exploratory activity in the Open Field test. It also causes increased immobilization in the Porsolt Swimming test (Bowman et al. (2002). Effect of Chronic Restraining Stress and Estradiol on Open Field Activity, Spatial Memory and Monoaminergic Neurotransmitters in Ovariectomized Rats. Neurology, 113 (2), 401-410; Guedri et al. (2017). Chronic Stress Deterrence Induced Neurobiologie Changes and Histological Changes in Rats. Toxicol. Environ. Sci., 9(2), 123-129). The results indicate a weak effect of the stress effect on animal behavior. Application of the peptide at a dose of 0.3 and 3 mg/kg had no effect on the emotionality of stressed animals in the Open Field test. A dose of 3 mg/kg had an antidepressant-like effect compared with the stress+ vehicle group, which may indicate a positive neurotrophic effect of chronic administration of FQSE (SEQ ID NO:10).

9.2.4. Results and Discussion of the Western Blot Analysis

Figure 62:
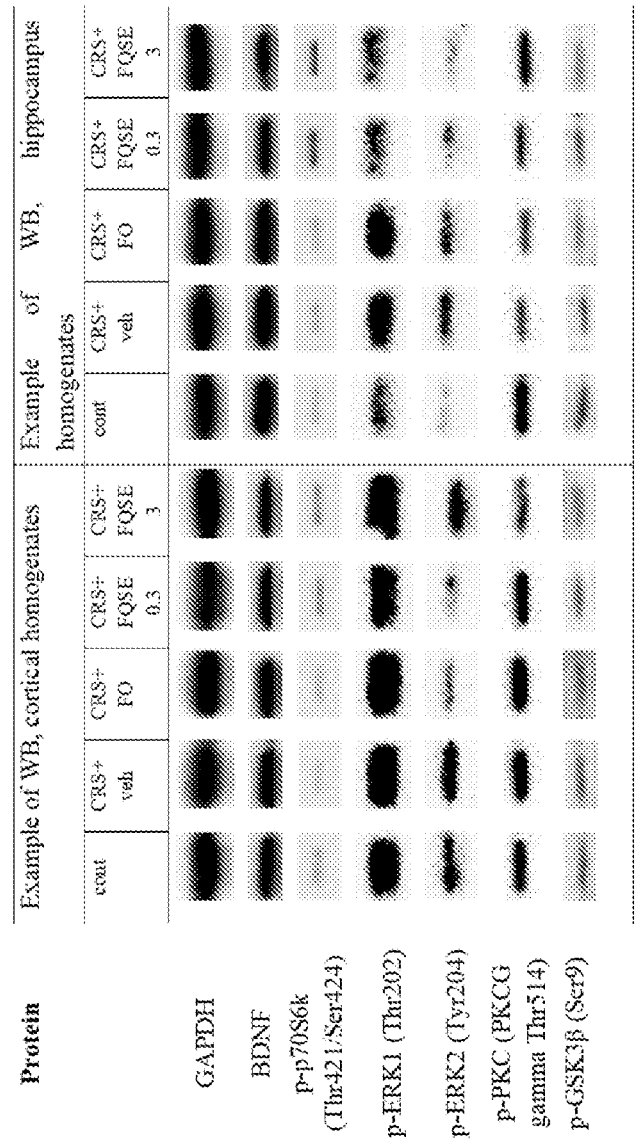
FIG. 62 illustrates an example of the Western Blot results in samples of the cortical and hippocampal homogenates of Sprague-Dawley rats after CRS and treatment.

Examples of blots obtained are presented in FIG. 62. According to the results obtained for the GAPDH reference gene (FIGS. 63A, 63B), no statistically significant differences were observed in any experimental group, which indicates a uniform distribution of proteins in the samples.

The stressful effect resulted in significant changes in the levels of p-ERK-1 (60% increase), p-ERK-2 (100% increase), p-GSK3β (40% decrease) and p-PKC (53% decrease) in the hippocampus, however, in the cerebral cortex, this effect alone did not affect the levels of the studied proteins. The results obtained may indicate mild stress (low-grade stress) in the used model. Levels of BDNF protein in the cerebral cortex (FIG. 64A) and the hippocampus (FIG. 64B) showed no relation to either stress or fluoxetine administration. Meanwhile, both doses of FQSE (SEQ ID NO:10) (0.3 mg/kg and 3 mg/kg) led to a decrease in BDNF levels in the cortex by 20 to 40% and a 40% decrease in the hippocampus.

This change corresponds to the effects of allosteric modulators of GABA-A receptors. It was shown that administering benzodiazepines leads to decreased levels of BDNF in the hippocampus, hypothalamus, and cerebral cortex in adult male rats (Kellogg et al. (2000). Sex-specific effects of intrauterine GABA receptor manipulation on pre- and postnatal BDNF expression in rats. Dev. Brain. Res., 121(2), 157-167; Chan et al. (2017). Sex Differences in Brain Neurotrophic Factor Signals and Functions. J. Neurosci. Res., 95 (1-2), 328-335). The same effects were observed in the cerebral cortex of mice (Huopaniemi et al. (2004). Adaptive plasticity induced by diazepam is revealed by profiling the specific expression of the α1 GABAA receptor. J. Neurochem., 88(5), 1059-1067). It also reduced serum levels of the BDNF protein (Ventrilla et al. (2013). Serum levels of brain neurotrophic factors in various neurological diseases. Biomed Res. Int., 2013). However, it should be mentioned that there is currently no research on the interaction of GABA-A and BDNF (Kim et al. (2017). Brain neurotropic factor and GABAergic transmission in neurodegeneration and neuroregeneration. Neural Regen. Res., 12 (10), 1733). Some papers have noted the BDNF shift in response to GABA-A stimulation which is related to embryonic or developing neurons (Porcher et al. (2011). Regulation of positive feedback between the signaling of the γ-aminobutyric acid receptor type A (GABAA) and the release of brain neurotrophic factor (BDNF) in developing neurons. J. Biol. Chem., 286(24), 21667-21677; Porscher et al. (2018). Mechanism of BDNF modulation in GABAergic synaptic transmission in healthy and diseased brains. Front. Cell. Neurosci., 12, 273). The nature of changes in BDNF levels as a response to GABA-A stimulation may depend on the type of neurons and brain regions studied, the mode and duration of GABA-A modulators, and the type of experimental model used (Kim et al. (2017). Brain neurotropic factor and GABAergic transmission in neurodegeneration and neuroregeneration. Neural Regen. Res., 12 (10), 1733). At the same time, the data obtained as a result of this study allows for the assumption, within a high degree of probability, that the change in the level of BDNF in response to administration of FQSE (SEQ ID NO:10) indicates modulation of the GABA system.

Levels of the phosphorylated form of p-p70S6k (Thr421/Ser424) showed no relation to either stress or fluoxetine in the cerebral cortex (FIG. 65A) or the hippocampus (FIG. 65B). In response to both doses of FQSE (SEQ ID NO:10), there was an 80% increase in levels of the protein in the cortex and a 170 to 200% increase in the hippocampus.

S6 kinase is one of the main effectors of the mTORC1 signaling cascade. It is associated with increased protein biosynthesis activity (Mao et al. (2018). The role of mTOR in glucose and lipid metabolism. Int. J. Mol. Sci., 19(7), 2043). Activation of the GABAA receptor results in inactivation of the mTORC1 cascade, especially an increase in p-p70S6k (Thr421/Ser424) (Thanapreedawat et al. (2013). Influence of GABA on brain protein synthesis mediated by the mammalian target on the rapamycin pathway. Biosci. Biotechnol. Biochem., 120808; Weston et al. (2012). Multiple roles for mammalian target of rapamycin signaling in both glutamatergic and GABAergic synaptic transmission. J. Neurosci. Res., 32(33), 11441-11452). Activation of S61 and mTROC1 has an antidepressant effect, studied on ketamine. In this case, the antidepressant effect of ketamine is neutralized by the use of rapamycin, which indicates a significant role of mTROC1 in mediating this effect (Dwyer et al. (2015). Ribosomal protein S6 kinase 1 signaling in prefrontal cortex controls depressive behavior. Proc. Natl. Acad. Sci., 112(19), 6188-6193). It can thus be concluded that the high level of phosphorylation of S6k in response to the introduction of FQSE (SEQ ID NO:10) indicates the activation of the mTORC1 cascade, which can hypothetically be initiated by the modulation of GABA-A receptors.

In the hippocampus, levels of p-ERK 1 protein phosphorylation (FIG. 66B) and p-ERK 2 (FIG. 66B) showed a respective 60% and 100% increase in response to stress. Both doses of FQSE (SEQ ID NO:10) resulted in normalized levels of p-ERK 1 and p-ERK 2 to intact control levels.

Some literature suggests that individual stress models show increased phosphorylation of p-ERK 1 and 2 in the brain (Kim et al. (2018). Social support rescues acute stress-induced cognitive impairments by modulating ERK½ phosphorylation in adolescent mice. Sci. Rep., 8(1), 1-13; Hebert et al. (2005). Single and repeated immobilization stress differentially trigger induction and phosphorylation of several transcription factors and mitogen-activated protein kinases in the rat locus coeruleus. J. Neurochem., 95(2), 484-498), evidence supporting results from this study. It is also known that allosteric modulators of GABA-A (particularly drugs of the benzodiazepine group) are able to inhibit the phosphorylation of the p-ERK system (Kim et al. (2012). Hippocampal extracellular signaling-regulated kinase signaling has a role in passive avoidance memory retrieval induced by GABA receptor modulation in mice. Neuropsychopharmacology, 37 (5), 1234).

Thus, the nature of FQSE (SEQ ID NO:10) corresponds to the profile of allosteric modulators GABA-A. However, it should be noted that in other models described in the literature a depressive state and severe chronic stress are associated with inhibition of p-ERK/2 and MAPK kinase cascade. The antidepressant effect, in particular, that of ketamine, is associated with activation of this system (Reus et al. (2014). MAPK signaling correlates with the antidepressant effects of ketamine. J. Psychiatr. Res., 55, 15-21). The data obtained clearly indicate the effects of FQSE (SEQ ID NO:10) on the MAPK signaling cascade, and a certain direction of changes may be observed in a mild stress model.

The level of p-ERK 1 (Thr 202) in the cerebral cortex showed no relation to any of the studied effects (FIG. 66A). Cortical levels of p-ERK 2 (Tyr204) showed no change in response to stress but decreased to fluoxetine and FQSE (SEQ ID NO:10) at a dose of 0.3 mg/kg against stress and control levels (FIG. 67A). This may be associated with GABA-A receptor modulation. Because stress did not affect ERK/2 phosphorylation levels in the cortex the findings require verification on a different stress model.

In the cerebral cortex, levels of the phosphorylated form of p-PKC (Thr 514) showed no changes after stress, fluoxetine, or FQSE (SEQ ID NO:10) 0.3 mg/kg administration (FIG. 68A). However, the administration of FQSE (SEQ ID NO:10) 3 mg/kg resulted in a 51% decrease in p-PKC. This effect can hypothetically be explained by the reduced level of BDNF in this group, due to the fact that p-PKC is involved with the cascade triggered by TrkB (Duman et al. (2012). Signaling pathways underlying the pathophysiology and treatment of depression: novel mechanisms for rapid-acting agents. Trends Neurosci., 35(1), 47-56). A 3 mg/kg dose of FQSE (SEQ ID NO:10) led to more pronounced decreases in BDNF than a 0.3 mg/kg dose (FIG. 64A). This may explain the ineffectiveness of lower doses on levels of p-PKC. Additionally, reduced levels of p-PKC may indirectly indicate inhibition of the mTORC2 dependent cascade (which is antagonistic to mtorc1 activation), for which p-PKC is an effector (Mao et al. (2018). The role of mTOR in glucose and lipid metabolism. Int. J. Mol. Sci., 19(7), 2043). However, the above results do not warrant any definite conclusions about the influence of FQSE (SEQ ID NO:10) on p-PKC.

CRS caused a significant decrease of p-PKC (FIG. 68B) in the hippocampus, which corresponds to a depressive state (Thiels et al. (2000). Protein phosphatase-mediated regulation of protein kinase C during long-term depression in the adult hippocampus in vivo. J. Neurosci., 20(19), 7199-7207; Shelton et al. (2009). Protein kinases A and C in post-mortem prefrontal cortex from persons with major depression and normal controls. Int. J. Neuropsychoph., 12(9), 1223-1232). At the same time, neither fluoxetine nor peptide FQSE (SEQ ID NO:10) contributed to the normalization of its levels: the values in these groups do not differ statistically from the control group. It should be noted that the lack of activation of p-PKC and FQSE (SEQ ID NO:10) in the hippocampus can be perceived as a positive effect.

It is known that the high activity of p-PKC associated with phosphorylation of benzodiazepine specific sites in GABA-A receptors (in particular the γ2 subunit), reducing the affinity of the modulators to the receptor and inhibiting their effects (Gao et al. (2005). Activation of protein kinase C reduces benzodiazepine potency at GABAA receptors in NT2-N neurons. Neuropharmacology, 48(3), 333-342; Qi et al. (2007). Protein kinase C∈ regulates γ-aminobutyrate type A receptor sensitivity to ethanol and benzodiazepines through phosphorylation of γ2 subunits. J. Biol. Chem., 282(45), 33052-33063). The mechanism described above may underlie increased tolerance to benzodiazepine drugs. Activation of p-PKC during chronic administration leads to phosphorylation of the GABA-A receptor and decreased sensitivity to these drugs (Vinkers et al. (2012). Mechanisms underlying tolerance after long-term benzodiazepine use: a future for subtype-selective GABAA receptor modulators? Adv. Pharmacol. Sci., 2012). The absence of PKC activation in this experiment may most likely indicate that the provision of the FQSE (SEQ ID NO:10) does not activate the mechanism of self-tolerance.

Levels of protein p-GSK3β showed no dependence on any of the effects in the cortex (FIG. 69A). The hippocampus (FIG. 69B) exhibited a 40% reduced response to stress while simultaneously showing no response to the administration of fluoxetine or FQSE (SEQ ID NO:10).

In summary, it can be concluded that the nature of FQSE (SEQ ID NO:10) levels in a number of proteins tested matches the profiles of positive allosteric modulators of GABA-A receptors. Decreased levels of BDNF and phosphorylated forms of ERK ½ are characteristic of benzodiazepines. The high level of phosphorylation of p70S6k in both the cortex and hippocampus in response to administration of FQSE (SEQ ID NO:10) indicates activation of the mTORC1 cascade and corresponds to a pronounced antidepressant effect. Increased phosphorylation of p70S6k may affect behavior, as observed by significant increases in active swimming and drift time as well as decreases in passive swimming time compared to rats in the control group. Observations from the Porsolt test may be the result of the activation of the mTORC1 cascade (Chen et al. (2015). AMPA receptor-mTOR activation is required for the antidepressant-like effects of sarcosine during the forced swim test in rats: Insertion of AMPA receptor may play a role. Front. Behav. Neurosci., 9, 162). This effect may also indicate GABA-A receptor modulation, during which the mTORC1 cascade begins and an increase in the level of p-p70S6k (Thr421/Ser424) should be observed.

However, it is impossible to not mention the markers analyzed are in fact participants of universal cascades regulated by a large number of influences. Therefore, it is impossible to state unequivocally the specific modulation of GABA-A receptors mediated by FQSE (SEQ ID NO:10).

9.2.5. Conclusion

Stressful effects led to significant changes in the levels of proteins p-ERK-1, p-ERK-2, p-GSK3β and p-PKC in the hippocampus. However, this did not affect the levels of the studied proteins in the cerebral cortex. The results obtained may indicate a mild mode of stress (low-grade stress) in the model used.

Administration of FQSE (SEQ ID NO:10) in both doses (0.3 mg/kg and 3 mg/kg) led to a decrease in BDNF levels in both the cortex (by 20-40%) and in the hippocampus (by 40%). This corresponds to the profile of allosteric modulators of the GABA-A receptor. The use of BDNF as a marker of GABA-A receptor modulation is possible in further experiments.

Example 10: Radioligand Binding Assay for Investigation of Specific Binding Sites for [$^3$H] FQSE (SEQ ID NO:10) In Vitro 10.1. Aim of the Study Stage 1. Estimate the IC50 value of the unlabeled FQSE (SEQ ID NO:10) peptide with respect to the [$^3$H]-SR 95531 (antagonist of GABAA receptors) binding when 50 μl of the test compound is added to the incubation medium at final concentrations of $10^{-10}$-$10^{-4}$ M.

Stage 2. Determine the binding sites of the FQSE (SEQ ID NO:10) peptide in brain structures (using tritium radiolabeled peptide) in the following experiments:

Isolation of plasma membranes with GABAA receptors of the cerebral cortex (modified methods of Ito (Ito et al. (1992). Effects of bicuculline on [³H] SR 95531 binding in discrete regions of rat brains. Neurochem. res., 17(4), 307-313; Hawkinson et al. (1996). Steroid inhibition of [³H] SR 95531 binding to the GABAA recognition site. Eur. J. Pharmacol., 304(1-3), 141-146).

Isolation of plasma membranes of the whole brain with the a+/b-GABAA receptor site (according to modified methods of Maldifassi et al. (2016). Molecular mode of action of CGS 9895 at α1β2γ2 GABAA receptors. J. Neurochem., 138(5), 722-730; Ramerstorfer et al. (2011). The GABAA receptor α+β− interface: a novel target for subtype selective drugs. J. Neurosci., 31(3), 870-877).

Isolation of plasma membranes of the brain by other methods.

Stage 3. To determine the binding sites of the FQSE (SEQ ID NO:10) peptide in brain structures (using tritium radiolabeled peptide) in ligand displacement experiments with different "classical" GABAA receptor ligands using rat cerebral cortex membrane under the following incubation conditions:

incubation at RT for 25 min;

increased incubation time;

pre-incubation with known "cold" ligands and the subsequent addition of a labeled peptide (it is supposed that binding to intact membranes by "hot" peptide will decrease because of a "cold" ligand will occupy its site—an indirect determination of competition).

Stage 4. To assess the binding to BZD-site of GABAA receptors in vivo by calculating IC50 of unlabeled peptide added in the range of concentrations $10^{-10}$-$10^{-4}$ M in relation to [³H] flunitrazepam and [³H] diazepam;

Stage 5. To assess the influence of various substances, binding to different sites of GABAA receptors, on specific binding of [³H]-FQSE (SEQ ID NO:10) to rat cortex membrane with different protocol modifications.

Stage 6. To obtain the data with a negative control for the binding sites of [³H]-FQSE (SEQ ID NO:10): isolation of membranes by a specific method (NMDA, with the addition of ligand MK-801), different from that obtained in previous experiments, and checking the absence of binding sites for the peptide in this protocol.

10.2. Materials and Methods

Studies were performed on Wistar male rats (250-300 gram). The animals were decapitated, the brain was removed, placed on ice and brain structures were isolated according to the generally accepted scheme (Glowinski et al. (1966). Regional studies of catecholamines in the rat brain-I: the disposition of [³H] norepinephrine, [³H] dopamine and [³H] dopa in various regions of the brain. J. Neurochem., 13(8), 655-669) for radioreceptor analysis. All procedures involving animals were conducted in accordance with the European (Directive 2010/63/EU of the European Parliament and of the Council of 22 Sep. 2010 on the protection of animals used for scientific purposes) and the Russian ("GOST 33216-2014 Guidelines for the maintenance and care of laboratory animals. Rules for the maintenance and care of laboratory rodents and rabbits") bioethical guidelines.

10.2.1. Series 1. Isolation of Plasma Membranes with GABAA-Receptors of the Cerebral Cortex.

The preparation of membrane samples containing GABAA-cerebral cortex receptors of rats was provided according to modified methods (Ito et al. (1992). Effects of bicuculline on [³H] SR 95531 binding in discrete regions of rat brains. Neurochem. res., 17(4), 307-313; Hawkinson et al. (1996). Steroid inhibition of [³H] SR 95531 binding to the GABAA recognition site. Eur. J. Pharmacol., 304(1-3), 141-146). After decapitation, the tissue was immediately frozen in liquid nitrogen and stored in a low-temperature refrigerator at −80° C. On the day of the experiment, the frontal cortex was homogenized in a Teflon-glass Potter homogenizer 1:20 W:V in ice-cold buffer (0.32 M Sucrose; pH 7.1). The homogenate was then centrifuged at 1,000 g for 10 minutes. The supernatant was re-centrifuged at 20,000 g for 20 min. The precipitate was resuspended in 20 ml of cold distilled water and centrifuged at 8000 g for 20 min. The supernatant was re-centrifuged at 48,000 g for 20 min. The precipitate was suspended in 0.05 M Tris-citrate buffer (pH 7.1) and centrifuged 48,000 g for 20 min. The resulting membrane fraction was frozen and stored at −80° C. On the day of the experiment, the membranes were suspended in 40 volumes of 0.05 M Tris-citrate buffer (pH 7.1) and centrifuged at 48,000 g for 20 minutes. The precipitate was suspended in 40 volumes of 0.05 M Tris-citrate buffer (pH 7.1) and incubated at 24° C. for 30 minutes. Then it was centrifuged again at 48,000 g for 20 min. The final precipitate was resuspended in a fresh buffer.

10.2.2. Radioligand Analysis of GABAA Receptors.

The incubation mixture (final volume 0.5 ml) contained 50 μl [³H] SR 95531, 250 μl of buffer and 200 μl of membrane protein suspension, 50 μl of unlabeled SR 95531 ligand (gabazine) or unlabeled FQSE (SEQ ID NO:10) peptide was added for non-specific binding. The reaction mixture was incubated at 40° C. for 1 hour.

10.2.3. Series 2. The Determination of the Binding Sites of the Studied Peptide in Brain Structures (Using Tritium Radiolabeled FQSE (SEQ ID NO:10) Peptide).

Plasma membranes were isolated according to various modified techniques (Ito et al. (1992). Effects of bicuculline on [³H] SR 95531 binding in discrete regions of rat brains. Neurochem. res., 17(4), 307-313; Hawkinson et al. (1996). Steroid inhibition of [³H] SR 95531 binding to the GABAA recognition site. Eur. J. Pharmacol., 304(1-3), 141-146; Asano et al. (1979). Identification of inosine and hypoxanthine as endogenous ligands for the brain benzodiazepine-binding sites. Proc. Nat. Acad. Sci., 76(2), 977-981; Maldifassi et al. (2016). Molecular mode of action of CGS 9895 at α1β2γ2 GABAA receptors. J. Neurochem., 138(5), 722-730; Ramerstorfer et al. (2011). The GABAA receptor α+β− interface: a novel target for subtype selective drugs. J. Neurosci., 31(3), 870-877). Then, radioligand analysis was performed on the isolated membranes using [3H] FQSE (SEQ ID NO:10) and its unlabeled form in vitro. As a result, the specific FQSE (SEQ ID NO:10) binding percentage of the total binding in the range from 0% to 47% was obtained. For further study, the technique with the highest percentage of specific binding was chosen. The protocol of the technique is described below.

10.2.4. Isolation of Plasma Membranes and Radioligand Analysis.

After decapitation, the tissues were immediately frozen in liquid nitrogen and stored in a low-temperature refrigerator at −80° C. On the day of the experiment, brain tissue (cortex, about 300 mg) was homogenized in a Teflon-glass Potter homogenizer 1:25 W:V in the buffer (50 mM Tris-HCl, pH 7.4). The homogenate was centrifuged at 40,000 g for 20 min. The obtained precipitate was homogenized in a buffer (50 mM Tris-HCl; pH=7.4) and centrifuged again at 40,000 g for 20 min. A similar procedure was performed again. The precipitate was resuspended in 15 ml of the same buffer and used for the radioligand analysis.

The incubation mixture (final volume 0.5 ml) contained 50 μl [$^3$H] FQSE (SEQ ID NO:10), 200 or 250 μl buffer (50 mM Tris-HCl, pH=7.4) and 200 μl of membrane protein suspension, 50 μl of unlabeled FQSE (SEQ ID NO:10) was added for non-specific binding.

After that, experimentally, through changes in time and temperature, the optimal incubation mode was selected for the FQSE (SEQ ID NO:10) binding to its own binding sites in the rat cortex: the reaction mixture was incubated at room temperature (RT) for 25 minutes (Table 6).

TABLE 6

Different experimental conditions of incubation in radioligand analysis.

| Experimental condition No | Incubation time, min | Incubation temperature, ° C. | % percentage of specific binding of total binding |
|---|---|---|---|
| 1 | 10 | 4 | 47 |
| 2 | 20 | 4 | 48 |
| 3 | 10 | 37 | 72 |
| 4 | 20 | 37 | 79 |
| 5 | 30 | 37 | 77 |
| 6 | 20 | 24 | 75 |
| 7* | 25 | 24 | 86 |
| 8 | 30 | 24 | 78 |

*Selected incubation condition.

When the incubation mode has been selected the composition of the buffer was changed by adding various salts—NaCl, KCl, KH$_2$PO$_4$, CaCl$_2$, MgCl$_2$. As a result, the percentage of specific binding decreased to 63%.

Further, applying this modification of plasma membrane extraction, the effect of ligands of known receptor sites (Table 7) on the [$^3$H] FQSE (SEQ ID NO:10) binding to their own specific binding sites was studied, in order to determine their nature.

TABLE 7

The effect of ligands of various receptors on the binding of [$^3$N]-FQSE (SEQ ID NO: 10) with FQSE (SEQ ID NO: 10)-binding cortical sites in vitro.

| Studied compound | Source | Target receptor |
|---|---|---|
| Spiperone | Sigma Aldrich | D2/D4 dopamine receptor antagonist; 1B adrenergic inhibitor; antagonist of 5-HT2A/5-HT1 receptors |
| Sulpiride | Sigma Aldrich | Selective antagonist of D2, D3 and 5-HT1A receptors |
| Ifenprodil | Santa Cruz | NMDA-receptor inhibitor, in particular, the Gly-site of subunit 1 (GluN1) and the Glu-binding site of subunit 2 (GluN2B) |
| Ketanserin | Sigma Aldrich | Non-selective 5HT2a-receptor antagonist |
| 7-OH-DPAT | Sigma Aldrich | Selective D3 receptor agonist |
| Haloperidol | Gedeon Richter | Antagonist of D2, D3, and D4 dopamine receptors. Sigma1 receptor ligand. |
| GBR-12909 | Tocris Bioscience | Competitive Dopamine Reuptake Inhibitor |
| CGS-9895 | Sigma Aldrich | Enhances GABA-induced currents in receptors containing the ab subunit. It is also a ligand of the a+/b-GABA receptor site |
| SR-95531 (gabazine) | Santa Cruz | Selective antagonist of the GABAA-receptor |
| Ro-256981 | Santa Cruz | Selective antagonist of the subunit GluN2B of the NMDA receptor. |
| Glutamate | Sigma Aldrich | Glutamate receptor agonist |
| Muscimol | Fluka | GABAA receptor agonist |
| Bicuculline | Fluka | Competitive antagonist of the GABA-receptor |
| Nicotine | Tocris Bioscience | nACh-receptor agonist |
| LY-354740 | Santa Cruz | Selective mGluII-receptor agonist |
| MK-801 | Sigma Aldrich | Noncompetitive NMDA-receptor antagonist |
| Glycine | Sigma Aldrich | NMDA-receptor glycine site agonist |
| Spermine | Sigma Aldrich | NMDA-receptor polyamine site ligand |
| Arcaine | Sigma Aldrich | NMDA-receptor polyamine site ligand |

10.2.5. Liquid Scintillation Spectrometry.

At the end of the incubation, the samples were filtered through Ge/C glass fiber filters (Whatman) previously moistened with 0.3% polyethyleneimine for 2 hours at room temperature. Each tube was washed twice with cold buffer, then the filters were washed twice with the same volume of buffer.

The filters were air-dried and transferred to scintillation vials. Filters were poured with 5 ml of toluene-based scintillation liquid (4 g PPO, 0.2 g POPOP per liter of toluene). The radioactivity of the samples was determined on a Tri-Carb 2900TR counter (Perkin Elmer) with a counting efficiency of 42-46%. Protein concentration was measured by the standard Lowry method (1951).

10.2.6. Series 3. The Determination of the Binding Sites of the Studied Peptide in Brain Structures (Using Tritium Radiolabeled FQSE (SEQ ID NO: 10) Peptide) in Ligand Displacement Experiments with Different "Classical" GABAA Receptor Ligands.

For sample preparation and the protocol of radioligand binding assay see 9.2.3.

TABLE 8

The list of "classical" GABAA ligands.

| Substance | Target |
|---|---|
| GABA | ligand of GABA site of GABA receptors |
| Diazepam | ligand of benzodiazepine (BZD) site of GABAA receptors (containing α$_{1-3}$ and to a lesser extent—α$_5$ subunits) |
| Zolpidem | agonist of BZD site of GABAA receptors (containing primarily α$_1$ subunits) |
| Pregnenolone | negative allosteric modulator (NAM) of neurosteroid site (NS) of GABAA receptors |
| Flumazenil | antagonist of BZD site of GABAA receptors with affinity to α$_5$ |

10.2.7. Series 4. Radioligand Analysis of GABAA Receptors (Benzodiazepine Site).

The incubation mixture (final volume 0.5 ml) contained 50 μl of [$^3$H] Flunitrazepam, 250 μl of buffer and 200 μl of protein suspension of the membranes, 50 μl of unlabeled diazepam ligand or unlabeled FQSE (SEQ ID NO:10) peptide were added for nonspecific binding.

The procedure of liquid scintillation spectrometry and processing of the results were carried out as described in 10.2.5.

The first modification of the in vitro radioligand analysis of benzodiazepine receptors was as follows: the incubation was carried out for 30 minutes at 40° C. and at 24° C.; for non-specific binding, the following combinations of unlabeled substances were used: 1) Diazepam $10^{-6}$M+FQSE $10^{-4}$M; 2) Diazepam $10^{-6}$M+FQSE $10^{-5}$M; 3) Diazepam $10^{-6}$M (control).

The second modification was similar to that described above but also with preincubation, which lasted 25 minutes, and unlabeled FQSE (SEQ ID NO:10) was added during preincubation, and Diazepam later only during incubation along with [$^3$H]-Flunitrazepam.

10.2.8. Series 5. The Influence of Various Substances, Binding to Different Sites of GABAA Receptors, on Specific Binding of [$^3$H]-FQSE (SEQ ID NO:10) to Rat Cortex Membrane.

For sample preparation and the protocol of radioligand binding assay see 9.2.3.

TABLE 9

The list of GABAA ligands

| Substance | Target |
|---|---|
| Isoguvacine | GABAA receptor agonist |
| SCS | GABAA receptor antagonist |
| Bretanezil | GABAA α1 subtype selective agonist |
| SL 651498 | GABAA α2 subtype-selective agonist |
| MK0343 | GABAA α3 subtype-selective agonist |
| THDOC | GABAA α4,6 subtype-selective agonist |
| TB21007 | GABAA α5 subtype-selective inverse agonist |
| Gaboxadol (THIP) | GABAA α4β3δ subtype partial agonist |
| FGIN-1-27 | specific ligand for mitochondrial DBI (Diazepam-binding inhibitor) receptor |
| Allopregnanolone | Neurosteroid, positive allosteric modulator of the GABAA receptor |

10.2.9. Series 6. Negative Control for the Binding Sites of [$^3$H]-FQSE (SEQ ID NO:10).

10.2.9.1. Isolation of Plasma Membranes with Hippocampal NMDA Receptors.

Hippocampal plasma membranes were isolated using modified methods (Zhou et al. (1997). (2S,4R)-4-methylglutamic acid (SYM 2081): a selective, high-affinity ligand for kainate receptors. J. Pharmacol. Exp. Ther., 280(1), 422-427, LePage et al. (2005). Differential binding properties of [$^3$H] dextrorphan and [$^3$H] MK-801 in heterologously expressed NMDA receptors. Neuropharmacol., 49(1), 1-16). After decapitation, the tissue was immediately frozen in liquid nitrogen and stored in a low-temperature refrigerator at −80° C. On the day of the experiment, the hippocampi were homogenized "Teflon-glass" in a Potter homogenizer in 10 volumes of buffer No. 1 (5 mM HEPES, 4.5 mM Tris, 0.32 M Sucrose, pH 7.6). The homogenate was diluted with 50 volumes of buffer No. 2 (5 mM HEPES, 4.5 mM Tris, pH 7.6) and centrifuged at 1000 g for 10 minutes on an Optima L-70K ultracentrifuge (Beckman Coulter). The supernatant was discarded and centrifuged again at 25000 g for 20 minutes. To increase the protein yield, this operation was performed twice. The resulting precipitate was resuspended in 50 volumes of buffer No. 2 and centrifuged at 8000 g for 20 minutes. The supernatant and the upper brown sedimentary layer were decanted and centrifuged at 25000 g for 20 minutes. The pellet was resuspended in 50 volumes of buffer No. 3 (5 mM HEPES, 4.5 mM Tris, 1 mM Na$_4$EDTA, pH 7.6) and centrifuged 3× times at 25,000 g for 20 minutes. The resulting precipitate was resuspended in 50 volumes of buffer No. 2 and centrifuged at 25,000 g for 20 minutes. The final sediment was resuspended in 5 volumes of buffer No. 2 and frozen in cryovials in liquid nitrogen. On the day of analysis, the tissue was thawed, diluted in 10 volumes of buffer No. 2, centrifuged at 25,000 g for 20 minutes. The sediment was resuspended in the required amount of buffer No. 2.

10.2.10. Radioligand Analysis of NMDA Receptors.

The incubation mixture (final volume 0.5 ml) contained 50 µl of [$^3$H] (+) MK-801, 250 µl of buffer and 200 µl of protein suspension of the membranes, 50 µl of unlabeled ligand ((+) MK-801, 1 was added for nonspecific binding mM). The reaction mixture was incubated at room temperature for 2 hours.

10.2.11. Analysis and Presentation of Results.

The IC50 value with respect to the binding of labeled ligands was determined by adding 50 µl of the test compounds to the incubation medium at final concentrations of $10^{-10}$-$10^{-4}$ M. The volume of the incubation mixture was 500 µl. To construct the curves of the radioactive ligand's displacement each concentration of the test substance was taken in 3 replications.

10.2.12. Statistical Analysis.

For analysis of the radioligand binding results the programs, GraphPad Prism 4 and Statistica 6.0 were used. Results are presented as mean±SE.M.

10.3. Results.

10.3.1. Series 1.

Figure 70:
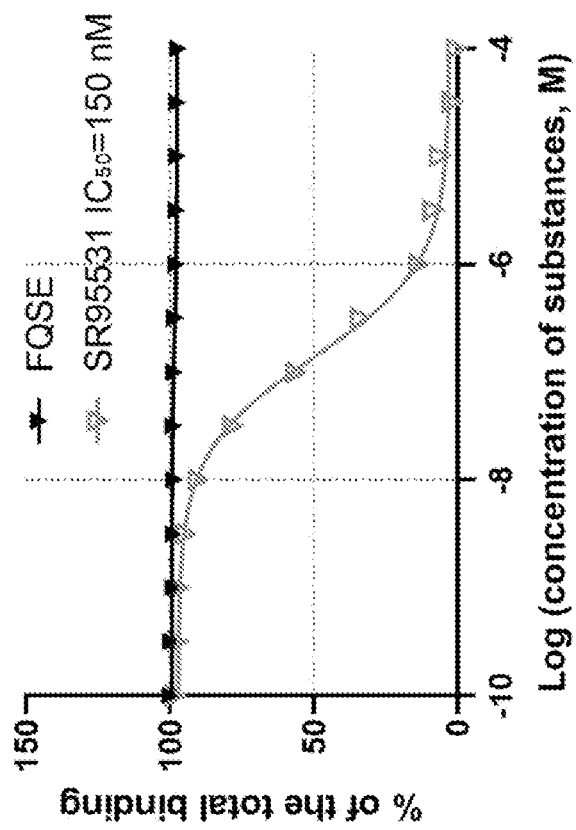
FIG. 70 illustrates the effect of SR 95531 and FQSE (SEQ ID NO:10) on the binding of [$^3$H]-SR 95531 to GABA receptors of the brain cortex of rats in vitro.

FQSE (SEQ ID NO:10) didn't affect the specific binding of [$^3$H] SR 95531 to the GABAA receptor in the whole range of concentrations used which indicates the absence of direct interaction of the studied compound with GABA site of GABAA receptor: the IC50 values were found to be bigger than 100 µmol/L (FIG. 70).

10.3.2. Series 2.

Figure 71:
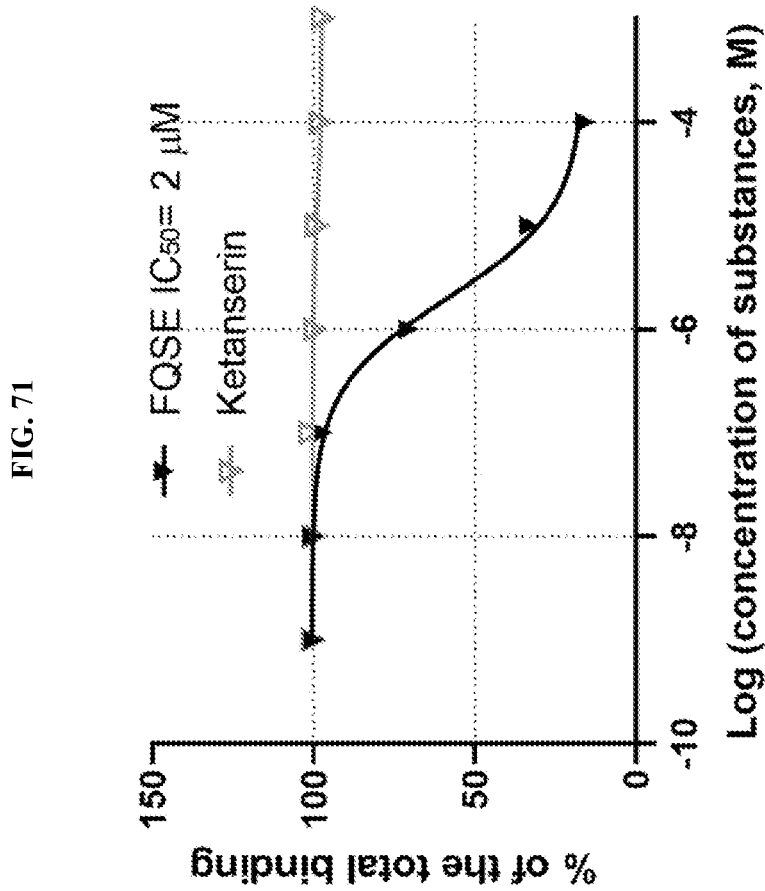
FIG. 71 illustrates the effect of FQSE (SEQ ID NO:10) and Ketanserin on the binding of [$^3$H]-FQSE (SEQ ID NO:10) with FQSE (SEQ ID NO:10)-binding cortical sites in vitro. Ketanserin curve was used as an example, it is similar for all selected ligands with an IC50>100 μmol/L.

The specific FQSE (SEQ ID NO:10) binding sites were found with IC50=2±0.1 µM (FIG. 71). None of the studied substances affected the specific binding of the labeled peptide in the entire range of concentrations used (IC50>100 µM for all ligands), which means that the receptors of chosen ligands are not the binding sites of the studied peptide (FIG. 71).

10.3.3. Series 3.

10.3.3.1. 25 Min Incubation at RT.

Figure 72:
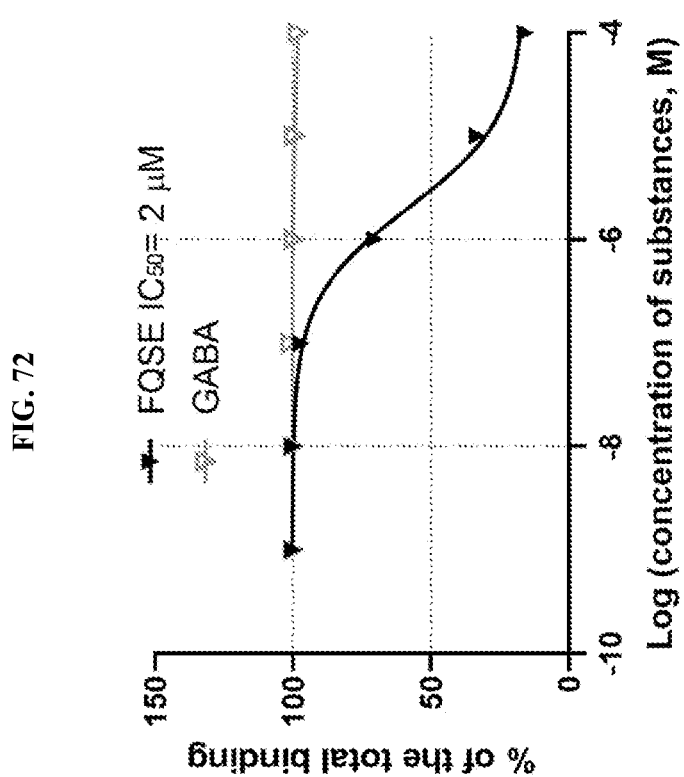
FIG. 72 illustrates the effect of FQSE (SEQ ID NO:10) and GABA on the binding of [$^3$H]-FQSE with FQSE (SEQ ID NO:10)-specific sites in the rat cortex in vitro. GABA curve was used as an example, it is similar for all selected ligands with an IC50>100 μmol/L.

None of the studied substances affected the specific binding of the labeled peptide in the entire range of concentrations used: the IC50 values were found to be bigger than 100 µmol/L (FIG. 72).

10.3.3.2. Increased Incubation Time.

Figure 73:
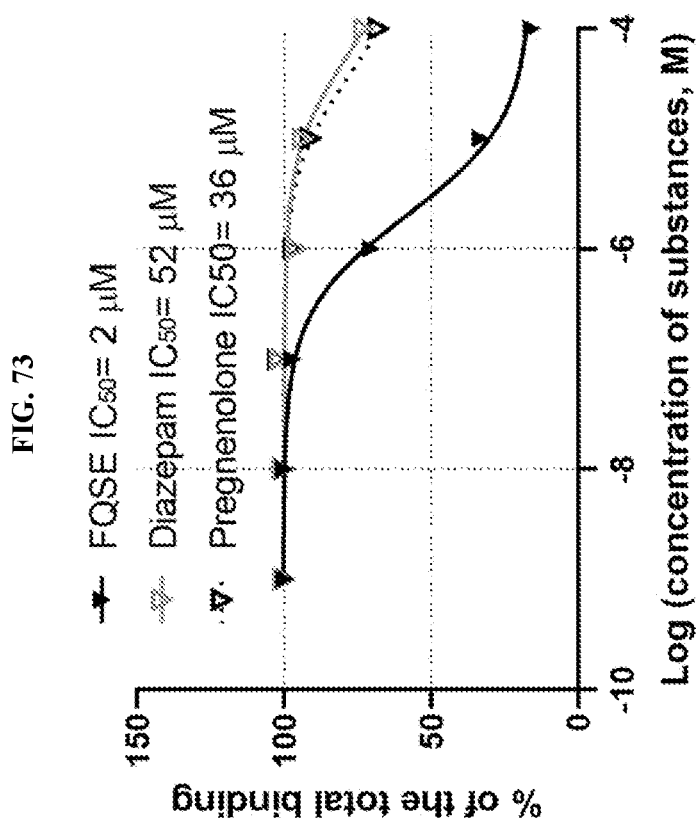
FIG. 73 illustrates the effect of FQSE (SEQ ID NO:10), Diazepam, and Pregnenolone on the binding of [$^3$H]-FQSE (SEQ ID NO:10) with FQSE (SEQ ID NO:10)-specific binding sites in the rat cortex in vitro.

Incubation in this series of the experiment was also carried out at RT, but the duration time was prolonged to 50 min, 1 h, 1 h 30 min. Among the studied substances only diazepam and pregnenolone affected specific binding of the labeled peptide (FIG. 73, Table 10).

TABLE 10

The potential of competitive binding of diazepam and pregnenolone with FQSE (SEQ ID NO: 10)-specific binding sites in the rat cortex (IC50, µmol/L).

| Substance | IC$_{50}$ after different incubation times | | |
|---|---|---|---|
| | 50 min | 1 h | 1 h 30 min |
| Diazepam | 52 ± 0.3 | 89 ± 0.3 | 95 ± 0.2 |
| Pregnenolone | 36 ± 0.2 | 77 ± 0.2 | 75 ± 0.3 |

Results presented as mean ± SE.M.

10.3.3.3. Pre-Incubation Protocol.

The experiments were carried out with 2 modifications of pre-incubation and incubation durations:
pre-incubation—20 min, incubation—25 min;
pre-incubation—1 h, incubation—30 min.

In both variants of incubation protocols, the amount of bound [$^3$H] FQSE (SEQ ID NO:10) was decreased only after pre-incubation with diazepam or pregnenolone ($p<0.05$, t-test) (Table 11).

TABLE 11

The influence of pre-incubation with diazepam and pregnenolone on the among of binding sites for [$^3$H] FQSE (SEQ ID NO: 10).

| Pre-incubation substance | Amount of bound [$^3$H] FQSE (SEQ ID NO: 10) after pre-incubation compared to control level, % | |
|---|---|---|
| | 20 min pre-incubation + 25 min incubation | 1 h pre-incubation + 30 min incubation |
| Diazepam | 90 | 86 |
| Pregnenolone | 87 | 81 |

The control level (100%) was calculated in probes pre-incubated without any added unlabeled ligand.

10.3.4. Series 4.

Specific binding was calculated as the difference between total and non-specific binding. The results obtained at this stage are presented in Table 12.

TABLE 12

The influence of FQSE (SEQ ID NO: 10) on benzodiazepines binding with the corresponding site of the GABAA receptor.

| | Specific binding of [$^3$H]-Flunitrazepam, relative to control levels, % | | | |
|---|---|---|---|---|
| | 30 min incubation | | 25 min pre-incubation + 30 min incubation | |
| Modifications | 4° C. | 24° C. | 4° C. | 24° C. |
| Diazepam 10$^{-6}$M | 100 | 100 | 100 | 100 |
| Diazepam 10$^{-6}$M + FQSE 10$^{-4}$M | 100.27 | 100.95 | 101.07 | 100.58 |
| Diazepam 10$^{-6}$M + FQSE 10$^{-5}$M | 100.04 | 100.70 | 101.07 | 99.78 |

For control level (100%), specific binding values are accepted, for which only Diazepam is used in non-specific binding in the corresponding modification of the radioligand analysis.

It was shown that FQSE (SEQ ID NO:10) in all modified protocols of radioligand binding assay didn't influence the BZD binding to specific sites of GABAA receptors.

10.3.5. Series 5.

Figure 74:
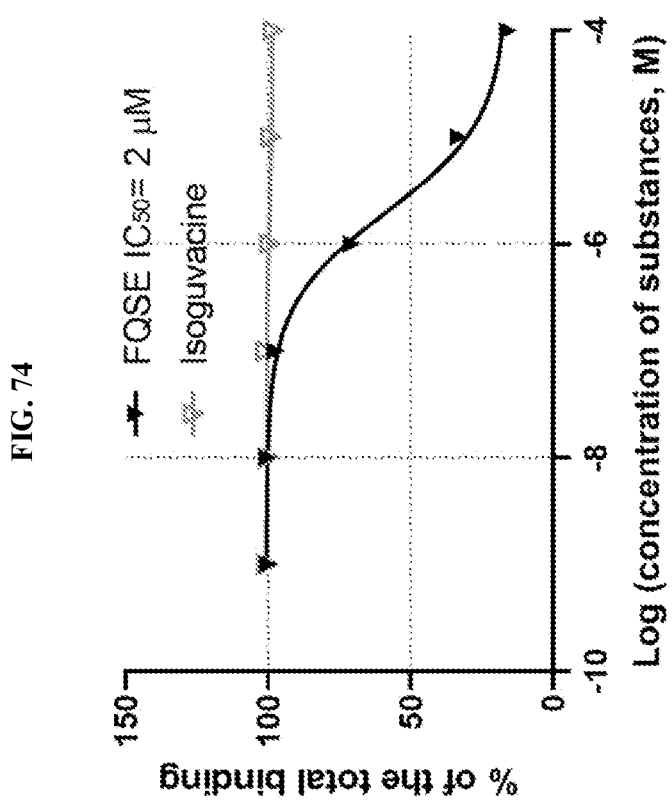
FIG. 74 illustrates the influence of FQSE (SEQ ID NO:10) and Isoguvacine on [$^3$H]-FQSE (SEQ ID NO:10) binding to the cortex FQSE (SEQ ID NO:10)-binding sites in vitro. Isoguvacine curve was used as an example, it is similar for all selected ligands with an IC50>100 μmol/L.

For the second part of the experiments, different incubation times were used—25 and 50 minutes at room temperature (these protocols were used according to the results obtained in the previous experiments). There were no effects of studied ligands (Table 9) on specific binding of the labeled peptide in the whole range of concentrations used, I050 values were >100 μmol/L (FIG. 74).

At the second stage, the incubation was carried out at room temperature, but the order of adding the components in the incubation mixture was different: first, a protein suspension of membranes and an unlabeled ligand of the GABAA receptor were added to the buffer in concentrations of 10$^{-4}$ or 10$^{-5}$M, and after 1 hour of preincubation [$^3$H]-FQSE (SEQ ID NO:10) was added. The incubation lasted 25 minutes. The indicated time intervals were selected based on data obtained in the previous experiment. If one of the studied substance binds to the FQSE (SEQ ID NO:10) sites, the amount of bound [$^3$H]-FQSE (SEQ ID NO:10) would decrease, which may indicate the affinity of the binding sites of the studied ligands with the FQSE (SEQ ID NO:10) binding sites.

In this modification of the experiment, none of the test substances did change the amount of bound [$^3$H]-FQSE (SEQ ID NO:10) ($p<0.05$, t-test) (Table 13).

TABLE 13

The influence of preincubation with studied substances on the number of binding sites for [$^3$H]-FQSE (SEQ ID NO: 10).

| Pre-incubation substance | | Amount of bound [$^3$H] FQSE (SEQ ID NO: 10) after pre-incubation compared to control level, % |
|---|---|---|
| Isoguvacine | 10$^{-4}$M | 102.56 |
| | 10$^{-5}$M | 104.33 |
| SCS | 10$^{-4}$M | 93.93 |
| | 10$^{-5}$M | 104.58 |
| Bretanezil | 10$^{-4}$M | 94.79 |
| | 10$^{-5}$M | 104.51 |
| SL 651498 | 10$^{-4}$M | 101.36 |
| | 10$^{-5}$M | 106.98 |
| MK0343 | 10$^{-4}$M | 98.58 |
| | 10$^{-5}$M | 104.65 |
| THDOC | 10$^{-4}$M | 100.59 |
| | 10$^{-5}$M | 103.38 |
| TB21007 | 10$^{-4}$M | 103.14 |
| | 10$^{-5}$M | 105.28 |
| Gaboxadol | 10$^{-4}$M | 99.31 |
| | 10$^{-5}$M | 100.25 |
| FGIN-1-27 | 10$^{-4}$M | 102.65 |
| | 10$^{-5}$M | 102.33 |
| Allopregnanolone | 10$^{-4}$M | 100.90 |
| | 10$^{-5}$M | 103.18 |

The control level (100%) was calculated in probes pre-incubated without any added unlabeled ligand.

10.3.6. Series 6.

Negative control data were obtained for the [$^3$H]-FQSE (SEQ ID NO:10) binding sites. For this, membranes with NMDA receptors were isolated with a special technique described in the methods section. The specific binding of the corresponding ligand MK-801 on these membranes was verified.

As a result of the in vitro radioligand analysis of NMDA receptors, a displacement curve was obtained with IC50=0.007+0.0004 μmol/L. A radioligand analysis using [$^3$H]-FQSE (SEQ ID NO:10) and unlabeled FQSE (SEQ ID NO:10) was performed on the same membranes, which showed the absence of binding sites for the studied peptide (the difference between total and non-specific binding was 11%).

10.4. Conclusions

The sites of specific binding of the [3H]-FQSE (SEQ ID NO:10) peptide in rat cortex membranes were determined with IC50=2*10$^{-6}$ M.

The FQSE (SEQ ID NO:10) peptide does not compete for the GABA site of GABAA-receptors with [$^3$H]-SR 95531.

The specific binding sites of [$^3$H]-FQSE (SEQ ID NO:10) differ from the binding sites of the known GABA-receptor ligands (muscimol, bicuculline, gabazine, CGS-9895) and dopamine (seroperidol, sulpiride, spiperone, 7-OH-DPAT), serotonin (ketanserin), acetylcholine (nicotine), glutamate (glutamate, glycine, Ro-256981, LY-354740, MK-801, spermine, arkain) receptors.

A partial affinity (IC50~$10^{-4}$ M) to the binding sites of [$^3$H]-FQSE (SEQ ID NO:10) has been shown for diazepam and pregnenolone.

FQSE (SEQ ID NO:10) has no effect on the binding of benzodiazepines to the corresponding GABAA receptor site.

The specific binding sites of [$^3$H]-FQSE (SEQ ID NO:10) differ from the binding sites of the known GABAA receptor ligands: Isoguvacine, SCS, Bretanezil, SL 651498, MK0343, THDOC, TB21007, Gaboxadol, FGIN-1-27, Allopregnanolone.

Negative control data were obtained for binding sites of [$^3$H]-FQSE (SEQ ID NO:10), which confirms the presence of specific binding sites of the peptide

Example 11: Study of the Effects of FQSE (SEQ ID NO:10) Peptide Administration Using the Bicuculline Model The objective of this study was to evaluate the potential neurotropic effect of the FQSE (SEQ ID NO:10) peptide intraperitoneal administration using the bicuculline model.

For the evaluation of the mechanisms of the peptide action in this research, the bicuculline model was used. Bicuculline is a natural alkaloid compound that was extracted from leaf of the plant *Dicentre cucullaria*, family Fumariaceae, by its nature is a competitive antagonist of GABA-A receptors. When administered intravenously at a dose of 0.1-0.4 mg/kg, it causes convulsions in mice lasting up to several hours due to the disruption of the Ca2+-dependent potassium channels (Khawaled (1999). Bicuculline block of small-conductance calcium-activated potassium channels. Pflugers Archiv, 438(3):314-321). During the intraperitoneal administration of the drug at a dose of 5 mg/kg, convulsions are not observed, but the behavioral tests reveal that the activity of drugs belonging to the GABA-A modulators group is greatly reduced in comparison with the values observed for these compounds without bicuculline, which confirms the functional effect of the studied substances on GABA-A receptors (Mizushige (2013). Aromatic amino acid-leucine dipeptides exhibit anxiolytic-like activity in young mice. Neurosci. lett., 543: 126-129). It can be proposed that the FQSE (SEQ ID NO:10) peptide used in the current study belongs to the GABA-A group of modulators.

The aim of the study was to evaluate the effect of i.p. administration of FQSE (SEQ ID NO:10) peptide on the behavior of BALB/C mice in the Elevated plus maze (EPM), Porsolt forced swim test (FST) using the bicuculline model.

11.1. Materials and Methods.

11.1.1. Animal Model

Forty-eight male BALB/C mice were used as subjects in this example. Body weight of each specimen at the beginning of the experiment was between about 18 grams and about 20 grams. All animals were free from species-specific pathogens (SPF status according to the FELASA list, 2014). The animals were kept in conditions of free access to water and food. The room was air-conditioned (exchange rate not less than 15 r/h) with a 12 h:12 h light-dark cycle (lights on at 09:00 am), air temperature 20-24°±2° C. (possible fluctuations of the limits no more than 2° C. per day), 30-70% humidity. All procedures involving animals were conducted in accordance with the European (Directive 2010/63/EU of the European Parliament and of the Council of 22 Sep. 2010 on the protection of animals used for scientific purposes) and the Russian ("GOST 33216-2014 Guidelines for the maintenance and care of laboratory animals. Rules for the maintenance and care of laboratory rodents and rabbits") bioethical guidelines. For the study, the mice were separated into four different groups and the tested substances were administered to the groups as shown in Table 2.

TABLE 14

Experimental groups

| Group name | Group size | Testing substance | Test |
| --- | --- | --- | --- |
| 1. Intact control | 12 | Intraperitoneal injections of solvent according to the experimental group study design | «Elevated plus maze test», «Porsolt swim test (two-day modification)» |
| 2. FQSE (SEQ ID NO: 10) peptide | 12 | Intraperitoneal injections of FQSE (SEQ ID NO: 10) at a dose of 20 mg/kg 30 minutes before testing the behavior. | |
| 3. Bicuculline | 12 | Intraperitoneal injections of Bicuculline at a dose of 5 mg/kg 30 minutes before testing the behavior. | |
| 4. FQSE (SEQ ID NO: 10) peptide + Bicuculline | 12 | Intraperitoneal injections of Bicuculline at a dose of 5 mg/kg and FQSE (SEQ ID NO: 10) at a dose of 20 mg/kg 30 minutes before testing the behavior. | |

All substances were administered intraperitoneally in a volume of 10 µl of solution per 1 g of animal weight 30 minutes before the behavioral tests (FQSE (SEQ ID NO:10) peptide at a dose of 20 mg/kg, bicuculline—5 mg/kg. No more than one test was performed per day. List and order of the planned tests: day 1—The Elevated plus maze test, days 8-9—The Porsolt swim (two-day modification) test.

11.1.2. Statistical Analysis

Statistical data analysis was performed using nonparametric criteria (Manna-Whitney) for not normally distributed samples or using one-way analysis of variance (ANOVA) followed by Fisher's LSD test for normally distributed samples.

11.1.3. The Elevated Plus Maze Test

In the elevated plus maze test, a test arena includes two open and two closed arms crossed in the middle. The arm length is 30 cm, the height of the closed arms side walls is 15 cm. The entire installation is raised 70 cm above the floor. The open arms have bright uniform illumination of about 400 lux, and the closed arms have illumination of about 30-40 lux. Mice were placed at the junction of the four arms of the maze (center), facing an open arm. The following behavioral parameters were automatically registered by the EthoVision, Noldus program within 5 minutes of the experiment: a total distance (cm), a time of motion (if the speed is more than 5 cm/s), an immobility (if the speed is less than 0.2 cm/sec), a mean and maximum velocity, and the number of episodes of motor activity and "freezing". The same set of parameters, as well as a latent period and the duration of stay, were measured for the central sector, open and closed arms separately. (Manufactured by OpenScience, Russia). In the EPM, the main behavioral parameters that characterize the anxiolytic effect of the drug administration in comparison with the control group are the "time on open arms", "open arms entries", and "Anxiety index". Anxiety index (AI) was calculated by the following formula: AI=100*(1−(time on open arms/total test time+open arms entries/total number of entries)/2). An increase in time spent on the open arms and in number of open arms entries in addition with associated decrease of anxiety index are the standard metrics of increased exploratory motivation and decreased anxiety. These parameters may indicate the anxiolytic action of the substance.

11.1.4. The Porsolt Swim Test (Two-Day Modification)

In the Porsolt Swim test, two tests were conducted in two days. The installation is a transparent cylinder, 30 cm in height, 10 cm in diameter, filled with water (temperature about 21-23° C.) to the mark of 25 cm height. On the first day each animal was placed into the cylinder for 10 minutes. Behavioral parameters were not registered. On the second day, the animals were placed into the cylinder for 5 minutes. The following parameters were measured: duration of active (vigorous movements of all limbs) and passive (weak movements of hind limbs) swimming, as well as immobility (immobilization) (Porsolt et al. (1977) Behavioral despair in mice: a primary screening test for antidepressants. Arch Int Pharmacodyn Ther. 229(2):327-36). After each test, the mice were placed into a heated cell to dry. FST (two-day modification) was used for the evaluation of the antidepressant-like properties of the drugs. This test is one of the main methods for the evaluation of the depressive component of animal behavior and the effect of the study drugs on it.

The experimental study was conducted in accordance with GOST 33215-2014 Rules for equipping premises and organizing procedures when working with laboratory animals; GOST 33216-2014 Rules for working with laboratory rodents and rabbits; Directive 2010/63/EU of the European Parliament and the European Union Council for the Protection of Animals used for Scientific Purposes. Translation of Rus-LASA, 2012.

Figure 75:
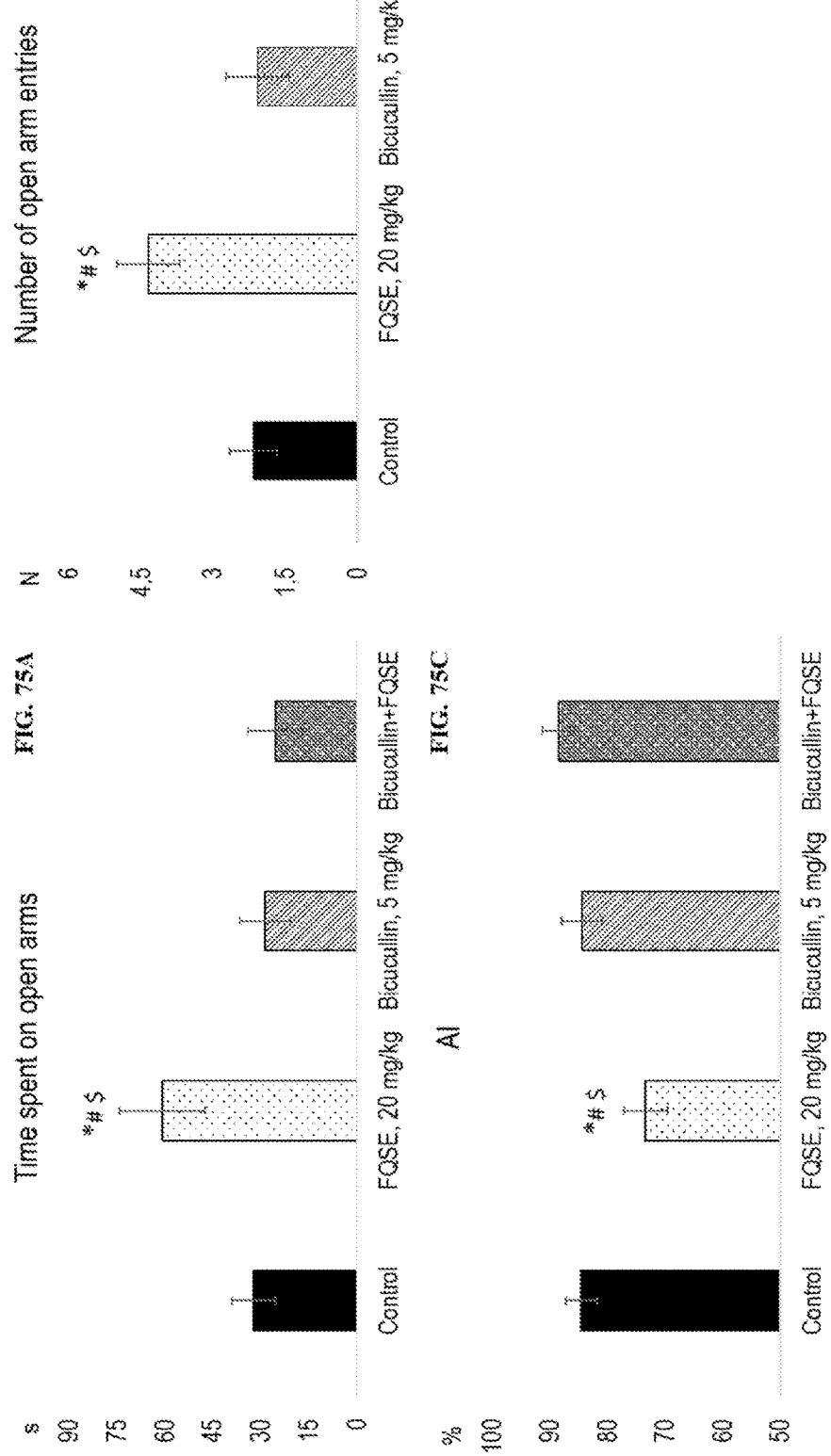
FIGS. 75A, 75B, 75C illustrate the behavior of mice in Elevated Plus Maze test after FQSE (SEQ ID NO:10), bicuculine and bicuculine+FQSE (SEQ ID NO:10) treatment.

11.2 Results 11.2.1. Evaluation of Effects of Test Substances on Mice Behavior Using the Elevated Plus Maze Test FQSE (SEQ ID NO:10) peptide administration increased the time spent on open arms (60.9±13.31 vs. 32.4±6.77 s in control group) (FIG. 75A) as well as the open arm entries (FIG. 75B) (4±0.65 vs 2.2±0.48 in control group). The changes in these parameters led to a decrease of "AI" in FQSE (SEQ ID NO:10)-treated animals in comparison with control (73±3.8 vs. 85±2.7% respectively) (FIG. 75C). The obtained results indicate a pronounced anxiolytic-like effect of the test substance at a dose of 20 mg/kg.

We didn't observe any differences in EPM test in the experimental group treated with bicuculline at a dose of 5 mg/kg. Co-administration of the peptide with bicuculline also did not reduce the anxiety-like behavior in mice.

The obtained results indicate a pronounced anxiolytic-like effect of the test substance at a dose of 20 mg/kg. These effects of FQSE (SEQ ID NO:10) were absent when the peptide was co-administered with bicuculline—a competitive antagonist of GABA-A receptors, which may propose the functional effect of FQSE (SEQ ID NO:10) through the interaction with GABA-A receptors.

Figure 76:
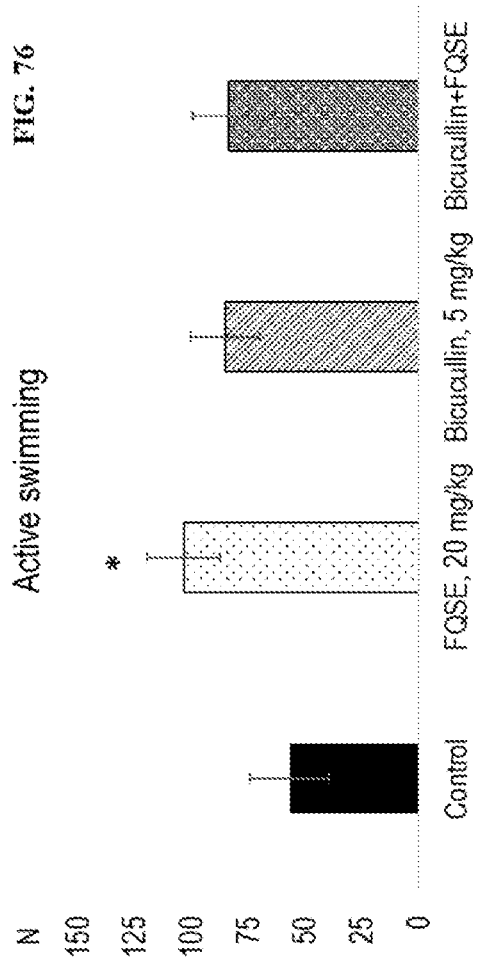
FIG. 76 illustrates the time spent active swimming in Porsolt forced swim test (two-day modification), s, after FQSE (SEQ ID NO:10), bicuculine and bicuculine+FQSE (SEQ ID NO:10) treatment. The results are expressed as the mean±SEM. * $p<0.05$ represents significant differences vs. control group, #$p<0.05$—vs. "bicuculline" group, $ $p<0.05$—vs. "bicuculline+FQSE (SEQ ID NO:10)" group. One-way ANOVA with Fisher's LSD post hoc test.

11.2.2. Evaluation of Effects of Test Substances on Mice Behavior Using the Porsolt Forced Swim Test The FQSE (SEQ ID NO:10) peptide treatment resulted in increased time spent active swimming (103.7±16 s) in comparison with the control group (57.1±17.62 s) (FIG. 76), which can be considered as the antidepressant-like effects of the test compound.

The administration of bicuculline alone didn't affect the behavior of mice in this test. These results are consistent with previous studies. In the work of Mizushige (Mizushige et al. (2013). Characterization of Tyr-Leu-Gly, a novel anxiolytic-like peptide released from bovine aS-casein. FASEB J., 27(7), 2911-2917), the i.p. administration of bicuculline at a dose of 5 mg/kg didn't affect the parameters of animals in FST. The mice which received FQSE (SEQ ID NO:10) together with bicuculline also didn't show any changes in the time spent active swimming. These results may propose that bicuculline may diminish the effects of peptide and the antidepressant-like properties of the FQSE (SEQ ID NO:10) may associate with interaction with GABA-A receptors.

11.3. Conclusions

Intraperitoneal injection of FQSE (SEQ ID NO:10) peptide at a dose of 20 mg/kg into BALB/C mice 30 minutes before the behavioral tests resulted in a pronounced anxiolytic-like and antidepressant-like effects.

Injection of bicuculline at a dose of 5 mg/kg into BALB/C mice 30 minutes before the behavioral tests did not affect the behavior of mice in EPM and FS tests.

Co-administration of FQSE (SEQ ID NO:10) with bicuculline significantly reduced the manifestation of the anxiolytic-like and antidepressant-like properties of the peptide, which may suggest the possible mechanism of the functional action of the drug through interaction with GABA-A receptors.

Example 12: The Effects of Novel Peptide FQSE (SEQ ID NO:10) on Neuroinflammation In Vitro Using Primary Glial Cells The aim of the study was to evaluate in vitro potential effect of FQSE (SEQ ID NO:10) peptide on LPS-induced neuroinflammation in murine primary glial cells.

12.1. Methods

The cells were divided into 10 groups and subjected to the following treatment.

Control Cells
+LPS (500 ng/mL, 24 hours)
+LPS+FQSE (SEQ ID NO:10), 0.04 µM
+LPS+FQSE (SEQ ID NO:10), 4 µM
+LPS+FQSE (SEQ ID NO:10), 40 µM
+LPS+FQSE (SEQ ID NO:10), 400 µM
+FQSE (SEQ ID NO:10), 0.04 µM
+FQSE (SEQ ID NO:10), 4 µM
+FQSE (SEQ ID NO:10), 40 µM
+FQSE (SEQ ID NO:10), 400 µM 12.1.1. Analyzed Parameters Expression levels (mRNA, qPCR) of the following inflammatory biomarkers: IL-6, Il-1b, TNFa, IKKb.

12.1.2. Experimental Procedures

The whole brain from 1-2-day-old neonatal C57/B16 mice was collected, without the meninges, and placed in HBSS modified medium without calcium or magnesium (Gibco 14190144) and processed according to the manufacturer's instructions from Miltenyi Biotech. All procedures were approved by the Wayne State University Institutional Animal Care and Use Committee in accordance with the National Institutes of Health Guidelines. The supernatant was discarded, and the pellet was re-suspended in 1-2 mL of Dulbecco's Modified Eagle Medium/Nutrient Mixture F-12, no phenol red (DMEM/F-12), (Gibco 21041025) enriched with 10% inactivated fetal bovine serum (FBS) (ThermoFischer 10082147) and 1% Antibiotic-Antimycotic (ThermoFischer 15240062). After homogenization, the cells were grown in Nunc™ Cell Culture Treated Flasks with Filter Caps, (ThermoFischer, 178905) containing 10 mL of the medium [DMEM/F-12; 10% FBS; 1% Antibiotic-Antimycotic] in a 5% CO2 incubator (Galaxy 170R, Eppendorf) at 37° C. The cells were maintained in culture for a period of 8-10 days, with a partial replacement of the incubation medium (70%) every 48-72 h. At 80% confluence, the cells were incubated in a shaker at 200 rpm for 2 h at 37° C. to separate the oligodendrocytes and neurons from the glial cell culture. The cells in suspension were discarded, and the adhered cells were washed with 1 mL of Dulbecco's Phosphate-Buffered Saline, without calcium or magnesium (DPBS), (Gibco 14190144). Then, 5 mL of 1× trypsin (ThermoFischer 15400054) were added, and the cells were maintained for 15 min in the incubator (5% CO2 at 37° C.). After this step, the same amount of complete medium was added to stop the trypsin action, and the cells were centrifuged at 1000 rpm for 10 min at room temperature. Cells were then cultured in 24-well (80 000 cells/well) and the treatment was performed 48 hours after seeding.

The cells were treated for 24 hours with the following conditions: LPS [250 ng/ml] and separately the drug FQSE (SEQ ID NO:10) [400 µM, 40 µM, 4 µM, 0.04 µM]. Also, the drug FQSE (SEQ ID NO:10) was used in all concentrations with LPS [400 µM+LPS, 40 µM+LPS, 4 µM+LPS, 0.04 µM+LPS]. N=3-4 samples per group. A complete medium was used as a control.

After the exposure the cells were washed with 1 ml of cold DPBS and immediately harvested with 1 ml of Trizol, following for RNA extraction. Gene expression for TNF-alpha, IL-1b, Il-6, IKKb was analyzed.

12.2. Results

Figure 77:
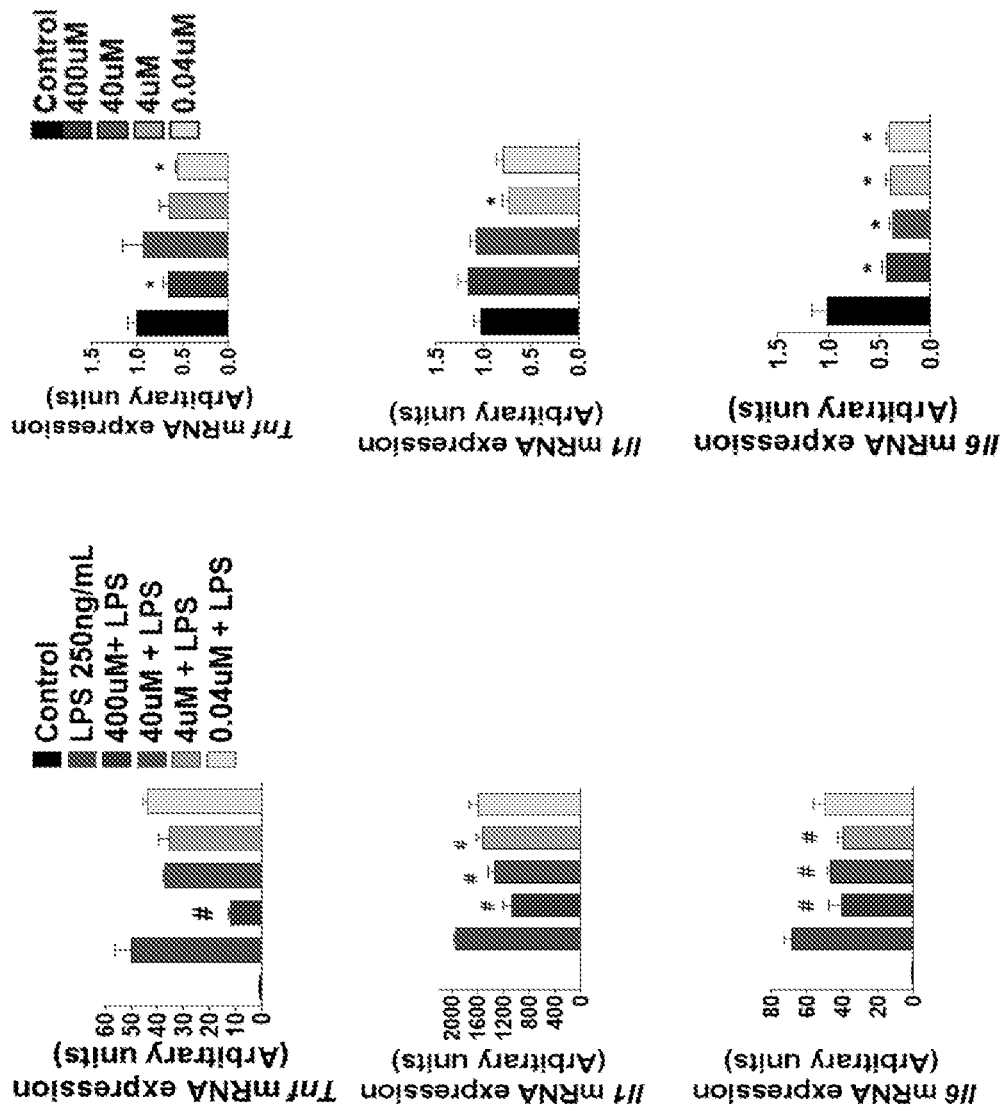
FIG. 77 illustrates that FQSE (SEQ ID NO:10) suppresses LPS-induced TNFa, Il-1b and IL-6 mRNA expression levels in murine primary glial cells. The results are expressed as the mean±SEM. All LPS groups demonstrated significant difference in respect to control without LPS. #–$p<0.05$ in respect to LPS control. *–$p<0.05$ in respect to control. Statistical analysis was performed using unpaired t-test.

The results of qPCR measurements of TNFa, IL-1b and Il-6 expression levels are represented on FIG. 77. FQSE (SEQ ID NO:10) demonstrates a significant dose-response effect on TNFa expression. On 400 µM it efficiently suppresses LPS-induced TNFa expression, however the effects of lower FQSE (SEQ ID NO:10) concentrations were statistically insignificant. It is possible that under chronic stimulation with potentially weaker stressors than LPS, lower concentrations of FQSE (SEQ ID NO:10) will still have anti-inflammatory effects. This assumption is supported by the fact that FQSE (SEQ ID NO:10) (even on 0.04 µM) is able to reduce basal TNFa and IL-6 expression levels in non-activated glial cells.

FQSE (SEQ ID NO:10) demonstrates high efficiency regarding suppression of LPS-induced expression of both IL-1b and IL-6 in a wide range of doses.

Figure 78:
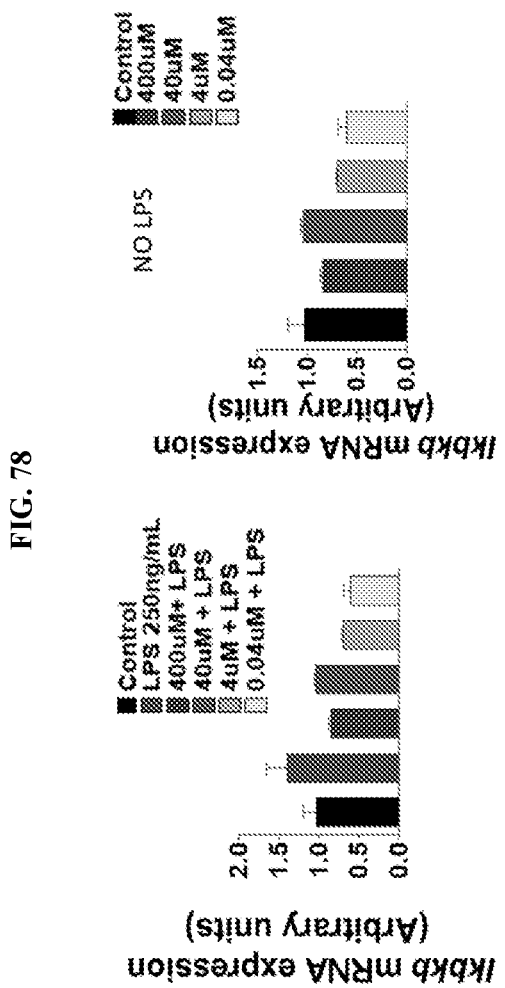
FIG. 78 illustrates that IKKb mRNA expression level depend neither on LPS nor on FQSE (SEQ ID NO:10) in murine primary glial cells. The results are expressed as the mean±SEM.

Expression of NFKb downstream signaling gene IKKb (FIG. 78) did not correlate with FQSE (SEQ ID NO:10), however the expression levels of the gene were relatively weak across all treatments. Also, it is important to mention that no significant changes in IKKb expression in response to LPS were detected, which indicates that this gene appears to be a non-relevant marker in this model.

12.3. Conclusions

FQSE (SEQ ID NO:10) suppresses LPS-induced expression of pro-inflammatory cytokines TNF-alpha, IL-1b and Il-6 in primary glial cells that could indicate its role in the regulation of neuroinflammation The obtained data highly correlate with the previous Western blot results where it was discovered that FQSE (SEQ ID NO:10) is able to normalize stress induced ERK½ (MAPK pathway participants) phosphorylation levels. Inhibited expression of proinflammatory cytokines observed in the present study could be also considered as a result of GABAa-triggered MAPK repression (Lee et al. (2013). Neurotransmitters and microglial-mediated neuroinflammation. Curr. Prot. Pept. Sci., 14(1), 21-32).

Example 13: The Study of FQSE (SEQ ID NO:10) Distribution in Brain Regions of Rats Following Intranasal Administration The aim of the pharmacokinetic study was to establish FQSE (SEQ ID NO:10) distribution in brain regions of rats following intranasal administration.

Study Design

Tritium-labeled peptide FQSE (SEQ ID NO:10) was administered intranasally (i.n.) at a dose of 500 µg/kg diluted in saline. The administered sample contained 2000 pKi of tritium-labeled peptide [$^3$H] FQSE (SEQ ID NO:10). In 6 minutes after the administration, test samples of brain, blood and urine were obtained.

Selection of Animal Species

Animal studies provide full toxicity information of the substance which is supposed for human use. The study is a part of the complex pharmacokinetic and pharmacological investigation of the drug intended for therapy of neurodegenerative diseases. Wistar male rats were selected for the study.

Number of Animals

The number of animals used in the study—5 Wistar male rats which is sufficient for significance of data on the tested effects.

Method of Administration and Selection of Doses

The substance was administered once, one-time (bolus injection) intranasally.

Dose Preparation

The study was carried out using tritium-labeled peptide FQSE (SEQ ID NO:10). For that, rats were administered with 2000 pKi [$^3$H] FQSE (SEQ ID NO:10) in dose 500 µg/kg (about 150 µg). The solutions administered to animals were prepared using saline solution. The volume of the solution for intranasal administration was 20 µl for rats.

Doses after preparation prior administration are kept at 4-2° C. for 3 hours.

Animal Maintenance

The animals were maintained in polycarbonate cages Type-3 (825 sq. cm) on the bedding; cages were covered with a steel grating feeder. As bedding, commercial bedding LIGNOCEL (JRS, Germany) out of specially prepared wooden chips was used. The bedding was routinely checked for microbiological contamination. The test data were kept in the laboratory documents.

Complete mixed feed for laboratory animals "Chara" (Range of Agro products, Russia) was provided ad libitum to the feeder in the cage cover. Periodic analysis of microbiological contamination of feeding specimens was performed. The analysis results, as well the data on composition and quality of the producer's feeding are filed in the laboratory documents.

Purified potable water was given ad libitum in standard drinking bottles. Water samples were periodically tested for microbiological contamination. The test results were filed in the current laboratory documents.

The animals were kept in controlled environmental conditions (18-26° C. and 30-70% relative humidity). Temperature and humidity were constantly monitored in each experimental room. In the rooms where animals were maintained, 12-hour light cycle and at least 10-fold air change in the room per hour were kept.

The animals were adapted in the laboratory for at least 3 days prior the dosing. During the period, animal appearance was daily examined. The animals having abnormalities found at the examination were not included to experimental groups.

Individual number was assigned to each animal which was marked by auricle prick and fixed on the cage label. All procedures involving animals were conducted in accordance with the European (Directive 2010/63/EU of the European Parliament and of the Council of 22 Sep. 2010 on the protection of animals used for scientific purposes) and the Russian ("GOST 33216-2014 Guidelines for the maintenance and care of laboratory animals. Rules for the maintenance and care of laboratory rodents and rabbits") bioethical guidelines.

13.1 Methods

Peptide Administration to Animals and Blood Sampling

In rat experiments, product FQSE (SEQ ID NO:10) was administered as a single, bolus, intranasal injection. Preliminarily, rats were anesthetized with chloral hydrate (300 mg/kg), and in 10 min, product FQSE (SEQ ID NO:10) was administered in volume 20 µl, in dose 500 µg/kg which contained 2000 pKi of labeled peptide [$^3$H]FQSE (SEQ ID NO:10). Rats were decapitated in 6 minutes after the product administration. Organ biopsies were rinsed in a saline solution for 5-7 seconds, transferred to weighted plastic vials, weighted and frozen by liquid nitrogen. FQSE (SEQ ID NO:10) solution intended for administration to animals was prepared using sterile saline solution (0.9% NaCl).

Preparation of Tissue Samples

Before preparing tissues for high performance liquid chromatography (HPLC) assay, frozen and weighted tissue samples in plastic tubes were freeze-dried for 2 days. To prepare the peptide extract, successive extractions with organic diluents, evaporation under reduced pressure and centrifugation were performed. Freeze-dried blood samples were heated at 65° C. for 30 minutes, after that the samples were dispersed in the same plastic vials with horizontal knives rotating with rate 5000 rot/min. The samples were first extracted with 90% water-acetonitrile containing 1% trifluoroacetic acid. Then, 10 µg of peptide FQSE (SEQ ID NO:10) intended for identification of the peptide fraction in chromatography was added to water-acetonitrile solution used for extraction. After centrifugation, the solution containing tritium-labeled peptide and plasma components was dried under the reduced pressure, re-extracted with methanol and re-centrifuged. The resulting solution containing tritium-labeled peptide and plasma components was dried under reduced pressure, re-extracted with 0.1% aqueous solution of heptafluorobutyric acid and further centrifuged. To verify the method for sample preparation, 10 pKi of peptide [$^3$H] FQSE (SEQ ID NO:10) in 10 µg of the solution was administered to 200 µl of freshly derived blood of rats, after that the sample was treated by the scheme described above. As a result of the analysis, 95% of initial labeled peptide [$^3$H] FQSE (SEQ ID NO:10) was found in the sample.

13.2 Results

The quantitative analysis of peptides was performed with HPLC on column Kromasil C18, 4×150 mm in methanol gradient (0-40%), presence of 0.08% TEA and 0.02% HBA (heptafluorobutyric acid). The fractions containing peptide FQSE (SEQ ID NO:10) were collected, and their radioactivity was determined with liquid scintillation counting. The distribution of peptide FQSE (SEQ ID NO:10) in tissues was shown in Table 15.

TABLE 15

Distribution of peptide FQSE (SEQ ID NO: 10) in brain tissues of rats in 6 min following intranasal administration of 2000 µKi [$^3$H] FQSE (SEQ ID NO: 10) at a dose of 500 µg/kg.

| Region | Weight, g | Count, DPM/g × 1000 | Concentration, ng/g |
|---|---|---|---|
| 1. Olfactory bulbs | 0.040 ± 0.003 | 930 ± 80 | 30.3 ± 2.6 |
| 2. Cerebellum | 0.246 ± 0.015 | 220 ± 30 | 7.2 ± 0.9 |
| 3. Hypothalamus | 0.084 ± 0.012 | 310 ± 35 | 10.2 ± 1.1 |
| 4. Prefrontal cortex | 0.096 ± 0.006 | 290 ± 30 | 9.5 ± 1.0 |
| 5. Habenula | 0.026 ± 0.002 | 155 ± 25 | 5.1 ± 0.8 |
| 6. Hippocampus | 0.096 ± 0.015 | 300 ± 40 | 10.8 ± 1.5 |
| 7. Occipital cortex | 0.125 ± 0.005 | 190 ± 25 | 6.1 ± 0.8 |
| 8. Striatum | 0.128 ± 0.012 | 165 ± 20 | 5.4 ± 0.7 |
| 9. Blood | 1.277 ± 0.25 | 1420 ± 170 | 45.2 ± 5.4 |
| 10. Urine | 0.130 ± 0.080 | 15 ± 3 | 0.5 ± 0.1 |

Concentrations are presented as the mean ± error of the mean.

It was found that the greatest affinity of peptide FQSE (SEQ ID NO:10) following intranasal administration is found in the olfactory bulbs where its contents are significantly higher than in other brain regions. It was also found that a higher level of peptide FQSE (SEQ ID NO:10) presented in the prefrontal cortex, hippocampus and hypothalamus compared to other brain regions. The concentration of peptide FQSE (SEQ ID NO:10) in tissues is lower than in blood: FQSE (SEQ ID NO:10) concentration in the brain 6 minutes after intranasal administration were about $^1\!/_5$-$^1\!/_{10}$ of its blood concentration.

13.3 Conclusions

It was found that the greatest affinity for peptide FQSE (SEQ ID NO:10) was found in olfactory bulbs where its contents were significantly higher than in other brain regions. It was also revealed that a higher level of peptide FQSE (SEQ ID NO:10) was presented in the prefrontal cortex, hippocampus and hypothalamus compared to other brain regions. These results suggest that peptide FQSE (SEQ ID NO:10) can penetrate blood-brain barrier.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features. Further, the term "substantially" means that the recited characteristic, parameter, or value need not be achieved exactly, but that deviations or variations including, for example, tolerances, measurement error, measurement accuracy limitations, manufacturing tolerances and other factors known to those of skill in the art, can occur in amounts that do not preclude the effect that characteristic, parameter, or value was intended to provide. In the description presented herein, the term "about" or "approximately" refers to a range of values within plus or minus 10% of the specified number.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

What is claimed is:

1. A method for treating a mood disorder, comprising administering to a subject in need thereof a composition comprising a synthetic neuromodulatory peptide defined by the general formula I:

$$R_1R_2R_3R_4 \quad (I)$$

wherein:
$R_1$ is selected from the amino acids F, W, and D;
$R_2$ is selected from the amino acids Q, D, and K;
$R_3$ is selected from the amino acids S, Q, and T; and
$R_4$ is selected from the amino acids E and V; and
the subject in need thereof is diagnosed with the mood disorder.

2. The method of claim 1, wherein:
R1 is F;
R2 is Q;
R3 is S; and
$R_4$ is E.

3. The method of claim 1, wherein:
$R_1$ is W;
R2 is D;
R3 is Q; and
R4 is V.

4. The method of claim 1, wherein:
R1 is D;
R2 is K;
R3 is T; and
R4 is E.

5. The method of claim 1, wherein the synthetic neuromodulatory peptide binds to a benzodiazepine binding site of a GABA-A receptor.

6. The method of claim 1, wherein the synthetic neuromodulatory peptide binds to a neurosteroid binding site of a GABA-A receptor.

7. The method of claim 1, wherein the synthetic neuromodulatory peptide binds to an α-β binding site of a GABA-A receptor.

8. The method of claim 1, wherein the composition further comprises a pharmaceutically acceptable carrier or delivery vehicle.

9. The method of claim 8, wherein the delivery vehicle is selected from a liposome, a nanoparticle, and a polysaccharide.

10. The method of claim 9, wherein the polysaccharide is selected from cyclodextrin, chitosan, cellulose, and alginate.

11. The method of claim 1, wherein the composition is administered orally, intranasally, intravenously or by inhalation.

12. The method of claim 1, wherein the mood disorder is depression.

13. The method of claim 12, wherein the depression is selected from major depressive disorder, dysthymia, breakthrough depression, treatment-refractory depression, depression associated with Parkinson's disease, depression associated with post-traumatic stress disorder, post-partum depression, bipolar depression, and suicidal ideation.

14. The method of claim 1, wherein the mood disorder is an anxiety disorder.

15. The method of claim 14, wherein the anxiety disorder is selected from separation anxiety disorder, selective mutism, specific phobia (SP), social anxiety disorder (SAD), panic disorder, agoraphobia, substance/medication-induced anxiety disorder, and anxiety disorder due to another medication condition, generalized anxiety disorder (GAD), post-traumatic stress disorder (PTSD), major depressive disorder (MDD), treatment-resistant depression (TRD), postpartum depression (PPD), bipolar disorder or bipolar depression, obsessive-compulsive disorder (OCD), and attention deficit hyperactivity disorder (ADHD), social phobia, agitation in Alzheimer's disease, aggression in Alzheimer's disease, and obsessive-compulsive disorder.

16. The method of claim 1, wherein the mood disorder is schizophrenia, a panic disorder, attention deficit hyperactivity disorder (ADHD), or a stress-related disorder.

17. The method of claim 1, wherein the treatment further comprises administering an antidepressant, wherein the antidepressant is selected from the group consisting of serotonin reuptake inhibitors, selective norepinephrine reuptake inhibitors, combined action SSRI/SNRI, serotonin-2 antagonist/reuptake inhibitors, an antidepressant with alpha-2 antagonism plus serotonin-2 and serotonin-3 antagonism, an antidepressant with serotonin/norepinephrine/dopamine reuptake inhibition, an antidepressant with norepinephrine and dopamine reuptake inhibition, 5-HT-1alpha antagonist, 5-HT-1beta antagonist, 5-HT1A receptor agonists, 5-HT1A receptor agonists and antagonists, 5-HT2 receptor antagonists, viloxazine hydrochloride, dehydroepiandosterone, NMDA receptor antagonists, AMPA receptor potentiators, substance P antagonists/neurokinin-1 receptor antagonists, nonpeptide Substance P antagonist, neurokinin 2 antagonists, neurokinin 3 antagonists, corticotropin-releasing factor receptor antagonists, antiglucocorticoid medications, glucocorticoid receptor antagonists, cortisol blocking agents, nitric oxide synthesize inhibitors, inhibitors of phosphodiesterase, enkephalinase inhibitors, GABA-A receptor agonists, free radical trapping agents, atypical MAOI's, selective MAOI inhibitors, hormones, folinic acid, leucovorin, tramadol, and tryptophan in combination with an antipsychotic drug, wherein said antipsychotic drug is selected from the group consisting of an atypical antipsychotic drug, and a dopamine system stabilizer.

18. The method of claim 1, wherein the treatment further comprises administering an additional depression treatment, wherein the additional depression treatment is selected from one or more of amoxapine, bupropion, citalopram, clomipramine, desipramine, desvenlafaxine, doxepin, duloxetine, escitalopram, fluoxetine, fluvoxamine, imipramine, isocarboxazid, levomilnacipran, mesylate, methylphenidate, maprotiline, milnacipran, mirtazapine, nefazodone, nortriptyline, olanzapine, paroxetine, phenelzine, protriptyline, selegiline, sertraline, tranylcypromine, trimipramine, trazodone, venlafaxine, vilazodone, vortioxetine.

19. The method of claim 1, wherein the treatment further comprises administering an additional anxiety treatment, wherein the additional anxiety treatment is selected from agent one or more of benzodiazepines selected from alprazolam, clonazepam, diazepam, lorazepam, oxazepam, and chlordiazepoxide; beta blockers selected from propranolol and atenolol; tricyclic antidepressants selected from imipramine, desipramine, nortriptyline, amitriptyline, doxepin, and clomipramine; monoamine oxidase inhibitors (MAOIs) selected from phenelzine, and tranylcypromine; selective serotonin reuptake inhibitors (SSRIs) selected from fluoxetine, fluvoxamine, sertraline, paroxetine, escitalopram oxalate, and citalopram; serotonin-norepinephrine reuptake inhibitors (SNRIs) selected from venlafaxine, venlafaxine extended release, and duloxetine; mild tranquilizers, the mild tranquilizer being buspirone; and anticonvulsants selected from valproate, pregabalin, and gabapentin.

20. The method of claim 1, wherein the synthetic neuromodulatory peptide modulates voltage-gated calcium channels (VGCC) activity.

* * * * *